United States Patent
Bradbury et al.

(10) Patent No.: US 11,920,258 B2
(45) Date of Patent: Mar. 5, 2024

(54) ANTIBODY LIBRARIES WITH MAXIMIZED ANTIBODY DEVELOPABILITY CHARACTERISTICS

(71) Applicant: SPECIFICA INC., Santa Fe, NM (US)

(72) Inventors: Andrew Raymon Morton Bradbury, Santa Fe, NM (US); Michael Frank Erasmus, Santa Fe, NM (US); Andre Teixeira, Santa Fe, NM (US)

(73) Assignee: RULES-BASED MEDICINE INC., Austin, TX (US)

( * ) Notice: Subject to any disclaimer, the term of this patent is extended or adjusted under 35 U.S.C. 154(b) by 406 days.

(21) Appl. No.: 17/163,170

(22) Filed: Jan. 29, 2021

(65) Prior Publication Data

US 2021/0171936 A1 Jun. 10, 2021

Related U.S. Application Data

(63) Continuation of application No. 16/505,358, filed on Jul. 8, 2019, now Pat. No. 10,954,508.

(60) Provisional application No. 62/822,671, filed on Mar. 22, 2019, provisional application No. 62/695,065, filed on Jul. 8, 2018.

(51) Int. Cl.
| | |
|---|---|
| *C40B 50/06* | (2006.01) |
| *C12N 15/10* | (2006.01) |
| *C12N 15/81* | (2006.01) |
| *C40B 40/10* | (2006.01) |
| *C40B 40/08* | (2006.01) |

(52) U.S. Cl.
CPC .......... *C40B 40/10* (2013.01); *C12N 15/1037* (2013.01); *C12N 15/81* (2013.01); *C40B 40/08* (2013.01); *C40B 50/06* (2013.01)

(58) Field of Classification Search
None
See application file for complete search history.

(56) References Cited

U.S. PATENT DOCUMENTS

| | | |
|---|---|---|
| 5,888,732 A | 3/1999 | Hartley et al. |
| 2003/0153038 A1 | 8/2003 | Ohlin et al. |
| 2006/0160178 A1 | 7/2006 | Rothberg et al. |

(Continued)

FOREIGN PATENT DOCUMENTS

| | | |
|---|---|---|
| WO | 00/70023 A1 | 11/2000 |
| WO | 02/83872 A2 | 10/2002 |

(Continued)

OTHER PUBLICATIONS

Boldicke, Antibody Engineering "2.3.2 Case study of synthetic antibody libraries: n-CoDeR". Feb. 1, 2018. 3 pages.

(Continued)

*Primary Examiner* — Christian C Boesen
(74) *Attorney, Agent, or Firm* — McDermott Will & Emery LLP; Michael Siekman; Yuhe Liu

(57) ABSTRACT

Antibody libraries comprising a plurality of heavy chain variable domains and/or a plurality of light chain variable domains, which comprise complementary determining regions (CDRs) found in naturally-occurring human antibodies, and methods of making such antibody libraries. The antibody libraries are free of members that comprise one or more liabilities affecting one or more features of such members. Further, the antibody libraries comprise members having heavy chain and/or light chain CDRs not found in the same naturally-occurring human antibody.

12 Claims, 58 Drawing Sheets

Specification includes a Sequence Listing.

(56) References Cited

U.S. PATENT DOCUMENTS

| | | |
|---|---|---|
| 2012/0077710 A1 | 3/2012 | Ohlin et al. |
| 2016/0194627 A1 | 7/2016 | Smider et al. |
| 2017/0362306 A1 | 12/2017 | Shim et al. |

FOREIGN PATENT DOCUMENTS

| | | |
|---|---|---|
| WO | 09/36379 A2 | 3/2009 |
| WO | 2019126227 A1 | 6/2019 |

OTHER PUBLICATIONS

Frenzel et al., Phage display-derived human antibodies in clinical development and therapy. MAbs. Oct. 2016;8(7):1177-1194. Epub Jul. 14, 2016.

Ponsel et al., High affinity, developability and functional size: the holy grail of combinatorial antibody library generation. Molecules. May 3, 2011;16(5):3675-700.

Urlinger, Ylanthia—A New Antibody Library Concept. Dec. 1, 2011. 33 pages.

Van Blarcom et al., Productive common light chain libraries yield diverse panels of high affinity bispecific antibodies. MAbs. Feb./Mar. 2018/10(2):256-268. Epub Dec. 14, 2017.

Bai, X. et al. "A Novel Human scFv Library with Non-Combinatorial Synthetic CDR Diversity" PLoS ONE. vol. 10, No. 10, pp. 1-18, Oct. 20, 2015.

Barbas, Carlos F., et al., "Assembly of combinatorial antibody libraries on phage surfaces: the gene III site," Proc. Natl. Acad. Sci. vol. 88, No. 18, pp. 7978-7982, Sep. 15, 1991.

D'Angelo, Sara, et al. "Many Routes to an Antibody Heavy-Chain CDR3: Necessary, Yet Insufficient, For Specific Binding" Frontiers in Immunology. vol. 9, pp. 1-13, Mar. 8, 2018.

Palazzolo, Michael J., et al., "Phage lambda cDNA cloning vectors for subtractive hybridization, fusion-protein synthesis and Cre-loxP automatic plasmid subcloning," Gene. vol. 88, No. 1, pp. 25-36, Mar. 30, 1990.

Soderlind, E., et al., "Recombining germline-derived CDR sequences for creating diverse single-framework antibody libraries" Nature vol. 18, No. 8, pp. 852-856, Aug. 2000.

Waterhouse, Peter, et al., "Combinatorial infection and in vivo recombination: a strategy for making large phage antibody repertoires," Nucleic Acids Research. vol. 21, No. 9, pp. 2265-2266, May 11, 1993.

Figure 3

Two BsaI sites in opposite orientations
- Scarless cloning
- Removes the exact portion of the CDR as well as the BsaI site

```
GTGTTACCATCACCTGTCGTGCTTCTagagaccatggccagtaagcttactctCTGGCTTGGTACAGCAGAAA
CACAATGGTAGTGGACACGAAGA...                              aGACCGAACCATGGTCGTCTTT
```

18 19 20 21 22 23 24 25 26  1 2 3 4 5 6 7 8 9  1 2 3 4 5 6 7

Internal SfiI site
- Minimize uncut vector background
- Serves as spacer between BsaI sites

Ochre stop codon and frame-shift
- Prevent expression of background sequences

Cysteines in CDRs should be paired and structurally placed

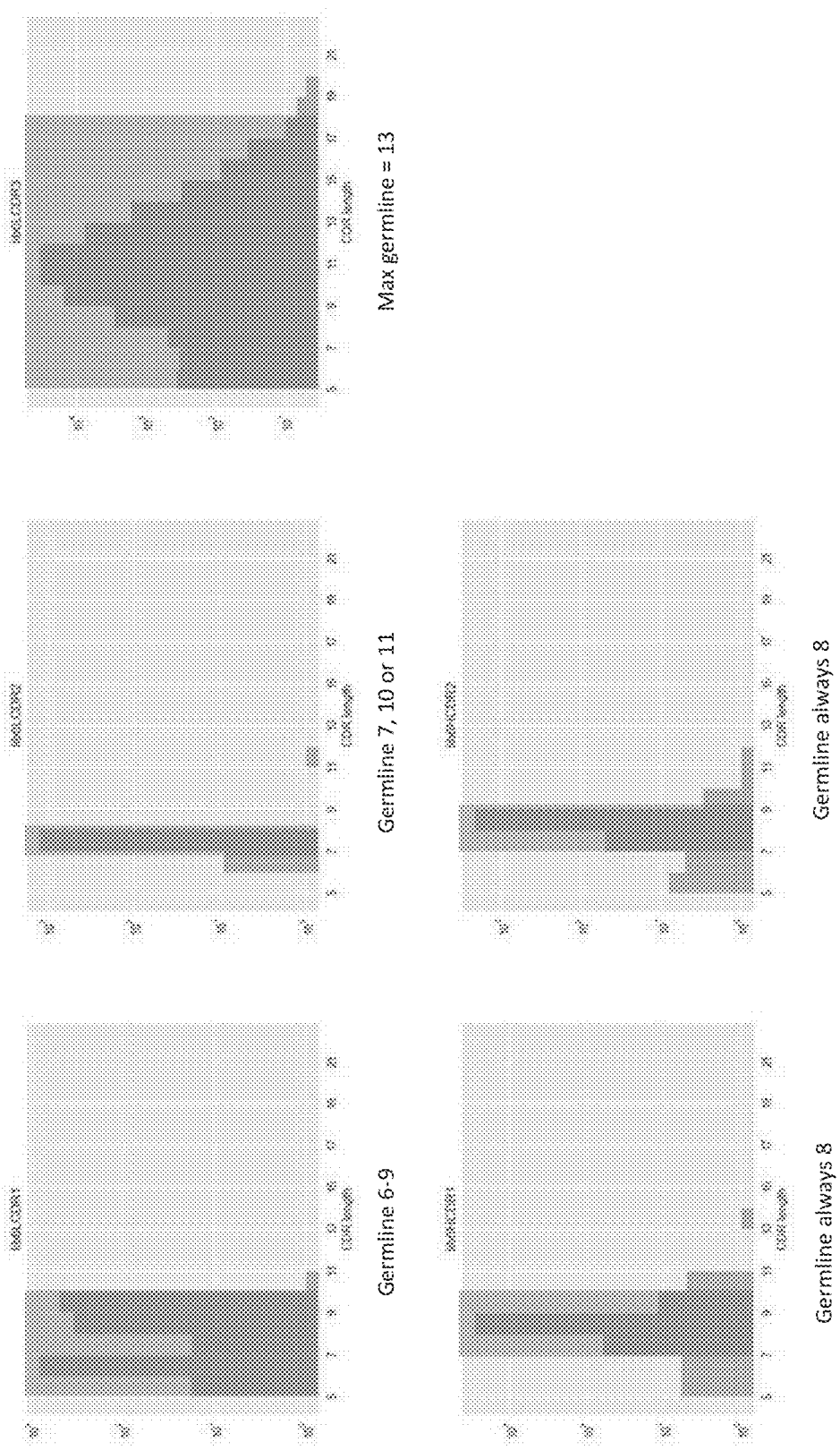

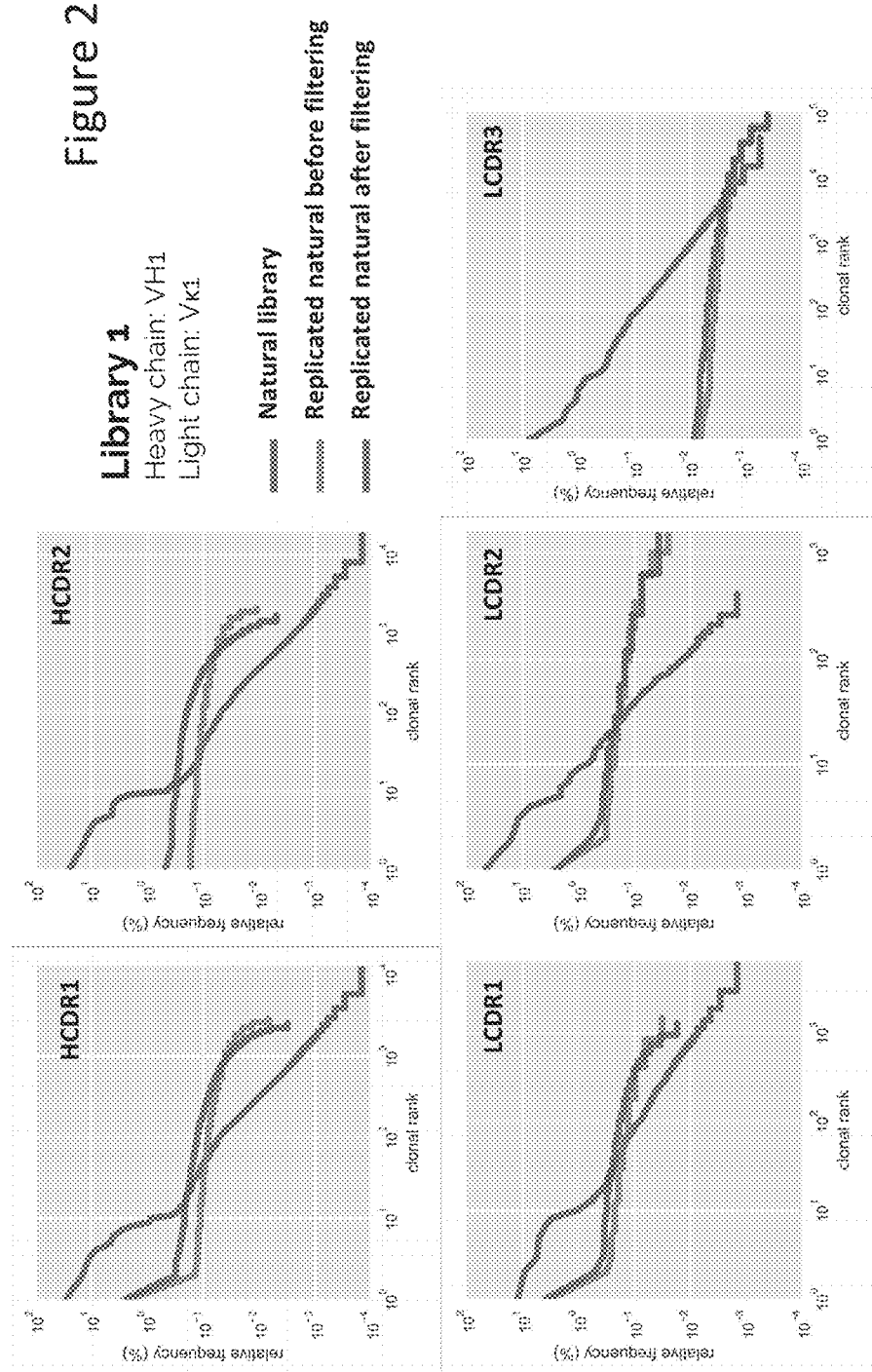

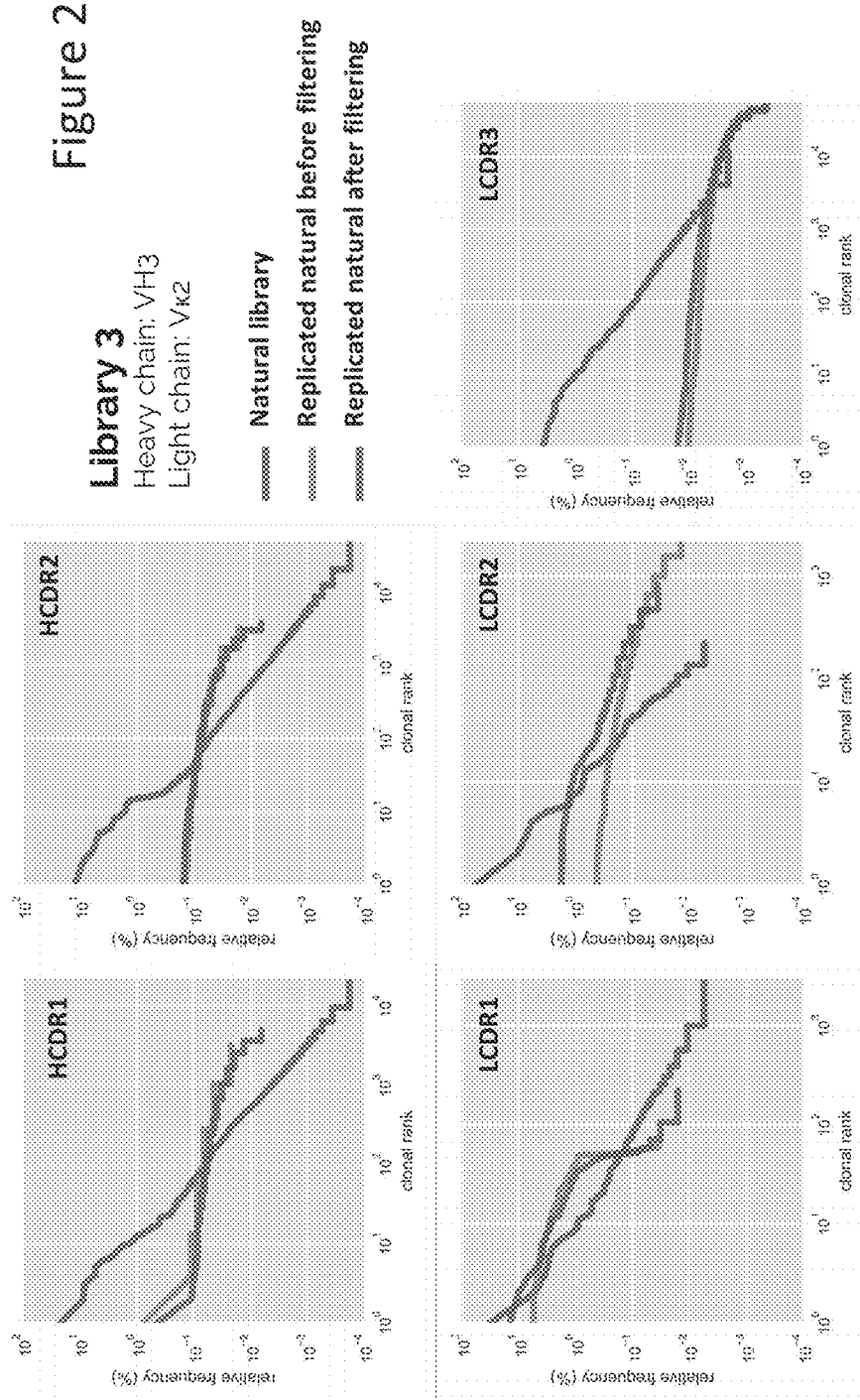

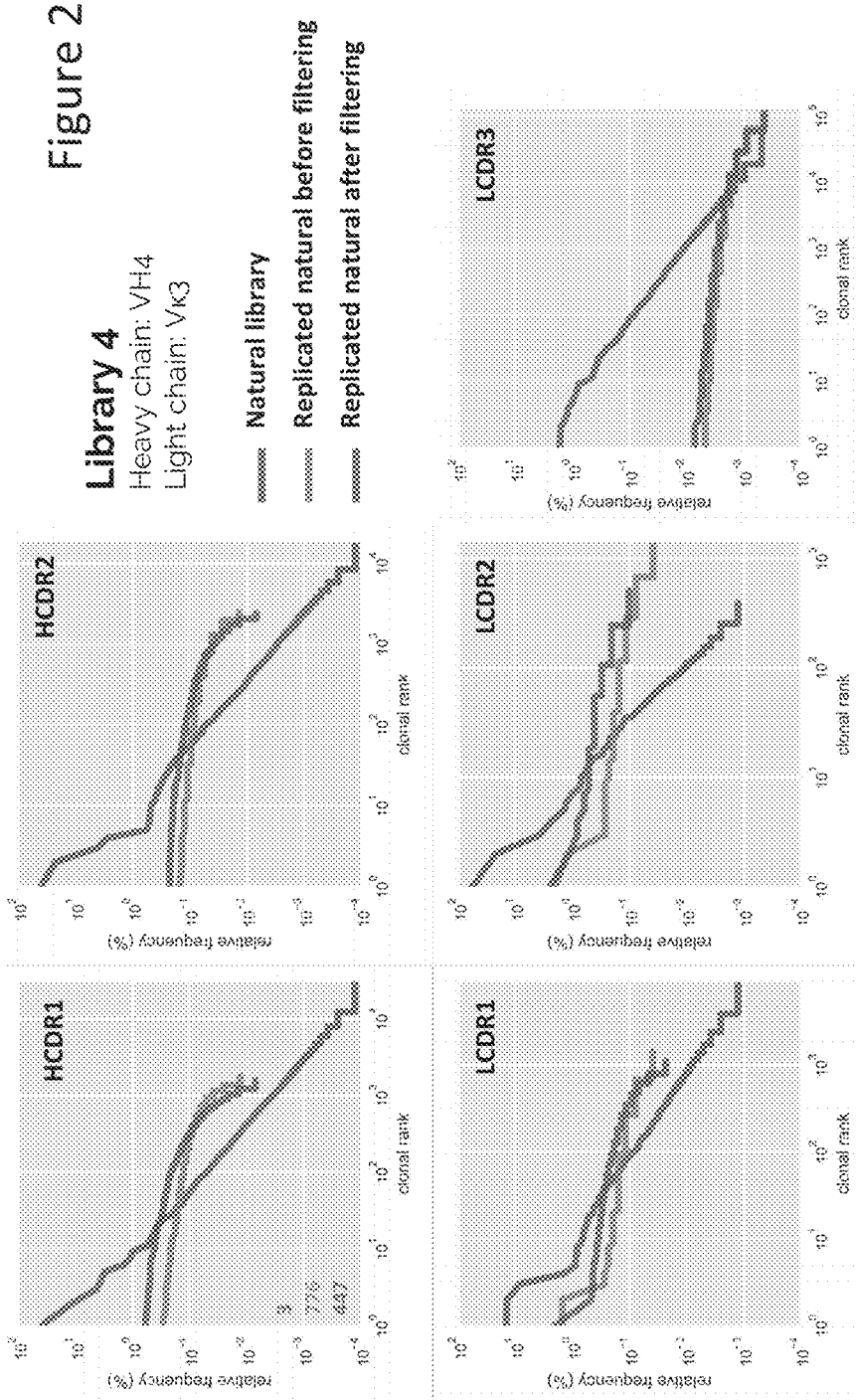

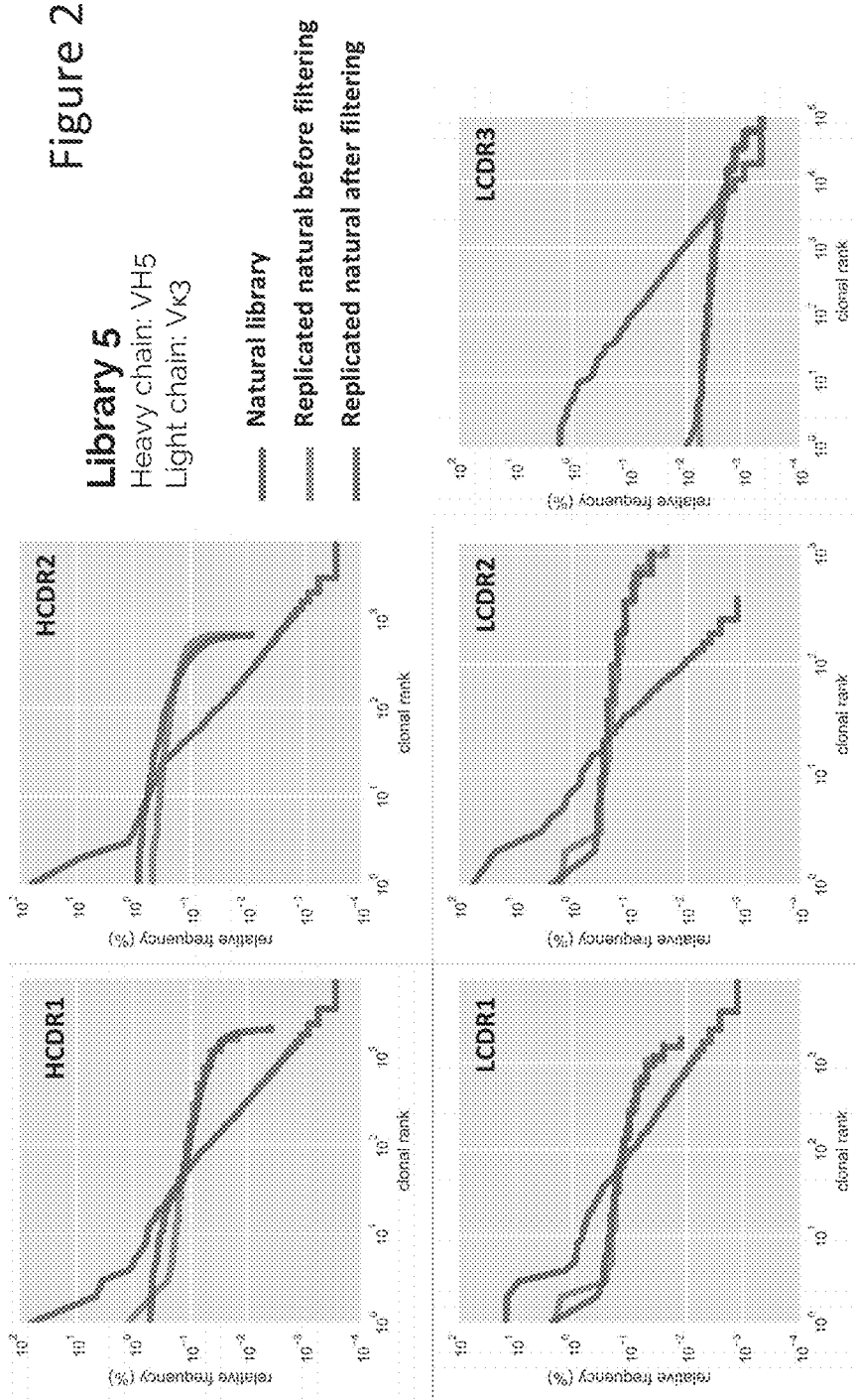

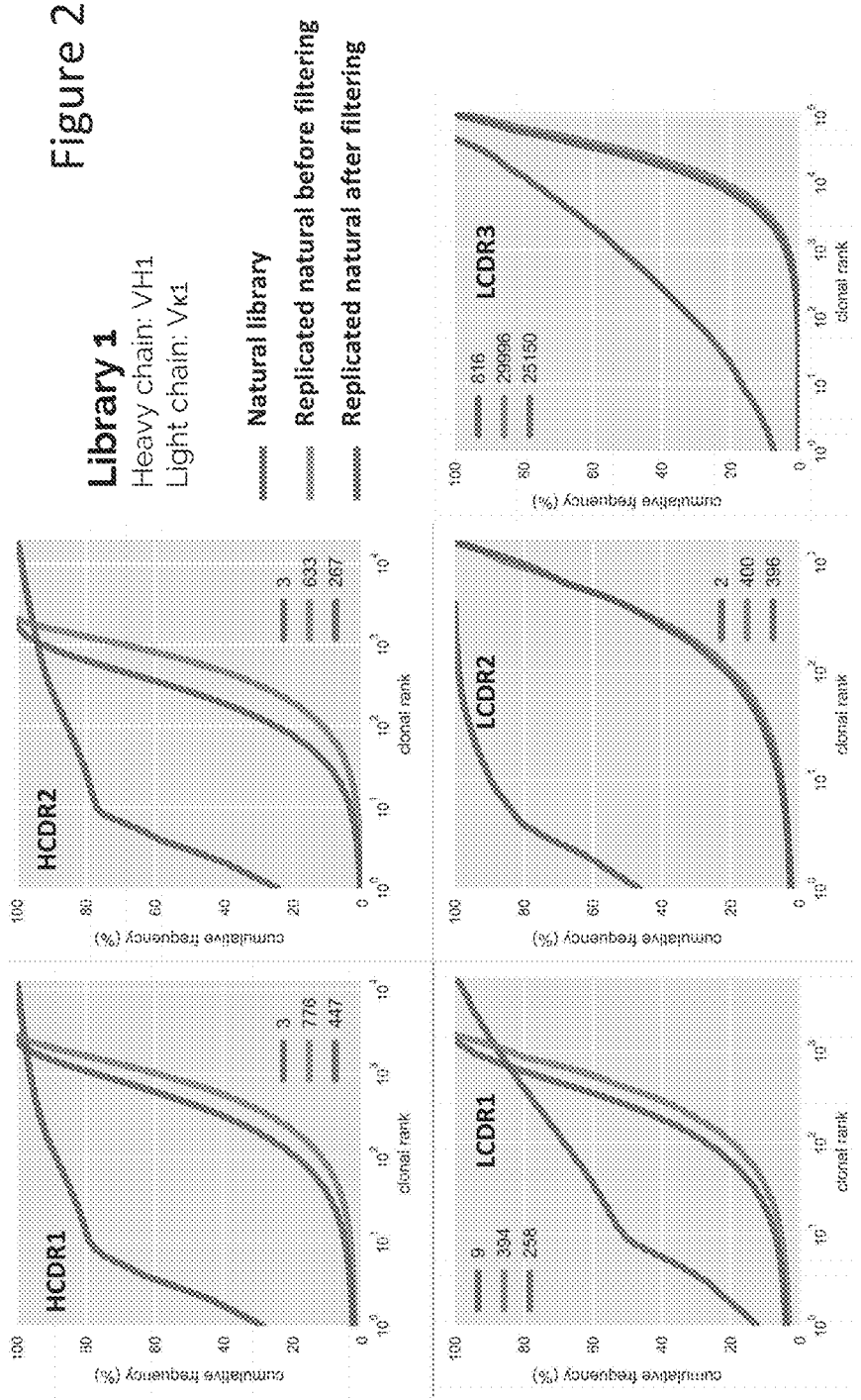

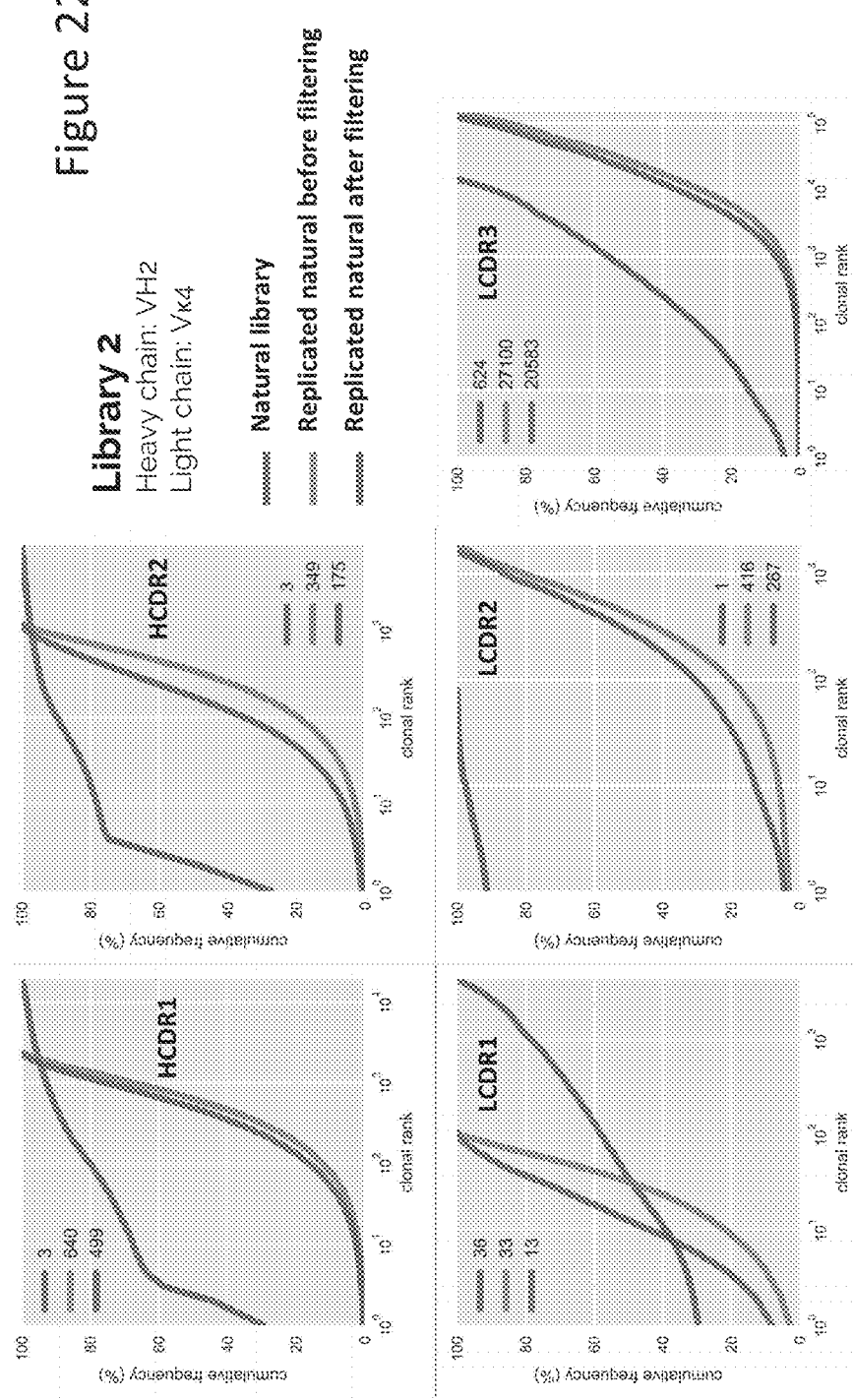

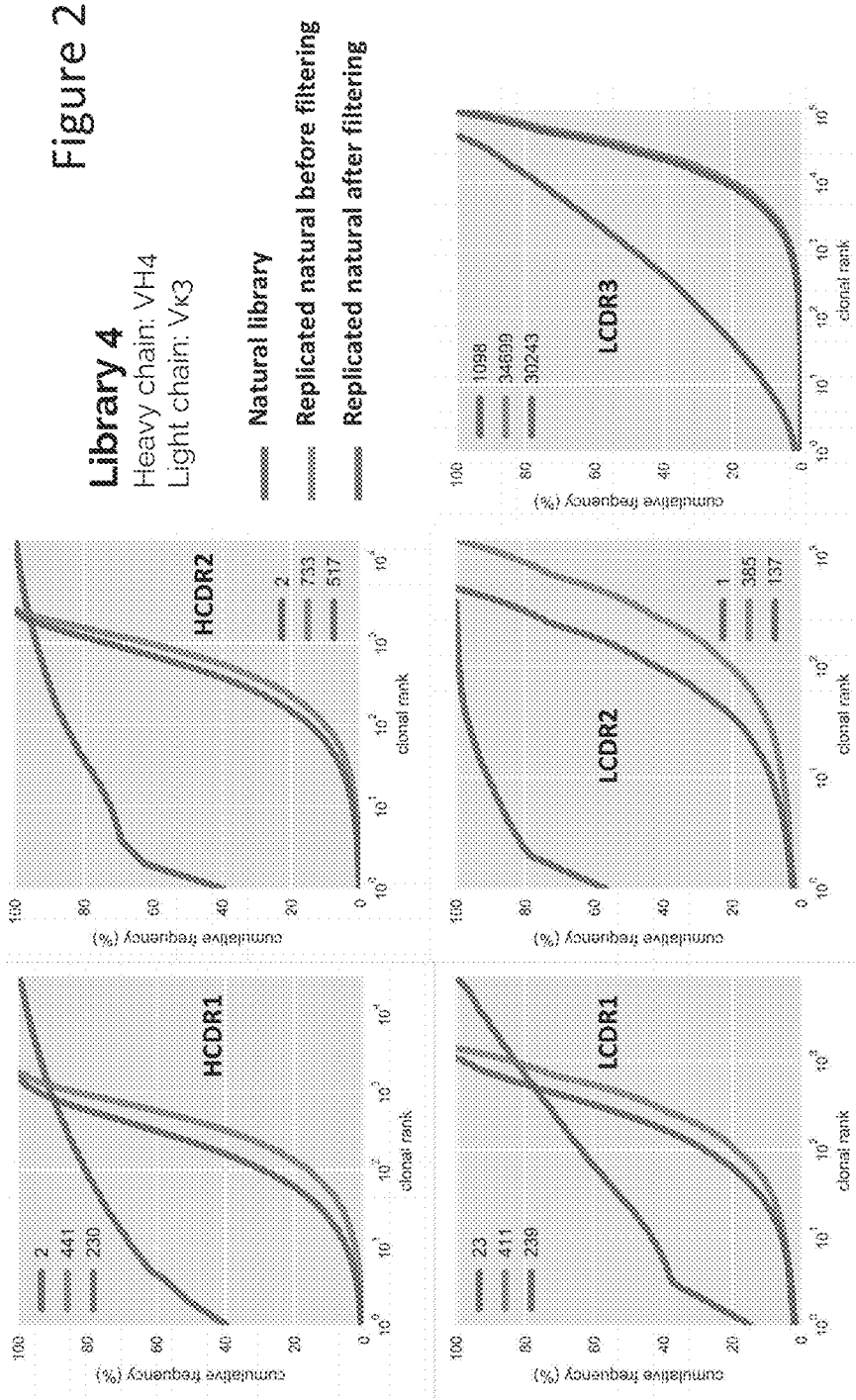

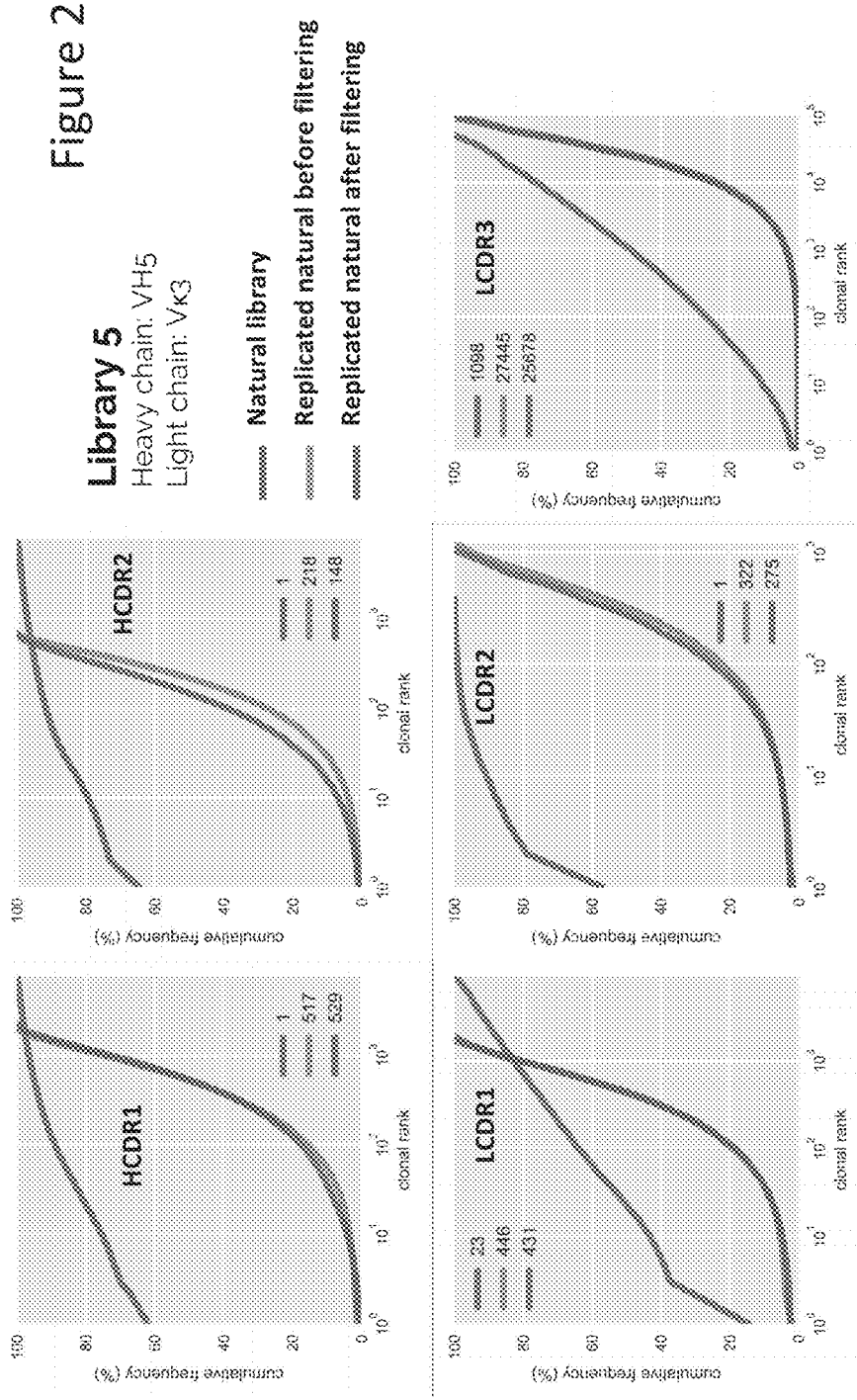

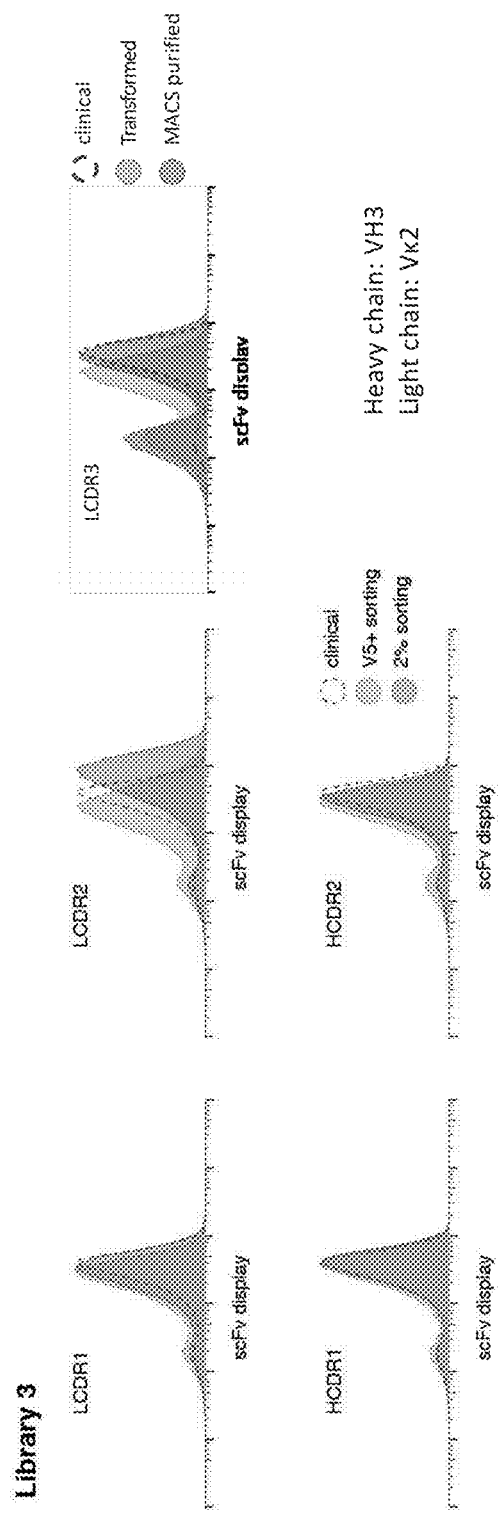

SEQUENCE LISTING

```
<160> NUMBER OF SEQ ID NOS: 298

<210> SEQ ID NO 1
<211> LENGTH: 76
<212> TYPE: DNA
<213> ORGANISM: Artificial Sequence
<220> FEATURE:
<223> OTHER INFORMATION: Cloning Vector

<400> SEQUENCE: 1
gtgttaccat cacctgtcgt gcttctagag accatggcca gtaaggccgg tctctctggc     60
ttggtaccag cagaaa                                                    76

<210> SEQ ID NO 2
<211> LENGTH: 76
<212> TYPE: DNA
<213> ORGANISM: Artificial Sequence
<220> FEATURE:
<223> OTHER INFORMATION: Cloning Vector

<400> SEQUENCE: 2
cacaatggta gtggacagca cgaagatctc tggtaccggt cattccggcc agagagaccg     60
aaccatggtc gtcttt                                                    76

<210> SEQ ID NO 3
<211> LENGTH: 24
<212> TYPE: PRT
<213> ORGANISM: Artificial Sequence
<220> FEATURE:
<223> OTHER INFORMATION: Cloning Vector

<400> SEQUENCE: 3

Arg Val Thr Ile Thr Cys Arg Ala Ser Arg Asp His Gly Gln Gly Arg
1               5                   10                  15

Ser Leu Ala Trp Tyr Gln Gln Lys
            20

<210> SEQ ID NO 4
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is Met, Ile, or Leu
<220> FEATURE:
<221> NAME/KEY: MISC_FEATURE
<222> LOCATION: (4)..(4)
<223> OTHER INFORMATION: Xaa at position 4 is Gly or Ala
<220> FEATURE:
<221> NAME/KEY: MISC_FEATURE
<222> LOCATION: (5)..(5)
<223> OTHER INFORMATION: Xaa at position 5 is Trp, Arg, Glu, or His
<220> FEATURE:
<221> NAME/KEY: MISC_FEATURE
<222> LOCATION: (7)..(7)
<223> OTHER INFORMATION: Xaa at position 7 is Ser, Asn, or Phe
<220> FEATURE:
<221> NAME/KEY: MISC_FEATURE
<222> LOCATION: (8)..(8)
<223> OTHER INFORMATION: Xaa at position 8 is optional or is Gly, Thr,
      Val, Ala, or Pro
```

```
<220> FEATURE:
<221> NAME/KEY: MISC_FEATURE
<222> LOCATION: (9)..(9)
<223> OTHER INFORMATION: Xaa at position 9 is Tyr, Asn, His, or Ser
<220> FEATURE:
<221> NAME/KEY: MISC_FEATURE
<222> LOCATION: (10)..(10)
<223> OTHER INFORMATION: Xaa at position 10 is Asn, Ser, or Thr
<220> FEATURE:
<221> NAME/KEY: MISC_FEATURE
<222> LOCATION: (11)..(11)
<223> OTHER INFORMATION: Xaa at position 11 is Gly or Asp
<220> FEATURE:
<221> NAME/KEY: MISC_FEATURE
<222> LOCATION: (12)..(12)
<223> OTHER INFORMATION: Xaa at position 12 is Asn, Asp, Lys, Ala, Gly,
      or Glu
<220> FEATURE:
<221> NAME/KEY: MISC_FEATURE
<222> LOCATION: (13)..(13)
<223> OTHER INFORMATION: Xaa at position 13 is Thr, Ala, Asn, or Lys
<220> FEATURE:
<221> NAME/KEY: MISC_FEATURE
<222> LOCATION: (14)..(14)
<223> OTHER INFORMATION: Xaa at position 14 is Asn, Lys, Asp, or Ser

<400> SEQUENCE: 4

Glu Trp Xaa Xaa Xaa Ile Xaa Xaa Xaa Xaa Xaa Xaa Xaa Xaa Tyr
1               5                   10                  15

<210> SEQ ID NO 5
<211> LENGTH: 15
<212> TYPE: PRT
<213> ORGANISM: Homo sapiens

<400> SEQUENCE: 5

Glu Trp Met Gly Trp Ile Ser Gly Tyr Asn Gly Asn Thr Asn Tyr
1               5                   10                  15

<210> SEQ ID NO 6
<211> LENGTH: 15
<212> TYPE: PRT
<213> ORGANISM: Homo sapiens

<400> SEQUENCE: 6

Glu Trp Met Gly Trp Ile Ser Thr Tyr Asn Gly Asn Thr Asn Tyr
1               5                   10                  15

<210> SEQ ID NO 7
<211> LENGTH: 15
<212> TYPE: PRT
<213> ORGANISM: Homo sapiens

<400> SEQUENCE: 7

Glu Trp Met Gly Trp Ile Ser Val Tyr Asn Gly Asn Thr Asn Tyr
1               5                   10                  15

<210> SEQ ID NO 8
<211> LENGTH: 15
<212> TYPE: PRT
<213> ORGANISM: Homo sapiens

<400> SEQUENCE: 8

Glu Trp Met Gly Trp Ile Ser Ala Tyr Asn Gly Asn Thr Lys Tyr
1               5                   10                  15

<210> SEQ ID NO 9
<211> LENGTH: 15
<212> TYPE: PRT
```

<213> ORGANISM: Homo sapiens

<400> SEQUENCE: 9

Glu Trp Met Gly Arg Ile Ser Ala Tyr Asn Gly Asn Thr Asn Tyr
1               5                   10                  15

<210> SEQ ID NO 10
<211> LENGTH: 15
<212> TYPE: PRT
<213> ORGANISM: Homo sapiens

<400> SEQUENCE: 10

Glu Trp Met Gly Trp Ile Ser Ala Tyr Asn Gly Asp Thr Asn Tyr
1               5                   10                  15

<210> SEQ ID NO 11
<211> LENGTH: 15
<212> TYPE: PRT
<213> ORGANISM: Homo sapiens

<400> SEQUENCE: 11

Glu Trp Met Gly Trp Ile Ser Ala Tyr Asn Gly Lys Thr Asn Tyr
1               5                   10                  15

<210> SEQ ID NO 12
<211> LENGTH: 15
<212> TYPE: PRT
<213> ORGANISM: Homo sapiens

<400> SEQUENCE: 12

Glu Trp Met Gly Trp Ile Ser Pro Tyr Asn Gly Asn Thr Asn Tyr
1               5                   10                  15

<210> SEQ ID NO 13
<211> LENGTH: 15
<212> TYPE: PRT
<213> ORGANISM: Homo sapiens

<400> SEQUENCE: 13

Glu Trp Met Gly Trp Ile Asn Pro Asn Ser Gly Asp Thr Asn Tyr
1               5                   10                  15

<210> SEQ ID NO 14
<211> LENGTH: 15
<212> TYPE: PRT
<213> ORGANISM: Homo sapiens

<400> SEQUENCE: 14

Glu Trp Met Gly Trp Ile Asn Pro Asn Ser Gly Ala Thr Asn Tyr
1               5                   10                  15

<210> SEQ ID NO 15
<211> LENGTH: 15
<212> TYPE: PRT
<213> ORGANISM: Homo sapiens

<400> SEQUENCE: 15

Glu Trp Met Gly Trp Ile Asn Pro Asn Ser Gly Gly Thr Asp Tyr
1               5                   10                  15

<210> SEQ ID NO 16
<211> LENGTH: 15
<212> TYPE: PRT
<213> ORGANISM: Homo sapiens

```
<400> SEQUENCE: 16

Glu Trp Met Gly Trp Ile Asn Pro Asn Ser Gly Gly Thr Ser Tyr
1               5                   10                  15

<210> SEQ ID NO 17
<211> LENGTH: 15
<212> TYPE: PRT
<213> ORGANISM: Homo sapiens

<400> SEQUENCE: 17

Glu Trp Met Gly Trp Ile Asn Pro Asn Ser Gly Gly Thr Lys Tyr
1               5                   10                  15

<210> SEQ ID NO 18
<211> LENGTH: 15
<212> TYPE: PRT
<213> ORGANISM: Homo sapiens

<400> SEQUENCE: 18

Glu Trp Met Gly Trp Ile Asn Pro Asn Ser Gly Gly Ala Asn Tyr
1               5                   10                  15

<210> SEQ ID NO 19
<211> LENGTH: 15
<212> TYPE: PRT
<213> ORGANISM: Homo sapiens

<400> SEQUENCE: 19

Glu Trp Met Gly Arg Ile Asn Pro Asn Ser Gly Gly Thr Asn Tyr
1               5                   10                  15

<210> SEQ ID NO 20
<211> LENGTH: 15
<212> TYPE: PRT
<213> ORGANISM: Homo sapiens

<400> SEQUENCE: 20

Glu Trp Met Gly Trp Ile Asn Pro Asn Asn Gly Gly Thr Asn Tyr
1               5                   10                  15

<210> SEQ ID NO 21
<211> LENGTH: 15
<212> TYPE: PRT
<213> ORGANISM: Homo sapiens

<400> SEQUENCE: 21

Glu Trp Met Gly Trp Ile Asn Pro Asn Thr Gly Gly Thr Asn Tyr
1               5                   10                  15

<210> SEQ ID NO 22
<211> LENGTH: 14
<212> TYPE: PRT
<213> ORGANISM: Homo sapiens

<400> SEQUENCE: 22

Glu Trp Ile Gly Glu Ile Asn His Ser Gly Asn Thr Asn Tyr
1               5                   10

<210> SEQ ID NO 23
<211> LENGTH: 14
<212> TYPE: PRT
<213> ORGANISM: Homo sapiens

<400> SEQUENCE: 23
```

-continued

```
Glu Trp Leu Ala His Ile Phe Ser Asn Asp Glu Asn Ser Tyr
1               5                   10
```

<210> SEQ ID NO 24
<211> LENGTH: 14
<212> TYPE: PRT
<213> ORGANISM: Homo sapiens

<400> SEQUENCE: 24

```
Glu Trp Leu Ala His Ile Phe Ser Asn Gly Glu Lys Ser Tyr
1               5                   10
```

<210> SEQ ID NO 25
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is Met or Leu
<220> FEATURE:
<221> NAME/KEY: MISC_FEATURE
<222> LOCATION: (4)..(4)
<223> OTHER INFORMATION: Xaa at position 4 is Gly or Ala
<220> FEATURE:
<221> NAME/KEY: MISC_FEATURE
<222> LOCATION: (5)..(5)
<223> OTHER INFORMATION: Xaa at position 5 is Val, Leu, Ile, Arg, or Phe
<220> FEATURE:
<221> NAME/KEY: MISC_FEATURE
<222> LOCATION: (6)..(6)
<223> OTHER INFORMATION: Xaa at position 6 is Ile or Val
<220> FEATURE:
<221> NAME/KEY: MISC_FEATURE
<222> LOCATION: (7)..(7)
<223> OTHER INFORMATION: Xaa at position 7 is Tyr or Asp
<220> FEATURE:
<221> NAME/KEY: MISC_FEATURE
<222> LOCATION: (8)..(8)
<223> OTHER INFORMATION: Xaa at position 8 is optional or is Pro
<220> FEATURE:
<221> NAME/KEY: MISC_FEATURE
<222> LOCATION: (9)..(9)
<223> OTHER INFORMATION: Xaa at position 9 is Gly, Ser, Ala, Asp, or Trp
<220> FEATURE:
<221> NAME/KEY: MISC_FEATURE
<222> LOCATION: (10)..(10)
<223> OTHER INFORMATION: Xaa at position 10 is Asp or Asn
<220> FEATURE:
<221> NAME/KEY: MISC_FEATURE
<222> LOCATION: (11)..(11)
<223> OTHER INFORMATION: Xaa at position 11 is Ser, Gly, or Asp
<220> FEATURE:
<221> NAME/KEY: MISC_FEATURE
<222> LOCATION: (12)..(12)
<223> OTHER INFORMATION: Xaa at position 12 is Asp or Glu
<220> FEATURE:
<221> NAME/KEY: MISC_FEATURE
<222> LOCATION: (13)..(13)
<223> OTHER INFORMATION: Xaa at position 13 is Thr, Ile, Lys, or Arg
<220> FEATURE:
<221> NAME/KEY: MISC_FEATURE
<222> LOCATION: (14)..(14)
<223> OTHER INFORMATION: Xaa at position 14 is Arg, Ser, Lys, or Thr

<400> SEQUENCE: 25

```
Glu Trp Xaa Xaa Xaa Xaa Xaa Xaa Xaa Xaa Xaa Xaa Xaa Xaa Tyr
1               5                   10                  15
```

<210> SEQ ID NO 26
<211> LENGTH: 15
<212> TYPE: PRT
<213> ORGANISM: Homo sapiens

<400> SEQUENCE: 26

Glu Trp Met Gly Val Ile Tyr Pro Gly Asp Ser Asp Thr Arg Tyr
1               5                   10                  15

<210> SEQ ID NO 27
<211> LENGTH: 15
<212> TYPE: PRT
<213> ORGANISM: Homo sapiens

<400> SEQUENCE: 27

Glu Trp Met Gly Leu Ile Tyr Pro Gly Asp Ser Asp Thr Arg Tyr
1               5                   10                  15

<210> SEQ ID NO 28
<211> LENGTH: 15
<212> TYPE: PRT
<213> ORGANISM: Homo sapiens

<400> SEQUENCE: 28

Glu Trp Met Gly Ile Ile Phe Pro Gly Asp Ser Asp Thr Arg Tyr
1               5                   10                  15

<210> SEQ ID NO 29
<211> LENGTH: 15
<212> TYPE: PRT
<213> ORGANISM: Homo sapiens

<400> SEQUENCE: 29

Glu Trp Met Gly Ile Ile Tyr Pro Gly Asp Ser Asp Ile Arg Tyr
1               5                   10                  15

<210> SEQ ID NO 30
<211> LENGTH: 15
<212> TYPE: PRT
<213> ORGANISM: Homo sapiens

<400> SEQUENCE: 30

Glu Trp Met Gly Ile Ile Tyr Pro Gly Asp Ser Glu Thr Arg Tyr
1               5                   10                  15

<210> SEQ ID NO 31
<211> LENGTH: 15
<212> TYPE: PRT
<213> ORGANISM: Homo sapiens

<400> SEQUENCE: 31

Glu Trp Met Gly Ile Ile Tyr Pro Gly Asp Ser Asp Thr Ser Tyr
1               5                   10                  15

<210> SEQ ID NO 32
<211> LENGTH: 15
<212> TYPE: PRT
<213> ORGANISM: Homo sapiens

<400> SEQUENCE: 32

Glu Trp Met Gly Ile Ile Tyr Pro Gly Asp Ser Asp Thr Lys Tyr
1               5                   10                  15

<210> SEQ ID NO 33
<211> LENGTH: 15
<212> TYPE: PRT
<213> ORGANISM: Homo sapiens

<400> SEQUENCE: 33

```
Glu Trp Met Gly Ile Ile Tyr Pro Gly Asp Ser Asp Thr Thr Tyr
1               5                   10                  15

<210> SEQ ID NO 34
<211> LENGTH: 15
<212> TYPE: PRT
<213> ORGANISM: Homo sapiens

<400> SEQUENCE: 34

Glu Trp Met Gly Ile Ile Tyr Pro Ser Asp Ser Asp Thr Arg Tyr
1               5                   10                  15

<210> SEQ ID NO 35
<211> LENGTH: 15
<212> TYPE: PRT
<213> ORGANISM: Homo sapiens

<400> SEQUENCE: 35

Glu Trp Met Gly Ile Ile Tyr Pro Ala Asp Ser Asp Thr Arg Tyr
1               5                   10                  15

<210> SEQ ID NO 36
<211> LENGTH: 15
<212> TYPE: PRT
<213> ORGANISM: Homo sapiens

<400> SEQUENCE: 36

Glu Trp Met Gly Ile Ile Tyr Pro Asp Asp Ser Asp Thr Arg Tyr
1               5                   10                  15

<210> SEQ ID NO 37
<211> LENGTH: 14
<212> TYPE: PRT
<213> ORGANISM: Homo sapiens

<400> SEQUENCE: 37

Glu Trp Leu Ala Leu Ile Tyr Trp Asp Gly Asp Lys Arg Tyr
1               5                   10

<210> SEQ ID NO 38
<211> LENGTH: 14
<212> TYPE: PRT
<213> ORGANISM: Homo sapiens

<400> SEQUENCE: 38

Glu Trp Leu Ala Leu Val Tyr Trp Asp Asp Asp Lys Arg Tyr
1               5                   10

<210> SEQ ID NO 39
<211> LENGTH: 14
<212> TYPE: PRT
<213> ORGANISM: Homo sapiens

<400> SEQUENCE: 39

Glu Trp Leu Ala Leu Ile Tyr Trp Asn Asp Asp Lys Arg Tyr
1               5                   10

<210> SEQ ID NO 40
<211> LENGTH: 14
<212> TYPE: PRT
<213> ORGANISM: Homo sapiens

<400> SEQUENCE: 40

Glu Trp Leu Ala Leu Ile Tyr Trp Asp Asp Asp Arg Arg Tyr
1               5                   10
```

<210> SEQ ID NO 41
<211> LENGTH: 14
<212> TYPE: PRT
<213> ORGANISM: Homo sapiens

<400> SEQUENCE: 41

Glu Trp Leu Ala Arg Ile Asp Trp Asp Asp Asp Lys Tyr Tyr
1               5                   10

<210> SEQ ID NO 42
<211> LENGTH: 14
<212> TYPE: PRT
<213> ORGANISM: Homo sapiens

<400> SEQUENCE: 42

Glu Trp Leu Ala Leu Ile Tyr Trp Asp Asp Asp Lys Tyr Tyr
1               5                   10

<210> SEQ ID NO 43
<211> LENGTH: 14
<212> TYPE: PRT
<213> ORGANISM: Homo sapiens

<400> SEQUENCE: 43

Glu Trp Leu Ala Val Ile Tyr Trp Asp Asp Asp Lys Arg Tyr
1               5                   10

<210> SEQ ID NO 44
<211> LENGTH: 14
<212> TYPE: PRT
<213> ORGANISM: Homo sapiens

<400> SEQUENCE: 44

Glu Trp Leu Ala Phe Ile Tyr Trp Asp Asp Asp Lys Arg Tyr
1               5                   10

<210> SEQ ID NO 45
<211> LENGTH: 14
<212> TYPE: PRT
<213> ORGANISM: Homo sapiens

<400> SEQUENCE: 45

Glu Trp Leu Ala Ile Ile Tyr Trp Asp Asp Asp Lys Arg Tyr
1               5                   10

<210> SEQ ID NO 46
<211> LENGTH: 16
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is Met, Ile, Leu, or Val
<220> FEATURE:
<221> NAME/KEY: MISC_FEATURE
<222> LOCATION: (4)..(4)
<223> OTHER INFORMATION: Xaa at position 4 is Gly, Ser, Ala, or Asp
<220> FEATURE:
<221> NAME/KEY: MISC_FEATURE
<222> LOCATION: (5)..(5)
<223> OTHER INFORMATION: Xaa at position 5 is optional or is Arg or Gly
<220> FEATURE:
<221> NAME/KEY: MISC_FEATURE
<222> LOCATION: (6)..(6)
<223> OTHER INFORMATION: Xaa at position 6 is Trp, Arg, Asn, Lys, Ile,
      Ser, Thr, Tyr, or Val
<220> FEATURE:

```
<221> NAME/KEY: MISC_FEATURE
<222> LOCATION: (7)..(7)
<223> OTHER INFORMATION: Xaa at position 7 is Ile or Ser
<220> FEATURE:
<221> NAME/KEY: MISC_FEATURE
<222> LOCATION: (8)..(8)
<223> OTHER INFORMATION: Xaa at position 8 is Asn, Ser, Trp, or Thr
<220> FEATURE:
<221> NAME/KEY: MISC_FEATURE
<222> LOCATION: (9)..(9)
<223> OTHER INFORMATION: Xaa at position 9 is Pro, Leu, Arg, His, Ala,
      Trp, Glu, Gly, Tyr, or Ile
<220> FEATURE:
<221> NAME/KEY: MISC_FEATURE
<222> LOCATION: (10)..(10)
<223> OTHER INFORMATION: Xaa at position 10 is Asn, Gly, Ser, Thr, Ala,
      Asp, Leu, or Phe
<220> FEATURE:
<221> NAME/KEY: MISC_FEATURE
<222> LOCATION: (11)..(11)
<223> OTHER INFORMATION: Xaa at position 11 is Arg, Asp, Gly, or Ser
<220> FEATURE:
<221> NAME/KEY: MISC_FEATURE
<222> LOCATION: (12)..(12)
<223> OTHER INFORMATION: Xaa at position 12 is Ser, Pro, Gly, or Arg
<220> FEATURE:
<221> NAME/KEY: MISC_FEATURE
<222> LOCATION: (13)..(13)
<223> OTHER INFORMATION: Xaa at position 13 is Gly, Asp, Ser, Thr, Phe,
      Ala, Lys, Asn, or Ile
<220> FEATURE:
<221> NAME/KEY: MISC_FEATURE
<222> LOCATION: (14)..(14)
<223> OTHER INFORMATION: Xaa at position 14 is Thr, Ile, Lys, or Ala
<220> FEATURE:
<221> NAME/KEY: MISC_FEATURE
<222> LOCATION: (15)..(15)
<223> OTHER INFORMATION: Xaa at position 15 is Ser, Thr, Asn, Arg, His,
      or Tyr

<400> SEQUENCE: 46

Glu Trp Xaa Xaa Xaa Xaa Xaa Xaa Xaa Xaa Xaa Xaa Xaa Xaa Tyr
1               5                   10                  15

<210> SEQ ID NO 47
<211> LENGTH: 15
<212> TYPE: PRT
<213> ORGANISM: Homo sapiens

<400> SEQUENCE: 47

Glu Trp Met Gly Trp Ile Asn Pro Asn Arg Ser Gly Thr Ser Tyr
1               5                   10                  15

<210> SEQ ID NO 48
<211> LENGTH: 15
<212> TYPE: PRT
<213> ORGANISM: Homo sapiens

<400> SEQUENCE: 48

Glu Trp Met Gly Trp Ile Asn Leu Asn Arg Ser Gly Thr Thr Tyr
1               5                   10                  15

<210> SEQ ID NO 49
<211> LENGTH: 15
<212> TYPE: PRT
<213> ORGANISM: Homo sapiens

<400> SEQUENCE: 49

Glu Trp Met Gly Arg Ile Asn Pro Asn Arg Ser Asp Thr Asn Tyr
1               5                   10                  15
```

```
<210> SEQ ID NO 50
<211> LENGTH: 15
<212> TYPE: PRT
<213> ORGANISM: Homo sapiens

<400> SEQUENCE: 50

Glu Trp Met Gly Asn Ile Ser Pro Gly Asp Pro Asp Thr Arg Tyr
1               5                   10                  15

<210> SEQ ID NO 51
<211> LENGTH: 15
<212> TYPE: PRT
<213> ORGANISM: Homo sapiens

<400> SEQUENCE: 51

Glu Trp Met Gly Lys Ile Asn Arg Ser Gly Gly Ser Thr Ser Tyr
1               5                   10                  15

<210> SEQ ID NO 52
<211> LENGTH: 15
<212> TYPE: PRT
<213> ORGANISM: Homo sapiens

<400> SEQUENCE: 52

Glu Trp Met Gly Ile Ile Asn His Ser Gly Gly Thr Thr Ser Tyr
1               5                   10                  15

<210> SEQ ID NO 53
<211> LENGTH: 15
<212> TYPE: PRT
<213> ORGANISM: Homo sapiens

<400> SEQUENCE: 53

Glu Trp Met Gly Ile Ile Asn Leu Ser Ser Arg Phe Thr Ser Tyr
1               5                   10                  15

<210> SEQ ID NO 54
<211> LENGTH: 15
<212> TYPE: PRT
<213> ORGANISM: Homo sapiens

<400> SEQUENCE: 54

Glu Trp Ile Gly Ile Ile Asn Leu Ser Ser Gly Ser Thr Ser Tyr
1               5                   10                  15

<210> SEQ ID NO 55
<211> LENGTH: 15
<212> TYPE: PRT
<213> ORGANISM: Homo sapiens

<400> SEQUENCE: 55

Glu Trp Met Gly Ile Ser Asn Leu Ser Gly Gly Ser Thr Ser Tyr
1               5                   10                  15

<210> SEQ ID NO 56
<211> LENGTH: 15
<212> TYPE: PRT
<213> ORGANISM: Homo sapiens

<400> SEQUENCE: 56

Glu Trp Leu Gly Ile Ile Asn Ala Ser Gly Gly Ser Thr Arg Tyr
1               5                   10                  15

<210> SEQ ID NO 57
<211> LENGTH: 15
```

```
<212> TYPE: PRT
<213> ORGANISM: Homo sapiens

<400> SEQUENCE: 57

Glu Trp Val Gly Ile Ile Asn Leu Thr Gly Gly Ala Thr Arg Tyr
1               5                   10                  15

<210> SEQ ID NO 58
<211> LENGTH: 15
<212> TYPE: PRT
<213> ORGANISM: Homo sapiens

<400> SEQUENCE: 58

Glu Trp Val Ser Ser Ile Asn Trp Ser Gly Gly Ser Thr Tyr Tyr
1               5                   10                  15

<210> SEQ ID NO 59
<211> LENGTH: 15
<212> TYPE: PRT
<213> ORGANISM: Homo sapiens

<400> SEQUENCE: 59

Glu Trp Val Ser Thr Ile Asn Glu Ser Gly Gly Lys Thr His Tyr
1               5                   10                  15

<210> SEQ ID NO 60
<211> LENGTH: 15
<212> TYPE: PRT
<213> ORGANISM: Homo sapiens

<400> SEQUENCE: 60

Glu Trp Val Ala Asn Ile Ser Gly Gly Gly Ala Ile Tyr Tyr
1               5                   10                  15

<210> SEQ ID NO 61
<211> LENGTH: 15
<212> TYPE: PRT
<213> ORGANISM: Homo sapiens

<400> SEQUENCE: 61

Glu Trp Val Ala Tyr Ile Asn Arg Ser Gly Ser Thr Ile Tyr Tyr
1               5                   10                  15

<210> SEQ ID NO 62
<211> LENGTH: 15
<212> TYPE: PRT
<213> ORGANISM: Homo sapiens

<400> SEQUENCE: 62

Glu Trp Val Asp Val Ile Trp Tyr Ala Gly Arg Asn Lys Ser Tyr
1               5                   10                  15

<210> SEQ ID NO 63
<211> LENGTH: 15
<212> TYPE: PRT
<213> ORGANISM: Homo sapiens

<400> SEQUENCE: 63

Glu Trp Val Ala Val Ile Ser His Asp Arg Ser Asn Lys Ser Tyr
1               5                   10                  15

<210> SEQ ID NO 64
<211> LENGTH: 15
<212> TYPE: PRT
<213> ORGANISM: Homo sapiens
```

<400> SEQUENCE: 64

Glu Trp Met Ser Trp Ile Asn Ala Ser Ser Gly Gly Thr Asn Tyr
1               5                   10                  15

<210> SEQ ID NO 65
<211> LENGTH: 15
<212> TYPE: PRT
<213> ORGANISM: Homo sapiens

<400> SEQUENCE: 65

Glu Trp Met Gly Arg Asn Ile Thr Ile Leu Gly Ile Ala Asn Tyr
1               5                   10                  15

<210> SEQ ID NO 66
<211> LENGTH: 15
<212> TYPE: PRT
<213> ORGANISM: Homo sapiens

<400> SEQUENCE: 66

Glu Trp Met Gly Gly Asn Ile Thr Ile Phe Gly Lys Ala Asn Tyr
1               5                   10                  15

<210> SEQ ID NO 67
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa at position 3 is Met, Val, Leu, Ile
<220> FEATURE:
<221> NAME/KEY: MISC_FEATURE
<222> LOCATION: (4)..(4)
<223> OTHER INFORMATION: Xaa at position 4 is Gly, Ala, Ser
<220> FEATURE:
<221> NAME/KEY: MISC_FEATURE
<222> LOCATION: (5)..(5)
<223> OTHER INFORMATION: Xaa at position 5 is Ile, Trp, Met, Gly, Cys,
      Val, His, Leu, Tyr, Ser, or Arg
<220> FEATURE:
<221> NAME/KEY: MISC_FEATURE
<222> LOCATION: (6)..(6)
<223> OTHER INFORMATION: Xaa at position 6 is Ile, Phe, or Ser
<220> FEATURE:
<221> NAME/KEY: MISC_FEATURE
<222> LOCATION: (7)..(7)
<223> OTHER INFORMATION: Xaa at position 7 is Asn, Tyr, Ile, Cys, Ser,
      or Glu
<220> FEATURE:
<221> NAME/KEY: MISC_FEATURE
<222> LOCATION: (8)..(8)
<223> OTHER INFORMATION: Xaa at position 8 is optional, or is Pro, Ala,
      His, Ser, Gln, Tyr, Cys, Gly, or Arg
<220> FEATURE:
<221> NAME/KEY: MISC_FEATURE
<222> LOCATION: (9)..(9)
<223> OTHER INFORMATION: Xaa at position 9 is Asn, Gly, Ile, Tyr, Asp,
      Ala, Lys, Cys, or Ser
<220> FEATURE:
<221> NAME/KEY: MISC_FEATURE
<222> LOCATION: (10)..(10)
<223> OTHER INFORMATION: Xaa at position 10 is Ser, Val, Asn, Phe, Asp,
      Tyr, or Gly
<220> FEATURE:
<221> NAME/KEY: MISC_FEATURE
<222> LOCATION: (11)..(11)
<223> OTHER INFORMATION: Xaa at position 11 is optional or is Gly, Cys,
      Ala, Ser, or Thr
<220> FEATURE:
<221> NAME/KEY: MISC_FEATURE
<222> LOCATION: (12)..(12)
<223> OTHER INFORMATION: Xaa at position 12 is optional or is Cys, Gly,

```
        Asp, Glu, Thr, Ala, Asn, Pro, Ser, or Tyr
<220> FEATURE:
<221> NAME/KEY: MISC_FEATURE
<222> LOCATION: (13)..(13)
<223> OTHER INFORMATION: Xaa at position 13 is Thr, Glu, Pro, Lys, Asn,
        Ile, or Ala
<220> FEATURE:
<221> NAME/KEY: MISC_FEATURE
<222> LOCATION: (14)..(14)
<223> OTHER INFORMATION: Xaa at position 14 is Asn, Ser, Lys, Tyr, Arg,
        Cys, or Ile

<400> SEQUENCE: 67

Glu Trp Xaa Xaa Xaa Xaa Xaa Xaa Xaa Xaa Xaa Xaa Xaa Xaa Tyr
1               5                   10                  15

<210> SEQ ID NO 68
<211> LENGTH: 15
<212> TYPE: PRT
<213> ORGANISM: Homo sapiens

<400> SEQUENCE: 68

Glu Trp Met Gly Ile Ile Asn Pro Asn Ser Gly Cys Thr Asn Tyr
1               5                   10                  15

<210> SEQ ID NO 69
<211> LENGTH: 15
<212> TYPE: PRT
<213> ORGANISM: Homo sapiens

<400> SEQUENCE: 69

Glu Trp Met Gly Trp Ile Asn Pro Asn Val Cys Gly Thr Asn Tyr
1               5                   10                  15

<210> SEQ ID NO 70
<211> LENGTH: 15
<212> TYPE: PRT
<213> ORGANISM: Homo sapiens

<400> SEQUENCE: 70

Glu Trp Met Gly Met Ile Tyr Pro Gly Asn Cys Asp Thr Ser Tyr
1               5                   10                  15

<210> SEQ ID NO 71
<211> LENGTH: 15
<212> TYPE: PRT
<213> ORGANISM: Homo sapiens

<400> SEQUENCE: 71

Glu Trp Met Gly Ile Ile Tyr Pro Gly Ser Cys Glu Thr Lys Tyr
1               5                   10                  15

<210> SEQ ID NO 72
<211> LENGTH: 15
<212> TYPE: PRT
<213> ORGANISM: Homo sapiens

<400> SEQUENCE: 72

Glu Trp Met Gly Gly Ile Ile Pro Ile Phe Cys Thr Glu Tyr Tyr
1               5                   10                  15

<210> SEQ ID NO 73
<211> LENGTH: 15
<212> TYPE: PRT
<213> ORGANISM: Homo sapiens

<400> SEQUENCE: 73
```

```
Glu Trp Met Gly Ile Ile Cys Pro Gly Asp Ala Ala Thr Arg Tyr
1               5                   10                  15
```

<210> SEQ ID NO 74
<211> LENGTH: 15
<212> TYPE: PRT
<213> ORGANISM: Homo sapiens

<400> SEQUENCE: 74

```
Glu Trp Met Gly Cys Ile Ser Ala Tyr Tyr Gly Asn Pro Asn Tyr
1               5                   10                  15
```

<210> SEQ ID NO 75
<211> LENGTH: 15
<212> TYPE: PRT
<213> ORGANISM: Homo sapiens

<400> SEQUENCE: 75

```
Glu Trp Val Gly Val Ile Ser His Asp Gly Gly Asn Glu Cys Tyr
1               5                   10                  15
```

<210> SEQ ID NO 76
<211> LENGTH: 15
<212> TYPE: PRT
<213> ORGANISM: Homo sapiens

<400> SEQUENCE: 76

```
Glu Trp Met Gly Cys Ile Asn Ala Ala Asp Gly Asn Thr Lys Tyr
1               5                   10                  15
```

<210> SEQ ID NO 77
<211> LENGTH: 15
<212> TYPE: PRT
<213> ORGANISM: Homo sapiens

<400> SEQUENCE: 77

```
Glu Trp Met Gly Cys Phe Glu Pro Lys Asp Gly Glu Thr Ile Tyr
1               5                   10                  15
```

<210> SEQ ID NO 78
<211> LENGTH: 14
<212> TYPE: PRT
<213> ORGANISM: Homo sapiens

<400> SEQUENCE: 78

```
Glu Trp Leu Ala His Ile Cys Ser Asn Asp Gly Lys Arg Tyr
1               5                   10
```

<210> SEQ ID NO 79
<211> LENGTH: 14
<212> TYPE: PRT
<213> ORGANISM: Homo sapiens

<400> SEQUENCE: 79

```
Glu Trp Ile Gly Leu Ile Asn Gln Cys Gly Ser Thr Asn Tyr
1               5                   10
```

<210> SEQ ID NO 80
<211> LENGTH: 14
<212> TYPE: PRT
<213> ORGANISM: Homo sapiens

<400> SEQUENCE: 80

```
Glu Trp Ile Gly Tyr Ile Tyr Tyr Cys Gly Ser Pro Asn Tyr
```

```
1               5                    10
```

<210> SEQ ID NO 81
<211> LENGTH: 15
<212> TYPE: PRT
<213> ORGANISM: Homo sapiens

<400> SEQUENCE: 81

```
Glu Trp Leu Ser Tyr Ser Ser Cys Ser Gly Thr Pro Ile Tyr Tyr
1               5                    10                  15
```

<210> SEQ ID NO 82
<211> LENGTH: 15
<212> TYPE: PRT
<213> ORGANISM: Homo sapiens

<400> SEQUENCE: 82

```
Glu Trp Val Ser Tyr Ile Cys Gly Ser Ser Thr Ile Tyr Tyr
1               5                    10                  15
```

<210> SEQ ID NO 83
<211> LENGTH: 15
<212> TYPE: PRT
<213> ORGANISM: Homo sapiens

<400> SEQUENCE: 83

```
Glu Trp Val Ser Ser Ile Ser Ser Cys Gly Ser Ser Thr Tyr Tyr
1               5                    10                  15
```

<210> SEQ ID NO 84
<211> LENGTH: 15
<212> TYPE: PRT
<213> ORGANISM: Homo sapiens

<400> SEQUENCE: 84

```
Glu Trp Val Ser Tyr Ile Ser Ser Cys Gly Ser Thr Ile Asn Tyr
1               5                    10                  15
```

<210> SEQ ID NO 85
<211> LENGTH: 14
<212> TYPE: PRT
<213> ORGANISM: Homo sapiens

<400> SEQUENCE: 85

```
Glu Trp Val Ser Ile Ile Tyr Arg Cys Gly Thr Thr Tyr Tyr
1               5                    10
```

<210> SEQ ID NO 86
<211> LENGTH: 14
<212> TYPE: PRT
<213> ORGANISM: Homo sapiens

<400> SEQUENCE: 86

```
Glu Trp Met Gly Tyr Ile Tyr Cys Ser Ser Ala Asn Tyr
1               5                    10
```

<210> SEQ ID NO 87
<211> LENGTH: 15
<212> TYPE: PRT
<213> ORGANISM: Homo sapiens

<400> SEQUENCE: 87

```
Glu Trp Met Gly Arg Ile Tyr Pro Cys Asp Ser Tyr Ile Asn Tyr
1               5                    10                  15
```

-continued

<210> SEQ ID NO 88
<211> LENGTH: 25
<212> TYPE: PRT
<213> ORGANISM: Homo sapiens

<400> SEQUENCE: 88

Ala Gly Pro Ser Ile Thr Glu Ser His Tyr Cys Leu Asp Cys Ala Ala
1               5                   10                  15

Lys Asp Tyr Tyr Tyr Gly Leu Asp Val
            20                  25

<210> SEQ ID NO 89
<211> LENGTH: 17
<212> TYPE: PRT
<213> ORGANISM: Homo sapiens

<400> SEQUENCE: 89

Ala Lys Asp Ala Arg Asp Cys Leu Leu Cys Ala Asp Trp His Phe Asp
1               5                   10                  15

Leu

<210> SEQ ID NO 90
<211> LENGTH: 16
<212> TYPE: PRT
<213> ORGANISM: Homo sapiens

<400> SEQUENCE: 90

Ala Lys Phe Ser Gly Lys Asp Cys Ser Gly Thr Ser Cys Arg Asp Tyr
1               5                   10                  15

<210> SEQ ID NO 91
<211> LENGTH: 18
<212> TYPE: PRT
<213> ORGANISM: Homo sapiens

<400> SEQUENCE: 91

Ala Arg Ala Pro Asp Cys Ala Asp Ala Asp Cys His Lys Gly Ala Phe
1               5                   10                  15

Gly Tyr

<210> SEQ ID NO 92
<211> LENGTH: 19
<212> TYPE: PRT
<213> ORGANISM: Homo sapiens

<400> SEQUENCE: 92

Ala Arg Asp Gly Gly His Gly Phe Cys Ser Ser Ala Ser Cys Phe Gly
1               5                   10                  15

Pro Asp Tyr

<210> SEQ ID NO 93
<211> LENGTH: 16
<212> TYPE: PRT
<213> ORGANISM: Homo sapiens

<400> SEQUENCE: 93

Ala Arg Arg Gly Ser Cys Asp Tyr Cys Gly Asp Phe Pro Trp Gln Tyr
1               5                   10                  15

<210> SEQ ID NO 94
<211> LENGTH: 17
<212> TYPE: PRT

<213> ORGANISM: Homo sapiens

<400> SEQUENCE: 94

Ala Arg Ser Pro Ser Tyr Ile Cys Ser Gly Gly Thr Cys Val Phe Asp
1               5                   10                  15

His

<210> SEQ ID NO 95
<211> LENGTH: 18
<212> TYPE: PRT
<213> ORGANISM: Homo sapiens

<400> SEQUENCE: 95

Ala Arg Val Gly Tyr Cys Ser Ser Thr Ser Cys Asn Arg Gly Ala Phe
1               5                   10                  15

Asp Ile

<210> SEQ ID NO 96
<211> LENGTH: 14
<212> TYPE: PRT
<213> ORGANISM: Homo sapiens

<400> SEQUENCE: 96

Val Arg Gly His Cys Asp Gly Thr Thr Cys Ser Arg Ala Tyr
1               5                   10

<210> SEQ ID NO 97
<211> LENGTH: 17
<212> TYPE: PRT
<213> ORGANISM: Homo sapiens

<400> SEQUENCE: 97

Val Arg Lys Gly Pro Ser Cys Pro His Cys Gly Asp Phe His Trp Gln
1               5                   10                  15

His

<210> SEQ ID NO 98
<211> LENGTH: 20
<212> TYPE: PRT
<213> ORGANISM: Homo sapiens

<400> SEQUENCE: 98

Val Arg Ser Val Thr Pro Arg Tyr Cys Gly Gly Phe Cys Tyr Gly
1               5                   10                  15

Glu Phe Asp Tyr
            20

<210> SEQ ID NO 99
<211> LENGTH: 18
<212> TYPE: PRT
<213> ORGANISM: Homo sapiens

<400> SEQUENCE: 99

Val Arg Thr Ala Asp Cys Glu Arg Asp Pro Cys Lys Gly Trp Val Phe
1               5                   10                  15

Pro His

<210> SEQ ID NO 100
<211> LENGTH: 18
<212> TYPE: PRT
<213> ORGANISM: Homo sapiens

<400> SEQUENCE: 100

Val Thr Leu Pro Asp Leu Cys Pro Gly Asp Asn Cys Thr Tyr Pro Asp
1               5                   10                  15

Ala Ser

<210> SEQ ID NO 101
<211> LENGTH: 25
<212> TYPE: PRT
<213> ORGANISM: Homo sapiens

<400> SEQUENCE: 101

Val Arg Gly Arg Ser Cys Cys Gly Gly Arg Arg His Cys Asn Gly Ala
1               5                   10                  15

Asp Cys Phe Asn Trp Asp Phe Gln His
            20                  25

<210> SEQ ID NO 102
<211> LENGTH: 37
<212> TYPE: PRT
<213> ORGANISM: Homo sapiens

<400> SEQUENCE: 102

Ala Lys Asp Leu Arg Glu Asp Glu Cys Glu Glu Trp Trp Ser Asp Tyr
1               5                   10                  15

Tyr Asp Phe Gly Lys Gln Leu Pro Cys Arg Lys Ser Arg Gly Val Ala
            20                  25                  30

Gly Ile Phe Asp Gly
        35

<210> SEQ ID NO 103
<211> LENGTH: 96
<212> TYPE: DNA
<213> ORGANISM: Artificial Sequence
<220> FEATURE:
<223> OTHER INFORMATION: Yeast Display Vector

<400> SEQUENCE: 103
ggtgatcgtg ttactattac ctgtcgtgct tctagagacc atggccagta aggccggtct    60
ctctggcttg gtaccagcag aaaccaggta aagctc                              96

<210> SEQ ID NO 104
<211> LENGTH: 96
<212> TYPE: DNA
<213> ORGANISM: Artificial Sequence
<220> FEATURE:
<223> OTHER INFORMATION: Yeast Display Vector

<400> SEQUENCE: 104
ccactagcac aatgataatg gacagcacga agatctctgg taccggtcat tccggccaga    60
gagaccgaac catggtcgtc tttggtccat tcgag                               96

<210> SEQ ID NO 105
<211> LENGTH: 29
<212> TYPE: DNA
<213> ORGANISM: Artificial Sequence
<220> FEATURE:
<223> OTHER INFORMATION: Yeast Display Vector

<400> SEQUENCE: 105
ggtgatcgtg ttactattac ctgtcgtgc                                      29

```
<210> SEQ ID NO 106
<211> LENGTH: 34
<212> TYPE: DNA
<213> ORGANISM: Artificial Sequence
<220> FEATURE:
<223> OTHER INFORMATION: Yeast Display Vector

<400> SEQUENCE: 106
ctggcttggt accagcagaa accaggtaaa gctc                    34

<210> SEQ ID NO 107
<211> LENGTH: 33
<212> TYPE: DNA
<213> ORGANISM: Artificial Sequence
<220> FEATURE:
<223> OTHER INFORMATION: Yeast Display Vector

<400> SEQUENCE: 107
ccactagcac aatgataatg gacagcacga aga                     33

<210> SEQ ID NO 108
<211> LENGTH: 30
<212> TYPE: DNA
<213> ORGANISM: Artificial Sequence
<220> FEATURE:
<223> OTHER INFORMATION: Yeast Display Vector

<400> SEQUENCE: 108
gaaccatggt cgtctttggt ccatttcgag                         30

<210> SEQ ID NO 109
<211> LENGTH: 33
<212> TYPE: DNA
<213> ORGANISM: Artificial Sequence
<220> FEATURE:
<223> OTHER INFORMATION: Amplified LCDR1 Oligo

<400> SEQUENCE: 109
ggtgatcgtg ttactattac ctgtcgtgct tct                     33

<210> SEQ ID NO 110
<211> LENGTH: 34
<212> TYPE: DNA
<213> ORGANISM: Artificial Sequence
<220> FEATURE:
<223> OTHER INFORMATION: Amplified LCDR1 Oligo

<400> SEQUENCE: 110
ctggcttggt accagcagaa accaggtaaa gctc                    34

<210> SEQ ID NO 111
<211> LENGTH: 33
<212> TYPE: DNA
<213> ORGANISM: Artificial Sequence
<220> FEATURE:
<223> OTHER INFORMATION: Amplified LCDR1 Oligo

<400> SEQUENCE: 111
ccactagcac aatgataatg gacagcacga aga                     33

<210> SEQ ID NO 112
<211> LENGTH: 34
<212> TYPE: DNA
<213> ORGANISM: Artificial Sequence
<220> FEATURE:
<223> OTHER INFORMATION: Amplified LCDR1 Oligo
```

<400> SEQUENCE: 112
gaccgaacca tggtcgtctt tggtccattt cgag                                34

<210> SEQ ID NO 113
<211> LENGTH: 33
<212> TYPE: DNA
<213> ORGANISM: Artificial Sequence
<220> FEATURE:
<223> OTHER INFORMATION: Cloned Construct

<400> SEQUENCE: 113
ggtgatcgtg ttactattac ctgtcgtgct tct                                 33

<210> SEQ ID NO 114
<211> LENGTH: 34
<212> TYPE: DNA
<213> ORGANISM: Artificial Sequence
<220> FEATURE:
<223> OTHER INFORMATION: Cloned Construct

<400> SEQUENCE: 114
ctggcttggt accagcagaa accaggtaaa gctc                                34

<210> SEQ ID NO 115
<211> LENGTH: 33
<212> TYPE: DNA
<213> ORGANISM: Artificial Sequence
<220> FEATURE:
<223> OTHER INFORMATION: Cloned Construct

<400> SEQUENCE: 115
ccactagcac aatgataatg gacagcacga aga                                 33

<210> SEQ ID NO 116
<211> LENGTH: 34
<212> TYPE: DNA
<213> ORGANISM: Artificial Sequence
<220> FEATURE:
<223> OTHER INFORMATION: Cloned Construct

<400> SEQUENCE: 116
gaccgaacca tggtcgtctt tggtccattt cgag                                34

<210> SEQ ID NO 117
<211> LENGTH: 4
<212> TYPE: PRT
<213> ORGANISM: Artificial Sequence
<220> FEATURE:
<223> OTHER INFORMATION: Streptavidin Binding Motif

<400> SEQUENCE: 117

Glu Pro Asp Trp
1

<210> SEQ ID NO 118
<211> LENGTH: 5
<212> TYPE: PRT
<213> ORGANISM: Artificial Sequence
<220> FEATURE:
<223> OTHER INFORMATION: Streptavidin Binding Motif
<220> FEATURE:
<221> NAME/KEY: MISC_FEATURE
<222> LOCATION: (3)..(3)
<223> OTHER INFORMATION: Xaa is any amino acid

<400> SEQUENCE: 118

```
Pro Trp Xaa Trp Leu
1               5

<210> SEQ ID NO 119
<211> LENGTH: 6
<212> TYPE: PRT
<213> ORGANISM: Artificial Sequence
<220> FEATURE:
<223> OTHER INFORMATION: Streptavidin Binding Motif

<400> SEQUENCE: 119

Gly Asp Trp Val Phe Ile
1               5

<210> SEQ ID NO 120
<211> LENGTH: 6
<212> TYPE: PRT
<213> ORGANISM: Artificial Sequence
<220> FEATURE:
<223> OTHER INFORMATION: Streptavidin Binding Motif

<400> SEQUENCE: 120

Pro Trp Pro Trp Leu Gly
1               5

<210> SEQ ID NO 121
<211> LENGTH: 107
<212> TYPE: PRT
<213> ORGANISM: Homo sapiens

<400> SEQUENCE: 121

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asn Tyr Tyr Cys Gln Gln Ala Asn Ser Phe Pro Trp
                85                  90                  95

Thr Phe Gly Gly Gly Thr Lys Val Glu Ile Lys
            100                 105

<210> SEQ ID NO 122
<211> LENGTH: 21
<212> TYPE: PRT
<213> ORGANISM: Artificial Sequence
<220> FEATURE:
<223> OTHER INFORMATION: Linker Sequence

<400> SEQUENCE: 122

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 123
<211> LENGTH: 118
<212> TYPE: PRT
<213> ORGANISM: Homo sapiens
```

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Asp Leu
            20                  25                  30

Ser Ile His Trp Val Arg Gln Ala Pro Gly Lys Gly Leu Glu Trp Met
        35                  40                  45

Gly Gly Phe Asp Pro Gln Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Lys Ser Glu Asp Thr Ala Val Tyr Tyr Cys
                85                  90                  95

Ala Thr Gly Ser Ser Ser Ser Trp Phe Asp Pro Trp Gly Gln Gly Thr
            100                 105                 110

Leu Val Thr Val Ser Ser
        115

<210> SEQ ID NO 124
<211> LENGTH: 113
<212> TYPE: PRT
<213> ORGANISM: Homo sapiens

<400> SEQUENCE: 124

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Val Glu Ile
            100                 105                 110

Lys

<210> SEQ ID NO 125
<211> LENGTH: 21
<212> TYPE: PRT
<213> ORGANISM: Artificial Sequence
<220> FEATURE:
<223> OTHER INFORMATION: Linker Sequence

<400> SEQUENCE: 125

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 126
<211> LENGTH: 118
<212> TYPE: PRT
<213> ORGANISM: Homo sapiens

<400> SEQUENCE: 126

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Thr
            100                 105                 110

Leu Val Thr Val Ser Ser
        115

<210> SEQ ID NO 127
<211> LENGTH: 112
<212> TYPE: PRT
<213> ORGANISM: Homo sapiens

<400> SEQUENCE: 127

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 128
<211> LENGTH: 21
<212> TYPE: PRT
<213> ORGANISM: Artificial Sequence
<220> FEATURE:
<223> OTHER INFORMATION: Linker Sequence

<400> SEQUENCE: 128

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 129
<211> LENGTH: 112
<212> TYPE: PRT
<213> ORGANISM: Homo sapiens

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 130
<211> LENGTH: 107
<212> TYPE: PRT
<213> ORGANISM: Homo sapiens

<400> SEQUENCE: 130

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Tyr Gly Ser Thr Pro Leu
                85                  90                  95

Thr Phe Gly Gly Gly Thr Lys Val Glu Ile Lys
            100                 105

<210> SEQ ID NO 131
<211> LENGTH: 21
<212> TYPE: PRT
<213> ORGANISM: Artificial Sequence
<220> FEATURE:
<223> OTHER INFORMATION: Linker Sequence

<400> SEQUENCE: 131

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 132
<211> LENGTH: 121
<212> TYPE: PRT
<213> ORGANISM: Homo sapiens

<400> SEQUENCE: 132

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly

```
                    20                  25                  30

Asp Tyr Tyr Trp Ser Trp Ile Arg Gln Pro Pro Gly Lys Gly Leu Glu
                35                  40                  45

Trp Ile Gly Tyr Ile Tyr Tyr Ser Gly Ser Thr Asp Tyr Asn Pro Ser
 50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
                100                 105                 110

Gln Gly Thr Leu Val Thr Val Ser Ser
                115                 120

<210> SEQ ID NO 133
<211> LENGTH: 108
<212> TYPE: PRT
<213> ORGANISM: Homo sapiens

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Leu Ser
 50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gly Gly Thr Lys Val Glu Ile Lys
                100                 105

<210> SEQ ID NO 134
<211> LENGTH: 21
<212> TYPE: PRT
<213> ORGANISM: Artificial Sequence
<220> FEATURE:
<223> OTHER INFORMATION: Linker Sequence

<400> SEQUENCE: 134

Ser Gly Gly Ser Thr Ile Thr Ser Tyr Asn Val Tyr Tyr Thr Lys Leu
1               5                   10                  15

Ser Ser Ser Gly Thr
                20

<210> SEQ ID NO 135
<211> LENGTH: 117
<212> TYPE: PRT
<213> ORGANISM: Homo sapiens

<400> SEQUENCE: 135

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
                20                  25                  30
```

Trp Ile Ala Trp Val Arg Gln Val Pro Gly Lys Gly Leu Glu Ser Met
              35                  40                  45

Gly Ile Ile Tyr Pro Gly Asp Ser Asp Ile Arg Tyr Ser Pro Ser Phe
 50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Ile Tyr Tyr Cys
                 85                  90                  95

Ala Arg His Asp Ile Glu Gly Phe Asp Tyr Trp Gly Arg Gly Thr Leu
             100                 105                 110

Val Thr Val Ser Ser
             115

<210> SEQ ID NO 136
<211> LENGTH: 109
<212> TYPE: PRT
<213> ORGANISM: Homo sapiens

<400> SEQUENCE: 136

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
             20                  25                  30

Asn Ser Val Ser Trp Tyr Gln Gln His Pro Gly Lys Ala Pro Lys Leu
         35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                 85                  90                  95

Ser Met Val Phe Gly Gly Gly Thr Lys Leu Thr Val Leu
            100                 105

<210> SEQ ID NO 137
<211> LENGTH: 21
<212> TYPE: PRT
<213> ORGANISM: Artificial Sequence
<220> FEATURE:
<223> OTHER INFORMATION: Linker Sequence

<400> SEQUENCE: 137

Ser Gly Gly Ser Thr Ile Thr Ser Tyr Asn Val Tyr Tyr Thr Lys Leu
1               5                   10                  15

Ser Ser Ser Gly Thr
             20

<210> SEQ ID NO 138
<211> LENGTH: 114
<212> TYPE: PRT
<213> ORGANISM: Homo sapiens

<400> SEQUENCE: 138

Val Gln Leu Val Gln Ser Gly Ala Glu Val Lys Lys Pro Gly Ala Ser
1               5                   10                  15

Val Lys Val Ser Cys Lys Ala Ser Gly Tyr Thr Leu Thr Ser Tyr Gly
             20                  25                  30

Ile Ser Trp Val Arg Gln Ala Pro Gly Gln Gly Leu Glu Trp Met Gly
         35                  40                  45

Trp Val Ser Phe Tyr Asn Gly Asn Thr Asn Tyr Ala Gln Lys Leu Gln
 50                  55                  60

Gly Arg Gly Thr Met Thr Thr Asp Pro Ser Thr Ser Thr Ala Tyr Met
 65                  70                  75                  80

Glu Leu Arg Ser Leu Arg Ser Asp Asp Thr Ala Val Tyr Tyr Cys Ala
                 85                  90                  95

Arg Gly Tyr Gly Met Asp Val Trp Gly Gln Gly Thr Thr Val Thr Val
             100                 105                 110

Ser Ser

<210> SEQ ID NO 139
<211> LENGTH: 816
<212> TYPE: DNA
<213> ORGANISM: Artificial Sequence
<220> FEATURE:
<223> OTHER INFORMATION: Oligonucleotide

<400> SEQUENCE: 139

| | | | | | | |
|---|---|---|---|---|---|---|
| cagttagata | aaagaggcgc | ggcagcaagc | ggcgcgcatg | ccgatatcca | gatgacccag | 60 |
| tctccatctt | ctgtttctgc | ttctgttggt | gatcgtgtta | ctattacctg | tcgtgcttct | 120 |
| cagggtatct | cttcttggct | ggcttggtac | cagcagaaac | caggtaaagc | tccaaaactg | 180 |
| ctgatctacg | gtgcttctaa | cctggaatct | ggtgttccat | ctcgtttctc | tggttctggt | 240 |
| tctggtaccg | atttcaccct | gaccatctct | tctctgcagc | cagaagattt | cgctaactac | 300 |
| tactgtcagc | aggctaactc | tttcccatgg | accttcggtg | gtggtaccaa | agttgaaatc | 360 |
| aaatccggag | ggtcgaccat | aacttcgtat | aatgtatact | atacgaagtt | atcctcgagc | 420 |
| ggtacccagg | ttcagctggt | tcagtctggt | gctgaagtta | aaaaaccagg | tgcttctgtt | 480 |
| aaagtttctt | gtaaagtttc | tggttacacc | ctgtctgatc | tgtctatcca | ctgggttcgt | 540 |
| caggctccag | gtaaaggtct | ggaatggatg | ggtggtttcg | atccacagga | tggtgaaacc | 600 |
| atctacgctc | agaaattcca | gggtcgtgtt | accatgaccg | aagatacctc | taccgatacc | 660 |
| gcttacatgg | aactgtcttc | tctgaaatct | gaggacacgg | ccgtgtatta | ctgtgctacc | 720 |
| ggttcttctt | cttcttggtt | cgatccatgg | ggtcagggaa | ccctggtcac | cgtctcctca | 780 |
| gctagcggca | aaccaatccc | aaacccactg | ctgggc | | | 816 |

<210> SEQ ID NO 140
<211> LENGTH: 827
<212> TYPE: DNA
<213> ORGANISM: Artificial Sequence
<220> FEATURE:
<223> OTHER INFORMATION: Oligonucleotide

<400> SEQUENCE: 140

| | | | | | | |
|---|---|---|---|---|---|---|
| cagttagata | aaagaggcgc | ggcagcaagc | ggcgcgcatg | ccgatatcca | gatgacccag | 60 |
| tctccatctt | ctgtttctgc | ttctgttggt | gatcgtgtta | ctattacctg | tcgtgcttct | 120 |
| agagaccatg | gccagtaagg | ccggtctctc | tggcttggta | ccagcagaaa | ccaggtaaag | 180 |
| ctccaaaact | gctgatctac | ggtgcttcta | acctggaatc | tggtgttcca | tctcgtttct | 240 |
| ctggttctgg | ttctggtacc | gatttcaccc | tgaccatctc | ttctctgcag | ccagaagatt | 300 |
| tcgctaacta | ctactgtcag | caggctaact | ctttcccatg | gaccttcggt | ggtggtacca | 360 |
| aagttgaaat | caaatccgga | gggtcgacca | taacttcgta | taatgtatac | tatacgaagt | 420 |
| tatcctcgag | cggtacccag | gttcagctgg | ttcagtctgg | tgctgaagtt | aaaaaaccag | 480 |

```
gtgcttctgt taaagtttct tgtaaagttt ctggttacac cctgtctgat ctgtctatcc    540
actgggttcg tcaggctcca ggtaaaggtc tggaatggat gggtggtttc gatccacagg    600
atggtgaaac catctacgct cagaaattcc agggtcgtgt taccatgacc gaagatacct    660
ctaccgatac cgcttacatg gaactgtctt ctctgaaatc tgaggacacg gccgtgtatt    720
actgtgctac cggttcttct tcttcttggt tcgatccatg gggtcaggga accctggtca    780
ccgtctcctc agctagcggc aaaccaatcc caaacccact gctgggc                 827

<210> SEQ ID NO 141
<211> LENGTH: 824
<212> TYPE: DNA
<213> ORGANISM: Artificial Sequence
<220> FEATURE:
<223> OTHER INFORMATION: Oligonucleotide

<400> SEQUENCE: 141
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
cagggtatct cttcttggct ggcttggtac cagcagaaac caggtaaagc tccaaaactg    180
ctgatctaca gagaccatgg ccagtaaggc cggtctctgg tgttccatct cgtttctctg    240
gttctggttc tggtaccgat ttcaccctga ccatctcttc tctgcagcca gaagatttcg    300
ctaactacta ctgtcagcag ctaactcttt cccatggac cttcggtggt ggtaccaaag    360
ttgaaatcaa atccggaggg tcgaccataa cttcgtataa tgtatactat acgaagttat    420
cctcgagcgg tacccaggtt cagctggttc agtctggtgc tgaagttaaa aaaccaggtg    480
cttctgttaa agtttcttgt aaagtttctg gttacaccct gtctgatctg tctatccact    540
gggttcgtca ggctccaggt aaaggtctgg aatggatggg tggtttcgat ccacaggatg    600
gtgaaaccat ctacgctcag aaattccagg gtcgtgttac catgaccgaa gatacctcta    660
ccgataccgc ttacatggaa ctgtcttctc tgaaatctga ggacacggcc gtgtattact    720
gtgctaccgg ttcttcttct tcttggttcg atccatgggg tcagggaacc ctggtcaccg    780
tctcctcagc tagcggcaaa ccaatcccaa acccactgct gggc                    824

<210> SEQ ID NO 142
<211> LENGTH: 818
<212> TYPE: DNA
<213> ORGANISM: Artificial Sequence
<220> FEATURE:
<223> OTHER INFORMATION: Oligonucleotide

<400> SEQUENCE: 142
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
cagggtatct cttcttggct ggcttggtac cagcagaaac caggtaaagc tccaaaactg    180
ctgatctacg gtgcttctaa cctggaatct ggtgttccat ctcgtttctc tggttctggt    240
tctggtaccg atttcaccct gaccatctct tctctgcagc cagaagattt cgctaactac    300
tactgtagag accatggcca gtaaggccgg tctctttcgg tggtggtacc aaagttgaaa    360
tcaaatccgg agggtcgacc ataacttcgt ataatgtata ctatacgaag ttatcctcga    420
gcggtaccca ggttcagctg gttcagtctg gtgctgaagt aaaaaaacca ggtgcttctg    480
ttaaagtttc ttgtaaagtt tctggttaca ccctgtctga tctgtctatc cactgggttc    540
gtcaggctcc aggtaaaggt ctggaatgga tgggtggttt cgatccacag gatggtgaaa    600
```

```
ccatctacgc tcagaaattc cagggtcgtg ttaccatgac cgaagatacc tctaccgata    660
ccgcttacat ggaactgtct tctctgaaat ctgaggacag gccgtgtat tactgtgcta     720 ccggttcttc ttcttcttgg ttcgatccat ggggtcaggg aaccctggtc accgtctcct    780
cagctagcgg caaaccaatc ccaaacccac tgctgggc                            818
```

<210> SEQ ID NO 143
<211> LENGTH: 821
<212> TYPE: DNA
<213> ORGANISM: Artificial Sequence
<220> FEATURE:
<223> OTHER INFORMATION: Oligonucleotide

<400> SEQUENCE: 143

```
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
cagggtatct cttcttggct ggcttggtac cagcagaaac caggtaaagc tccaaaactg    180
ctgatctacg gtgcttctaa cctggaatct ggtgttccat ctcgtttctc tggttctggt    240
tctggtaccg atttcaccct gaccatctct tctctgcagc cagaagattt cgctaactac    300
tactgtcagc aggctaactc tttcccatgg accttcggtg tgtgtaccaa agttgaaatc    360
aaatccggag gtcgaccat aacttcgtat aatgtatact atacgaagtt atcctcgagc     420
ggtacccagg ttcagctggt tcagtctggt gctgaagtta aaaaaccagg tgcttctgtt    480
aaagtttctt gtaaagtttc tagagaccat ggccagtaag gccggtctct atccactggg    540
ttcgtcaggc tccaggtaaa ggtctggaat ggatgggtgg tttcgatcca caggatggtg    600
aaaccatcta cgctcagaaa ttccagggtc gtgttaccat gaccgaagat acctctaccg    660
ataccgctta catggaactg tcttctctga atctgaggac acggccgtg tattactgtg     720 ctaccggttc ttcttcttct tggttcgatc catggggtca gggaaccctg gtcaccgtct    780
cctcagctag cggcaaacca atcccaaacc cactgctggg c                        821
```

<210> SEQ ID NO 144
<211> LENGTH: 821
<212> TYPE: DNA
<213> ORGANISM: Artificial Sequence
<220> FEATURE:
<223> OTHER INFORMATION: Oligonucleotide

<400> SEQUENCE: 144

```
cagttagata aaagaggcgc ggcagcaagc ggcgcgcatg ccgatatcca gatgacccag     60
tctccatctt ctgtttctgc ttctgttggt gatcgtgtta ctattacctg tcgtgcttct    120
cagggtatct cttcttggct ggcttggtac cagcagaaac caggtaaagc tccaaaactg    180
ctgatctacg gtgcttctaa cctggaatct ggtgttccat ctcgtttctc tggttctggt    240
tctggtaccg atttcaccct gaccatctct tctctgcagc cagaagattt cgctaactac    300
tactgtcagc aggctaactc tttcccatgg accttcggtg tgtgtaccaa agttgaaatc    360
aaatccggag gtcgaccat aacttcgtat aatgtatact atacgaagtt atcctcgagc     420
ggtacccagg ttcagctggt tcagtctggt gctgaagtta aaaaaccagg tgcttctgtt    480
aaagtttctt gtaaagtttc tggttacacc ctgtctgatc tgtctatcca ctgggttcgt    540
caggctccag gtaaaggtct ggaatggatg ggtggtagag accatggcca gtaaggccgg    600
tctctatcta cgctcagaaa ttccagggtc gtgttaccat gaccgaagat acctctaccg    660
```

| ataccgctta catggaactg tcttctctga atctgagga cacggccgtg tattactgtg | 720 |
| ctaccggttc ttcttcttct tggttcgatc catggggtca gggaaccctg gtcaccgtct | 780 |
| cctcagctag cggcaaacca atcccaaacc cactgctggg c | 821 |

<210> SEQ ID NO 145
<211> LENGTH: 803
<212> TYPE: DNA
<213> ORGANISM: Artificial Sequence
<220> FEATURE:
<223> OTHER INFORMATION: Oligonucleotide

<400> SEQUENCE: 145

| cagttagata aagaggcgc ggcagcaagc ggcgcgcatg ccgatatcca gatgacccag | 60 |
| tctccatctt ctgtttctgc ttctgttggt gatcgtgtta ctattacctg tcgtgcttct | 120 |
| cagggtatct cttcttggct ggcttggtac cagcagaaac caggtaaagc tccaaaactg | 180 |
| ctgatctacg gtgcttctaa cctggaatct ggtgttccat ctcgtttctc tggttctggt | 240 |
| tctggtaccg atttcaccct gaccatctct tctctgcagc cagaagattt cgctaactac | 300 |
| tactgtcagc aggctaactc tttcccatgg accttcggtg gtggtaccaa agttgaaatc | 360 |
| aaatccggag ggtcgaccat aacttcgtat aatgtatact atacgaagtt atcctcgagc | 420 |
| ggtacccagg ttcagctggt tcagtctggt gctgaagtta aaaaaccagg tgcttctgtt | 480 |
| aaagtttctt gtaaagtttc tggttacacc ctgtctgatc tgtctatcca ctgggttcgt | 540 |
| caggctccag gtaaaggtct ggaatggatg ggtggtttcg atccacagga tggtgaaacc | 600 |
| atctacgctc agaaattcca gggtcgtgtt accatgaccg aagatacctc taccgatacc | 660 |
| gcttacatgg aactgtcttc tctgaaatct gaggacacgg ccgtgtatta ctgtagagac | 720 |
| catggccagt aaggccggtc tctggaaccc tggtcaccgt ctcctcagct agcggcaaac | 780 |
| caatcccaaa cccactgctg ggc | 803 |

<210> SEQ ID NO 146
<211> LENGTH: 834
<212> TYPE: DNA
<213> ORGANISM: Artificial Sequence
<220> FEATURE:
<223> OTHER INFORMATION: Oligonucleotide

<400> SEQUENCE: 146

| cagttagata aagaggcgc ggcagcaagc ggcgcgcatg ccgatatcgt tatgacccag | 60 |
| tctccagatt ctctggctgt ttctctgggt aacgtgcta ccatcaactg caaatcttct | 120 |
| cagtctctgc tgaactctgg taaccagaaa aactacctgg cttggtacca gcagaaacca | 180 |
| ggtcagccac caaaactgct gatctacggt gcttctaccc gtgaatctgg tgttccagat | 240 |
| cgtttctctg gttctggttc tggtaccgat ttcacccctga ccatctcttc tctgcaggct | 300 |
| gaagatgttg ctgtttacta ctgtcagaac gttcactctt tcccattcac cttcggtggt | 360 |
| ggtaccaaag ttgaaatcaa atccggaggg tcgaccataa cttcgtataa tgtatactat | 420 |
| acgaagttat cctcgagcgg tacccaggtt accctgcgtg aatctggtcc agctctggtt | 480 |
| aaaccaaccc agaccctgac cctgacctgt accgtttctg gtttctctct gtctgcttac | 540 |
| tctgttaact ggatccgtca gccaccaggt aaagctctgg aatggctggc tatgatctgg | 600 |
| ggtgatggta aatcgttta caactctgct ctgaaatctc gtctgaccat ctctaaagat | 660 |
| acctctaaaa accaggttgt tctgaccatg accaacatgg atcctgtgga cacagccaca | 720 |
| tattactgtg ctggtgatgg ttactaccca tacgctatgg ataactgggg tcagggaacc | 780 |

```
ctggtcaccg tctcctcagc tagcggcaaa ccaatcccaa acccactgct gggc         834
```

<210> SEQ ID NO 147
<211> LENGTH: 827
<212> TYPE: DNA
<213> ORGANISM: Artificial Sequence
<220> FEATURE:
<223> OTHER INFORMATION: Oligonucleotide

<400> SEQUENCE: 147

```
cagttagata aagaggcgc ggcagcaagc ggcgcgcatg ccgatatcgt tatgacccag      60
tctccagatt ctctggctgt ttctctgggt aacgtgcta ccatcaactg caaatcttct    120
agagaccatg ccagtaagg ccggtctctc tggcttggta ccagcagaaa ccaggtcagc    180
caccaaaact gctgatctac ggtgcttcta cccgtgaatc tggtgttcca gatcgtttct    240
ctggttctgg ttctggtacc gatttcaccc tgaccatctc ttctctgcag ctgaagatg    300
ttgctgttta ctactgtcag aacgttcact cttttcccatt caccttcggt ggtggtacca    360
aagttgaaat caaatccgga gggtcgacca taacttcgta taatgtatac tatacgaagt    420
tatcctcgag cggtacccag gttaccctgc gtgaatctgg tccagctctg gttaaaccaa    480
cccagaccct gaccctgacc tgtaccgttt ctggtttctc tctgtctgct tactctgtta    540
actggatccg tcagccacca ggtaaagctc tggaatggct ggctatgatc tggggtgatg    600
gtaaaatcgt ttacaactct gctctgaaat ctcgtctgac catctctaaa gatacctcta    660
aaaccaggt tgttctgacc atgaccaaca tggatcctgt ggacacagcc acatattact    720
gtgctggtga tggttactac ccatacgcta tggataactg gggtcaggga accctggtca    780
ccgtctcctc agctagcggc aaaccaatcc caaacccact gctgggc                827
```

<210> SEQ ID NO 148
<211> LENGTH: 842
<212> TYPE: DNA
<213> ORGANISM: Artificial Sequence
<220> FEATURE:
<223> OTHER INFORMATION: Oligonucleotide

<400> SEQUENCE: 148

```
cagttagata aagaggcgc ggcagcaagc ggcgcgcatg ccgatatcgt tatgacccag      60
tctccagatt ctctggctgt ttctctgggt aacgtgcta ccatcaactg caaatcttct    120
cagtctctgc tgaactctgg taaccagaaa aactacctgg cttggtacca gcagaaacca    180
ggtcagccac caaaactgct gatctacaga gaccatggcc agtaaggccg gtctctggtg    240
ttccagatcg tttctctggt tctggttctg gtaccgattt caccctgacc atctcttctc    300
tgcaggctga agatgttgct gtttactact gtcagaacgt tcactctttc ccattcacct    360
tcggtggtgg taccaaagtt gaaatcaaat ccggagggtc gaccataact tcgtataatg    420
tatactatac gaagttatcc tcgagcggta cccaggttac cctgcgtgaa tctggtccag    480
ctctggttaa ccaacccag accctgaccc tgacctgtac cgtttctggt ttctctctgt    540
ctgcttactc tgttaactgg atccgtcagc caccaggtaa agctctggaa tggctggcta    600
tgatctgggg tgatggtaaa atcgtttaca actctgctct gaaatctcgt ctgaccatct    660
ctaaagatac ctctaaaaac caggttgttc tgaccatgac caacatggat cctgtggaca    720
cagccacata ttactgtgct ggtgatggtt actacccata cgctatggat aactgggtc     780
agggaaccct ggtcaccgtc tcctcagcta gcggcaaacc aatcccaaac ccactgctgg    840
```

| | |
|---|---:|
| gc | 842 |

<210> SEQ ID NO 149
<211> LENGTH: 836
<212> TYPE: DNA
<213> ORGANISM: Artificial Sequence
<220> FEATURE:
<223> OTHER INFORMATION: Oligonucleotide

<400> SEQUENCE: 149

| | |
|---|---:|
| cagttagata aaagaggcgc ggcagcaagc ggcgcgcatg ccgatatcgt tatgacccag | 60 |
| tctccagatt ctctggctgt ttctctgggt gaacgtgcta ccatcaactg caaatcttct | 120 |
| cagtctctgc tgaactctgg taaccagaaa aactacctgg cttggtacca gcagaaacca | 180 |
| ggtcagccac caaaactgct gatctacggt gcttctaccc gtgaatctgg tgttccagat | 240 |
| cgtttctctg gttctggttc tggtaccgat ttcaccctga ccatctcttc tctgcaggct | 300 |
| gaagatgttg ctgtttacta ctgtagagac catggccagt aaggccggtc tctttcggtg | 360 |
| gtggtaccaa agttgaaatc aaatccggag gtcgaccat aacttcgtat aatgtatact | 420 |
| atacgaagtt atcctcgagc ggtacccagg ttaccctgcg tgaatctggt ccagctctgg | 480 |
| ttaaaccaac ccagaccctg accctgacct gtaccgtttc tggtttctct ctgtctgctt | 540 |
| actctgttaa ctggatccgt cagccaccag gtaaagctct ggaatggctg gctatgatct | 600 |
| ggggtgatgg taaaatcgtt tacaactctg ctctgaaatc tcgtctgacc atctctaaag | 660 |
| atacctctaa aaccaggtt gttctgacca tgaccaacat ggatcctgtg gacacagcca | 720 |
| catattactg tgctggtgat ggttactacc catacgctat ggataactgg ggtcagggaa | 780 |
| ccctggtcac cgtctcctca gctagcggca aaccaatccc aaacccactg ctgggc | 836 |

<210> SEQ ID NO 150
<211> LENGTH: 837
<212> TYPE: DNA
<213> ORGANISM: Artificial Sequence
<220> FEATURE:
<223> OTHER INFORMATION: Oligonucleotide

<400> SEQUENCE: 150

| | |
|---|---:|
| cagttagata aaagaggcgc ggcagcaagc ggcgcgcatg ccgatatcgt tatgacccag | 60 |
| tctccagatt ctctggctgt ttctctgggt gaacgtgcta ccatcaactg caaatcttct | 120 |
| cagtctctgc tgaactctgg taaccagaaa aactacctgg cttggtacca gcagaaacca | 180 |
| ggtcagccac caaaactgct gatctacggt ttctacccgt gaatctggtg ttccagatcg | 240 |
| tttctctggt tctggttctg gtaccgattt caccctgacc atctcttctc tgcaggctga | 300 |
| agatgttgct gtttactact gtcagaacgt tcactctttc ccattcacct cggtggtgg | 360 |
| taccaaagtt gaaatcaaat ccggagggtc gaccataact tcgtataatg tatactatac | 420 |
| gaagttatcc tcgagcggta cccaggttac cctgcgtgaa tctggtccag ctctggttaa | 480 |
| accaacccag accctgaccc tgacctgtac cgtttctaga gaccatggcc agtaaggccg | 540 |
| gtctctgtta actggatccg tcagccacca ggtaaagctc tggaatggct ggctatgatc | 600 |
| tggggtgatg gtaaaatcgt ttacaactct gctctgaaat ctcgtctgac catctctaaa | 660 |
| gatacctcta aaaccaggt tgttctgacc atgaccaaca tggatcctgt ggacacagcc | 720 |
| acatattact gtgctggtga tggttactac ccatacgcta tggataactg gggtcaggga | 780 |
| accctggtca ccgtctcctc agctagcggc aaaccaatcc caaacccact gctgggc | 837 |

<210> SEQ ID NO 151
<211> LENGTH: 845
<212> TYPE: DNA
<213> ORGANISM: Artificial Sequence
<220> FEATURE:
<223> OTHER INFORMATION: Oligonucleotide

<400> SEQUENCE: 151

| | | | | | |
|---|---|---|---|---|---|
| cagttagata | aaagaggcgc | ggcagcaagc | ggcgcgcatg | ccgatatcgt | tatgacccag | 60 |
| tctccagatt | ctctggctgt | ttctctgggt | aacgtgcta | ccatcaactg | caaatcttct | 120 |
| cagtctctgc | tgaactctgg | taaccagaaa | aactacctgg | cttggtacca | gcagaaacca | 180 |
| ggtcagccac | aaaaactgct | gatctacggt | gcttctaccc | gtgaatctgg | tgttccagat | 240 |
| cgtttctctg | gttctggttc | tggtaccgat | ttcaccctga | ccatctcttc | tctgcaggct | 300 |
| gaagatgttg | ctgtttacta | ctgtcagaac | gttcactctt | tcccattcac | cttcggtggt | 360 |
| ggtaccaaag | ttgaaatcaa | atccggaggg | tcgaccataa | cttcgtataa | tgtatactat | 420 |
| acgaagttat | cctcgagcgg | tacccaggtt | accctgcgtg | aatctggtcc | agctctggtt | 480 |
| aaaccaaccc | agaccctgac | cctgacctgt | accgtttctg | gtttctctct | gtctgcttac | 540 |
| tctgttaact | ggatccgtca | gccaccaggt | aaagctctgg | aatggctggc | tatgagagac | 600 |
| catggccagt | aaggccggtc | tctatcgttt | acaactctgc | tctgaaatct | cgtctgacca | 660 |
| tctctaaaga | tacctctaaa | aaccaggttg | ttctgaccat | gaccaacatg | gatcctgtgg | 720 |
| acacagccac | atattactgt | gctggtgatg | gttactaccc | atacgctatg | gataactggg | 780 |
| gtcagggaac | cctggtcacc | gtctcctcag | ctagcggcaa | accaatccca | aacccactgc | 840 |
| tgggc | | | | | 845 |

<210> SEQ ID NO 152
<211> LENGTH: 818
<212> TYPE: DNA
<213> ORGANISM: Artificial Sequence
<220> FEATURE:
<223> OTHER INFORMATION: Oligonucleotide

<400> SEQUENCE: 152

| | | | | | |
|---|---|---|---|---|---|
| cagttagata | aaagaggcgc | ggcagcaagc | ggcgcgcatg | ccgatatcgt | tatgacccag | 60 |
| tctccagatt | ctctggctgt | ttctctgggt | aacgtgcta | ccatcaactg | caaatcttct | 120 |
| cagtctctgc | tgaactctgg | taaccagaaa | aactacctgg | cttggtacca | gcagaaacca | 180 |
| ggtcagccac | aaaaactgct | gatctacggt | gcttctaccc | gtgaatctgg | tgttccagat | 240 |
| cgtttctctg | gttctggttc | tggtaccgat | ttcaccctga | ccatctcttc | tctgcaggct | 300 |
| gaagatgttg | ctgtttacta | ctgtcagaac | gttcactctt | tcccattcac | cttcggtggt | 360 |
| ggtaccaaag | ttgaaatcaa | atccggaggg | tcgaccataa | cttcgtataa | tgtatactat | 420 |
| acgaagttat | cctcgagcgg | tacccaggtt | accctgcgtg | aatctggtcc | agctctggtt | 480 |
| aaaccaaccc | agaccctgac | cctgacctgt | accgtttctg | gtttctctct | gtctgcttac | 540 |
| tctgttaact | ggatccgtca | gccaccaggt | aaagctctgg | aatggctggc | tatgatctgg | 600 |
| ggtgatggta | aaatcgttta | caactctgct | ctgaaatctc | gtctgaccat | ctctaaagat | 660 |
| acctctaaaa | accaggttgt | tctgaccatg | accaacatgg | atcctgtgga | cacagccaca | 720 |
| tattactgta | gagaccatgg | ccagtaaggc | cggtctctgg | aaccctggtc | accgtctcct | 780 |
| cagctagcgg | caaaccaatc | ccaaacccac | tgctgggc | | | 818 |

<210> SEQ ID NO 153

<211> LENGTH: 813
<212> TYPE: DNA
<213> ORGANISM: Artificial Sequence
<220> FEATURE:
<223> OTHER INFORMATION: Oligonucleotide

<400> SEQUENCE: 153

| | | | | | | |
|---|---|---|---|---|---|---|
| cagttagata | aaagaggcgc | ggcagcaagc | ggcgcgcatg | ccgatatcgt | tatgacccag | 60 |
| tctccactgt | ctctgccagt | taccccaggt | gaaccagctt | ctatttcttg | tcgttcttct | 120 |
| cagtctctgg | tttactctaa | cggtgatacc | tacctgcact | ggtacctgca | gaaaccaggt | 180 |
| cagtctccac | agctgctgat | ctacaaagtt | tctaaccgtt | ctctggtgt | tccagatcgt | 240 |
| ttctctggtt | ctggttctgg | taccgatttc | accctgaaaa | tctctcgtgt | tgaagctgaa | 300 |
| gatgttggtg | tttactactg | ttctcagtct | acccacgttc | catggacctt | cggtggtggt | 360 |
| accaaagttg | aaatcaaatc | cggagggtcg | accataactt | cgtataatgt | atactatacg | 420 |
| aagttatcct | cgagcggtac | cgaagttcag | ctggttgaat | ctggtggtgg | tctggttcag | 480 |
| ccaggtggtt | ctctgcgtct | gtcttgtgct | gcttctggtt | tcaccttctc | ttcttacggt | 540 |
| atgtcttggg | ttcgtcaggc | tccaggtaaa | ggtctggaac | tggttgcttc | tatcaactct | 600 |
| aacggtggtt | ctacctacta | cccagattct | gttaaaggtc | gtttcaccat | ctctcgtgat | 660 |
| aacgctaaaa | actctctgta | cctgcagatg | aactctctgc | gtgccgagga | cacggctgtg | 720 |
| tattactgtg | cttctggtga | ttactggggt | caggggacca | cggtcaccgt | ctcctcagct | 780 |
| agcggcaaac | caatcccaaa | cccactgctg | ggc | | | 813 |

<210> SEQ ID NO 154
<211> LENGTH: 809
<212> TYPE: DNA
<213> ORGANISM: Artificial Sequence
<220> FEATURE:
<223> OTHER INFORMATION: Oligonucleotide

<400> SEQUENCE: 154

| | | | | | | |
|---|---|---|---|---|---|---|
| cagttagata | aaagaggcgc | ggcagcaagc | ggcgcgcatg | ccgatatcgt | tatgacccag | 60 |
| tctccactgt | ctctgccagt | taccccaggt | gaaccagctt | ctatttcttg | tcgttcttct | 120 |
| agagaccatg | ccagtaagg | ccggtctctc | tgcactggta | cctgcagaaa | ccaggtcagt | 180 |
| ctccacagct | gctgatctac | aaagtttcta | accgtttctc | tggtgttcca | gatcgtttct | 240 |
| ctggttctgg | ttctggtacc | gatttcaccc | tgaaaatctc | tcgtgttgaa | gctgaagatg | 300 |
| ttggtgttta | ctactgttct | cagtctaccc | acgttccatg | gaccttcggt | ggtggtacca | 360 |
| aagttgaaat | caaatccgga | gggtcgacca | taacttcgta | taatgtatac | tatacgaagt | 420 |
| tatcctcgag | cggtaccgaa | gttcagctgg | ttgaatctgg | tggtggtctg | gttcagccag | 480 |
| gtggttctct | gcgtctgtct | tgtgctgctt | ctggtttcac | cttctcttct | tacggtatgt | 540 |
| cttgggttcg | tcaggctcca | ggtaaaggtc | tggaactggt | tgcttctatc | aactctaacg | 600 |
| gtggttctac | ctactaccca | gattctgtta | aaggtcgttt | caccatctct | cgtgataacg | 660 |
| ctaaaaactc | tctgtacctg | cagatgaact | ctctgcgtgc | cgaggacacg | gctgtgtatt | 720 |
| actgtgcttc | tggtgattac | tggggtcagg | gaccacggt | caccgtctcc | tcagctagcg | 780 |
| gcaaaccaat | cccaaaccca | ctgctgggc | | | | 809 |

<210> SEQ ID NO 155
<211> LENGTH: 821
<212> TYPE: DNA
<213> ORGANISM: Artificial Sequence

```
<220> FEATURE:
<223> OTHER INFORMATION: Oligonucleotide

<400> SEQUENCE: 155
cagttagata aaagaggcgc ggcagcaagc ggcgcgcatg ccgatatcgt tatgacccag      60
tctccactgt ctctgccagt tacccaggt gaaccagctt ctatttcttg tcgttcttct     120
cagtctctgg tttactctaa cggtgatacc tacctgcact ggtacctgca gaaaccaggt    180
cagtctccac agctgctgat ctacagagac atggccagt aaggccggtc tctggtgttc     240
cagatcgttt ctctggttct ggttctggta ccgatttcac cctgaaaatc tctcgtgttg    300
aagctgaaga tgttggtgtt tactactgtt ctcagtctac ccacgttcca tggaccttcg    360
gtggtggtac caaagttgaa atcaaatccg agggtcgac cataacttcg tataatgtat     420
actatacgaa gttatcctcg agcggtaccg aagttcagct ggttgaatct ggtggtggtc    480
tggttcagcc aggtggttct ctgcgtctgt cttgtgctgc ttctggtttc accttctctt    540
cttacggtat gtcttgggtt cgtcaggctc aggtaaagg tctggaactg gttgcttcta    600
tcaactctaa cggtggttct acctactacc agattctgt taaaggtcgt ttcaccatct    660
ctcgtgataa cgctaaaaac tctctgtacc tgcagatgaa ctctctgcgt gccgaggaca    720
cggctgtgta ttactgtgct tctggtgatt actggggtca ggggaccacg gtcaccgtct    780
cctcagctag cggcaaacca atcccaaacc cactgctggg c                        821

<210> SEQ ID NO 156
<211> LENGTH: 815
<212> TYPE: DNA
<213> ORGANISM: Artificial Sequence
<220> FEATURE:
<223> OTHER INFORMATION: Oligonucleotide

<400> SEQUENCE: 156
cagttagata aaagaggcgc ggcagcaagc ggcgcgcatg ccgatatcgt tatgacccag      60
tctccactgt ctctgccagt tacccaggt gaaccagctt ctatttcttg tcgttcttct     120
cagtctctgg tttactctaa cggtgatacc tacctgcact ggtacctgca gaaaccaggt    180
cagtctccac agctgctgat ctacaaagtt tctaaccgtt tctctggtgt tccagatcgt    240
ttctctggtt ctggttctgg taccgatttc accctgaaaa tctctcgtgt tgaagctgaa    300
gatgttggtg tttactactg tagagaccat ggccagtaag gccggtctct ttcggtggtg    360
gtaccaaagt tgaaatcaaa tccggagggt cgaccataac ttcgtataat gtatactata    420
cgaagttatc ctcgagcggt accgaagttc agctggttga atctggtggt ggtctggttc    480
agccaggtgg ttctctgcgt ctgtcttgtg ctgcttctgg tttcaccttc tcttcttacg    540
gtatgtcttg ggttcgtcag gctccaggta aaggtctgga actggttgct tctatcaact    600
ctaacggtgg ttctacctac tacccagatt ctgttaaagg tcgtttcacc atctctcgtg    660
ataacgctaa aaactctctg tacctgcaga tgaactctct gcgtgccgag gacacggctg    720
tgtattactg tgcttctggt gattactggg gtcagggac cacggtcacc gtctcctcag    780
ctagcggcaa accaatccca aacccactgc tgggc                               815

<210> SEQ ID NO 157
<211> LENGTH: 818
<212> TYPE: DNA
<213> ORGANISM: Artificial Sequence
<220> FEATURE:
<223> OTHER INFORMATION: Oligonucleotide
```

<400> SEQUENCE: 157

```
cagttagata aaagaggcgc ggcagcaagc ggcgcgcatg ccgatatcgt tatgacccag      60
tctccactgt ctctgccagt taccccaggt gaaccagctt ctatttcttg tcgttcttct     120
cagtctctgg tttactctaa cggtgatacc tacctgcact ggtacctgca gaaaccaggt     180
cagtctccac agctgctgat ctacaaagtt tctaaccgtt ctctggtgt tccagatcgt      240
ttctctggtt ctggttctgg taccgatttc accctgaaaa tctctcgtgt tgaagctgaa     300
gatgttggtg tttactactg ttctcagtct acccacgttc catggacctt cggtggtggt     360
accaaagttg aaatcaaatc cggagggtcg accataactt cgtataatgt atactatacg     420
aagttatcct cgagcggtac cgaagttcag ctggttgaat ctggtggtgg tctggttcag     480
ccaggtggtt ctctgcgtct gtcttgtgct gcttctagag accatggcca gtaaggccgg     540
tctctatgtc ttgggttcgt caggctccag gtaaaggtct ggaactggtt gcttctatca     600
actctaacgg tggttctacc tactacccag attctgttaa aggtcgtttc accatctctc     660
gtgataacgc taaaaactct ctgtacctgc agatgaactc tctgcgtgcc gaggacacgg     720
ctgtgtatta ctgtgcttct ggtgattact ggggtcaggg gaccacggtc accgtctcct     780
cagctagcgg caaaccaatc ccaaacccac tgctgggc                             818
```

<210> SEQ ID NO 158
<211> LENGTH: 818
<212> TYPE: DNA
<213> ORGANISM: Artificial Sequence
<220> FEATURE:
<223> OTHER INFORMATION: Oligonucleotide

<400> SEQUENCE: 158

```
cagttagata aaagaggcgc ggcagcaagc ggcgcgcatg ccgatatcgt tatgacccag      60
tctccactgt ctctgccagt taccccaggt gaaccagctt ctatttcttg tcgttcttct     120
cagtctctgg tttactctaa cggtgatacc tacctgcact ggtacctgca gaaaccaggt     180
cagtctccac agctgctgat ctacaaagtt tctaaccgtt ctctggtgt tccagatcgt      240
ttctctggtt ctggttctgg taccgatttc accctgaaaa tctctcgtgt tgaagctgaa     300
gatgttggtg tttactactg ttctcagtct acccacgttc catggacctt cggtggtggt     360
accaaagttg aaatcaaatc cggagggtcg accataactt cgtataatgt atactatacg     420
aagttatcct cgagcggtac cgaagttcag ctggttgaat ctggtggtgg tctggttcag     480
ccaggtggtt ctctgcgtct gtcttgtgct gcttctggtt tcaccttctc ttcttacggt     540
atgtcttggg ttcgtcaggc tccaggtaaa ggtctggaac tggttgcttc tagagaccat     600
ggccagtaag gccggtctct tactacccag attctgttaa aggtcgtttc accatctctc     660
gtgataacgc taaaaactct ctgtacctgc agatgaactc tctgcgtgcc gaggacacgg     720
ctgtgtatta ctgtgcttct ggtgattact ggggtcaggg gaccacggtc accgtctcct     780
cagctagcgg caaaccaatc ccaaacccac tgctgggc                             818
```

<210> SEQ ID NO 159
<211> LENGTH: 818
<212> TYPE: DNA
<213> ORGANISM: Artificial Sequence
<220> FEATURE:
<223> OTHER INFORMATION: Oligonucleotide

<400> SEQUENCE: 159

```
cagttagata aaagaggcgc ggcagcaagc ggcgcgcatg ccgatatcgt tatgacccag      60
```

```
tctccactgt ctctgccagt taccccaggt gaaccagctt ctatttcttg tcgttcttct    120
cagtctctgg tttactctaa cggtgatacc tacctgcact ggtacctgca gaaaccaggt    180
cagtctccac agctgctgat ctacaaagtt tctaaccgtt tctctggtgt tccagatcgt    240
ttctctggtt ctggttctgg taccgatttc accctgaaaa tctctcgtgt tgaagctgaa    300
gatgttggtg tttactactg ttctcagtct acccacgttc catggacctt cggtggtggt    360
accaaagttg aaatcaaatc cggagggtcg accataactt cgtataatgt atactatacg    420
aagttatcct cgagcggtac cgaagttcag ctggttgaat ctggtggtgg tctggttcag    480
ccaggtggtt ctctgcgtct gtcttgtgct gcttctggtt tcaccttctc ttcttacggt    540
atgtcttggg ttcgtcaggc tccaggtaaa ggtctggaac tggttgcttc tatcaactct    600
aacggtggtt ctacctacta cccagattct gttaaaggtc gtttcaccat ctctcgtgat    660
aacgctaaaa actctctgta cctgcagatg aactctctgc gtgccgagga cacggctgtg    720
tattactgta gagaccatgg ccagtaaggc cggtctctgg gaccacggtc accgtctcct    780
cagctagcgg caaaccaatc ccaaacccac tgctgggc                            818
```

`<210> SEQ ID NO 160`
`<211> LENGTH: 825`
`<212> TYPE: DNA`
`<213> ORGANISM: Artificial Sequence`
`<220> FEATURE:`
`<223> OTHER INFORMATION: Oligonucleotide`

`<400> SEQUENCE: 160`

```
cagttagata aagaggcgc ggcagcaagc ggcgcgcatg ccgaaatcgt tatgacccag     60
tctccagcta ccctgtctct gtctccaggt gaacgtgcca ctctgtcttg tcgtgcttct    120
cagtctgttt cttcttacct ggcttggtac cagcagaaac aggtcaggc tccacgtctg     180 ctgatctacg atgcttctaa ccgtgctacc ggtatcccag ctcgtttctc tggttctggt    240
tctggtaccg atttcaccct gaccatctct tctctggaac agaagatttt cgctgtttac    300
tactgtcacc agtacggttc tacccccactg accttcggtg gtggtaccaa agttgaaatc    360
aaatccggag gtcgaccat aacttcgtat aatgtatact atacgaagtt atcctcgagc     420
ggtacccagg ttcagctgca ggaatctggt ccaggtctgg ttaaaccatc tcagaccctg    480
tctctgacct gtaccgtttc tggtggttct atctcttctg gtgattacta ctggtcttgg    540
atccgtcagc caccaggtaa aggtctggaa tggatcggtt acatctacta ctctggttct    600
accgattaca acccatctct gaaatctcgt gttaccatgt ctgttgatac ctctaaaaac    660
cagttctctc tgaaagttaa ctctgttacc gccgcggaca cggctgtgta ttactgtgct    720
cgtgtttcta tcttcggtgt tggtaccttc gattactggg gtcagggaac cctggtcacc    780
gtctcctcag ctagcggcaa accaatccca aacccactgc tgggc                    825
```

`<210> SEQ ID NO 161`
`<211> LENGTH: 836`
`<212> TYPE: DNA`
`<213> ORGANISM: Artificial Sequence`
`<220> FEATURE:`
`<223> OTHER INFORMATION: Oligonucleotide`

`<400> SEQUENCE: 161`

```
cagttagata aagaggcgc ggcagcaagc ggcgcgcatg ccgaaatcgt tatgacccag     60
tctccagcta ccctgtctct gtctccaggt gaacgtgcca ctctgtcttg tcgtgcttct    120
```

| | |
|---|---:|
| agagaccatg gccagtaagg ccggtctctc tggcttggta ccagcagaaa ccaggtcagg | 180 |
| ctccacgtct gctgatctac gatgcttcta accgtgctac cggtatccca gctcgtttct | 240 |
| ctggttctgg ttctggtacc gatttcaccc tgaccatctc ttctctggaa ccagaagatt | 300 |
| tcgctgttta ctactgtcac cagtacggtt ctaccccact gaccttcggt ggtggtacca | 360 |
| aagttgaaat caaatccgga gggtcgacca taacttcgta taatgtatac tatacgaagt | 420 |
| tatcctcgag cggtacccag gttcagctgc aggaatctgg tccaggtctg gttaaaccat | 480 |
| ctcagaccct gtctctgacc tgtaccgttt ctggtggttc tatctcttct ggtgattact | 540 |
| actggtcttg gatccgtcag ccaccaggta aaggtctgga atggatcggt tacatctact | 600 |
| actctggttc taccgattac aacccatctc tgaaatctcg tgttaccatg tctgttgata | 660 |
| cctctaaaaa ccagttctct ctgaaagtta actctgttac cgccgcggac acggctgtgt | 720 |
| attactgtgc tcgtgtttct atcttcggtg ttggtacctt cgattactgg ggtcagggaa | 780 |
| ccctggtcac cgtctcctca gctagcggca accaatccc aaacccactg ctgggc | 836 |

<210> SEQ ID NO 162
<211> LENGTH: 833
<212> TYPE: DNA
<213> ORGANISM: Artificial Sequence
<220> FEATURE:
<223> OTHER INFORMATION: Oligonucleotide

<400> SEQUENCE: 162

| | |
|---|---:|
| cagttagata aagaggcgc ggcagcaagc ggcgcgcatg ccgaaatcgt tatgacccag | 60 |
| tctccagcta ccctgtctct gtctccaggt gaacgtgcca ctctgtcttg tcgtgcttct | 120 |
| cagtctgttt cttcttacct ggcttggtac cagcagaaac caggtcaggc tccacgtctg | 180 |
| ctgatctaca gagaccatgg ccagtaaggc cggtctctgg tatcccagct cgtttctctg | 240 |
| gttctggttc tggtaccgat ttcaccctga ccatctcttc tctggaacca gaagatttcg | 300 |
| ctgtttacta ctgtcaccag tacggttcta ccccactgac cttcggtggt ggtaccaaag | 360 |
| ttgaaatcaa atccggaggg tcgaccataa cttcgtataa tgtatactat acgaagttat | 420 |
| cctcgagcgg tacccaggtt cagctgcagg aatctggtcc aggtctggtt aaaccatctc | 480 |
| agaccctgtc tctgacctgt accgtttctg gtggtctat ctcttctggt gattactact | 540 |
| ggtcttggat ccgtcagcca ccaggtaaag gtctggaatg gatcggttac atctactact | 600 |
| ctggttctac cgattacaac ccatctctga atctcgtgt taccatgtct gttgatacct | 660 |
| ctaaaaacca gttctctctg aaagttaact ctgttaccgc cgcggacacg gctgtgtatt | 720 |
| actgtgctcg tgtttctatc ttcggtgttg gtaccttcga ttactggggt cagggaaccc | 780 |
| tggtcaccgt ctcctcagct agcggcaaac caatcccaaa cccactgctg ggc | 833 |

<210> SEQ ID NO 163
<211> LENGTH: 827
<212> TYPE: DNA
<213> ORGANISM: Artificial Sequence
<220> FEATURE:
<223> OTHER INFORMATION: Oligonucleotide

<400> SEQUENCE: 163

| | |
|---|---:|
| cagttagata aagaggcgc ggcagcaagc ggcgcgcatg ccgaaatcgt tatgacccag | 60 |
| tctccagcta ccctgtctct gtctccaggt gaacgtgcca ctctgtcttg tcgtgcttct | 120 |
| cagtctgttt cttcttacct ggcttggtac cagcagaaac caggtcaggc tccacgtctg | 180 |
| ctgatctacg atgcttctaa ccgtgctacc ggtatcccag ctcgtttctc tggttctggt | 240 |

```
tctggtaccg atttcaccct gaccatctct tctctggaac cagaagattt cgctgtttac        300
tactgtagag accatggcca gtaaggccgg tctctttcgg tggtggtacc aaagttgaaa        360
tcaaatccgg agggtcgacc ataacttcgt ataatgtata ctatacgaag ttatcctcga        420
gcggtaccca ggttcagctg caggaatctg gtccaggtct ggttaaacca tctcagaccc        480
tgtctctgac ctgtaccgtt tctggtggtt ctatctcttc tggtgattac tactggtctt        540
ggatccgtca gccaccaggt aaaggtctgg aatggatcgg ttacatctac tactctggtt        600
ctaccgatta caacccatct ctgaaatctc gtgttaccat gtctgttgat acctctaaaa        660
accagttctc tctgaaagtt aactctgtta ccgccgcgga cacggctgtg tattactgtg        720
ctcgtgtttc tatcttcggt gttggtacct cgattactg gggtcaggga accctggtca         780
ccgtctcctc agctagcggc aaaccaatcc caaacccact gctgggc                      827

<210> SEQ ID NO 164
<211> LENGTH: 824
<212> TYPE: DNA
<213> ORGANISM: Artificial Sequence
<220> FEATURE:
<223> OTHER INFORMATION: Oligonucleotide

<400> SEQUENCE: 164
cagttagata aaagaggcgc ggcagcaagc ggcgcgcatg ccgaaatcgt tatgacccag         60
tctccagcta ccctgtctct gtctccaggt gaacgtgcca ctctgtcttg tcgtgcttct       120
cagtctgttt cttcttacct ggcttggtac cagcagaaac caggtcaggc tccacgtctg       180
ctgatctacg atgcttctaa ccgtgctacc ggtatcccag ctcgtttctc tggttctggt       240
tctggtaccg atttcaccct gaccatctct tctctggaac cagaagattt cgctgtttac       300
tactgtcacc agtacggttc taccccactg accttcggtg tggtaccaa agttgaaatc        360 aaatccggag ggtcgaccat aacttcgtat aatgtatact atacgaagtt atcctcgagc       420
ggtacccagg ttcagctgca ggaatctggt ccaggtctgg ttaaaccatc tcagaccctg       480
tctctgacct gtaccgtttc tagagaccat ggccagtaag gccggtctct ggtcttgga       540 tccgtcagcc accaggtaaa ggtctggaat ggatcggtta catctactac tctggttcta       600
ccgattacaa cccatctctg aaatctcgtg ttaccatgtc tgttgatacc tctaaaaacc       660
agttctctct gaaagttaac tctgttaccg ccgcggacac ggctgtgtat tactgtgctc       720
gtgtttctat cttcggtgtt ggtaccttcg attactgggg tcagggaacc ctggtcaccg       780
tctcctcagc tagcggcaaa ccaatcccaa acccactgct gggc                         824

<210> SEQ ID NO 165
<211> LENGTH: 833
<212> TYPE: DNA
<213> ORGANISM: Artificial Sequence
<220> FEATURE:
<223> OTHER INFORMATION: Oligonucleotide

<400> SEQUENCE: 165
cagttagata aaagaggcgc ggcagcaagc ggcgcgcatg ccgaaatcgt tatgacccag         60
tctccagcta ccctgtctct gtctccaggt gaacgtgcca ctctgtcttg tcgtgcttct       120
cagtctgttt cttcttacct ggcttggtac cagcagaaac caggtcaggc tccacgtctg       180
ctgatctacg atgcttctaa ccgtgctacc ggtatcccag ctcgtttctc tggttctggt       240
tctggtaccg atttcaccct gaccatctct tctctggaac cagaagattt cgctgtttac       300
```

| | |
|---|---|
| tactgtcacc agtacggttc taccccactg accttcggtg gtggtaccaa agttgaaatc | 360 |
| aaatccggag gtcgaccat aacttcgtat aatgtatact atacgaagtt atcctcgagc | 420 |
| ggtacccagg ttcagctgca ggaatctggt ccaggtctgg ttaaaccatc tcagaccctg | 480 |
| tctctgacct gtaccgtttc tggtggttct atctcttctg gtgattacta ctggtcttgg | 540 |
| atccgtcagc caccaggtaa aggtctggaa tggatcggtt acagagacca tggccagtaa | 600 |
| ggccggtctc tgattacaac ccatctctga atctcgtgt taccatgtct gttgatacct | 660 |
| ctaaaaacca gttctctctg aaagttaact ctgttaccgc cgcggacacg gctgtgtatt | 720 |
| actgtgctcg tgtttctatc ttcggtgttg gtaccttcga ttactggggt cagggaaccc | 780 |
| tggtcaccgt ctcctcagct agcggcaaac caatcccaaa cccactgctg ggc | 833 |

<210> SEQ ID NO 166
<211> LENGTH: 806
<212> TYPE: DNA
<213> ORGANISM: Artificial Sequence
<220> FEATURE:
<223> OTHER INFORMATION: Oligonucleotide

<400> SEQUENCE: 166

| | |
|---|---|
| cagttagata aagaggcgc ggcagcaagc ggcgcgcatg ccgaaatcgt tatgacccag | 60 |
| tctccagcta ccctgtctct gtctccaggt gaacgtgcca ctctgtcttg tcgtgcttct | 120 |
| cagtctgttt cttcttacct ggcttggtac cagcagaaac aggtcaggc tccacgtctg | 180 |
| ctgatctacg atgcttctaa ccgtgctacc ggtatcccag ctcgtttctc tggttctggt | 240 |
| tctggtaccg atttcaccct gaccatctct tctctggaac cagaagattt cgctgtttac | 300 |
| tactgtcacc agtacggttc taccccactg accttcggtg gtggtaccaa agttgaaatc | 360 |
| aaatccggag gtcgaccat aacttcgtat aatgtatact atacgaagtt atcctcgagc | 420 |
| ggtacccagg ttcagctgca ggaatctggt ccaggtctgg ttaaaccatc tcagaccctg | 480 |
| tctctgacct gtaccgtttc tggtggttct atctcttctg gtgattacta ctggtcttgg | 540 |
| atccgtcagc caccaggtaa aggtctggaa tggatcggtt acatctacta ctctggttct | 600 |
| accgattaca acccatctct gaaatctcgt gttaccatgt ctgttgatac ctctaaaaac | 660 |
| cagttctctc tgaaagttaa ctctgttacc gccgcggaca cggctgtgta ttactgtaga | 720 |
| gaccatggcc agtaaggccg gtctctggaa ccctggtcac cgtctcctca gctagcggca | 780 |
| aaccaatccc aaacccactg ctgggc | 806 |

<210> SEQ ID NO 167
<211> LENGTH: 816
<212> TYPE: DNA
<213> ORGANISM: Artificial Sequence
<220> FEATURE:
<223> OTHER INFORMATION: Oligonucleotide

<400> SEQUENCE: 167

| | |
|---|---|
| cagttagata aagaggcgc ggcagcaagc ggcgcgcatg ccgaaatcgt tctgacccag | 60 |
| tctccaggta ccctgtctct gtctccaggt gaacgtgcca ctctgtcttg tcgtgcttct | 120 |
| cagtctgttt cttcttcttt cctggcttgg taccagcaga aaccaggtca ggctccacgt | 180 |
| ctgctgatct acggtgcttc ttctcgtgct accggtatcc cagatcgtct gtctggttct | 240 |
| ggttctggta ccgatttcac cctgaccatc accgtctgg aaccagaaga tttcgctgtt | 300 |
| tactactgtc agcagtacga ttcttctgct atccccttcg gtggtggtac caaagttgaa | 360 |
| atcaaatccg gagggtcgac cataacttcg tataatgtat actatacgaa gttatcctcg | 420 |

```
agcggtaccg aagttcagct ggttcagtct ggtgctgaag ttaaaaaacc aggtgaatct    480
ctgaaaatct cttgtaaagg ttctggttac atcttcacca actactggat cgcttgggtt    540
cgtcaggttc caggtaaagg tctggaatct atgggtatca tctacccagg tgattctgat    600
atccgttact ctccatcttt ccagggtcag gttaccatct ctgctgataa atctatcacc    660
accgcttacc tgcagtggtc ttctctgaaa gcctcggaca ccgccattta ttactgtgct    720
cgtcacgata tcgaaggttt cgattactgg ggtcgtggaa ccctggtcac cgtctcctca    780
gctagcggca aaccaatccc aaacccactg ctgggc    816
```

<210> SEQ ID NO 168
<211> LENGTH: 824
<212> TYPE: DNA
<213> ORGANISM: Artificial Sequence
<220> FEATURE:
<223> OTHER INFORMATION: Oligonucleotide

<400> SEQUENCE: 168

```
cagttagata aagaggcgc ggcagcaagc ggcgcgcatg ccgaaatcgt tctgacccag     60
tctccaggta ccctgtctct gtctccaggt gaacgtgcca ctctgtcttg tcgtgcttct    120
agagaccatg gccagtaagg ccggtctctc tggcttggta ccagcagaaa ccaggtcagg    180
ctccacgtct gctgatctac ggtgcttctt ctcgtgctac cggtatccca gatcgtctgt    240
ctggttctgg ttctggtacc gatttcaccc tgaccatcac ccgtctggaa ccagaagatt    300
tcgctgttta ctactgtcag cagtacgatt cttctgctat caccttcggt ggtggtacca    360 agttgaaat caaatccgga gggtcgacca taacttcgta taatgtatac tatacgaagt    420
tatcctcgag cggtaccgaa gttcagctgg ttcagtctgg tgctgaagtt aaaaaaccag    480
gtgaatctct gaaaatctct tgtaaaggtt ctggttacat cttcaccaac tactggatcg    540
cttgggttcg tcaggttcca ggtaaaggtc tggaatctat gggtatcatc tacccaggtg    600
attctgatat ccgttactct ccatctttcc agggtcaggt taccatctct gctgataaat    660
ctatcaccac cgcttacctg cagtggtctt ctctgaaagc ctcggacacc gccatttatt    720
actgtgctcg tcacgatatc gaaggtttcg attactgggg tcgtggaacc ctggtcaccg    780
tctcctcagc tagcggcaaa ccaatcccaa acccactgct gggc    824
```

<210> SEQ ID NO 169
<211> LENGTH: 824
<212> TYPE: DNA
<213> ORGANISM: Artificial Sequence
<220> FEATURE:
<223> OTHER INFORMATION: Oligonucleotide

<400> SEQUENCE: 169

```
cagttagata aagaggcgc ggcagcaagc ggcgcgcatg ccgaaatcgt tctgacccag     60
tctccaggta ccctgtctct gtctccaggt gaacgtgcca ctctgtcttg tcgtgcttct    120
cagtctgttt cttcttcttt cctggcttgg taccagcaga accaggtca ggctccacgt    180 ctgctgatct acagagacca tggccagtaa ggccggtctc tggtatccca gatcgtctgt    240
ctggttctgg ttctggtacc gatttcaccc tgaccatcac ccgtctggaa ccagaagatt    300
tcgctgttta ctactgtcag cagtacgatt cttctgctat caccttcggt ggtggtacca    360 agttgaaat caaatccgga gggtcgacca taacttcgta taatgtatac tatacgaagt    420
tatcctcgag cggtaccgaa gttcagctgg ttcagtctgg tgctgaagtt aaaaaaccag    480
```

```
gtgaatctct gaaaatctct tgtaaaggtt ctggttacat cttcaccaac tactggatcg      540
cttgggttcg tcaggttcca ggtaaaggtc tggaatctat gggtatcatc tacccaggtg      600
attctgatat ccgttactct ccatctttcc agggtcaggt taccatctct gctgataaat      660
ctatcaccac cgcttacctg cagtggtctt ctctgaaagc ctcggacacc gccatttatt      720
actgtgctcg tcacgatatc gaaggtttcg attactgggg tcgtggaacc ctggtcaccg      780
tctcctcagc tagcggcaaa ccaatcccaa acccactgct gggc                       824
```

```
<210> SEQ ID NO 170
<211> LENGTH: 818
<212> TYPE: DNA
<213> ORGANISM: Artificial Sequence
<220> FEATURE:
<223> OTHER INFORMATION: Oligonucleotide

<400> SEQUENCE: 170
cagttagata aaagaggcgc ggcagcaagc ggcgcgcatg ccgaaatcgt tctgacccag       60
tctccaggta ccctgtctct gtctccaggt gaacgtgcca ctctgtcttg tcgtgcttct      120
cagtctgttt cttcttcttt cctggcttgg taccagcaga aaccaggtca ggctccacgt      180
ctgctgatct acggtgcttc ttctcgtgct accggtatcc cagatcgtct gtctggttct      240
ggttctggta ccgatttcac cctgaccatc acccgtctgg aaccagaaga tttcgctgtt      300
tactactgta gagaccatgg ccagtaaggc cggtctcttt cggtggtggt accaaagttg      360
aaatcaaatc cggagggtcg accataactt cgtataatgt atactatacg aagttatcct      420
cgagcggtac cgaagttcag ctggttcagt ctggtgctga agttaaaaaa ccaggtgaat      480
ctctgaaaat ctcttgtaaa ggttctggtt acatcttcac caactactgg atcgcttggg      540
ttcgtcaggt tccaggtaaa ggtctggaat ctatgggtat catctaccca ggtgattctg      600
atatccgtta ctctccatct ttccagggtc aggttaccat ctctgctgat aaatctatca      660
ccaccgctta cctgcagtgg tcttctctga agcctcgga caccgccatt tattactgtg      720
ctcgtcacga tatcgaaggt ttcgattact ggggtcgtgg aaccctggtc accgtctcct      780
cagctagcgg caaaccaatc ccaaacccac tgctgggc                              818
```

```
<210> SEQ ID NO 171
<211> LENGTH: 821
<212> TYPE: DNA
<213> ORGANISM: Artificial Sequence
<220> FEATURE:
<223> OTHER INFORMATION: Oligonucleotide

<400> SEQUENCE: 171
cagttagata aaagaggcgc ggcagcaagc ggcgcgcatg ccgaaatcgt tctgacccag       60
tctccaggta ccctgtctct gtctccaggt gaacgtgcca ctctgtcttg tcgtgcttct      120
cagtctgttt cttcttcttt cctggcttgg taccagcaga aaccaggtca ggctccacgt      180
ctgctgatct acggtgcttc ttctcgtgct accggtatcc cagatcgtct gtctggttct      240
ggttctggta ccgatttcac cctgaccatc acccgtctgg aaccagaaga tttcgctgtt      300
tactactgtc agcagtacga ttcttctgct atcaccttcg gtggtggtac caaagttgaa      360
atcaaatccg gagggtcgac cataacttcg tataatgtat actatacgaa gttatcctcg      420
agcggtaccg aagttcagct ggttcagtct ggtgctgaag ttaaaaaacc aggtgaatct      480
ctgaaaatct cttgtaaagg ttctagagac catggccagt aaggccggtc tctatcgctt      540
gggttcgtca ggttccaggt aaaggtctgg aatctatggg tatcatctac caggtgatt      600
```

```
ctgatatccg ttactctcca tctttccagg gtcaggttac catctctgct gataaatcta    660
tcaccaccgc ttacctgcag tggtcttctc tgaaagcctc ggacaccgcc atttattact    720
gtgctcgtca cgatatcgaa ggtttcgatt actggggtcg tggaaccctg gtcaccgtct    780
cctcagctag cggcaaacca atcccaaacc cactgctggg c                        821
```

<210> SEQ ID NO 172
<211> LENGTH: 820
<212> TYPE: DNA
<213> ORGANISM: Artificial Sequence
<220> FEATURE:
<223> OTHER INFORMATION: Oligonucleotide

<400> SEQUENCE: 172

```
cagttagata aaagaggcgc ggcagcaagc ggcgcgcatg ccgaaatcgt tctgacccag     60
tctccaggta ccctgtctct gtctccaggt gaacgtgcca ctctgtcttg tcgtgcttct    120
cagtctgttt cttcttcttt cctggcttgg taccagcaga aaccaggtca ggctccacgt    180
ctgctgatct acggtgcttc ttctcgtgct accggtatcc agatcgtct gtctggttct    240 ggttctggta ccgatttcac cctgaccatc acccgtctgg aaccagaaga tttcgctgtt    300
tactactgtc agcagtacga ttcttctgct atcaccttcg gtggtggtac caaagttgaa    360
atcaaatccg agggtcgac cataacttcg tataatgtat actatacgaa gttatcctcg    420
agcggtaccg aagttcagct ggttcagtct ggtgctgaag ttaaaaaacc aggtgaatct    480
ctgaaaatct cttgtaaagg ttctggttac atcttcacca actactggat cgcttgggtt    540
cgtcaggttc aggtaaaagg tctggaatct atgggtatca gagaccatgg ccagtaaggc    600
cggtctctcg ttactctcca tctttccagg gtcaggttac catctctgct gataaatcta    660
tcaccaccgc ttacctgcag tggtcttctc tgaaagcctc gacaccgcca tttattactg    720
tgctcgtcac gatatcgaag gtttcgatta ctggggtcgt ggaaccctgg tcaccgtctc    780
ctcagctagc ggcaaaccaa tcccaaaccc actgctgggc                          820
```

<210> SEQ ID NO 173
<211> LENGTH: 806
<212> TYPE: DNA
<213> ORGANISM: Artificial Sequence
<220> FEATURE:
<223> OTHER INFORMATION: Oligonucleotide

<400> SEQUENCE: 173

```
cagttagata aaagaggcgc ggcagcaagc ggcgcgcatg ccgaaatcgt tctgacccag     60
tctccaggta ccctgtctct gtctccaggt gaacgtgcca ctctgtcttg tcgtgcttct    120
cagtctgttt cttcttcttt cctggcttgg taccagcaga aaccaggtca ggctccacgt    180
ctgctgatct acggtgcttc ttctcgtgct accggtatcc agatcgtct gtctggttct    240 ggttctggta ccgatttcac cctgaccatc acccgtctgg aaccagaaga tttcgctgtt    300
tactactgtc agcagtacga ttcttctgct atcaccttcg gtggtggtac caaagttgaa    360
atcaaatccg agggtcgac cataacttcg tataatgtat actatacgaa gttatcctcg    420
agcggtaccg aagttcagct ggttcagtct ggtgctgaag ttaaaaaacc aggtgaatct    480
ctgaaaatct cttgtaaagg ttctggttac atcttcacca actactggat cgcttgggtt    540
cgtcaggttc aggtaaaagg tctggaatct atgggtatca tctacccagg tgattctgat    600
atccgttact ctccatcttt ccagggtcag gttaccatct ctgctgataa atctatcacc    660
```

| | |
|---|---|
| accgcttacc tgcagtggtc ttctctgaaa gcctcggaca ccgccattta ttactgtaga | 720 |
| gaccatggcc agtaaggccg gtctctggaa ccctggtcac cgtctcctca gctagcggca | 780 |
| aaccaatccc aaacccactg ctgggc | 806 |

<210> SEQ ID NO 174
<211> LENGTH: 813
<212> TYPE: DNA
<213> ORGANISM: Artificial Sequence
<220> FEATURE:
<223> OTHER INFORMATION: Oligonucleotide

<400> SEQUENCE: 174

| | |
|---|---|
| cagttagata aagaggcgc ggcagcaagc ggcgcgcatg ccgaatctgc tctgacccag | 60 |
| ccagcttctg tttctggttc tccaggtcag tctatcacca tctcttgtac cggtacctct | 120 |
| tctgatgttg gtggttacaa ctctgtttct tggtaccagc agcacccagg taaagctcca | 180 |
| aaactgatga tctacgaagt ttctaaccgt ccatctggtg tttctaaccg tttctctggt | 240 |
| tctaaatctg gtaacaccgc ttctctgacc atctctggtc tgcaggctga agatgaagct | 300 |
| gattactact gtaactctta cacctctacc tctatggttt tcggtggtgg taccaaactg | 360 |
| accgttctgt ccggagggtc gaccataact tcgtataatg tatactatac gaagttatcc | 420 |
| tcgagcggta ccgaagttca gctggttcag tctggtgctg aagttaaaaa accaggtgct | 480 |
| tctgttaaag tttcttgtaa agcttctggt tacacccctga cctcttacgg tatctcttgg | 540 |
| gttcgtcagg ctccaggtca gggtctggaa tggatgggtt gggtttcttt ctacaacggt | 600 |
| aacaccaact acgctcagaa actgcagggt cgtggtacca tgaccaccga tccatctacc | 660 |
| tctaccgctt acatggaact gcgttctctg cgttctgacg acacggccgt gtattactgt | 720 |
| gctcgtggtt acggtatgga tgtttgggt caggggacca cggtcaccgt ctcctcagct | 780 |
| agcggcaaac caatcccaaa cccactgctg ggc | 813 |

<210> SEQ ID NO 175
<211> LENGTH: 815
<212> TYPE: DNA
<213> ORGANISM: Artificial Sequence
<220> FEATURE:
<223> OTHER INFORMATION: Oligonucleotide

<400> SEQUENCE: 175

| | |
|---|---|
| cagttagata aagaggcgc ggcagcaagc ggcgcgcatg ccgaatctgc tctgacccag | 60 |
| ccagcttctg tttctggttc tccaggtcag tctatcacca tctcttgtac cggtaccaga | 120 |
| gaccatggcc agtaaggccg gtctctgttt cttggtacca gcagcaccca ggtaaagctc | 180 |
| caaaactgat gatctacgaa gtttctaacc gtccatctgg tgtttctaac cgtttctctg | 240 |
| gttctaaatc tggtaacacc gcttctctga ccatctctgg tctgcaggct gaagatgaag | 300 |
| ctgattacta ctgtaactct tacacctcta cctctatggt tttcggtggt ggtaccaaac | 360 |
| tgaccgttct gtccggaggg tcgaccataa cttcgtataa tgtatactat acgaagttat | 420 |
| cctcgagcgg taccgaagtt cagctggttc agtctggtgc tgaagttaaa aaaccaggtg | 480 |
| cttctgttaa agtttcttgt aaagcttctg gttacacccct gacctcttac ggtatctctt | 540 |
| gggttcgtca ggctccaggt cagggtctgg aatggatggg ttgggtttct ttctacaacg | 600 |
| gtaacaccaa ctacgctcag aaactgcagg gtcgtggtac catgaccacc gatccatcta | 660 |
| cctctaccgc ttacatggaa ctgcgttctc tgcgttctga cgacacggcc gtgtattact | 720 |
| gtgctcgtgg ttacggtatg gatgtttggg gtcaggggac cacggtcacc gtctcctcag | 780 |

<210> SEQ ID NO 176
<211> LENGTH: 821
<212> TYPE: DNA
<213> ORGANISM: Artificial Sequence
<220> FEATURE:
<223> OTHER INFORMATION: Oligonucleotide

<400> SEQUENCE: 176

```
cagttagata aaagaggcgc ggcagcaagc ggcgcgcatg ccgaatctgc tctgacccag      60
ccagcttctg tttctggttc tccaggtcag tctatcacca tctcttgtac cggtacctct     120
tctgatgttg gtggttacaa ctctgtttct tggtaccagc agcacccagg taaagctcca     180
aaactgatga tctacagaga ccatggccag taaggccggt ctctggtgtt tctaaccgtt     240
tctctggttc taaatctggt aacaccgctt ctctgaccat ctctggtctg caggctgaag     300
atgaagctga ttactactgt aactcttaca cctctacctc tatggttttc ggtggtggta     360
ccaaactgac cgttctgtcc ggagggtcga ccataacttc gtataatgta tactatacga     420
agttatcctc gagcggtacc gaagttcagc tggttcagtc tggtgctgaa gttaaaaaac     480
caggtgcttc tgttaaagtt tcttgtaaag cttctggtta caccctgacc tcttacggta     540
tctcttgggt tcgtcaggct ccaggtcagg gtctggaatg gatgggttgg gtttctttct     600
acaacggtaa caccaactac gctcagaaac tgcagggtcg tggtaccatg accaccgatc     660
catctacctc taccgcttac atggaactgc gttctctgcg ttctgacgac acggccgtgt     720
attactgtgc tcgtggttac ggtatggatg tttggggtca ggggaccacg gtcaccgtct     780
cctcagctag cggcaaacca atcccaaacc cactgctggg c                        821
```

<210> SEQ ID NO 177
<211> LENGTH: 815
<212> TYPE: DNA
<213> ORGANISM: Artificial Sequence
<220> FEATURE:
<223> OTHER INFORMATION: Oligonucleotide

<400> SEQUENCE: 177

```
cagttagata aaagaggcgc ggcagcaagc ggcgcgcatg ccgaatctgc tctgacccag      60
ccagcttctg tttctggttc tccaggtcag tctatcacca tctcttgtac cggtacctct     120
tctgatgttg gtggttacaa ctctgtttct tggtaccagc agcacccagg taaagctcca     180
aaactgatga tctacgaagt ttctaaccgt ccatctggtg tttctaaccg tttctctggt     240
tctaaatctg gtaacaccgc ttctctgacc atctctggtc tgcaggctga agatgaagct     300
gattactact gtagagacca tggccagtaa ggccggtctc tttcggtggt ggtaccaaac     360
tgaccgttct gtccggaggg tcgaccataa cttcgtataa tgtatactat acgaagttat     420
cctcgagcgg taccgaagtt cagctggttc agtctggtgc tgaagttaaa aaaccaggtg     480
cttctgttaa agtttcttgt aaagcttctg gttacaccct gacctcttac ggtatctctt     540
gggttcgtca ggctccaggt cagggtctgg aatggatggg ttgggtttct ttctacaacg     600
gtaacaccaa ctacgctcag aaactgcagg gtcgtggtac catgaccacc gatccatcta     660
cctctaccgc ttacatggaa ctgcgttctc tgcgttctga cgacacggcc gtgtattact     720
gtgctcgtgg ttacggtatg gatgtttggg gtcaggggac cacggtcacc gtctcctcag     780
ctagcggcaa accaatccca aacccactgc tgggc                                815
```

<210> SEQ ID NO 178
<211> LENGTH: 818
<212> TYPE: DNA
<213> ORGANISM: Artificial Sequence
<220> FEATURE:
<223> OTHER INFORMATION: Oligonucleotide

<400> SEQUENCE: 178

```
cagttagata aaagaggcgc ggcagcaagc ggcgcgcatg ccgaatctgc tctgacccag      60
ccagcttctg tttctggttc tccaggtcag tctatcacca tctcttgtac cggtacctct     120
tctgatgttg gtggttacaa ctctgtttct tggtaccagc agcacccagg taaagctcca     180
aaactgatga tctacgaagt ttctaaccgt ccatctggtg tttctaaccg tttctctggt     240
tctaaatctg gtaacaccgc ttctctgacc atctctggtc tgcaggctga agatgaagct     300
gattactact gtaactctta cacctctacc tctatggttt tcggtggtgg taccaaactg     360
accgttctgt ccggagggtc gaccataact tcgtataatg tatactatac gaagttatcc     420
tcgagcggta ccgaagttca gctggttcag tctggtgctg aagttaaaaa accaggtgct     480
tctgttaaag tttcttgtaa agcttctaga gaccatggcc agtaaggccg gtctctatct     540
cttgggttcg tcaggctcca ggtcagggtc tggaatggat gggttgggtt ctttctaca      600
acggtaacac caactacgct cagaaactgc agggtcgtgg taccatgacc accgatccat     660
ctacctctac cgcttacatg gaactgcgtt ctctgcgttc tgacgacacg gccgtgtatt     720
actgtgctcg tggttacggt atggatgttt ggggtcaggg gaccacggtc accgtctcct     780
cagctagcgg caaaccaatc ccaaacccac tgctgggc                              818
```

<210> SEQ ID NO 179
<211> LENGTH: 818
<212> TYPE: DNA
<213> ORGANISM: Artificial Sequence
<220> FEATURE:
<223> OTHER INFORMATION: Oligonucleotide

<400> SEQUENCE: 179

```
cagttagata aaagaggcgc ggcagcaagc ggcgcgcatg ccgaatctgc tctgacccag      60
ccagcttctg tttctggttc tccaggtcag tctatcacca tctcttgtac cggtacctct     120
tctgatgttg gtggttacaa ctctgtttct tggtaccagc agcacccagg taaagctcca     180
aaactgatga tctacgaagt ttctaaccgt ccatctggtg tttctaaccg tttctctggt     240
tctaaatctg gtaacaccgc ttctctgacc atctctggtc tgcaggctga agatgaagct     300
gattactact gtaactctta cacctctacc tctatggttt tcggtggtgg taccaaactg     360
accgttctgt ccggagggtc gaccataact tcgtataatg tatactatac gaagttatcc     420
tcgagcggta ccgaagttca gctggttcag tctggtgctg aagttaaaaa accaggtgct     480
tctgttaaag tttcttgtaa agcttctggt tacaccctga cctcttacgg tatctcttgg     540
gttcgtcagg ctccaggtca gggtctggaa tggatgggtt ggagagacca tggccagtaa     600
ggccggtctc taactacgct cagaaactgc agggtcgtgg taccatgacc accgatccat     660
ctacctctac cgcttacatg gaactgcgtt ctctgcgttc tgacgacacg gccgtgtatt     720
actgtgctcg tggttacggt atggatgttt ggggtcaggg gaccacggtc accgtctcct     780
cagctagcgg caaaccaatc ccaaacccac tgctgggc                              818
```

<210> SEQ ID NO 180
<211> LENGTH: 809

```
<212> TYPE: DNA
<213> ORGANISM: Artificial Sequence
<220> FEATURE:
<223> OTHER INFORMATION: Oligonucleotide

<400> SEQUENCE: 180
cagttagata aaagaggcgc ggcagcaagc ggcgcgcatg ccgaatctgc tctgacccag      60
ccagcttctg tttctggttc tccaggtcag tctatcacca tctcttgtac cggtacctct     120
tctgatgttg gtggttacaa ctctgtttct tggtaccagc agcacccagg taaagctcca     180
aaactgatga tctacgaagt ttctaaccgt ccatctggtg tttctaaccg tttctctggt     240
tctaaatctg gtaacaccgc ttctctgacc atctctggtc tgcaggctga agatgaagct     300
gattactact gtaactctta cacctctacc tctatggttt tcggtggtgg taccaaactg     360
accgttctgt ccggagggtc gaccataact tcgtataatg tatactatac gaagttatcc     420
tcgagcggta ccgaagttca gctggttcag tctggtgctg aagttaaaaa accaggtgct     480
tctgttaaag tttcttgtaa agcttctggt tacacccctga cctcttacgg tatctcttgg     540
gttcgtcagg ctccaggtca gggtctggaa tggatgggtt gggtttcttt ctacaacggt     600
aacaccaact acgctcagaa actgcagggt cgtggtacca tgaccaccga tccatctacc     660
tctaccgctt acatggaact gcgttctctg cgttctgacg acacggccgt gtattactgt     720
agagaccatg ccagtaagg ccggtctctg ggaccacggt caccgtctcc tcagctagcg     780
gcaaaccaat cccaaaccca ctgctgggc                                        809

<210> SEQ ID NO 181
<211> LENGTH: 42
<212> TYPE: DNA
<213> ORGANISM: Artificial Sequence
<220> FEATURE:
<223> OTHER INFORMATION: Primer

<400> SEQUENCE: 181
gcttctgttg gtgatcgtgt tactattacc tgtcgtgctt ct                          42

<210> SEQ ID NO 182
<211> LENGTH: 42
<212> TYPE: DNA
<213> ORGANISM: Artificial Sequence
<220> FEATURE:
<223> OTHER INFORMATION: Primer

<400> SEQUENCE: 182
gtttctctgg gtgaacgtgc taccatcaac tgcaaatctt ct                          42

<210> SEQ ID NO 183
<211> LENGTH: 42
<212> TYPE: DNA
<213> ORGANISM: Artificial Sequence
<220> FEATURE:
<223> OTHER INFORMATION: Primer

<400> SEQUENCE: 183
gttaccccag gtgaaccagc ttctatttct tgtcgttctt ct                          42

<210> SEQ ID NO 184
<211> LENGTH: 42
<212> TYPE: DNA
<213> ORGANISM: Artificial Sequence
<220> FEATURE:
<223> OTHER INFORMATION: Primer
```

```
<400> SEQUENCE: 184
ctgtctccag gtgaacgtgc cactctgtct tgtcgtgctt ct        42

<210> SEQ ID NO 185
<211> LENGTH: 42
<212> TYPE: DNA
<213> ORGANISM: Artificial Sequence
<220> FEATURE:
<223> OTHER INFORMATION: Primer

<400> SEQUENCE: 185
ctgtctccag gtgaacgtgc cactctgtct tgtcgtgctt ct        42

<210> SEQ ID NO 186
<211> LENGTH: 42
<212> TYPE: DNA
<213> ORGANISM: Artificial Sequence
<220> FEATURE:
<223> OTHER INFORMATION: Primer

<400> SEQUENCE: 186
ggttctccag gtcagtctat caccatctct tgtaccggta cc        42

<210> SEQ ID NO 187
<211> LENGTH: 42
<212> TYPE: DNA
<213> ORGANISM: Artificial Sequence
<220> FEATURE:
<223> OTHER INFORMATION: Primer

<400> SEQUENCE: 187
cagttttgga gctttacctg gtttctgctg gtaccaagcc ag        42

<210> SEQ ID NO 188
<211> LENGTH: 42
<212> TYPE: DNA
<213> ORGANISM: Artificial Sequence
<220> FEATURE:
<223> OTHER INFORMATION: Primer

<400> SEQUENCE: 188
cagttttggt ggctgacctg gtttctgctg gtaccaagcc ag        42

<210> SEQ ID NO 189
<211> LENGTH: 42
<212> TYPE: DNA
<213> ORGANISM: Artificial Sequence
<220> FEATURE:
<223> OTHER INFORMATION: Primer

<400> SEQUENCE: 189
cagctgtgga gactgacctg gtttctgcag gtaccagtgc ag        42

<210> SEQ ID NO 190
<211> LENGTH: 42
<212> TYPE: DNA
<213> ORGANISM: Artificial Sequence
<220> FEATURE:
<223> OTHER INFORMATION: Primer

<400> SEQUENCE: 190
cagacgtgga gcctgacctg gtttctgctg gtaccaagcc ag        42

<210> SEQ ID NO 191
<211> LENGTH: 42
```

<212> TYPE: DNA
<213> ORGANISM: Artificial Sequence
<220> FEATURE:
<223> OTHER INFORMATION: Primer

<400> SEQUENCE: 191
cagacgtgga gcctgacctg gtttctgctg gtaccaagcc ag                42

<210> SEQ ID NO 192
<211> LENGTH: 42
<212> TYPE: DNA
<213> ORGANISM: Artificial Sequence
<220> FEATURE:
<223> OTHER INFORMATION: Primer

<400> SEQUENCE: 192
cagtttggga gctttacctg ggtgctgctg gtaccaagaa ac                42

<210> SEQ ID NO 193
<211> LENGTH: 42
<212> TYPE: DNA
<213> ORGANISM: Artificial Sequence
<220> FEATURE:
<223> OTHER INFORMATION: Primer

<400> SEQUENCE: 193
taccagcaga aaccaggtaa agctccaaaa ctgctgatct ac                42

<210> SEQ ID NO 194
<211> LENGTH: 42
<212> TYPE: DNA
<213> ORGANISM: Artificial Sequence
<220> FEATURE:
<223> OTHER INFORMATION: Primer

<400> SEQUENCE: 194
taccagcaga aaccaggtca gccaccaaaa ctgctgatct ac                42

<210> SEQ ID NO 195
<211> LENGTH: 42
<212> TYPE: DNA
<213> ORGANISM: Artificial Sequence
<220> FEATURE:
<223> OTHER INFORMATION: Primer

<400> SEQUENCE: 195
tacctgcaga aaccaggtca gtctccacag ctgctgatct ac                42

<210> SEQ ID NO 196
<211> LENGTH: 42
<212> TYPE: DNA
<213> ORGANISM: Artificial Sequence
<220> FEATURE:
<223> OTHER INFORMATION: Primer

<400> SEQUENCE: 196
taccagcaga aaccaggtca ggctccacgt ctgctgatct ac                42

<210> SEQ ID NO 197
<211> LENGTH: 42
<212> TYPE: DNA
<213> ORGANISM: Artificial Sequence
<220> FEATURE:
<223> OTHER INFORMATION: Primer

<400> SEQUENCE: 197

-continued

```
taccagcaga aaccaggtca ggctccacgt ctgctgatct ac          42

<210> SEQ ID NO 198
<211> LENGTH: 42
<212> TYPE: DNA
<213> ORGANISM: Artificial Sequence
<220> FEATURE:
<223> OTHER INFORMATION: Primer

<400> SEQUENCE: 198
taccagcagc acccaggtaa agctccaaaa ctgatgatct ac          42

<210> SEQ ID NO 199
<211> LENGTH: 42
<212> TYPE: DNA
<213> ORGANISM: Artificial Sequence
<220> FEATURE:
<223> OTHER INFORMATION: Primer

<400> SEQUENCE: 199
atcggtacca gaaccagaac cagagaaacg agatggaaca cc          42

<210> SEQ ID NO 200
<211> LENGTH: 42
<212> TYPE: DNA
<213> ORGANISM: Artificial Sequence
<220> FEATURE:
<223> OTHER INFORMATION: Primer

<400> SEQUENCE: 200
atcggtacca gaaccagaac cagagaaacg atctggaaca cc          42

<210> SEQ ID NO 201
<211> LENGTH: 42
<212> TYPE: DNA
<213> ORGANISM: Artificial Sequence
<220> FEATURE:
<223> OTHER INFORMATION: Primer

<400> SEQUENCE: 201
atcggtacca gaaccagaac cagagaaacg atctggaaca cc          42

<210> SEQ ID NO 202
<211> LENGTH: 42
<212> TYPE: DNA
<213> ORGANISM: Artificial Sequence
<220> FEATURE:
<223> OTHER INFORMATION: Primer

<400> SEQUENCE: 202
atcggtacca gaaccagaac cagagaaacg agctgggata cc          42

<210> SEQ ID NO 203
<211> LENGTH: 42
<212> TYPE: DNA
<213> ORGANISM: Artificial Sequence
<220> FEATURE:
<223> OTHER INFORMATION: Primer

<400> SEQUENCE: 203
atcggtacca gaaccagaac cagacagacg atctgggata cc          42

<210> SEQ ID NO 204
<211> LENGTH: 42
<212> TYPE: DNA
<213> ORGANISM: Artificial Sequence
```

<220> FEATURE:
<223> OTHER INFORMATION: Primer

<400> SEQUENCE: 204
ggtgttacca gatttagaac cagagaaacg gttagaaaca cc         42

<210> SEQ ID NO 205
<211> LENGTH: 42
<212> TYPE: DNA
<213> ORGANISM: Artificial Sequence
<220> FEATURE:
<223> OTHER INFORMATION: Primer

<400> SEQUENCE: 205
atctcttctc tgcagccaga agatttcgct aactactact gt         42

<210> SEQ ID NO 206
<211> LENGTH: 42
<212> TYPE: DNA
<213> ORGANISM: Artificial Sequence
<220> FEATURE:
<223> OTHER INFORMATION: Primer

<400> SEQUENCE: 206
atctcttctc tgcaggctga agatgttgct gtttactact gt         42

<210> SEQ ID NO 207
<211> LENGTH: 42
<212> TYPE: DNA
<213> ORGANISM: Artificial Sequence
<220> FEATURE:
<223> OTHER INFORMATION: Primer

<400> SEQUENCE: 207
atctctcgtg ttgaagctga agatgttggt gtttactact gt         42

<210> SEQ ID NO 208
<211> LENGTH: 42
<212> TYPE: DNA
<213> ORGANISM: Artificial Sequence
<220> FEATURE:
<223> OTHER INFORMATION: Primer

<400> SEQUENCE: 208
atctcttctc tggaaccaga agatttcgct gtttactact gt         42

<210> SEQ ID NO 209
<211> LENGTH: 42
<212> TYPE: DNA
<213> ORGANISM: Artificial Sequence
<220> FEATURE:
<223> OTHER INFORMATION: Primer

<400> SEQUENCE: 209 atcaccegtc tggaaccaga agatttcgct gtttactact gt         42

<210> SEQ ID NO 210
<211> LENGTH: 42
<212> TYPE: DNA
<213> ORGANISM: Artificial Sequence
<220> FEATURE:
<223> OTHER INFORMATION: Primer

<400> SEQUENCE: 210
atctctggtc tgcaggctga agatgaagct gattactact gt         42

<210> SEQ ID NO 211
<211> LENGTH: 42
<212> TYPE: DNA
<213> ORGANISM: Artificial Sequence
<220> FEATURE:
<223> OTHER INFORMATION: Primer

<400> SEQUENCE: 211
cgaccctccg gatttgattt caactttggt accaccaccg aa    42

<210> SEQ ID NO 212
<211> LENGTH: 42
<212> TYPE: DNA
<213> ORGANISM: Artificial Sequence
<220> FEATURE:
<223> OTHER INFORMATION: Primer

<400> SEQUENCE: 212
cgaccctccg gacagaacgg tcagtttggt accaccaccg aa    42

<210> SEQ ID NO 213
<211> LENGTH: 42
<212> TYPE: DNA
<213> ORGANISM: Artificial Sequence
<220> FEATURE:
<223> OTHER INFORMATION: Primer

<400> SEQUENCE: 213
aaaaaaccag gtgcttctgt taaagtttct tgtaaagttt ct    42

<210> SEQ ID NO 214
<211> LENGTH: 42
<212> TYPE: DNA
<213> ORGANISM: Artificial Sequence
<220> FEATURE:
<223> OTHER INFORMATION: Primer

<400> SEQUENCE: 214
gttaaaccaa cccagaccct gaccctgacc tgtaccgttt ct    42

<210> SEQ ID NO 215
<211> LENGTH: 42
<212> TYPE: DNA
<213> ORGANISM: Artificial Sequence
<220> FEATURE:
<223> OTHER INFORMATION: Primer

<400> SEQUENCE: 215
gttcagccag gtggttctct gcgtctgtct tgtgctgctt ct    42

<210> SEQ ID NO 216
<211> LENGTH: 42
<212> TYPE: DNA
<213> ORGANISM: Artificial Sequence
<220> FEATURE:
<223> OTHER INFORMATION: Primer

<400> SEQUENCE: 216
gttaaaccat ctcagaccct gtctctgacc tgtaccgttt ct    42

<210> SEQ ID NO 217
<211> LENGTH: 42
<212> TYPE: DNA
<213> ORGANISM: Artificial Sequence
<220> FEATURE:
<223> OTHER INFORMATION: Primer

<400> SEQUENCE: 217
aaaaaaccag gtgaatctct gaaaatctct tgtaaaggtt ct                            42

<210> SEQ ID NO 218
<211> LENGTH: 42
<212> TYPE: DNA
<213> ORGANISM: Artificial Sequence
<220> FEATURE:
<223> OTHER INFORMATION: Primer

<400> SEQUENCE: 218
aaaaaaccag gtgcttctgt taaagtttct tgtaaagctt ct                            42

<210> SEQ ID NO 219
<211> LENGTH: 42
<212> TYPE: DNA
<213> ORGANISM: Artificial Sequence
<220> FEATURE:
<223> OTHER INFORMATION: Primer

<400> SEQUENCE: 219
ccattccaga cctttacctg gagcctgacg aacccagtgg at                            42

<210> SEQ ID NO 220
<211> LENGTH: 42
<212> TYPE: DNA
<213> ORGANISM: Artificial Sequence
<220> FEATURE:
<223> OTHER INFORMATION: Primer

<400> SEQUENCE: 220
ccattccaga gctttacctg gtggctgacg gatccagtta ac                            42

<210> SEQ ID NO 221
<211> LENGTH: 42
<212> TYPE: DNA
<213> ORGANISM: Artificial Sequence
<220> FEATURE:
<223> OTHER INFORMATION: Primer

<400> SEQUENCE: 221
cagttccaga cctttacctg gagcctgacg aacccaagac at                            42

<210> SEQ ID NO 222
<211> LENGTH: 42
<212> TYPE: DNA
<213> ORGANISM: Artificial Sequence
<220> FEATURE:
<223> OTHER INFORMATION: Primer

<400> SEQUENCE: 222
ccattccaga cctttacctg gtggctgacg gatccaagac ca                            42

<210> SEQ ID NO 223
<211> LENGTH: 42
<212> TYPE: DNA
<213> ORGANISM: Artificial Sequence
<220> FEATURE:
<223> OTHER INFORMATION: Primer

<400> SEQUENCE: 223
agattccaga cctttacctg gaacctgacg aacccaagcg at                            42

<210> SEQ ID NO 224

```
<211> LENGTH: 42
<212> TYPE: DNA
<213> ORGANISM: Artificial Sequence
<220> FEATURE:
<223> OTHER INFORMATION: Primer

<400> SEQUENCE: 224
ccattccaga ccctgacctg gagcctgacg aacccaagag at                            42

<210> SEQ ID NO 225
<211> LENGTH: 42
<212> TYPE: DNA
<213> ORGANISM: Artificial Sequence
<220> FEATURE:
<223> OTHER INFORMATION: Primer

<400> SEQUENCE: 225
gttcgtcagg ctccaggtaa aggtctggaa tggatgggtg gt                            42

<210> SEQ ID NO 226
<211> LENGTH: 42
<212> TYPE: DNA
<213> ORGANISM: Artificial Sequence
<220> FEATURE:
<223> OTHER INFORMATION: Primer

<400> SEQUENCE: 226
atccgtcagc caccaggtaa agctctggaa tggctggcta tg                            42

<210> SEQ ID NO 227
<211> LENGTH: 42
<212> TYPE: DNA
<213> ORGANISM: Artificial Sequence
<220> FEATURE:
<223> OTHER INFORMATION: Primer

<400> SEQUENCE: 227
gttcgtcagg ctccaggtaa aggtctggaa ctggttgctt ct                            42

<210> SEQ ID NO 228
<211> LENGTH: 42
<212> TYPE: DNA
<213> ORGANISM: Artificial Sequence
<220> FEATURE:
<223> OTHER INFORMATION: Primer

<400> SEQUENCE: 228
atccgtcagc caccaggtaa aggtctggaa tggatcggtt ac                            42

<210> SEQ ID NO 229
<211> LENGTH: 42
<212> TYPE: DNA
<213> ORGANISM: Artificial Sequence
<220> FEATURE:
<223> OTHER INFORMATION: Primer

<400> SEQUENCE: 229
gttcgtcagg ttccaggtaa aggtctggaa tctatgggta tc                            42

<210> SEQ ID NO 230
<211> LENGTH: 42
<212> TYPE: DNA
<213> ORGANISM: Artificial Sequence
<220> FEATURE:
<223> OTHER INFORMATION: Primer

<400> SEQUENCE: 230
```

```
gttcgtcagg ctccaggtca gggtctggaa tggatgggtt gg                              42
```

<210> SEQ ID NO 231
<211> LENGTH: 42
<212> TYPE: DNA
<213> ORGANISM: Artificial Sequence
<220> FEATURE:
<223> OTHER INFORMATION: Primer

<400> SEQUENCE: 231

```
ttcggtcatg gtaacacgac cctggaattt ctgagcgtag at                              42
```

<210> SEQ ID NO 232
<211> LENGTH: 42
<212> TYPE: DNA
<213> ORGANISM: Artificial Sequence
<220> FEATURE:
<223> OTHER INFORMATION: Primer

<400> SEQUENCE: 232

```
agagatggtc agacgagatt tcagagcaga gttgtaaacg at                              42
```

<210> SEQ ID NO 233
<211> LENGTH: 42
<212> TYPE: DNA
<213> ORGANISM: Artificial Sequence
<220> FEATURE:
<223> OTHER INFORMATION: Primer

<400> SEQUENCE: 233

```
acgagagatg gtgaaacgac ctttaacaga atctgggtag ta                              42
```

<210> SEQ ID NO 234
<211> LENGTH: 42
<212> TYPE: DNA
<213> ORGANISM: Artificial Sequence
<220> FEATURE:
<223> OTHER INFORMATION: Primer

<400> SEQUENCE: 234

```
aacagacatg gtaacacgag atttcagaga tgggttgtaa tc                              42
```

<210> SEQ ID NO 235
<211> LENGTH: 42
<212> TYPE: DNA
<213> ORGANISM: Artificial Sequence
<220> FEATURE:
<223> OTHER INFORMATION: Primer

<400> SEQUENCE: 235

```
agcagagatg gtaacctgac cctggaaaga tggagagtaa cg                              42
```

<210> SEQ ID NO 236
<211> LENGTH: 42
<212> TYPE: DNA
<213> ORGANISM: Artificial Sequence
<220> FEATURE:
<223> OTHER INFORMATION: Primer

<400> SEQUENCE: 236

```
ggtggtcatg gtaccacgac cctgcagttt ctgagcgtag tt                              42
```

<210> SEQ ID NO 237
<211> LENGTH: 42
<212> TYPE: DNA

<210> SEQ ID NO 237
<211> LENGTH: 42
<212> TYPE: DNA
<213> ORGANISM: Artificial Sequence
<220> FEATURE:
<223> OTHER INFORMATION: Primer

<400> SEQUENCE: 237
ctgtcttctc tgaaatctga ggacacggcc gtgtattact gt        42

<210> SEQ ID NO 238
<211> LENGTH: 42
<212> TYPE: DNA
<213> ORGANISM: Artificial Sequence
<220> FEATURE:
<223> OTHER INFORMATION: Primer

<400> SEQUENCE: 238
atgaccaaca tggatcctgt ggacacagcc acatattact gt        42

<210> SEQ ID NO 239
<211> LENGTH: 42
<212> TYPE: DNA
<213> ORGANISM: Artificial Sequence
<220> FEATURE:
<223> OTHER INFORMATION: Primer

<400> SEQUENCE: 239
atgaactctc tgcgtgccga ggacacggct gtgtattact gt        42

<210> SEQ ID NO 240
<211> LENGTH: 42
<212> TYPE: DNA
<213> ORGANISM: Artificial Sequence
<220> FEATURE:
<223> OTHER INFORMATION: Primer

<400> SEQUENCE: 240
gttaactctg ttaccgccgc ggacacggct gtgtattact gt        42

<210> SEQ ID NO 241
<211> LENGTH: 42
<212> TYPE: DNA
<213> ORGANISM: Artificial Sequence
<220> FEATURE:
<223> OTHER INFORMATION: Primer

<400> SEQUENCE: 241
tggtcttctc tgaaagcctc ggacaccgcc atttattact gt        42

<210> SEQ ID NO 242
<211> LENGTH: 42
<212> TYPE: DNA
<213> ORGANISM: Artificial Sequence
<220> FEATURE:
<223> OTHER INFORMATION: Primer

<400> SEQUENCE: 242
ctgcgttctc tgcgttctga cgacacggcc gtgtattact gt        42

<210> SEQ ID NO 243
<211> LENGTH: 42
<212> TYPE: DNA
<213> ORGANISM: Artificial Sequence
<220> FEATURE:
<223> OTHER INFORMATION: Primer

<400> SEQUENCE: 243
gattggtttg ccgctagctg aggagacggt gaccagggtt cc        42

<210> SEQ ID NO 244
<211> LENGTH: 42
<212> TYPE: DNA
<213> ORGANISM: Artificial Sequence
<220> FEATURE:
<223> OTHER INFORMATION: Primer

<400> SEQUENCE: 244
gattggtttg ccgctagctg aggagacggt gaccgtggtc cc                42

<210> SEQ ID NO 245
<211> LENGTH: 24
<212> TYPE: DNA
<213> ORGANISM: Artificial Sequence
<220> FEATURE:
<223> OTHER INFORMATION: Primer

<400> SEQUENCE: 245
gtagatcagc agttttggag cttt                                   24

<210> SEQ ID NO 246
<211> LENGTH: 21
<212> TYPE: DNA
<213> ORGANISM: Artificial Sequence
<220> FEATURE:
<223> OTHER INFORMATION: Primer

<400> SEQUENCE: 246
gtagatcagc agttttggtg g                                      21

<210> SEQ ID NO 247
<211> LENGTH: 21
<212> TYPE: DNA
<213> ORGANISM: Artificial Sequence
<220> FEATURE:
<223> OTHER INFORMATION: Primer

<400> SEQUENCE: 247
gtagatcagc agctgtggag a                                      21

<210> SEQ ID NO 248
<211> LENGTH: 20
<212> TYPE: DNA
<213> ORGANISM: Artificial Sequence
<220> FEATURE:
<223> OTHER INFORMATION: Primer

<400> SEQUENCE: 248
gtagatcagc agacgtggag                                        20

<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
gtagatcagc agacgtggag                                        20

<210> SEQ ID NO 250
<211> LENGTH: 25
<212> TYPE: DNA
<213> ORGANISM: Artificial Sequence
<220> FEATURE:

<223> OTHER INFORMATION: Primer

<400> SEQUENCE: 250
gtagatcatc agttttggag cttta                                              25

<210> SEQ ID NO 251
<211> LENGTH: 21
<212> TYPE: DNA
<213> ORGANISM: Artificial Sequence
<220> FEATURE:
<223> OTHER INFORMATION: Primer

<400> SEQUENCE: 251
ctggcttggt accagcagaa a                                                  21

<210> SEQ ID NO 252
<211> LENGTH: 21
<212> TYPE: DNA
<213> ORGANISM: Artificial Sequence
<220> FEATURE:
<223> OTHER INFORMATION: Primer

<400> SEQUENCE: 252
ctggcttggt accagcagaa a                                                  21

<210> SEQ ID NO 253
<211> LENGTH: 21
<212> TYPE: DNA
<213> ORGANISM: Artificial Sequence
<220> FEATURE:
<223> OTHER INFORMATION: Primer

<400> SEQUENCE: 253
ctgcactggt acctgcagaa a                                                  21

<210> SEQ ID NO 254
<211> LENGTH: 21
<212> TYPE: DNA
<213> ORGANISM: Artificial Sequence
<220> FEATURE:
<223> OTHER INFORMATION: Primer

<400> SEQUENCE: 254
ctggcttggt accagcagaa a                                                  21

<210> SEQ ID NO 255
<211> LENGTH: 21
<212> TYPE: DNA
<213> ORGANISM: Artificial Sequence
<220> FEATURE:
<223> OTHER INFORMATION: Primer

<400> SEQUENCE: 255
ctggcttggt accagcagaa a                                                  21

<210> SEQ ID NO 256
<211> LENGTH: 21
<212> TYPE: DNA
<213> ORGANISM: Artificial Sequence
<220> FEATURE:
<223> OTHER INFORMATION: Primer

<400> SEQUENCE: 256
gtttcttggt accagcagca c                                                  21

```
<210> SEQ ID NO 257
<211> LENGTH: 25
<212> TYPE: DNA
<213> ORGANISM: Artificial Sequence
<220> FEATURE:
<223> OTHER INFORMATION: Primer

<400> SEQUENCE: 257
acagtagtag ttagcgaaat cttct                                    25

<210> SEQ ID NO 258
<211> LENGTH: 25
<212> TYPE: DNA
<213> ORGANISM: Artificial Sequence
<220> FEATURE:
<223> OTHER INFORMATION: Primer

<400> SEQUENCE: 258
acagtagtaa acagcaacat cttca                                    25

<210> SEQ ID NO 259
<211> LENGTH: 25
<212> TYPE: DNA
<213> ORGANISM: Artificial Sequence
<220> FEATURE:
<223> OTHER INFORMATION: Primer

<400> SEQUENCE: 259
acagtagtaa acaccaacat cttca                                    25

<210> SEQ ID NO 260
<211> LENGTH: 25
<212> TYPE: DNA
<213> ORGANISM: Artificial Sequence
<220> FEATURE:
<223> OTHER INFORMATION: Primer

<400> SEQUENCE: 260
acagtagtaa acagcgaaat cttct                                    25

<210> SEQ ID NO 261
<211> LENGTH: 25
<212> TYPE: DNA
<213> ORGANISM: Artificial Sequence
<220> FEATURE:
<223> OTHER INFORMATION: Primer

<400> SEQUENCE: 261
acagtagtaa acagcgaaat cttct                                    25

<210> SEQ ID NO 262
<211> LENGTH: 25
<212> TYPE: DNA
<213> ORGANISM: Artificial Sequence
<220> FEATURE:
<223> OTHER INFORMATION: Primer

<400> SEQUENCE: 262
acagtagtaa tcagcttcat cttca                                    25

<210> SEQ ID NO 263
<211> LENGTH: 21
<212> TYPE: DNA
<213> ORGANISM: Artificial Sequence
<220> FEATURE:
<223> OTHER INFORMATION: Primer
```

```
<400> SEQUENCE: 263
ggtgttccat ctcgtttctc t                                              21

<210> SEQ ID NO 264
<211> LENGTH: 21
<212> TYPE: DNA
<213> ORGANISM: Artificial Sequence
<220> FEATURE:
<223> OTHER INFORMATION: Primer

<400> SEQUENCE: 264
ggtgttccag atcgtttctc t                                              21

<210> SEQ ID NO 265
<211> LENGTH: 21
<212> TYPE: DNA
<213> ORGANISM: Artificial Sequence
<220> FEATURE:
<223> OTHER INFORMATION: Primer

<400> SEQUENCE: 265
ggtgttccag atcgtttctc t                                              21

<210> SEQ ID NO 266
<211> LENGTH: 21
<212> TYPE: DNA
<213> ORGANISM: Artificial Sequence
<220> FEATURE:
<223> OTHER INFORMATION: Primer

<400> SEQUENCE: 266
ggtatcccag ctcgtttctc t                                              21

<210> SEQ ID NO 267
<211> LENGTH: 21
<212> TYPE: DNA
<213> ORGANISM: Artificial Sequence
<220> FEATURE:
<223> OTHER INFORMATION: Primer

<400> SEQUENCE: 267
ggtatcccag atcgtctgtc t                                              21

<210> SEQ ID NO 268
<211> LENGTH: 22
<212> TYPE: DNA
<213> ORGANISM: Artificial Sequence
<220> FEATURE:
<223> OTHER INFORMATION: Primer

<400> SEQUENCE: 268
ggtgtttcta accgtttctc tg                                             22

<210> SEQ ID NO 269
<211> LENGTH: 20
<212> TYPE: DNA
<213> ORGANISM: Artificial Sequence
<220> FEATURE:
<223> OTHER INFORMATION: Primer

<400> SEQUENCE: 269
accacccatc cattccagac                                                20

<210> SEQ ID NO 270
<211> LENGTH: 20
```

```
<212> TYPE: DNA
<213> ORGANISM: Artificial Sequence
<220> FEATURE:
<223> OTHER INFORMATION: Primer

<400> SEQUENCE: 270
catagccagc cattccagag                                              20

<210> SEQ ID NO 271
<211> LENGTH: 21
<212> TYPE: DNA
<213> ORGANISM: Artificial Sequence
<220> FEATURE:
<223> OTHER INFORMATION: Primer

<400> SEQUENCE: 271
agaagcaacc agttccagac c                                            21

<210> SEQ ID NO 272
<211> LENGTH: 21
<212> TYPE: DNA
<213> ORGANISM: Artificial Sequence
<220> FEATURE:
<223> OTHER INFORMATION: Primer

<400> SEQUENCE: 272
gtaaccgatc cattccagac c                                            21

<210> SEQ ID NO 273
<211> LENGTH: 24
<212> TYPE: DNA
<213> ORGANISM: Artificial Sequence
<220> FEATURE:
<223> OTHER INFORMATION: Primer

<400> SEQUENCE: 273
gatacccata gattccagac cttt                                         24

<210> SEQ ID NO 274
<211> LENGTH: 20
<212> TYPE: DNA
<213> ORGANISM: Artificial Sequence
<220> FEATURE:
<223> OTHER INFORMATION: Primer

<400> SEQUENCE: 274
ccaacccatc cattccagac                                              20

<210> SEQ ID NO 275
<211> LENGTH: 19
<212> TYPE: DNA
<213> ORGANISM: Artificial Sequence
<220> FEATURE:
<223> OTHER INFORMATION: Primer

<400> SEQUENCE: 275
atccactggg ttcgtcagg                                               19

<210> SEQ ID NO 276
<211> LENGTH: 21
<212> TYPE: DNA
<213> ORGANISM: Artificial Sequence
<220> FEATURE:
<223> OTHER INFORMATION: Primer

<400> SEQUENCE: 276
```
gttaactgga tccgtcagcc a                    21

<210> SEQ ID NO 277
<211> LENGTH: 21
<212> TYPE: DNA
<213> ORGANISM: Artificial Sequence
<220> FEATURE:
<223> OTHER INFORMATION: Primer

<400> SEQUENCE: 277
atgtcttggg ttcgtcaggc t                    21

<210> SEQ ID NO 278
<211> LENGTH: 19
<212> TYPE: DNA
<213> ORGANISM: Artificial Sequence
<220> FEATURE:
<223> OTHER INFORMATION: Primer

<400> SEQUENCE: 278
tggtcttgga tccgtcagc                       19

<210> SEQ ID NO 279
<211> LENGTH: 21
<212> TYPE: DNA
<213> ORGANISM: Artificial Sequence
<220> FEATURE:
<223> OTHER INFORMATION: Primer

<400> SEQUENCE: 279
atcgcttggg ttcgtcaggt t                    21

<210> SEQ ID NO 280
<211> LENGTH: 21
<212> TYPE: DNA
<213> ORGANISM: Artificial Sequence
<220> FEATURE:
<223> OTHER INFORMATION: Primer

<400> SEQUENCE: 280
atctcttggg ttcgtcaggc t                    21

<210> SEQ ID NO 281
<211> LENGTH: 21
<212> TYPE: DNA
<213> ORGANISM: Artificial Sequence
<220> FEATURE:
<223> OTHER INFORMATION: Primer

<400> SEQUENCE: 281
acagtaatac acggccgtgt c                    21

<210> SEQ ID NO 282
<211> LENGTH: 23
<212> TYPE: DNA
<213> ORGANISM: Artificial Sequence
<220> FEATURE:
<223> OTHER INFORMATION: Primer

<400> SEQUENCE: 282
acagtaatat gtggctgtgt cca                  23

<210> SEQ ID NO 283
<211> LENGTH: 21
<212> TYPE: DNA
<213> ORGANISM: Artificial Sequence
<220> FEATURE:
<223> OTHER INFORMATION: Primer

<400> SEQUENCE: 283
acagtaatac acagccgtgt c                                              21

<210> SEQ ID NO 284
<211> LENGTH: 21
<212> TYPE: DNA
<213> ORGANISM: Artificial Sequence
<220> FEATURE:
<223> OTHER INFORMATION: Primer

<400> SEQUENCE: 284
acagtaatac acagccgtgt c                                              21

<210> SEQ ID NO 285
<211> LENGTH: 22
<212> TYPE: DNA
<213> ORGANISM: Artificial Sequence
<220> FEATURE:
<223> OTHER INFORMATION: Primer

<400> SEQUENCE: 285
acagtaataa atggcggtgt cc                                             22

<210> SEQ ID NO 286
<211> LENGTH: 21
<212> TYPE: DNA
<213> ORGANISM: Artificial Sequence
<220> FEATURE:
<223> OTHER INFORMATION: Primer

<400> SEQUENCE: 286
acagtaatac acggccgtgt c                                              21

<210> SEQ ID NO 287
<211> LENGTH: 22
<212> TYPE: DNA
<213> ORGANISM: Artificial Sequence
<220> FEATURE:
<223> OTHER INFORMATION: Primer

<400> SEQUENCE: 287
atctacgctc agaaattcca gg                                             22

<210> SEQ ID NO 288
<211> LENGTH: 24
<212> TYPE: DNA
<213> ORGANISM: Artificial Sequence
<220> FEATURE:
<223> OTHER INFORMATION: Primer

<400> SEQUENCE: 288
gtttacaact ctgctctgaa atct                                           24

<210> SEQ ID NO 289
<211> LENGTH: 24
<212> TYPE: DNA
<213> ORGANISM: Artificial Sequence
<220> FEATURE:
<223> OTHER INFORMATION: Primer

<400> SEQUENCE: 289
tactacccag attctgttaa aggt                                           24

<210> SEQ ID NO 290
<211> LENGTH: 24
<212> TYPE: DNA
<213> ORGANISM: Artificial Sequence
<220> FEATURE:
<223> OTHER INFORMATION: Primer

<400> SEQUENCE: 290
gattacaacc catctctgaa atct                                          24

<210> SEQ ID NO 291
<211> LENGTH: 21
<212> TYPE: DNA
<213> ORGANISM: Artificial Sequence
<220> FEATURE:
<223> OTHER INFORMATION: Primer

<400> SEQUENCE: 291
cgttactctc catctttcca g                                             21

<210> SEQ ID NO 292
<211> LENGTH: 21
<212> TYPE: DNA
<213> ORGANISM: Artificial Sequence
<220> FEATURE:
<223> OTHER INFORMATION: Primer

<400> SEQUENCE: 292
aactacgctc agaaactgca g                                             21

<210> SEQ ID NO 293
<211> LENGTH: 23
<212> TYPE: DNA
<213> ORGANISM: Artificial Sequence
<220> FEATURE:
<223> OTHER INFORMATION: Primer

<400> SEQUENCE: 293
cggattgtct tcaaccaaca caa                                           23

<210> SEQ ID NO 294
<211> LENGTH: 20
<212> TYPE: DNA
<213> ORGANISM: Artificial Sequence
<220> FEATURE:
<223> OTHER INFORMATION: Primer

<400> SEQUENCE: 294
ctcctcctgt tgaatccagg                                               20

<210> SEQ ID NO 295
<211> LENGTH: 21
<212> TYPE: DNA
<213> ORGANISM: Artificial Sequence
<220> FEATURE:
<223> OTHER INFORMATION: Primer

<400> SEQUENCE: 295
cagttagata aaagaggcgc g                                             21

<210> SEQ ID NO 296
<211> LENGTH: 18
<212> TYPE: DNA
<213> ORGANISM: Artificial Sequence
<220> FEATURE:
<223> OTHER INFORMATION: Primer

```
<400> SEQUENCE: 296
gcccagcagt gggtttgg                                                    18

<210> SEQ ID NO 297
<211> LENGTH: 19
<212> TYPE: DNA
<213> ORGANISM: Artificial Sequence
<220> FEATURE:
<223> OTHER INFORMATION: Primer

<400> SEQUENCE: 297
tccggagggt cgaccataa                                                   19

<210> SEQ ID NO 298
<211> LENGTH: 21
<212> TYPE: DNA
<213> ORGANISM: Artificial Sequence
<220> FEATURE:
<223> OTHER INFORMATION: Primer

<400> SEQUENCE: 298
ggtaccgctc gaggataact t                                                21
```

ANTIBODY LIBRARIES WITH MAXIMIZED ANTIBODY DEVELOPABILITY CHARACTERISTICS

CROSS REFERENCE TO RELATED APPLICATIONS

The present application is a continuation of, and claims the benefit of and priority to, U.S. patent application Ser. No. 16/505,358, filed on Jul. 8, 2019, which claims the benefit of, and priority to, U.S. Provisional Application No. 62/822,671, filed on Mar. 22, 2019, and U.S. Provisional Application No. 62/695,065, filed on Jul. 8, 2018, the entire contents of each of which are incorporated by reference herein.

REFERENCE TO SUBMISSION OF A SEQUENCE LISTING AS AN ASCII TEXT FILE

This application includes a Sequence Listing as a text file named "S2061.70000US02_SequenceListing" created on Jul. 31, 2019 and containing 116,415 bytes. The material contained in this text file is hereby incorporated by reference in its entirety for all purposes.

BACKGROUND OF THE INVENTION

There are currently three recombinant antibody platforms used to generate human antibodies for human therapeutic use: (1) the "humanization" of murine monoclonal antibodies; (2) the immunization of transgenic mice containing human antibody genes; and (3) in vitro selection from vast human antibody libraries. Immunization approaches depend upon the occurrence of appropriate in vivo immune responses, and may not yield antibodies with desired characteristics. In contrast, in vitro selection has the advantage that antibodies with specific properties can be directly selected, and once selected, can be easily improved in terms of affinity or specificity.

In general, there are two types of antibody libraries: synthetic and natural antibody libraries. Synthetic antibody libraries can be constructed by introducing randomized complementarity determining region (CDR) sequences into antibody frameworks. Such antibody libraries can have vast potential genetic diversity and improved expression via selection of well-behaved frameworks. However, synthetic antibody libraries also include many non-functional antibody members and exclude much natural diversity due to the formulaic manner used to generate diversity within a restricted set of framework scaffolds. Antibody libraries created from natural sources, known as natural antibody libraries, have the advantage that the rearranged V genes undergo quality control in the B cell, and consequently a far higher proportion of the V genes are biologically functional, even if the potential diversity is lower. Disadvantages include the challenges of obtaining large numbers of B-cells to increase diversity, and the poor expression and biophysical properties of some antibodies expressed recombinantly in *E. coli*, yeast or mammalian cells.

SUMMARY OF THE INVENTION

Provided herein are antibody libraries that comprise diversified heavy chain variable domains (VH) and/or light chain variable domains (VL), which comprise complementary determining regions (CDRs) obtained from naturally-occurring antibodies (e.g., naturally-occurring human antibodies or naturally-occurring camelid antibodies). Optionally, any of the VH CDRs and/or VL CDRs excludes at least members carrying one or more liabilities that affect one or more features of an antibody carrying such. Such antibody libraries, comprising CDRs from natural antibodies such as human antibodies, would have a high number of functional members and reflect natural diversity of human antibodies. Excluding members carrying one or more liabilities as described herein would enhance the percentage of members having desired properties, for example, high yield when produced by recombinant technology, high stability, reduced aggregation capacity, reduced liabilities as described below etc. Thus, the antibody libraries described herein would maximize antibody developability characteristics.

Accordingly, one aspect of the present disclosure features an antibody heavy chain library, comprising a plurality of nucleic acids or a plurality of genetic packages comprising the nucleic acids. The plurality of nucleic acids encode a population of antibody heavy chain variable domains, which collectively (in combination) comprise a population of heavy chain CDR1s, a population of heavy chain CDR2s, and/or a population of heavy chain CDR3s located at the CDR1 region, the CDR2 region, and the CDR3 region of a common antibody heavy chain variable domain gene. The heavy chain CDR1s, CDR2s, and/or CDR3s may be derived from naturally-occurring antibodies of a mammalian species, for example, human or camelid. In some embodiments, the plurality of nucleic acids encode a population of antibody heavy chain variable domains (e.g., human antibody heavy chain variable domains), which collectively (in combination) comprise a population of heavy chain CDR1s, a population of heavy chain CDR2s, and a population of heavy chain CDR3s.

In some embodiments, the common antibody heavy chain variable domain gene may be a human antibody heavy chain variable domain gene. Examples include VH1-24, VH2-70, VH3-7, VH4-30-4, VH5-51, VH1-18, VH1-69, VH3-23, VH5-10-1, VH3-9, or VH3-11. In some instances, the human antibody heavy chain variable region gene may be derived from a therapeutic antibody, for example, abrilumab, mepolizumab, crenezumab, necitumumab, anifrolumab, evoculumab, abituzumab, adalimumab, alemtuzumab, alirocumab, bapineuzumab, benralizumab, brodalumab, canakinumab, certolizumab, clazakizumab, dacetuzumab, daclizumab, daratumumab, eculizumab, efalizumab, elotuzumab, epratuzumab, farletuzumab, fasinumab, ficlatuzumab, fletikumab, fresolimumab, fulranumab, gevokizumab, ibalizumab, lintuzumab, matuzumab, mavrilimumab, mogamulizumab, motavizumab, natalizumab, nivolumab, obinutuzumab, ofatumumab, olokizumab, omalizumab, onartuzumab, otelixizumab, otlertuzumab, palivizumab, panitumumab, panobacumab, pertuzumab, pinatuzumab, polatuzumab, radretumab, ramucirumab, reslizumab, romosozumab, sarilumab, secukinumab, sifalimumab, tabalumab, tigatuzumab, tildrakizumab, tocilizumab, tovetumab, trastuzumab, vedolizumab, veltuzumab, zalutumumab, or zanolimumab.

In some embodiments, the population of heavy chain CDR1s, the population of heavy chain CDR2s, and/or the population of heavy chain CDR3s can be free (e.g., substantially free) of members comprising one or more of the following liabilities:
  (i) a glycosylation site (e.g., comprising the motif NXS, NXT, or NXC, in which X represents any naturally-occurring amino acid residue except for proline), (ii) a deamidation site (e.g., comprising the motif of NG, NS, NT, NN, NA, NH, ND, GNF, GNY, GNT, or GNG),
(iii) an isomerization site (e.g., comprising the motif of DT, DH, DS, DG, or DD),
(iv) an unpaired cysteine,
(v) net charge greater than 1 (e.g., in LCDR1-2 and/or HCDR1-2),
(vi) a tripeptide motif containing at least two aromatic residues (e.g., HYF or HWH), which may affect viscosity;
(vii) a motif that promotes aggregation (e.g., comprising the motif of FHW);
(viii) a polyspecificity site (e.g., GG, GGG, RR, VG, W, WV, WW, WWW, YY, or WXW, X referring to any amino acid residue),
(ix) a protease sensitive site (e.g., comprising the motif DX, in which X can be P, G, S, V, Y, F, Q, K, L, or D),
(x) an integrin binding site (e.g., comprising the motif RGD, LDV, or KGD),
(xi) a lysine glycation site such as a lysine glycation site (e.g., KE, EK, or ED),
(xii) a metal catalyzed fragmentation site (e.g., comprises the motif of HS, SH, KT, HXS, or SXH, in which X represents any amino acid residue),
(xiii) a polyspecificity aggregation site (e.g., the motif of $X_1X_2X_3$, wherein each of $X_1$, $X_2$, and $X_3$ independently is F, I, L, V, W, or Y), and/or
(xiv) a streptavidin binding motif of (e.g., comprises the motif HPQ, EPDW (SEQ ID NO: 117), PWXWL (SEQ ID NO: 118), in which X represents any amino acid residue, GDWVFI (SEQ ID NO: 119), or PWPWLG (SEQ ID NO: 120)).

Alternatively, or in addition, the population of heavy chain CDR1s, the population of heavy chain CDR2s, and/or the population of heavy chain CDR3s in the antibody library described herein is free of non-functional members.

In some embodiments, the population of antibody heavy chain CDR1 fragments, the population of antibody heavy chain CDR2 fragments, and/or the population of antibody heavy chain CDR3 fragments is free of members comprising at least two of (i)-(xiv). In some examples, at least the population of antibody heavy chain CDR1 fragments, the population of antibody heavy chain CDR2 fragments, and/or the population of antibody heavy chain CDR3 fragments is free of members comprising (i)-(ix), and optionally free of members comprising one or more of (x)-(xiv).

In some embodiments, the antibody library described herein comprise a population of heavy chain CDR1s and/or a population of heavy chain CDR2s that is free of members comprising one or more of (i)-(xiv), and a population of heavy chain CDR3s is derived from naturally-occurring human antibodies (without removal of one or more the liability (i)-(xiv) disclosed herein), for example, derived from human B lymphocytes or precursor cells thereof.

In some instances, members of the antibody library described herein comprise heavy chain CDR1, heavy chain CDR2, and/or heavy chain CDR3 that are not from the same naturally-occurring antibody. For examples, at least 50% of the members in the antibody library do not comprise heavy chain CDR1, heavy chain CDR2, and/or heavy chain CDR3 that are from the same naturally-occurring antibody.

In another aspect, the instant disclosure provides an antibody light chain library, comprising a plurality of nucleic acids or a plurality of genetic packages comprising the plurality of nucleic acids. The plurality of nucleic acids encode a population of antibody light chain variable domains (e.g., human antibody light chain variable domains), which collectively (in combination) comprise a population of light chain CDR1s, a population of light chain CDR2s, and/or a population of light chain CDR3s located at the CDR1 region, the CDR2 region, and the CDR3 region of a common antibody light chain variable domain gene (e.g., a human antibody light chain variable domain gene). The light chain CDR1s, CDR2s, and CDR3s, and optionally the common light chain variable domain gene may be derived from naturally-occurring antibodies of the same mammal species, for example, human. In some embodiments, the population of human antibody light chain variable domains collectively comprises a population of light chain CDR1s, a population of light chain CDR2s, and a population of light chain CDR3s. In some embodiments, the population of light chain CDR1s, the population of light chain CDR2s, and/or the population of light chain CDR3s is free of members comprising one or more of the liabilities described herein (e.g., (i)-(xiv) described herein).

In some embodiments, the antibody light chain library described herein may comprise members having light chain CDR1, light chain CDR2, and/or light chain CDR3 that are not from the same naturally-occurring antibody. For example, at least 50% of the members in the antibody light chain library do not comprise light chain CDR1, light chain CDR2, and/or light chain CDR3 that are from the same naturally-occurring antibody.

In some embodiments, the common antibody light chain variable domain gene used in the antibody light chain library may be a human antibody light chain variable domain gene. Examples include K1-12, K4-1, K2D-29, K3-11, K3-20, or L2-14. In some instances, the human antibody heavy chain variable region gene is derived from a therapeutic antibody such as those described herein.

Also provided herein is an antibody library that comprises (i) a first plurality of nucleic acids encoding the population of antibody heavy chain variable domains of the antibody heavy chain library described herein, and (ii) a second plurality of nucleic acids encoding the population of antibody light chain variable domains of the antibody light chain library described herein. Alternatively, the antibody library provided herein may comprise (i) a first plurality of nucleic acids encoding the population of antibody heavy chain variable domains of the antibody heavy chain library described herein, and (ii) a common light chain variable domain, which may be VK3-20.

Any of the antibody libraries disclosed herein may be of a suitable format, for example, a library of full-length antibodies, a library of antigen-binding fragments such as Fab fragments, a library of single-chain antibodies, or a library of single-domain antibodies (e.g., VHH antibodies). In some examples, the antibody library disclosed herein may be a human antibody library. In other examples, the antibody library disclosed herein may be a camelid VHH antibody library.

In another aspect, the present disclosure features a method for producing an antibody library, comprising:
providing (a) a first plurality of nucleic acids encoding a population of naturally-occurring antibody heavy chain complementary determining region 1 (CDR1) fragments, and/or (b) a second plurality of nucleic acids encoding a population of naturally-occurring antibody heavy chain complementary determining region 2 (CDR2) fragments; and inserting the first plurality of nucleic acids and/or the second plurality of nucleic acids into the CDR1 region and/or the CDR2 region, respectively, of an antibody heavy chain variable domain gene (e.g., those described herein), thereby producing an antibody library.

The method may further comprise:
provide a third plurality of nucleic acids encoding a population of naturally-occurring heavy chain complementary determining region 3 (CDR3) fragments, and inserting the third plurality of nucleic acids into the CDR3 region of the heavy chain variable region gene.

The heavy chain CDR1 fragments, the heavy chain CDR2 fragments, and the heavy chain CDR3 fragments may be derived from naturally-occurring antibodies of a mammalian species as disclosed herein. In some embodiments, the heavy chain CDR1, CDR2, and CDR3 fragments can be derived from the same mammalian species. Optionally, the common heavy chain variable region gene may also be derived from the same mammalian species.

In some embodiments, the antibody library comprises members in each of which the heavy chain CDR1, the heavy chain CDR2, and/or the heavy chain CDR3 are not from the same naturally-occurring antibody. For example, at least 50% of the members in the antibody library do not contain heavy chain CDR1, the heavy chain CDR2, and/or the heavy chain CDR3 from the same naturally-occurring antibody.

In some embodiments, the population of antibody heavy chain CDR1 fragments, the population of antibody heavy chain CDR2 fragments, and/or the population of antibody heavy chain CDR3 fragments is free of members comprising one or more of the liabilities described herein, e.g., (i)-(xiv) disclosed herein. For example, the population of antibody heavy chain CDR1 fragments, the population of antibody heavy chain CDR2 fragments, and/or the population of antibody heavy chain CDR3 fragments may be free of members comprising at least two of (i)-(xiv). In some instances, the population of antibody heavy chain CDR1 fragments, the population of antibody heavy chain CDR2 fragments, and/or the population of antibody heavy chain CDR3 fragments is free of members comprising any of (i)-(ix), optionally further free of one or more of (x)-(xiv).

In other embodiments, the population of antibody heavy chain CDR1 fragments and/or the population of antibody heavy chain CDR2 fragments is free of members comprising one or more of the liabilities described herein (e.g., at least two of (i) to (xiv) or all of (i) to (xiv)) and the population of human antibody heavy chain CDR3 fragments are from naturally-occurring human antibodies (e.g., derived from B cells), which may not have the one or more liabilities excluded.

In some embodiments, the first plurality of nucleic acids, the second plurality of nucleic acids, and/or the third plurality of nucleic acids is produced by a process comprising:
(a) obtaining amino acid sequences of the heavy chain CDR1 regions, the heavy chain CDR2 regions, and/or the heavy chain CDR3 regions of a population of naturally-occurring antibodies (e.g., naturally-occurring human antibodies);
(b) excluding from (a) the heavy chain CDR1 amino acid sequences, the heavy chain CDR2 amino acid sequences, and/or the heavy chain CDR3 amino acid sequences that comprise one or more of liabilities (i) to (xiv) to obtain liability-free heavy chain CDR1 sequences, heavy chain CDR2 sequences, and/or heavy chain CDR3 sequences; and
(c) synthesizing the first plurality of nucleic acids that encode the liability-free heavy chain CDR1 regions, the second plurality of nucleic acids that encode the liability-free heavy chain CDR2 regions, and/or the third plurality of nucleic acids that encode the liability-free heavy chain CDR3 regions.

In some instances, the process described above may further comprise (d) isolating functional members from the liability-free heavy chain CDR1, CDR2, and/or CDR3 regions. For example, the functional members of the liability-free heavy chain CDR1, CDR2, and/or CDR3 can be isolated by expressing antibodies comprising the liability-free heavy chain CDR1, CDR2, and/or CDR3 regions in host cells in a manner that the antibodies are displayed on surface of the host cells, isolating the antibodies that display on the host cells, show improved folding, and/or show reduced binding to polyspecificity reagents and identifying the CDR1, CDR2, and/or CDR3 regions in the displayed antibodies, which are functional members of the liability-free heavy chain CDR1, CDR2, and/or CDR3 regions.

The method for producing an antibody library as described herein may further comprise:
(i) providing a fourth plurality of nucleic acids encoding a population of naturally-occurring antibody light chain complementary determining region 1 (CDR1) fragments, a fifth plurality of nucleic acids encoding a population of naturally-occurring antibody light chain complementary determining region 2 (CDR2) fragments, and/or a sixth plurality of nucleic acids encoding a population of naturally-occurring human antibody light chain complementary determining region 3 (CDR3) fragments, and
(ii) inserting the fourth plurality of nucleic acids, the fifth plurality of nucleic acids, and/or the sixth plurality of nucleic acids into the CDR1 region, the CDR2 region, and the CDR3 region, respectively, of an antibody light chain variable domain gene (e.g., those described herein).

The light chain CDR1 fragments, the light chain CDR2 fragments, and the light chain CDR3 fragments may be derived from naturally-occurring antibodies of a mammalian species as disclosed herein. In some embodiments, the light chain CDR1, CDR2, and CDR3 fragments can be derived from the same mammalian species. Optionally, the common light chain variable region gene may also be derived from the same mammalian species.

The population of naturally-occurring antibody light chain CDR1 fragments, the population of antibody light chain CDR2 fragments, and/or the population of antibody light chain CDR3 fragments may be free of members comprising one or more of the liabilities described herein (e.g., at least two or all of (i) to (xiv) described herein). The antibody library may comprise members, each of which comprises a light chain CDR1, a light chain CDR2, and/or a light chain CDR3 that are not found in the same naturally-occurring antibody. For example, at least 50% of the members in the antibody library comprise light chain CDR1, light chain CDR2, and/or light chain CDR3 that are not found in the same naturally-occurring antibody.

In some embodiments, the fourth plurality of nucleic acids, the fifth plurality of nucleic acids, and/or the sixth plurality of nucleic acids is produced by a process comprising:
(a) obtaining amino acid sequences of the light chain CDR1, CDR2, and/or CDR3 regions of a population of naturally-occurring antibodies (e.g., naturally-occurring human antibodies),
(b) excluding from (a) the light chain CDR1, CDR2, and/or CDR3 amino acid sequences that comprise one or more of (i) to (x) to obtain liability-free light chain CDR1, CDR2, and/or CDR3 sequences, and (c) synthesizing the fourth plurality of nucleic acids, the fifth plurality of the nucleic acids, and/or the sixth plurality of nucleic acids that encode the liability-free light chain CDR1, CDR2, and/or CDR3 regions.

The above process may further comprise (d) isolating functional members from the liability-free light chain CDR1, CDR2, and/or CDR3 regions. For example, the functional members of the liability-free light chain CDR1, CDR2, and/or CDR3 are isolated by expressing antibodies comprising the liability-free light chain CDR1, CDR2, and/or CDR3 regions in host cells in a manner that the antibodies are displayed on surface of the host cells, isolating the antibodies that display on the host cells, show improved folding, and/or show reduced binding to polyspecificity reagents and identifying the CDR1, CDR2, and/or CDR3 regions in the displayed antibodies, which are functional members of the liability-free light chain CDR1, CDR2, and/or CDR3 regions.

Further, the present disclosure features a method for making an antibody light chain library, the method comprising:

(i) providing a first plurality of nucleic acids encoding a population of naturally-occurring antibody light chain complementary determining region 1 (CDR1) fragments, a second plurality of nucleic acids encoding a population of naturally-occurring antibody light chain complementary determining region 2 (CDR2) fragments, and/or a third plurality of nucleic acids encoding a population of naturally-occurring antibody light chain complementary determining region 3 (CDR3) fragments, and (ii) inserting the first plurality of nucleic acids, the second plurality of nucleic acids, and/or the third plurality of nucleic acids into the CDR1 region, the CDR2 region, and the CDR3 region, respectively, of an antibody light chain variable domain gene (e.g., those described herein).

The light chain CDR1 fragments, the light chain CDR2 fragments, and the light chain CDR3 fragments may be derived from naturally-occurring antibodies of a mammalian species as disclosed herein. In some embodiments, the light chain CDR1, CDR2, and CDR3 fragments can be derived from the same mammalian species. Optionally, the common light chain variable region gene may also be derived from the same mammalian species.

Also within the scope of the present disclosure are antibody libraries (e.g., antibody heavy chain libraries, antibody light chain libraries, or a combination thereof) produced by any of the methods described herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The instant application contains at least one drawing executed in color.

FIG. 3 is a schematic illustrating an exemplary design of cloning LCDR1 (as an example) into a selected light chain scaffold. Exemplary vector nucleic acids and corresponding amino acids are shown. The nucleic acid sequences correspond to SEQ ID NO: 1 (top) and SEQ ID NO: 2 (bottom). The amino acid sequence corresponds to SEQ ID NO: 3.

FIG. 5 illustrates exemplary HCDR2 sequences comprising liabilities, such as deamidation sites, isomerization sites, glycosylation sites, or unpaired cysteine (highlighted). The first sequence of each column shows a graphical representation of a consensus sequence, which is followed by exemplary variant sequences. The depicted sequences in the "Deamidation column" correspond to SEQ ID NOs: 4-24 (top to bottom). The depicted sequences in the "Isomerization column" correspond to SEQ ID NOs: 25-45 (top to bottom). The depicted sequences in the "Glycosylation column" correspond to SEQ ID NOs: 46-66 (top to bottom). The depicted sequences in the "Unpaired Cysteine column" correspond to SEQ ID NOs: 67-87 (top to bottom).

FIG. 21 includes graphs showing the length distribution of CDRs in Library 6 (using scaffold derived from evoculumab). The germline length for each CDR is indicated under each graph and the CDRs outside of the highlighted region are eliminated for anomalous length.

FIGS. 22A-22F includes graphs showing natural distribution (blue) and replicated natural designed distributions before (red) and after (green) filtering for well folded sequences. Data is shows for 6 different scaffolds/germlines at each of LCDR1-3 and HCDR1-2. The results are based on sequencing the libraries illustrated in FIG. 25B-G.

FIGS. 22G-22L includes cumulative plots for the diversity at each CDR position assessed for a natural distribution (natural library—blue), and replicated natural designed distributions before (red) and after (green) filtering for well folded sequences. The results are based on sequencing the libraries illustrated in FIG. 25B-25G.

FIGS. 25B-25G illustrate the results of applying the exemplary process of isolating displayed single CDR loop libraries for each of the CDR (HCDR1-1, LCDR1-3) libraries displayed in yeast. The X axis indicates the level of antibody display, while the Y axis indicates the number of clones at each particular display level. For all histograms the display level of the clinical candidate is shown as a dotted blue line. For LCDR1-2 and HCDR1-2, fluorescence activated cell sorting was used to sort the most fluorescent 2% of yeast, corresponding to yeast displaying the most highly expressed antibodies. The display levels for the SV5 sorted (blue plot) and the most fluorescent 2% (red plot) are shown. For LCDR3, magnetic activated cell sorting was used to sort yeast displaying the most highly expressed antibodies. The transformed yeast clones (blue plot) are compared to the magnetic activated cell sorted yeast clones (red).

DETAILED DESCRIPTION OF THE INVENTION

Figure 1:
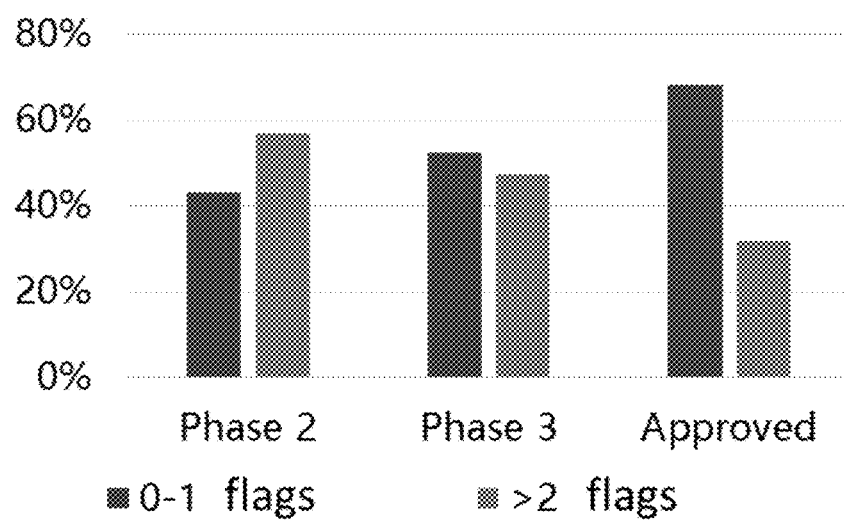
FIG. 1 is a chart showing the percentages of therapeutic antibodies in Phase 2 or Phase 3 clinical trials or approved therapeutic antibodies that are suitable or non-suitable for use as scaffold for antibody library construction. Suitable scaffolds for each of Phase 2, Phase 3, and Approved: 0-1 flags (left bar). Non-suitable scaffolds for each of Phase 2, Phase 3, and Approved: >2 flags (right bar).

It is generally accepted that the larger or more diverse an antibody library, measured in terms of the number of different antibodies, the better the antibodies that can be selected from it. Griffiths et al., *EMBO J* 13(14):3245-3260, 1994 and Perelson et al., *J Theor Biol.*, 81(4):645-70, 1979. The diversity of most antibody libraries has been estimated by counting the number of transformants, assuming that each colony represents a different antibody.

It was generally assumed that the VH gene diversity was the same as the number of colonies obtained, e.g., ~$10^8$ for the library described in Sblattero et al., *Nat Biotechnol.*, 18(1):75-80, 2000. However, next-generation sequencing (NGS) showed that the VH clonal diversity (unique HCDR3 amino acid sequences) was actually ~30 fold lower ($3 \times 10^6$). D'Angelo et al., *MAbs.*, 6(1):160-72, 2014. Notwithstanding this apparent low diversity, many antibodies have been selected from this library. See, e.g., Sblattero et al., *Nat Biotechnol.*, 18(1):75-80, 2000; Glanville et al., *Curr Opin Struct Biol.*, 33:146-60, 2015; Lou et al., *Journal of immunological methods;* 253(1-2):233-42, 2001; Kehoe et al., *Mol Cell Proteomics,* 5(12):2350-63, 2006; Ayriss et al., *J Proteome Res.* 6(3):1072-82, 2007; Velappan et al., *Journal of immunological methods,* 321(1-2):60-9, 2007; Lillo et al., *PLoS One,* 6(12):e27756, 2011; Ferrara et al., *PLoS One,* 7(11):e49535, 2012; Close et al., *BMC Microbiol.* 13:270, 2013; and Ferrara et al., *MAbs,* 7(1):32-41, 2015.

NGS sequencing of another natural antibody library showed an even lower measured VH diversity ($2\times10^5$), even though the number of donors used (654) was extremely high, and the estimated number of colonies was $3\times10^{10}$. Glanville et al., *Proceedings of the National Academy of Sciences of the United States of America,* 106(48):20216-21, 2009. Further, Fantini et al. *PLoS One.* 12(5):e0177574, 2017 described three libraries with maximal diversities (numbers of colonies) $6-16\times10^6$, and estimated NGS diversities of $3-9\times10^6$.

While genetic diversity is essential, effective functional diversity is even more important: a high genetic diversity is of no utility if the encoded antibodies are non-functional and unable to fold properly. Indeed, a single amino acid change in an antibody can result in dramatic changes in expression levels and stability. Some publications have shown the superiority of natural antibody libraries over synthetic ones. Hugo et al., *Protein Eng.,* 16(5):381-6, 2003; Wang et al., *Proteins,* 82(10):2620-30, 2014; and Chan et al., *Journal of immunological methods,* 373(1-2):79-88, 2011. Natural diversity has the advantage that it has been prescreened for functionality by the immune system. However, it has the disadvantage that some antibodies are poorly expressed and folded in in vitro display systems, and that diversity can be dominated by a small number of clones.

The present disclosure aims, at least in part, at constructing antibody libraries comprising natural diversity such that the members of the libraries would be prescreened by the immune system for functionality, while excluding members that contain potential liabilities, would be poorly expressed, aggregating and/or poorly folded in a common screening system (e.g., yeast display, phage display, or a folding reporter such as ß-lactamase; see, e.g., Saunders et al., *Nat. Che Biol.,* 12:94-101; 1988; and D'Angelo et al., *BMC genomics* 12, suppl. 1, S1-S5; 2011; or green fluorescent protein; see e.g. Waldo, et al., *Nat. Biotechnol.,* 17: 691-5; 1999; Cabantous, et al., *PLoS ONE.,* 3:e2387; 2008; and Cabantous, et al., *J Struct Funct Genomics,* 6:113-9; 2005). The present disclosure thus features, in some embodiments, a method to create extremely diverse, highly functional antibody libraries by combining naturally occurring CDRs, including naturally occurring CDRs containing somatic mutations generated in vivo, within antibody scaffolds such that members of the antibody libraries are expected to be well expressed and/or folded, and lacking liabilities.

As used herein, the term "liability" refers to a motif in an antibody (e.g., located in a heavy chain or light chain CDR region) that would negatively affect one or more desired features of the antibody (e.g., stability, good expression in an expression or display system, proper folding, no or reduced aggregation, solubility, no or reduced integrin binding, no or reduced glycosylation, no or reduced deamidation, no or reduced isomerization, no unpaired cysteine, or no or reduced protease sensitivity, etc.). By virtue of being comprised of highly functional members, such an antibody library would be expected to be functionally much larger than libraries of similar genetic size, in which antibodies are present that contain any of these liabilities. In other words, the antibody libraries disclosed herein would have a much larger effective diversity.

I. Antibody Libraries and Methods of Construction

Provided herein are antibody libraries comprising the heavy chain and/or light chain CDR populations as described herein, wherein the heavy chain CDRs and/or light chain CDRs are inserted into a pre-selected heavy chain variable domain gene and/or a pre-selected light chain variable domain gene as also described herein, as well as methods of producing such antibody libraries. The heavy chain CDR1s, CDR2s, and/or CDR3s, and the pre-selected heavy chain variable domain may be of a mammalian species, for example, human, mouse, rat, rabbit, dog, pig, or camelid such as camel or llama. In some instances, the heavy chain CDR1s, CDR2s, and CDR3s may be derived from antibodies of the same mammalian species (e.g., human or camelid). Optionally, the pre-selected heavy chain variable domain gene may be from the same mammalian species. Alternatively, the heavy chain CDR1s, CDR2s, and/or CDR3s, and optionally the pre-selected heavy chain variable domain gene may be derived from naturally-occurring antibodies of different mammalian species.

Similarly, the light chain CDR1s, CDR2s, and CDR3s, as well as the pre-selected light chain variable domain gene may be of a mammalian species such as those described herein. In some instances, the light chain CDR1s, CDR2s, and CDR3s may be derived from antibodies of the same mammalian species (e.g., human or camelid). Optionally, the pre-selected light chain variable domain gene may be from the same mammalian species. Alternatively, the light chain CDR1s, CDR2s, and/or CDR3s, and optionally the pre-selected light chain variable domain gene may be derived from naturally-occurring antibodies of different mammalian species.

In some embodiments, the heavy chain CDRs and the pre-selected variable domain gene, and the light chain CDRs and the pre-selected variable domain gene are all of the same mammal species, for example, human.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody encompasses not only intact (e.g., full-length) antibodies, but also antigen-binding fragments thereof (such as Fab, Fab', F(ab')2, Fv), single-chain antibody (scFv), fusion proteins comprising an antibody portion, diabodies, nanobodies, single domain antibodies (also known as nanobodies, e.g., a $V_H$ only antibody such as the VhH antibodies found in camelids), or multi-specific antibodies (e.g., bispecific antibodies).

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition,* U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs).

Single-domain antibodies, also known as nanobodies, are also within the scope of the present disclosure. In some embodiments, a single-domain antibody contains only a heavy chain (VHH). Heavy chain only antibodies (HcAb) are naturally produced by camelids and sharks. The antigen binding portion of the HcAb is comprised of the VHH fragment. Vincke et al., *Methods Mol Biol.* 911:15-26 (2012).

The antibody libraries disclosed herein may contain a population of antibodies of any suitable format. In some embodiments, the antibody library discloses herein comprise a population of full-length antibodies, which may be of any suitable family (e.g., IgG, or IgA). In other embodiments, the antibody library disclosed herein comprise a population of antigen-binding fragments, for example Fab fragments. In yet other embodiments, the antibody library disclosed herein comprise a population of single-chain antibodies. Alternatively, the antibody library disclosed herein may comprise a population of single-domain antibodies such as VHH fragments.

Exemplary steps for constructing the antibody libraries described herein may include:
(1) Identifying suitable VH/VL pairs for use as variable gene scaffolds;
(2) Generating vectors based on the scaffolds containing a single insertion site for each CDR, the remaining CDRs may remain unchanged;
(3) Identifying naturally occurring CDRs by analysis of a database of naturally occurring antibody sequences (which may be obtained from sequencing members of a natural antibody library);
(4) Eliminating from the database of naturally occurring CDR sequences those sequences likely to encode liabilities;
(5) Synthesize the remaining set of CDRs as oligonucleotides;
(6) Inserting the CDRs at their appropriate sites within the previously modified scaffolds, each scaffold containing CDRs at only one site (e.g., the identified collection of HCDR1s is inserted at the HCDR1 site of the modified scaffold).

In some embodiments, the CDRs (e.g., CDR1, CDR2, CDR3, or a combination thereof) identified as described herein may be experimentally screened or selected for good folding and/or expression and screened or selected against liabilities such as poor folding, poor expression, polyreactivity or aggregation. The selected CDRs may be inserted into complete V domains within the context of the scaffolds. The resultant complete V domains could be further screened and selected for good folding and/or expression, and/or screened and selected against liabilities such as poor folding or expression, polyreactivity or aggregation. The selected VH/VL complete scaffold pairs can be assembled and cloned into an appropriate display vector (e.g., phage or yeast) for screening of antibodies having desired binding specificity.

A. Selection of Heavy Chain and Light Chain Variable Domain Framework Scaffolds

In some embodiments, the heavy chain and/or light chain framework scaffolds used in constructing the antibody libraries described here may be derived from commercially available therapeutic antibodies (e.g., those whose marketing authorization has been approved by the US Food and Drug Administration or/or the European Medicines Agency) or therapeutic antibodies that are currently in clinical trials, for example, in phase II or phase III trials. As used herein, a therapeutic antibody refers to the antibody molecule of an approved drug product (e.g., in the US, in EP, or in other jurisdictions such as CA or JP), or an antibody molecule that has been or is currently in a clinical trial in a suitable jurisdiction, for example, in the US or in Europe.

The germline heavy chain variable domain and light chain variable domain genes used in such therapeutic antibodies can be examined for features such as aggregation, hydrophobic interaction, polyspecificity, monomericity, level of expression in mammalian host cells (e.g., in HEK cells or CHO cells), Tm of its Fab form, and purification characteristics. See Table 1. Those having desired features, for example, high expression levels in mammalian cells (e.g., ≥50 mg/L in HEK cells), high Fab Tm (e.g., >64° C.), low slope for accelerated stability (e.g., <0.09), etc. can be selected as framework scaffolds for library constructions. Additional features and selection criterion are provided in Table 1, which shows as exemplary examples those therapeutic antibodies with the best properties, as well as three additional antibodies with poor therapeutic properties. This data is derived from Jain, T. et al. Biophysical properties of the clinical-stage antibody landscape. *Proceedings of the National Academy of Sciences of the United States of America* 114, 944-949, doi:10.1073/pnas.1616408114 (2017).

For each characteristic being evaluated, the worst 10% of the evaluated therapeutic antibodies can be assigned with a flag. See FIG. 1. In some instances, those therapeutic antibodies having less than 2 flags (e.g., having 1 flag or none) may be selected for use as the heavy chain and/or light chain framework scaffold.

In some embodiments, the heavy chain variable domain gene for use as the heavy chain framework scaffold can be VH1-24, VH2-70, VH3-7, VH4-30-4, VH5-51, VH1-18, VH1-69, VH3-23, VH5-10-1, VH3-9, or VH3-11. Alternatively, or in addition, the light chain variable domain gene for use as the light chain framework scaffold can be K1-12, K4-1, K2D-29, K3-11, K3-20, or L2-14. Such heavy chain and/or light chain framework scaffolds may be germline VH and/or VL genes. Alternatively, the heavy chain and/or light chain framework scaffolds may contain one or more mutations in one or more framework regions (e.g., FR1, FR2, FR3, or FR4) as compared with the germline gene counterpart. Such mutations may be present within the therapeutic antibody, or may be introduced to avoid specific liabilities, e.g., methionine oxidation, aggregation, integrin binding, glycosylation, deamidation, isomerization, unpaired cysteine, or protease sensitivity. In specific examples, the antibody library described herein uses the following VH and VL framework scaffold pairs: VH1-24/VK1-12, VH2-70/VK4-1, VH3-7/VK2D-29, VH4-30-4/VK3-11, VH5-51/VK3-20, or VH1-18/VL2-14.

In some specific examples, the VH and/or VL framework scaffolds used in the antibody library described herein are derived from abrilumab, mepolizumab, crenezumab, necitumumab, anifrolumab, or evoculumab, the characteristics of each of which are provided in Table 2. As used herein, "derived from" refers to the use of the VH and/or VL genes of any of these therapeutic antibodies, either with no modification, or with one or more mutations introduced into one or more of the framework regions, for example, up to 5 amino acid substitutions (e.g., up to 4, 3, 2, or 1 amino acid substitutions) in the VH gene (e.g., in one or more of the framework regions) and/or in the VL gene (e.g., in one or more of the framework regions).

In some instances, the mutations introduced into a germline VH and/or VL gene or introduced into the VH and/or VL gene of a reference therapeutic antibody (e.g., those listed in Table 2) may be conservative substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The amino acid sequences of exemplary VH and VL framework scaffolds are provided below (with CDRs that are modified indicated in boldface and mutations relative to parent therapeutic antibodies listed in Table 2 underlined):

```
Scaffold derived from abrilumab:
CDRs are bold and underlined
Mutations from the original antibody are
italicized (all Jκ have been replaced for Jκ4).
VL:
                                      (SEQ ID NO: 121)
DIQMTQSPSSVSASVGDRVTITCRASQGISSWLAWYQQKPGKAPKLLIYGA

SNLESGVPSRFSGSGSGTDFTLTISSLQPEDFANYYCQQANSFPWTFGGGT

KVEIK

Linker:
                                      (SEQ ID NO: 122)
SGGSTITSYNVYYTKLSSSGT VH:
                                      (SEQ ID NO: 123)
QVQLVQSGAEVKKPGASVKVSCKVSGYTLSDLSIHWVRQAPGKGLEWMGGF

DPQDGETIYAQKFQGRVTMTEDTSTDTAYMELSSLKSEDTAVYYCATGSSS

SWFDPWGQGTLVTVSS

Scaffold derived from mepolizumab:
VL:
                                      (SEQ ID NO: 124)
DIVMTQSPDSLAVSLGERATINCKSSQSLLNSGNQKNYLAWYQQKPGQPPK

LLIYGASTRESGVPDRFSGSGSGTDFTLTISSLQAEDVAVYYCQNVHSFPF

TFGGGTKVEIK

Linker:
                                      (SEQ ID NO: 125)
SGGSTITSYNVYYTKLSSSGT VH:
                                      (SEQ ID NO: 126)
QVTLRESGPALVKPTQTLTLTCTVSGFSLSAYSVNWIRQPPGKALEWLAMI

WGDGKIVYNSALKSRLTISKDTSKNQVVLTMTNMDPVDTATYYCAGDGYYP

YAMDNWGQGTLVTVSS

Scaffold derived from crenezumab:
VL:
                                      (SEQ ID NO: 127)
DIVMTQSPLSLPVTPGEPASISCRSSQSLVYSNGDTYLHWYLQKPGQSPQL

LIYKVSNRFSGVPDRFSGSGSGTDFTLKISRVEAEDVGVYYCSQSTHVPWT

FGGGTKVEIK

Linker:
                                      (SEQ ID NO: 128)
SGGSTITSYNVYYTKLSSSGT VH:
                                      (SEQ ID NO: 129)
EVQLVESGGGLVQPGGSLRLSCAASGFTFSSYGMSWVRQAPGKGLELVASI

NSNGGSTYYPDSVKGRFTISRDNAKNSLYLQMNSLRAEDTAVYYCASGDYW

GQGTTVTVSS

Scaffold derived from necitumumab:
VL:
                                      (SEQ ID NO: 130)
EIVMTQSPATLSLSPGERATLSCRASQSVSSYLAWYQQKPGQAPRLLIYDA

SNRATGIPARFSGSGSGTDFTLTISSLEPEDFAVYYCHQYGSTPLTFGGGT

KVEIK

Linker:
                                      (SEQ ID NO: 131)
SGGSTITSYNVYYTKLSSSGT VH:
                                      (SEQ ID NO: 132)
QVQLQESGPGLVKPSQTLSLTCTVSGGSISSGDYYWSWIRQPPGKGLEWIG

YIYYSGSTDYNPSLKSRVTMSVDTSKNQFSLKVNSVTAADTAVYYCARVSI

FGVGTFDYWGQGTLVTVSS

Scaffold derived from anifrolumab:
VL:
                                      (SEQ ID NO: 133)
EIVLTQSPGTLSLSPGERATLSCRASQSVSSSFLAWYQQKPGQAPRLLIYG

ASSRATGIPDRLSGSGSGTDFTLTITRLEPEDFAVYYCQQYDSSAITFGGG

TKVEIK

Linker:
                                      (SEQ ID NO: 134)
SGGSTITSYNVYYTKLSSSGT VH:
                                      (SEQ ID NO: 135)
EVQLVQSGAEVKKPGESLKISCKGSGYIFTNYWIAWVRQVPGKGLESMGIII

YPGDSDIRYSPSFQGQVTISADKSITTAYLQWSSLKASDTAIYYCARHDIE

GFDYWGRGTLVTVSS

Scaffold derived from evolocumab:
VL:
                                      (SEQ ID NO: 136)
ESALTQPASVSGSPGQSITISCTGTSSDVGGYNSVSWYQQHPGKAPKLMIY

EVSNRPSGVSNRFSGSKSGNTASLTISGLQAEDEADYYCNSYTSTSMVFGG

GTKLTVL

Linker:
                                      (SEQ ID NO: 137)
SGGSTITSYNVYYTKLSSSGT
```

-continued

VH:
(SEQ ID NO: 138)
EVQLVQSGAEVKKPGASVKVSCKASGYTLTSYGISWVRQAPGQGLEWMGWV

SFYNGNTNYAQKLQGRGTMTTDPSTSTAYMELRSLRSDDTAVYYCARGYGM

DVWGQGTTVTVSS

Any of the VH and/or VL framework scaffolds described herein can be used to construct a cassette that allows for cloning of one or more of pluralities of nucleic acids each encoding a diverse population of a heavy chain CDR or a light chain CDR into the corresponding framework scaffold at the corresponding CDR position.

In some instances, restriction sites can be introduced into a heavy chain scaffold flanking the CDR1 region, the CDR2 region, or the CDR3 region for cloning a plurality of nucleic acids encoding a diverse population of heavy chain CDR1s, heavy chain CDR2s, or heavy chain CDR3s, respectively. In some instances, restriction sites can be introduced into a heavy chain framework scaffold flanking at least two or the CDR1, CDR2, and CDR3 (e.g., CDR1+CDR2, CDR1+CDR3, or CDR2+CDR3) for cloning a combination of the corresponding CDR regions into the framework scaffold. In one example, restriction sites can be introduced into a heavy chain framework scaffold flanking all of the CDR1, CDR2, and CDR3 regions for cloning diverse heavy chain CDR1s, CDR2s, and CDR3s at the corresponding locations.

In some instances, restriction sites can be introduced into a light chain scaffold flanking the CDR1 region, the CDR2 region, or the CDR3 region for cloning a plurality of nucleic acids encoding a diverse population of light chain CDR1s, heavy chain CDR2s, or heavy chain CDR3s, respectively. In some instances, restriction sites can be introduced into a light chain framework scaffold flanking at least two or the CDR1, CDR2, and CDR3 (e.g., CDR1+CDR2, CDR1+CDR3, or CDR2+CDR3) for cloning a combination of the corresponding CDR regions into the framework scaffold. In one example, restriction sites can be introduced into a light chain framework scaffold flanking all of the CDR1, CDR2, and CDR3 regions for cloning diverse light chain CDR1s, CDR2s, and CDR3s at the corresponding locations.

Figure 2:
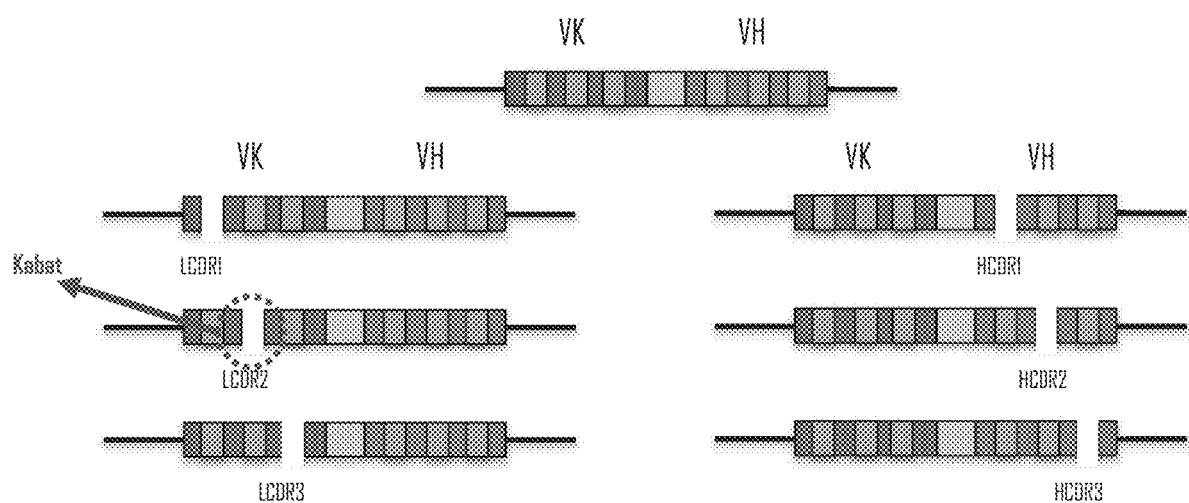
FIG. 2 is a schematic showing the seven scaffolds developed from the VH and/or VL gene of a selected therapeutic antibody. Except for LCDR2, all CDRs are as described by IMGT. LCDR2 uses the Kabat description.

FIGS. 2 and 3 illustrate an exemplary scheme for construction of cassettes for introducing heavy chain CDR1, CDR2, or CDR3 diversities into a heavy chain scaffold and/or cassette for introducing light chain CDR1, CDR2, or CDR3 diversities into a light chain scaffold.

The resultant cassettes can be located in a suitable expression vector for producing the encoded antibodies in a suitable expression, display or folding reporter system.

B. Heavy Chain and Light Chain CDR Populations

The heavy chain and/or light chain CDR1, CDR2, and/or CDR3 populations in the antibody libraries can be derived from naturally-occurring human antibodies. Such CDR sequences can be obtained by sequencing naturally-occurring antibodies (e.g., human antibodies) in existing natural antibody libraries and analyzing the heavy chain and light chain sequences thus obtained by conventional methods to identify heavy chain and/or light chain CDR sequences. Alternatively, or in addition, naturally-occurring antibody CDR sequences can be obtained by analyzing sequences of such antibodies in publicly available databases of naturally-occurring antibody sequences (e.g., human antibody sequences or camelid VHH antibody sequences), e.g., the NCBI database, the IMGT database, sequences from Jackson et al., J. Immunol. Methods, 324:26, 2007, and/or the sequences from Lee et al., Immunogenetics, 57:917, 2006, The Observed Antibody Space (antibodymap.org) described in Kovaltsuk, A. et al. Observed Antibody Space: A Resource for Data Mining Next-Generation Sequencing of Antibody Repertoires. *Journal of Immunology*, doi:10.4049/jimmunol.1800708 (2018), and/or the iReceptor database (ireceptor.irmacs.sfu.ca) described in Corrie, B. D. et al. iReceptor: A platform for querying and analyzing antibody/B-cell and T-cell receptor repertoire data across federated repositories. *Immunol Rev* 284, 24-41, doi:10.1111/imr.12666 (2018), and/or the sequence database described in Briney, B. et al., Commonality despite exceptional diversity in the baseline human antibody repertoire. *Nature*, doi: 10.1038/s41586-019-0879-y (2019).

The extent of the framework region and CDRs can be precisely identified using methodology known in the art, for example, by the Kabat definition, the IMGT definition, the Chothia definition, the AbM definition, and/or the contact definition, all of which are well known in the art. See, e.g. Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; Lefranc, M. P. et al. IMGT unique numbering for immunoglobulin and T cell receptor variable domains and Ig superfamily V-like domains. *Dev Comp Immunol* 27, 55-77 (2003) and Almagro, J. Mol. Recognit. 17:132-143 (2004). See also hgmp.mrc.ac.uk, IMGT.org and bioinf.org.uk/abs.

The heavy chain and/or light chain CDR1, CDR2, and/or CDR3 sequences thus obtained may be further analyzed to remove those that comprise a liability, e.g., those listed in Table 4. In some instances, heavy chain and/or light chain CDR1, CDR2, and/or CDR3 sequences comprising one of the liabilities listed in Table 4 (e.g., a glycosylation site, a deamidation site, an isomerization site, an unpaired cysteine, a net charge greater than 1 (e.g., in LCDR1-2 and/or HC CDR1-2), a tripeptide motif containing at least two aromatic residues (which may affect viscosity), a motif that promotes aggregation, (viii) a polyspecificity site such as those containing a motif of GG, GGG, RR, VG, W, WV, WW, WWW, YY, or, WXW, in which X represents any amino acid residue; a protease sensitive site (fragmentation sensitive site), or an integrin binding site) and/or FIG. 5 (using HC CDR2 as an example) can be removed such that the resultant antibody library is free (substantially free or completely free) of members comprising the excluded liability.

Alternatively or in addition, potential glycation sites such as lysine glycation sites may be removed. A glycation site refers to a site in a protein molecule that can be linked to a sugar molecule via a nonenzymatic process. Exemplary glycation sites include, but are not limited to, KE, EK, and ED. Additional liabilities include metal catalyzed fragmentation site (e.g., HS, SH, KT, HXS, or SXH, in which X represents any amino acid residue), polyspecificity aggregation site (e.g., having a motif of $X_1X_2X_3$, in which each of $X_1$, $X_2$, and $X_3$ is independently F, I, L, V, W, or Y), and streptavidin binding motif (e.g., HPQ, EPDW (SEQ ID NO: 117), PWXWL (SEQ ID NO: 118), in which X represents any amino acid residue, GDWVFI (SEQ ID NO: 119), and PWPWLG (SEQ ID NO: 120)).

Substantially free means that the number of a heavy or light chain CDR comprising the liability is less than 20% in the library, e.g., less than 15% or less than 10%.

In some examples, heavy chain and/or light chain CDR1, CDR2, and/or CDR3 sequences comprising two or more (e.g., 3, 4, 5, 6, 7, or more) of the liabilities noted above can be removed such that the resultant library is free of (substantially free of or completely free of) members comprising the excluded liabilities. In one example, heavy chain and/or light chain CDR1, CDR2, and/or CDR3 sequences comprising all of the liabilities listed in Table 4 can be removed such that the resultant library is free of (substantially free of or completely free of) members comprising any of the liabilities. Alternatively or in addition, heavy chain and/or light chain CDR1, CDR2, and/or CDR3 sequences comprising all of the liabilities listed in FIG. 5 can be removed such that the resultant library is free of (substantially free of or completely free of) members comprising any of the liabilities. In one specific example, heavy chain and/or light chain CDR1, CDR2, and/or CDR3 sequences comprising all of the liabilities disclosed herein can be removed such that the resultant library is free of (substantially free of or completely free of) members comprising any of the liabilities.

Figure 5:
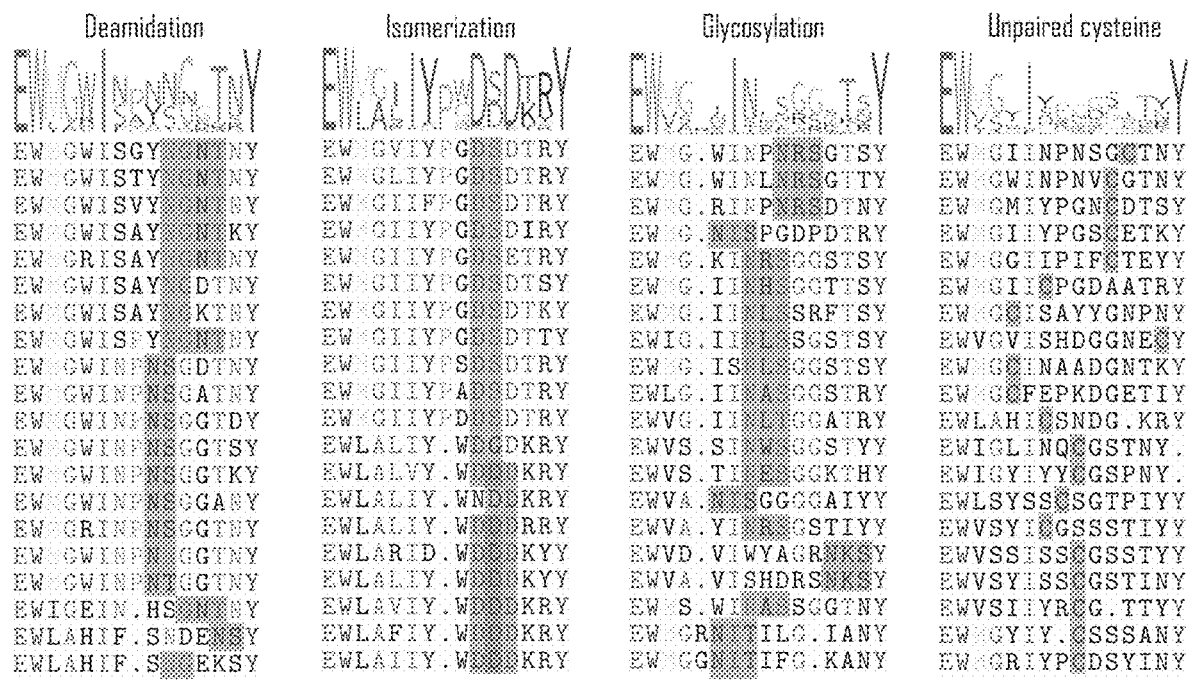

In some examples, heavy chain CDR1 and CDR2 sequences comprising one or more of liabilities, e.g., those listed in Table 4 and/or FIG. 5, can be removed, while heavy chain CDR3 sequences can be derived from naturally-occurring human antibodies without removal of members having the liabilities. Alternatively, heavy chain CDR3 sequences comprising one or more liabilities can also be removed. Alternatively, or in addition, light chain CDR1, CDR2, and CDR3 sequences comprising one or more of liabilities, e.g., those listed in Table 4 and illustrated by way of example in FIG. 5, can be removed.

In some examples, heavy and/or light chain CDR1, CDR2, and/or CDR3 sequences having anomalous lengths can also be excluded. For example, light chain CDR1 and/or CDR2 having a length that is beyond the scope of germline length ±2-aa could be excluded. See FIGS. 16-21.

In some examples, heavy chain CDR1 and CDR2 members containing deamidation sites (e.g., NG, NS, NT, NN, GNF, GNY, GNT, GNG), isomerization sites (e.g., DG, DS, DD), aggregation site (FHW); motifs affecting viscosity (e.g., HYF and HWH), motifs indicating poor developability (e.g., net charge ≥+1 in LCDR1-2 and/or HCDR1-2), unpaired cysterine, polyspecificity site (e.g., GGG, RR, VG, VV, VVV, WW, WWW, YY, WXW, X referring to any amino acid residue, and GG), and glycosylation sites (e.g., NXS or NXT, in which X is any amino acid residue except for proline) can be excluded. In some examples, one or more of the following liabilities in heavy chain CDR1 and heavy chain CDR2 members can also be excluded: additional glycosylation sites (e.g., NXC, X being any amino acid residue except for proline), additional deamination sites (e.g., NA, NH, and/or ND), additional isomerization sites (e.g., DT and/or DH), lysine glycation sites (e.g., KE, EK, and ED), integrin binding sites (e.g., RGD, RYD, LDV, and KGD), protease sensitive sites (fragmentation site) (e.g., DP, DG, DS, DV, DY, DF, DQ, DK, DL, and DD), metal catalyzed fragmentation sites (e.g., HS, SH, KT, HXS, and SXH, in which X represents any amino acid residue), polyspecificity aggregatin sites (e.g., having a motif of $X_1X_2X_3$, in which each of $X_1$, $X_2$, and $X_3$ independently is F, I, L, V, W, or Y), and/or streptavidin binding sites (e.g., HPQ, EPDW (SEQ ID NO: 117), PWXWL (SEQ ID NO: 118), in which X represents any amino acid residue, GDWVFI (SEQ ID NO: 119), and PWPWLG (SEQ ID NO: 120)).

In some examples, the heavy chain CDR3 members having the one or more liabilities described herein can also be excluded. Alternatively, the heavy chain CDR3 members may include those derived from naturally-occurring antibodies directly without removal of the one or more liabilities described herein.

Alternatively or in addition, light chain CDR1, CDR2, and/or CDR3 members containing deamidation sites (e.g., NG, NS, NT, NN, GNF, GNY, GNT, GNG), isomerization sites (e.g., DG, DS, DD), aggregation site (FHW); motifs affecting viscosity (e.g., HYF and HWH), motifs indicating poor developability (e.g., net charge ≥+1 in LCDR1-2, HCDR1-2), unpaired cysterine, polyspecificity site (e.g., GGG, RR, VG, VV, VVV, WW, WWW, YY, WXW, X referring to any amino acid residue, and GG), and glycosylation sites (e.g., NXS or NXT, in which X is any amino acid residue except for proline) can be excluded. In some examples, one or more of the following liabilities in light chain CDR1, CDR2, and/or CDR3 members can also be excluded: additional glycosylation sites (e.g., NXC, X being any amino acid residue except for proline), additional deamidation sites (e.g., NA, NH, and/or ND), additional isomerization sites (e.g., DT and/or DH), lysine glycation sites (e.g., KE, EK, and ED), integrin binding sites (e.g., RGD, RYD, LDV, and KGD), protease sensitive sites (fragmentation site) (e.g., DP, DG, DS, DV, DY, DF, DQ, DK, DL, and DD), metal catalyzed fragmentation sites (e.g., HS, SH, KT, HXS, and SXH, in which X represents any amino acid residue), polyspecificity aggregatin sites (e.g., having a motif of $X_1X_2X_3$, wherein each of $X_1$, $X_2$, and $X_3$ independently is F, I, L, V, W, or Y), and/or streptavidin binding sites (e.g., HPQ, EPDW (SEQ ID NO: 117), PWXWL (SEQ ID NO: 118), in which X represents any amino acid residue, GDWVFI (SEQ ID NO: 119), and PWPWLG (SEQ ID NO: 120)).

In some examples, the one or more liabilities described herein may be excluded from all of the light chain CDR1, CDR2, and CDR3 members.

The resultant heavy chain and/or light chain CDR1, CDR2, and/or CDR3 sequences obtained from naturally-occurring antibodies, either excluding sequences comprising one or more liabilities or maintaining all sequences, can be used as templates to synthesis nucleic acids encoding, and replicating, the CDR sequences. Such nucleic acids can be inserted into the corresponding CDR position in the VH and/or VL scaffolds disclosed herein, and are termed "replicated natural CDRs".

When desired, expression vectors carrying the VH and/or VL scaffolds with one or more heavy chain and or light chain CDRs inserted can be introduced into a suitable expression/display system for isolating functional members. Functional members include those having one or more superior features, for example, good expression and display in a suitable display system, improved folding, reduced aggregation or polyreactivity, and/or greater Tm. Such functional members can be identified by collecting host cells displaying antibodies produced from the expression vectors, and sequencing the corresponding heavy and/or light chain CDR sequences encoded by the expression vectors in the collected host cells.

For example, an initial antibody library may also be sorted for yeast displaying antibodies that have been stained with conformational probes that detect correct antibody folding. Traxlmayr et al., Arch Biochem Biophys. 526(2):174-80, 2012. Examples of such conformational probes include protein A (Hillson et al., The Journal of experimental medicine. 178(1):331-6, 1993; Akerstrom et al., 1994; J. Imm Methods, 177(1-2):151-63, 1994; and Roben et al., J. Immunology 154(12):6437-45, 1995) or protein L (Charbit et al., Gene, 70(1):181-9, 1988; Graille et al., Structure, 9(8):679-87, 2001; and Enever et al., Journal of molecular biology, 347(1):107-20, 2005), that are able to bind to VH3 and VK domains respectively, and derivatives of indole 3-butyric acid (Alves et al., Langmuir, 28(25):9640-8, 2012; Alves et al., Anal Chem., 84(18):7721-8, 2012; Alves et al., Bioconjug Chem., 25(7):1198-202, 2014; and Mustafaoglu et al., Biotechnol Bioeng., 112(7):1327-34, 2015) that binds to the "nucleotide binding site" found in all antibodies (Rajagopalan et al., Proceedings of the National Academy of Sciences of the United States of America, 93(12):6019-24, 1993).

The previous use of conformational probes has been shown to predict high expression and thermostability (Traxlmayr et al., 2012; Shusta et al., J Mol Biol. 292(5):949-56, 1999; Traxlmayr et al., Biochim Biophys Acta., 1824(4):542-9, 2012; Traxlmayr et al., Protein Eng Des Sel., 26(4):255-65, 2013; and Hasenhindl et al., Protein Eng Des Sel., 26(10):675-82, 2013) in yeast display. This approach selects for antibody fragments that are well expressed and well folded. Rather than positive selection for good display, each individual CDR library can be depleted of CDRs that contain liabilities. For example, adapting screens used for antibody screening (Yang et al., MAbs., 5(5):787-94, 2013; Kelly et al., MAbs, 7(4):770-7, 2015; Kohli et al., MAbs. 7(4):752-8, 2015; Obrezanova et al., MAbs., 7(2):352-63, 2015; Wu et al, Protein Eng Des Sel., 28(10):403-14, 2015; Yang et al., MAbs., 9(4):646-53, 2017; Xu et al., Protein Eng Des Sel., 26(10):663-70, 2013; and Kelly et al., MAbs., 9(7):1036-40, 2017) to yeast display sorting, and isolating those yeast displaying antibodies that correspond to the more "developable" phenotype selects for suitable CDRs that can then be combined to create highly functional libraries.

Examples of such selections include polyspecificity reagents, heparin or chaperones and only retaining those antibodies that do not bind such substances. Further stability increases can be generated by applying a heat shock step (Traxlmayr et al., 2012; Shusta et al., J Mol Biol. 292(5):949-56, 1999; Traxlmayr et al., Biochim Biophys Acta., 1824(4):542-9, 2012; Traxlmayr et al., Protein Eng Des Sel., 26(4):255-65, 2013; and Hasenhindl et al., Protein Eng Des Sel., 26(10):675-82, 2013). See also FIG. 23.

The sequences encoding functional members of the heavy and/or light CDR1, CDR2, and/or CDR3 can be used as templates for synthesizing nucleic acids coding for such functional members, or used directly. The resultant nucleic acids can then be inserted into the VH and/or VL scaffold as described herein to produce antibody libraries as also described herein. In some embodiments, the antibody library disclosed herein is substantially free of non-functional members, e.g., having less than 10% (e.g., less than 8%, less than 5%, less than 3%, less than 1%, or lower) non-functional members.

C. Antibody Libraries

The antibody libraries described herein may comprise a plurality of nucleic acids encoding a plurality of antibody heavy chain and/or antibody light chain variable domains, which collectively comprise a common VH and/or VL framework scaffold (e.g., those described herein) with a diverse population of heavy or light chain CDR1s, a diverse population of heavy or light chain CDR2s, and/or a diverse population of heavy or light chain CDRs inserted at the corresponding CDR positions.

In some embodiments, the antibody library described herein is a heavy chain library comprising a plurality of nucleic acids encoding a plurality of antibody heavy chain variable domains. In some examples, the heavy chain library may comprise at least $10^2$ diversity of heavy chain CDR1s (having at least $10^2$ unique heavy chain CDR1 sequences), for example, at least $10^3$, $10^4$, $10^5$ diversity or at least $10^6$ diversity. Alternatively, or in addition, the heavy chain library may comprise at least $10^2$ diversity of heavy chain CDR2s (having at least $10^2$ unique heavy chain CDR2 sequences), for example, at least $10^3$, $10^4$, $10^5$ diversity or at least $10^6$ diversity. In other examples, the heavy chain library may comprise at least $10^2$ diversity of heavy chain CDR3s (having at least $10^2$ unique heavy chain CDR3 sequences), for example, at least $10^3$, $10^4$, $10^5$ diversity, at least $10^6$ diversity, at least $10^7$ diversity, or at least $10^8$ diversity.

In some examples, the heavy chain library may comprise diversity only in the heavy chain CDR1s, the heavy chain CDR2s, or the heavy chain CDR3s. In other examples, the heavy chain library may comprise diversity in at least two of the heavy chain CDR1, CDR2, and CDR3 regions (e.g., CDR1+CDR2, CDR1+CDR3, or CDR2+CDR3). In one specific example, the heavy chain library comprises diversity in all of the heavy chain CDR1, CDR2, and CDR3 regions.

In some embodiments, the heavy chain library is a secondary library generated for affinity maturation of a pre-selected antibody (the parent antibody) with binding activity to a target antigen. Such a secondary library may comprise diversity in one or two of the heavy chain CDR regions, while keeping the other CDR sequence(s) of the parent antibody. For example, the secondary library may comprise the same heavy CDR1 and CDR2 sequences as the parent antibody, and a diverse population of heavy chain CDR3 sequences. Alternatively, the secondary library may comprise the same heavy CDR3 sequence as the parent antibody and a diverse population of heavy chain CDR1 and/or CDR2 sequences.

Any of the heavy chain libraries disclosed herein may be paired with a common light chain variable region. Alternatively, it may be paired with any of the light chain antibody libraries as also described herein.

Also provided herein are antibody light chain libraries that comprise a plurality of nucleic acids encoding a plurality of antibody light chain variable domains. In some examples, the light chain library may comprise at least $10^2$ diversity of light chain CDR1s (having at least $10^2$ unique light chain CDR1 sequences), for example, at least $10^3$, $10^4$, $10^5$ diversity or at least $10^6$ diversity. Alternatively, or in addition, the light chain library may comprise at least $10^2$ diversity of light chain CDR2s (having at least $10^2$ unique light chain CDR2 sequences), for example, at least $10^3$, $10^4$, $10^5$ diversity or at least $10^6$ diversity. In other examples, the light chain library may comprise at least $10^2$ diversity of light chain CDR3s (having at least $10^2$ unique light chain CDR3 sequences), for example, at least $10^3$, $10^4$, $10^5$ diversity, at least $10^6$ diversity, at least $10^7$ diversity, or at least $10^8$ diversity.

In some examples, the light chain library may comprise diversity only in the light chain CDR1s, the light chain CDR2s, or the light chain CDR3s. In other examples, the light chain library may comprise diversity in at least two of the light chain CDR1, CDR2, and CDR3 regions (e.g., CDR1+CDR2, CDR1+CDR3, or CDR2+CDR3). In one specific example, the light chain library comprises diversity in all of the light chain CDR1, CDR2, and CDR3 regions.

In some embodiments, the light chain library is a secondary library generated for affinity maturation of a pre-selected antibody (the parent antibody) with binding activity to a target antigen. Such a secondary library may comprise diversity in one or two of the light chain CDR regions, while keeping the other CDR sequence(s) of the parent antibody. For example, the secondary library may comprise the same light CDR1 and CDR2 sequences as the parent antibody, and a diverse population of light chain CDR3 sequences. Alternatively, the secondary library may comprise the same light CDR3 sequence as the parent antibody and a diverse population of light chain CDR1 and/or CDR2 sequences.

Figure 35:
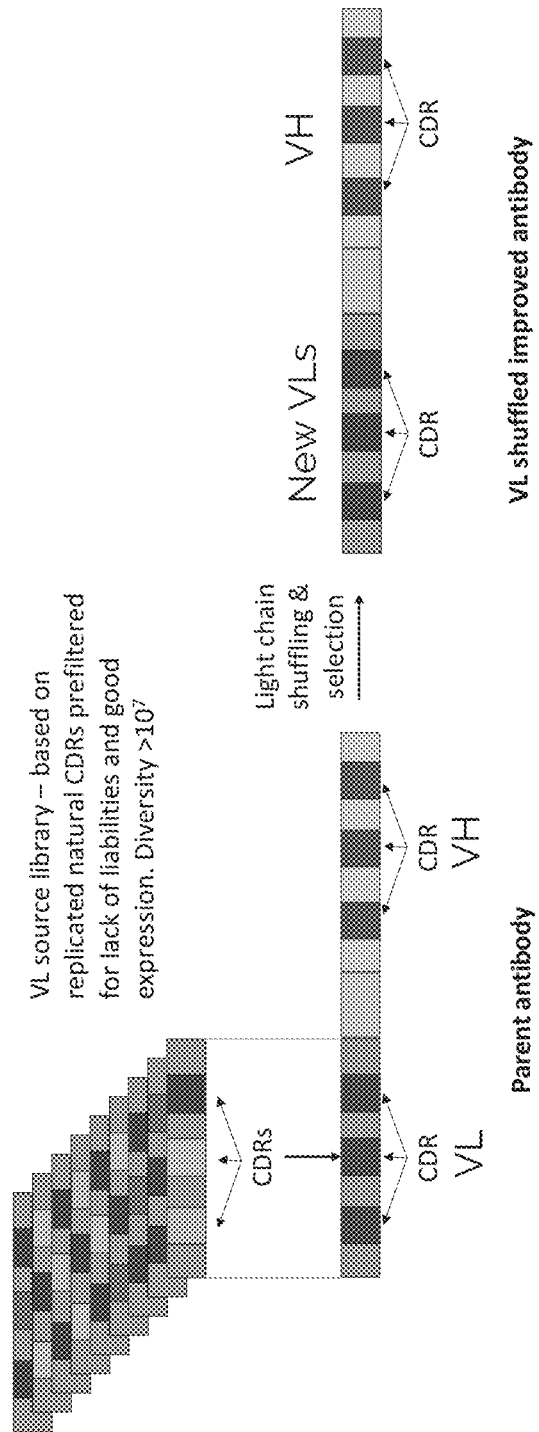
FIG. 35 is a diagram illustrating an exemplary affinity maturation approach via VL shuffling.
Figure 36:
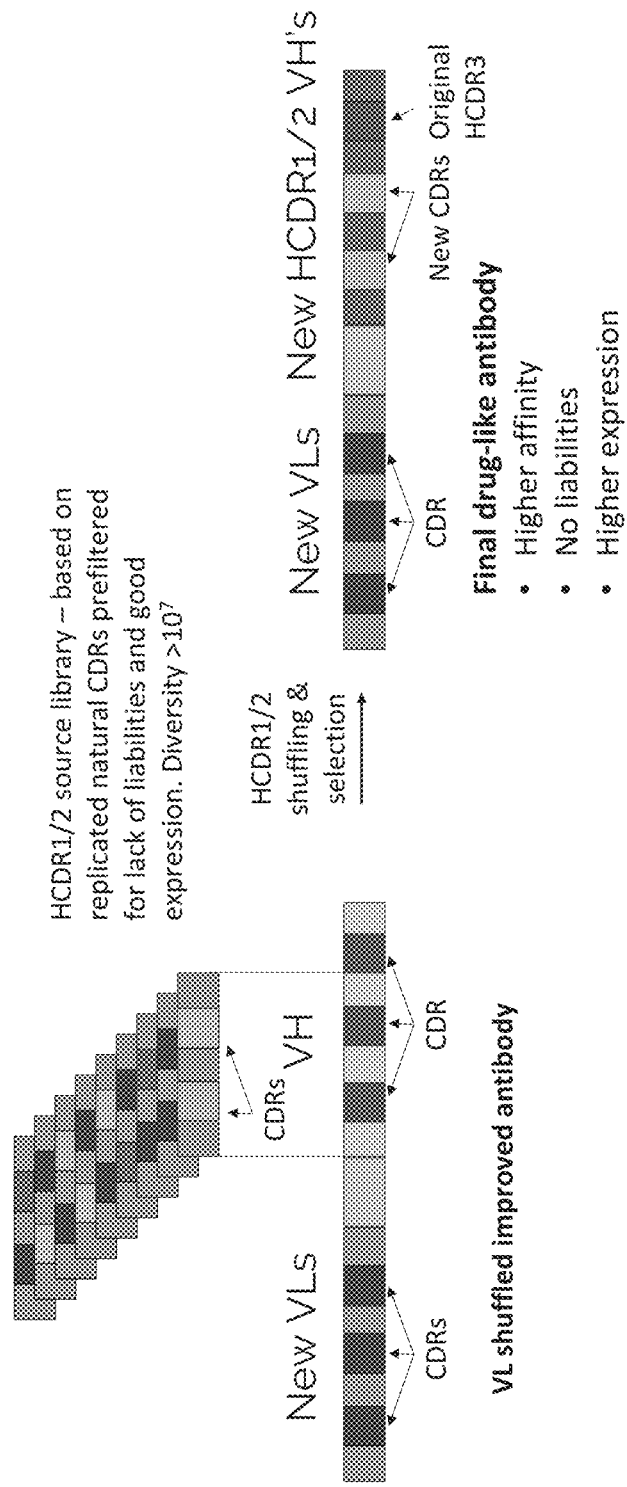
FIG. 36 is a diagram illustrating further HC CDR1 and HC CDR2 shuffling, following the VL shuffling depicted in FIG. 32.

As illustrated in FIG. 35 and FIG. 36, a secondary library may be generated via VL shuffling and/or VH CDR1 and/or CDR2 shuffling.

Any of the light chain libraries disclosed herein may be paired with a common heavy chain variable region. See, e.g., FIG. 26. Alternatively, it may be paired with any of the heavy chain antibody libraries as also described herein. See, e.g., FIG. 27.

II. Antibody Library Screening

Any of the antibody libraries described herein may be used to screen for antibodies having binding specificity to an antigen of interest. Antibodies encoded by the nucleic acids in the library can be expressed and displayed using a suitable expressing/display system, for example, a cell-free display system (e.g., ribosome display), a phage display system, a prokaryotic cell-based display system (e.g., bacterial display), or a eukaryotic cell-based display system (e.g., yeast display or mammalian cell display). In certain embodiments, the antibody libraries are expressed and displayed on yeast cells. In other embodiments, the antibody libraries are expressed and displayed on phage particles (phage display). In other embodiments two or more display systems are used, e.g. phage display followed by yeast display.

The library of antibodies may be expressed/displayed in a suitable system, e.g., those described herein, in any format. Examples include intact antibodies (full-length antibodies), antigen-binding fragments thereof (e.g., Fab), or single chain antibodies (scFv).

Phage display is a protein display format using bacteriophages (e.g., phage f1, fd, and M13). In this system, at least one antibody chain (e.g., the heavy chain and/or the light chain) is typically covalently linked to a bacteriophage coat protein, for example, a gene III protein, a gene VIII protein, or a major coat protein (see, e.g., WO 00/71694). Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; and Hoogenboom et al. (1991) *Nuc Acid Res* 19:4133-4137.

Bacteriophage displaying the protein component can be grown and harvested using standard phage preparatory methods, e.g., PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

In other embodiments, a eukaryotic expression/display system, e.g., yeast cells or mammalian cells, can be used for expressing and displaying the library of antibodies as described herein. Yeast display is a protein display format, in which a protein component (e.g., an antibody component) is linked to a yeast cell wall protein (e.g., Aga1p or Aga2p) directly or indirectly. In some instances, one chain of an antibody can be covalently fused to the yeast cell wall protein for direct display. In other instances, the association between an antibody component and a yeast cell wall component can be mediated by an intermediate agent. Yeast display is described in, e.g., Cho et al., J. Immunol. Methods, 220(1-2):179-188, 1998; Boder et al., Methods Enzymol. 192(2):243-248, 2000; van den Beucken et al., FEBS Lett 546(2-3):288-294, 2003; and Boder et al., Arch Biochem Biophys 526(2):99-106, 2012.

To screen an antibody library as described herein for isolating antibodies capable of binding to a target antigen, the library of antibodies can be in contact with the target antigen under suitable conditions allowing for antibody-antigen binding. Phage particles or host cells displaying antibodies binding to the target antigen can be isolated, for example, by retention or a support member on which the target antigen is immobilized, amplified if needed, and the nucleic acids coding for the displayed antibodies can be determined. The screening process can be repeated multiple time, and display systems can be used in combination. When needed different antigens can be used for selecting antibody members having desired binding specificity or for negative selection to exclude antibody members having binding activity to a non-target antigen.

The screening of the antibodies derived from the libraries described herein can be carried out by any appropriate means. For example, binding activity can be evaluated by standard immunoassay and/or affinity chromatography. Determining the ability of candidate antibodies to bind therapeutic targets can be assayed in vitro using, e.g., a BIACORE™ instrument, which measures binding rates of an antibody to a given target antigen based on surface plasmon resonance. In vivo assays can be conducted using any of a number of animal models and then subsequently tested, as appropriate, in humans. Cell-based biological assays are also contemplated.

A lead antibody identified from antibody library screening may be subject to affinity maturation as described herein. A secondary library resulting from affinity maturation may be screened for binders having desired features, e.g., high binding affinity and/or binding specificity, following routine practice and/or disclosures provided herein.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Identifying Suitable VH VL Pairs for Use as Scaffolds

Suitable VH/VL pairs as scaffold for CDR insertions are crucial for creating highly diverse, highly functional antibody libraries. The usual rational for selecting scaffolds are: (i) the scaffolds are commonly used in nature (e.g., VH1-69, VH3-23); (ii) the scaffolds are chosen from known antibodies; (iii) the scaffolds are widely used by others; (iv) the scaffolds contains consensus germline sequences; and (v) the VH and VL pairs in the scaffold are considered to be stable, well expressed and non-aggregating.

Provided herein is an alternative approach for identifying suitable VH/VL pairs for use as a scaffold for antibody library construction. A recent publication describing certain approved antibodies and antibodies that are currently approved, or in Phase 2 or Phase 3 clinical trials (Jain, T. et al. Biophysical properties of the clinical-stage antibody landscape. *Proceedings of the National Academy of Sciences of the United States of America* 114, 944-949, doi:10.1073/pnas.1616408114 (2017)) was analyzed. The VH and VL germline genes of these antibodies were determined. Based on the developability data (e.g., aggregation, hydrophobic interaction, polyspecificity, monomericity, expression level in HEK cells, and Fab Tm) provided for each clinical antibody in the paper, the frequency and developability of these germline genes in clinical antibodies was assessed. The antibodies displaying the value in the worst 10% for each of the standard tested was flagged (highlighted in bold and italics in Table 1) and only antibodies with ≤1 flag were considered developable. In Table 1 all the clinical antibodies containing ≤1 flag are indicated in rows 2-69. In rows 70-72 examples of antibodies with >2 flags are indicated (Table 1). The antibodies chosen as exemplary examples are highlighted in bold. The correlation between the clinical development stage of the antibodies and the percentage of flags in these antibodies is shown in FIG. 1.

Six therapeutic antibodies (abrilumab, mepolizumab, crenezumab, necitumumab, anifrolumab, and evoculumab) are selected as our final scaffold choices (Highlighted in bold and italics in Table 1, and further described in Table 2). They are well expressed, showing no or minimal liabilities, containing few framework mutations and having low immunogenicity indicating the presence of suitable antibody scaffolds in these antibodies.

For each of the therapeutic antibodies listed in Table 2, seven vectors were designed and synthesized, as described in Example 2. The diagrammatic representation of vectors encoding the original scaffold, the heavy chain CDR1, heavy chain CDR2, heavy CDR3, light chain CDR1, light chain CDR2, and light chain CDR3 scaffolds derived from the six original scaffolds listed in Table 2 is shown in FIG. 2. The scaffolds represent five VH gene families (VH1-5) and five VL families (VK1-4; Vλ2). Table 2. Naturally occurring replicated CDRs can be inserted into these selected exemplary antibody scaffolds, which were identified as being well expressed, folded and lacking liabilities, for further testing.

TABLE 1

Analysis of Therapeutic Antibodies.

| Row | Name | HEK Titer (mg/L) < 50 | Fab Tm by DSF (° C.) ≤ 64 | SGAC-SINS AS100 $(NH_4)_2SO_4$ mM) ≤ 300 | HIC Retention Time (Min) ≥ 11.8 | SMAC Retention Time (Min) ≥ 13.0 | Slope for Accelerated Stability ≥ 0.09 | Poly-Specificity Reagent (PSR) SMP (0-1) ≥ 0.27 | Affinity-Capture Self-Interaction Nanoparticle Spectroscopy (AC-SINS) ΔλMax (nm) Average ≥ 13.1 | CIC Retention Time (Min) > 10 | CSI-BLI Delta Response (nm) ≥ 0.02 | ELISA > 2.0 | BVP ELISA ≥ 4.35 |
|---|---|---|---|---|---|---|---|---|---|---|---|---|---|
| 2 | abituzumab | 89.6 | 75.5 | 900.0 | 9.2 | 8.7 | 0.06 | 0.17 | 1.5 | 8.6 | 0.00 | 1.14 | 2.72 |
| 3 | *abrilumab* | 100.2 | 71.0 | 900.0 | 9.4 | 8.7 | 0.03 | 0.00 | −0.9 | 8.4 | −0.02 | 1.12 | 1.82 |
| 4 | adalimumab | 134.9 | 71.0 | 900.0 | 8.8 | 8.7 | 0.05 | 0.00 | 1.1 | 8.9 | −0.01 | 1.08 | 1.49 |
| 5 | alemtuzumab | 144.7 | 74.5 | 1000.0 | 8.8 | 8.7 | 0.06 | 0.00 | −0.8 | 8.5 | −0.02 | 1.16 | 1.46 |

TABLE 1-continued

Analysis of Therapeutic Antibodies.

| Row | Name | HEK Titer (mg/L) < 50 | Fab Tm by DSF (° C.) ≤ 64 | SGAC-SINS AS100 (NH₄)₂SO₄ (mM) ≤ 300 | HIC Retention Time (Min) ≥ 11.8 | SMAC Retention Time (Min) ≥ 13.0 | Slope for Accelerated Stability ≥ 0.09 | Poly-Specificity Reagent (PSR) SMP (0-1) ≥ 0.27 | Affinity-Capture Self-Interaction Nanoparticle Spectroscopy (AC-SINS) Δλmax (nm) Average ≥ 13.1 | CIC Retention Time (Min) > 10 | CSI-BLI Delta Response (nm) ≥ 0.02 | ELISA > 2.0 | BVP ELISA ≥ 4.35 |
|---|---|---|---|---|---|---|---|---|---|---|---|---|---|
| 6 | alirocumab | 69.2 | 71.5 | 900.0 | 9.0 | 8.7 | 0.03 | 0.00 | 1.2 | 8.8 | −0.01 | 1.20 | 2.18 |
| 7 | *anifrolumab* | 82.0 | *62.5* | 700.0 | 8.8 | 8.6 | 0.07 | 0.00 | −0.6 | 8.5 | −0.02 | 1.16 | 1.62 |
| 8 | bapineuzumab | 151.1 | 73.0 | 1000.0 | 8.9 | 8.7 | 0.07 | 0.00 | −0.7 | 8.6 | *0.06* | 1.21 | 3.55 |
| 9 | benralizumab | 146.7 | 76.0 | 800.0 | 9.5 | 9.1 | 0.02 | *0.35* | 6.0 | 9.6 | −0.01 | 1.23 | 1.42 |
| 10 | brodalumab | 150.9 | 74.5 | 900.0 | 9.1 | 8.7 | 0.02 | *0.27* | 11.2 | 9.0 | −0.01 | 1.48 | 2.93 |
| 11 | canakinumab | *45.7* | 72.0 | 800.0 | 9.3 | 8.7 | 0.04 | 0.00 | 0.7 | 8.6 | 0.00 | 1.20 | 2.55 |
| 12 | certolizumab | 186.7 | 81.5 | 500.0 | 11.5 | 10.8 | 0.04 | 0.00 | 0.2 | 9.3 | −0.01 | 1.14 | 1.65 |
| 13 | clazakizumab | 113.5 | 69.5 | 800.0 | 9.6 | 8.9 | 0.05 | 0.00 | 0.9 | 8.7 | −0.03 | 1.28 | 4.12 |
| 14 | *crenezumab* | 149.3 | 72.0 | 700.0 | 10.0 | 8.7 | 0.05 | 0.10 | 6.4 | 8.9 | 0.00 | 1.13 | 2.78 |
| 15 | dacetuzumab | 128.5 | 68.0 | 1000.0 | 8.5 | 8.6 | 0.00 | 0.00 | 0.0 | 8.5 | −0.04 | 1.08 | 1.34 |
| 16 | daclizumab | 245.1 | 74.0 | 900.0 | 9.3 | 8.8 | 0.03 | 0.00 | −0.1 | 8.5 | −0.02 | 1.18 | 1.41 |
| 17 | daratumumab | 233.3 | 71.0 | 800.0 | 9.5 | 8.9 | 0.06 | 0.00 | 1.8 | 8.9 | 0.00 | 1.21 | 3.15 |
| 18 | eculizumab | 226.5 | 66.0 | 700.0 | 10.4 | 9.3 | 0.01 | 0.00 | 0.0 | 8.5 | −0.04 | 0.96 | 3.00 |
| 19 | efalizumab | 167.0 | 72.5 | 900.0 | 8.7 | 8.6 | 0.00 | 0.00 | 0.7 | 8.5 | −0.02 | 0.98 | 1.24 |
| 20 | elotuzumab | 213.2 | 83.5 | 700.0 | 10.3 | 9.3 | 0.00 | 0.00 | −0.2 | 8.5 | −0.03 | 0.98 | 1.26 |
| 21 | epratuzumab | 78.2 | 65.0 | 900.0 | 9.2 | 8.6 | 0.03 | 0.13 | 3.0 | 8.7 | −0.01 | 1.47 | 2.34 |
| 22 | *evolocumab* | 260.7 | 65.0 | 700.0 | 10.4 | 9.1 | 0.03 | 0.20 | 2.2 | 9.3 | −0.01 | 1.75 | 1.75 |
| 23 | farletuzumab | 220.8 | 75.5 | 800.0 | 9.5 | 9.1 | 0.01 | 0.00 | −0.5 | 8.7 | −0.01 | 1.07 | 1.32 |
| 24 | fasinumab | 110.4 | 71.0 | 900.0 | 10.0 | 8.7 | 0.07 | 0.00 | −0.7 | 8.4 | −0.02 | 1.16 | 2.53 |
| 25 | ficlatuzumab | 249.0 | 75.0 | 900.0 | 9.4 | 8.9 | 0.05 | 0.00 | −0.9 | 8.5 | −0.02 | 1.13 | 1.23 |
| 26 | fletikumab | 220.4 | 71.5 | 700.0 | 11.0 | 9.1 | 0.02 | 0.00 | −0.1 | 8.5 | −0.02 | 1.02 | 1.41 |
| 27 | fresolimumab | 166.0 | 74.0 | 700.0 | 10.9 | 9.1 | 0.06 | 0.00 | −0.5 | 8.5 | −0.02 | 1.30 | 3.51 |
| 28 | fulranumab | 142.0 | 68.5 | 900.0 | 9.3 | 9.3 | 0.07 | 0.19 | 11.6 | 9.3 | 0.00 | 1.85 | *6.92* |
| 29 | gevokizumab | 136.4 | 71.5 | 1000.0 | 8.8 | 8.6 | 0.07 | 0.00 | −0.5 | 8.6 | −0.03 | 1.18 | 1.93 |
| 30 | ibalizumab | 133.3 | 72.0 | 800.0 | 10.2 | 9.8 | 0.04 | 0.00 | −0.3 | 8.7 | −0.03 | 0.99 | 1.13 |
| 31 | lintuzumab | 230.0 | 75.5 | 700.0 | 10.9 | 9.4 | 0.05 | 0.00 | 0.9 | 8.9 | −0.02 | 1.05 | 1.25 |
| 32 | matuzumab | 224.3 | 72.0 | 900.0 | 9.8 | 8.8 | 0.02 | 0.00 | −0.9 | 8.6 | −0.03 | 1.06 | 1.03 |
| 33 | mavrilimumab | 150.5 | 68.5 | 700.0 | 10.3 | 8.7 | 0.05 | 0.00 | −0.8 | 8.5 | −0.01 | 1.21 | 2.16 |
| 34 | *mepolizumab* | 221.5 | 78.5 | 900.0 | 9.2 | 8.8 | 0.04 | 0.00 | −1.0 | 8.4 | −0.04 | 1.13 | 1.05 |
| 35 | mogamulizumab | 89.8 | 68.5 | 800.0 | 9.6 | 8.8 | 0.04 | 0.00 | −0.5 | 8.6 | −0.02 | 1.12 | 2.17 |
| 36 | motavizumab | 133.6 | 86.0 | 800.0 | 9.7 | 8.8 | 0.04 | 0.00 | 2.5 | 8.7 | −0.01 | 1.23 | *5.36* |
| 37 | natalizumab | 251.7 | 79.5 | 900.0 | 9.7 | 8.8 | 0.02 | 0.00 | 0.8 | 8.8 | −0.01 | 1.06 | 1.52 |
| 38 | *necitumumab* | 198.6 | 76.5 | 600.0 | 10.8 | 9.9 | 0.02 | 0.00 | 1.3 | 8.8 | −0.02 | 1.05 | 1.31 |
| 39 | nivolumab | 178.8 | 66.0 | 900.0 | 9.0 | 8.7 | 0.03 | 0.14 | 2.4 | 8.9 | −0.01 | 1.15 | 1.32 |
| 40 | obinutuzumab | 176.4 | 73.0 | 600.0 | 10.6 | 9.0 | 0.01 | 0.11 | 1.8 | 8.8 | −0.01 | 0.95 | 1.63 |
| 41 | ofatumumab | 249.8 | 68.0 | 800.0 | 9.7 | 9.5 | 0.03 | 0.00 | 1.2 | 9.2 | −0.02 | 1.12 | 1.18 |
| 42 | olokizumab | 115.3 | 69.0 | 700.0 | 9.9 | 9.0 | 0.04 | 0.00 | −0.5 | 8.7 | −0.03 | 1.11 | 1.23 |
| 43 | omalizumab | 150.4 | 77.5 | 800.0 | 9.5 | 8.7 | 0.05 | 0.00 | −0.4 | 8.5 | −0.02 | 1.12 | 1.17 |
| 44 | onartuzumab | 147.9 | 80.0 | 800.0 | 9.9 | 8.9 | 0.04 | 0.00 | 0.0 | 8.9 | −0.02 | 1.12 | 1.19 |
| 45 | otelixizumab | 152.1 | 75.5 | 1000.0 | 9.1 | 8.7 | *0.09* | 0.00 | 4.4 | 8.7 | −0.02 | 1.13 | 1.40 |
| 46 | otlertuzumab | 149.6 | 68.5 | 600.0 | 11.0 | 10.3 | 0.07 | 0.00 | 2.3 | 9.5 | −0.03 | 1.17 | 1.78 |
| 47 | palivizumab | 243.1 | 79.5 | 900.0 | 9.3 | 8.7 | 0.04 | 0.00 | −0.9 | 8.5 | −0.03 | 1.12 | 2.88 |
| 48 | panitumumab | 179.6 | 78.5 | 900.0 | 9.5 | 8.8 | 0.04 | 0.00 | −1.1 | 8.4 | −0.03 | 1.06 | 1.18 |
| 49 | panobacumab | 107.6 | 69.0 | 900.0 | 9.8 | 8.9 | 0.02 | 0.00 | −0.4 | 9.0 | −0.01 | 1.21 | 1.90 |
| 50 | pertuzumab | *31.4* | 78.5 | 700.0 | 10.1 | 8.9 | 0.04 | 0.00 | −0.2 | 8.6 | −0.04 | 1.21 | 1.69 |
| 51 | pinatuzumab | 130.6 | 79.0 | 800.0 | 9.2 | 8.8 | 0.07 | 0.01 | 0.6 | 8.8 | −0.02 | 1.27 | 2.49 |
| 52 | polatuzumab | 225.1 | 74.0 | 1000.0 | 8.8 | 8.7 | 0.06 | 0.00 | −1.0 | 8.3 | −0.05 | 1.36 | 3.62 |
| 53 | radretumab | 151.2 | 77.0 | 900.0 | 9.5 | 8.7 | 0.00 | 0.13 | 3.4 | 8.9 | 0.00 | 1.26 | 3.29 |
| 54 | ramucirumab | 90.7 | 66.0 | 900.0 | 9.4 | 8.7 | 0.02 | 0.00 | 0.0 | 8.6 | −0.02 | 1.05 | 1.25 |
| 55 | reslizumab | 191.6 | 75.5 | 700.0 | 9.8 | 8.9 | 0.06 | 0.23 | 1.7 | 8.9 | 0.00 | 1.25 | 2.02 |
| 56 | romosozumab | 227.7 | 76.0 | 1000.0 | 9.2 | 8.6 | 0.03 | 0.00 | −1.0 | 8.4 | −0.03 | 1.01 | 1.47 |
| 57 | sarilumab | 181.8 | *64.0* | 900.0 | 9.0 | 8.7 | 0.05 | 0.00 | 1.1 | 8.7 | −0.01 | 1.19 | 2.17 |
| 58 | secukinumab | 149.0 | 72.0 | 800.0 | 11.4 | 8.9 | 0.05 | 0.00 | −0.6 | 8.4 | −0.04 | 1.09 | 1.69 |
| 59 | sifalimumab | 158.6 | 67.0 | 800.0 | 9.7 | 8.8 | 0.01 | 0.06 | 2.1 | 9.0 | −0.02 | *2.60* | 2.50 |
| 60 | tabalumab | 121.6 | *64.0* | 700.0 | 10.8 | 9.9 | 0.06 | 0.00 | 2.0 | 9.1 | −0.01 | 1.26 | 3.68 |
| 61 | tigatuzumab | 179.2 | 64.5 | 700.0 | 10.0 | 8.7 | 0.02 | 0.13 | 5.5 | 8.7 | −0.01 | 1.17 | 1.70 |
| 62 | tildrakizumab | 181.9 | 77.5 | 600.0 | 11.1 | 9.9 | −0.01 | 0.00 | 0.8 | 8.7 | −0.01 | 1.19 | 1.77 |
| 63 | tocilizumab | 139.6 | 91.5 | 900.0 | 9.1 | 8.8 | 0.05 | 0.00 | 1.3 | 8.9 | 0.00 | 1.14 | 2.81 |
| 64 | tovetumab | 277.2 | *63.5* | 900.0 | 8.7 | 8.6 | 0.01 | 0.00 | 2.2 | 8.8 | −0.01 | 1.35 | 2.95 |
| 65 | trastuzumab | 159.5 | 78.5 | 800.0 | 9.7 | 8.8 | 0.04 | 0.00 | 2.0 | 8.8 | −0.02 | 1.06 | 1.34 |
| 66 | vedolizumab | 221.8 | 80.5 | 600.0 | 10.9 | 12.3 | 0.07 | 0.00 | 0.4 | 9.0 | −0.02 | 1.15 | 1.58 |

TABLE 1-continued

Analysis of Therapeutic Antibodies.

| Row | Name | HEK Titer (mg/L) < 50 | Fab Tm by DSF (° C.) ≤ 64 | SGAC-SINS AS100 $(NH_4)_2SO_4$ mM) ≤ 300 | HIC Retention Time (Min) ≥ 11.8 | SMAC Retention Time (Min) ≥ 13.0 | Slope for Accelerated Stability ≥ 0.09 | Poly-Specificity Reagent (PSR) SMP (0-1) ≥ 0.27 | Affinity-Capture Self-Interaction Nanoparticle Spectroscopy (AC-SINS) Δλmax (nm) Average ≥ 13.1 | CIC Retention Time (Min) > 10 | CSI-BLI Delta Response (nm) ≥ 0.02 | ELISA > 2.0 | BVP ELISA ≥ 4.35 |
|---|---|---|---|---|---|---|---|---|---|---|---|---|---|
| 67 | veltuzumab | 225.0 | 70.0 | 700.0 | 11.1 | 9.7 | 0.04 | 0.00 | 4.8 | 8.8 | −0.02 | 0.89 | 1.21 |
| 68 | zalutumumab | 200.5 | 72.5 | 900.0 | 9.3 | 8.7 | 0.05 | 0.00 | −0.8 | 8.4 | −0.03 | 1.28 | 2.90 |
| 69 | zanolimumab | 116.6 | 80.5 | 700.0 | 9.6 | 8.8 | 0.03 | 0.13 | 1.5 | 8.6 | −0.01 | 1.10 | 1.46 |
| 70 | atezolizumab | 164.1 | 73.5 | *300.0* | *13.4* | *19.3* | 0.06 | 0.07 | *15.0* | *10.8* | *0.06* | 1.29 | *6.20* |
| 71 | belimumab | *10.5* | *60.0* | 800.0 | 10.5 | 9.3 | *0.13* | 0.00 | 0.8 | 8.6 | −0.03 | *3.61* | *12.23* |
| 72 | bevacizumab | 50.0 | *63.5* | 700.0 | *11.8* | 11.1 | *0.22* | 0.00 | 0.8 | 9.8 | −0.02 | 1.29 | 2.78 |

TABLE 2

Summary of Final Scaffold Choices.

| Therapeutic | Target | Phase | Type | VH gene | VK gene | Framework VH mutations | Framework VL mutations | % Immunogenicity* | Fab Tm° C. | Phage display used |
|---|---|---|---|---|---|---|---|---|---|---|
| Abrilumab | a4-β7 integrin | Phase 2 | Human | 1-24 | 1-12 1 | | 1 | 0 | 71.0 | Other H1-24 & K1-12 |
| Mepolizumab | IL-5 | Approved | Humanized | 2-70 | 4-1 4 | | 0 | 6 | 78.5 | Other H2-70 & K4-1 |
| Crenezumab | Aβ | Phase 3 | Humanized | 3-7 | 2D-29 2 | | 3 | ND | 72.0 | None |
| Necitumumab | EGFR | Approved | Human | 4-30-4 | 3-11 3 | | 1 | 4.1 | 76.5 | For Necitumumab |
| Anifrolumab | Interferon receptor | Phase 3 | Human | 5-51 | 3-20 1^ | | 2 | 3.3 | 62.5 | Other H5-51 & K3-20 |
| Evocolumab | PCSK9 | Approved | Human | 1-18 | 12-14 2 | | 1 | 0.3 | 65 | Other H1-18 |

*These identified CDRs are identical, but synthesized with different flanking regions corresponding to different VH1 genes (VH1-18 and VH1-24).
^These identified CDRs are identical, but synthesized with different flanking regions corresponding to different VK3 genes (VK3-20 and VK3-11).

Example 2: Creating Vectors for Experimental CDR Screening

For each of the six libraries created using the six scaffolds shown in Table 2, seven polynucleotides encoding single-chain variable fragment (scFv) corresponding to each of the scaffolds were synthesized. One of the seven synthesized polynucleotides encodes for the non-modified scFv, and the other six polynucleotides were modified to have one of the original CDRs replaced by a combination of restriction sites including two inverted BsaI sites (a type Hs enzyme that cuts outside of its recognition sequence), an additional SfiI site to ensure cleavage of the vector and serve as a spacer between the BsaI sites, a frameshift and an ochre stop codon to prevent expression of background sequence (FIGS. 2-3). Each of these modified polynucleotides encoding the scaffolds was cloned into a yeast display vector, and the presence of the stop codon in this sequence prevented the expression of the scaffold on the yeast surface until the modified CDR is replaced with a functional CDR.

Figure 4:
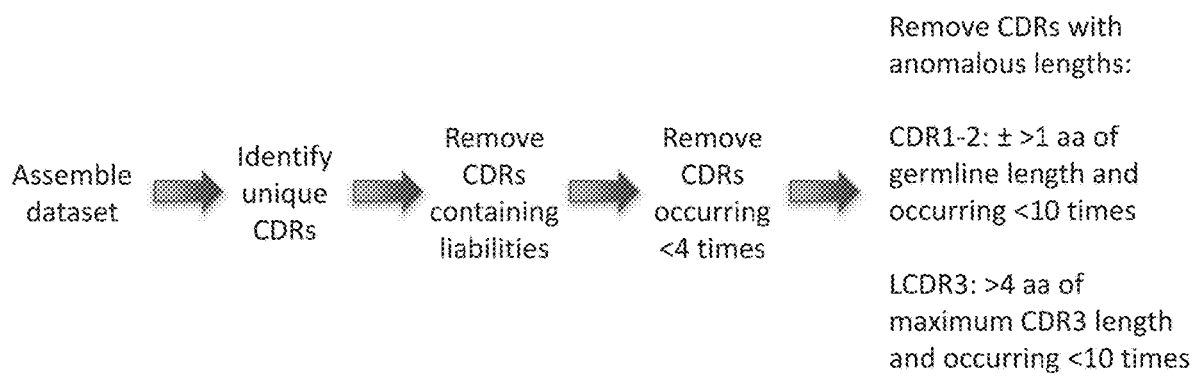
FIG. 4 is a flow chart describing an exemplary process of identifying unique CDRs and informatically removing CDRs based on liabilities, occurrence rate, and/or anomalous length.

Example 3: Generating a Database of CDR Sequences and Informatic Elimination of CDRs Demonstrating Potential Liabilities The process taken to identify suitable CDRs for use in the libraries exemplified herein is illustrated in FIG. 4. To generate a database of naturally occurring CDRs (CDRs found in naturally-occurring antibodies such as human antibodies), next generation sequencing (NGS) of the variable genes derived from a total of 40 donors was carried out, comprising a total of >140 million reads. NovaSeq analysis was applied to LCDR3 sequencing data and MiSeq analysis was applied to heavy chain and light chain CDR1 and CDR2 sequencing data.

Analysis of the variable gene sequences allowed identification of the numbers of CDRs shown in Table 3.

Figure 6:
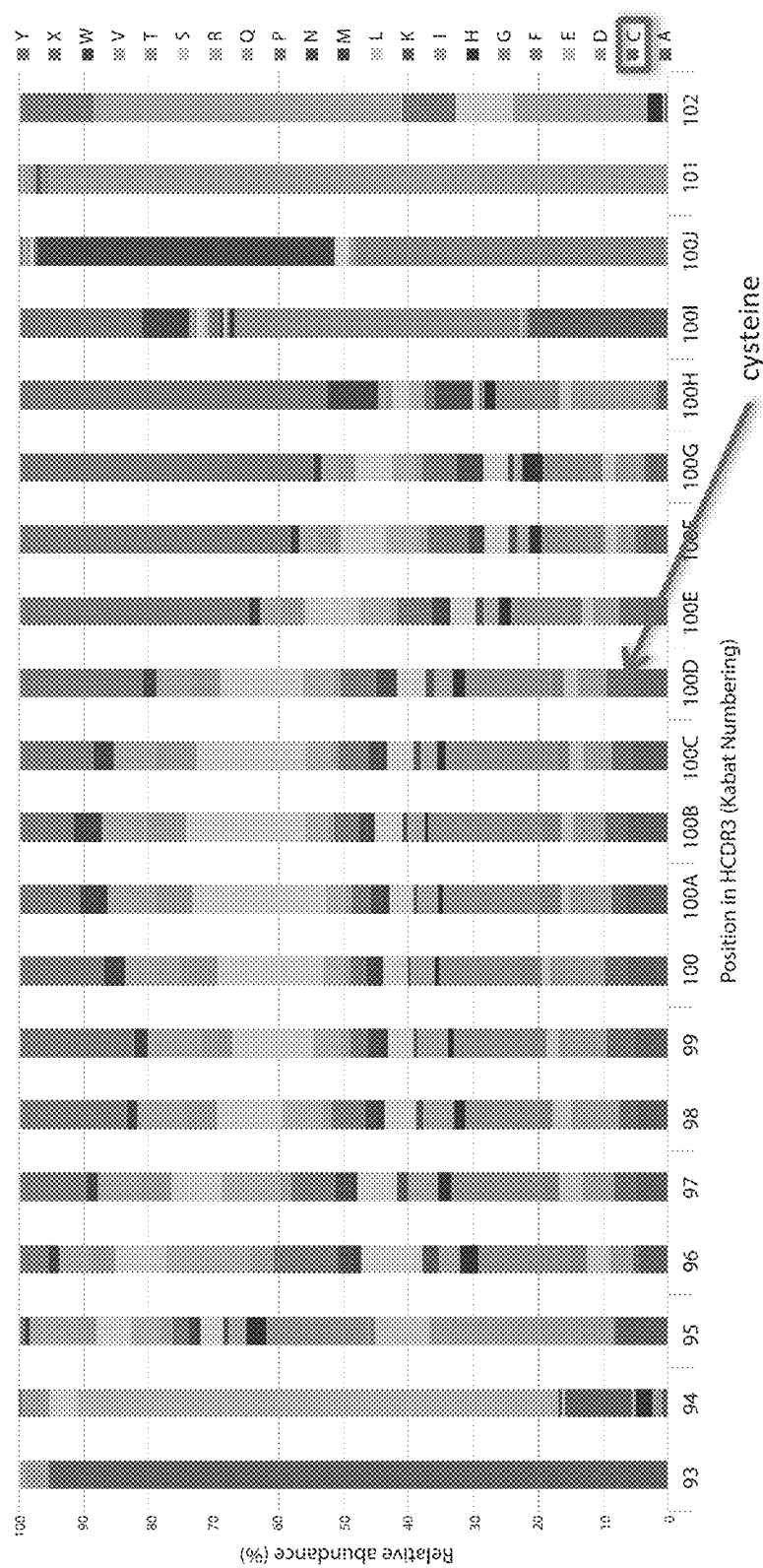
FIG. 6 is a diagram showing presence of cysteine residues in heavy chain CDR3.
Figure 7:
FIG. 7 shows presence of cysteine residues in heavy chain CDR3. Sequences correspond to SEQ ID NOs: 88-102 (from top to bottom).
Figure 8:
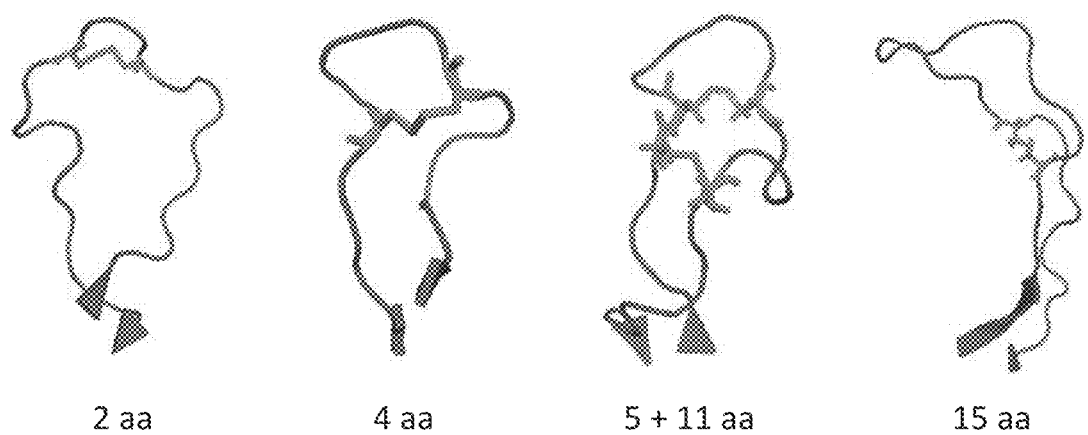
FIG. 8 is a diagram illustrating paired cysteine residues in CDRs.
Figure 9:
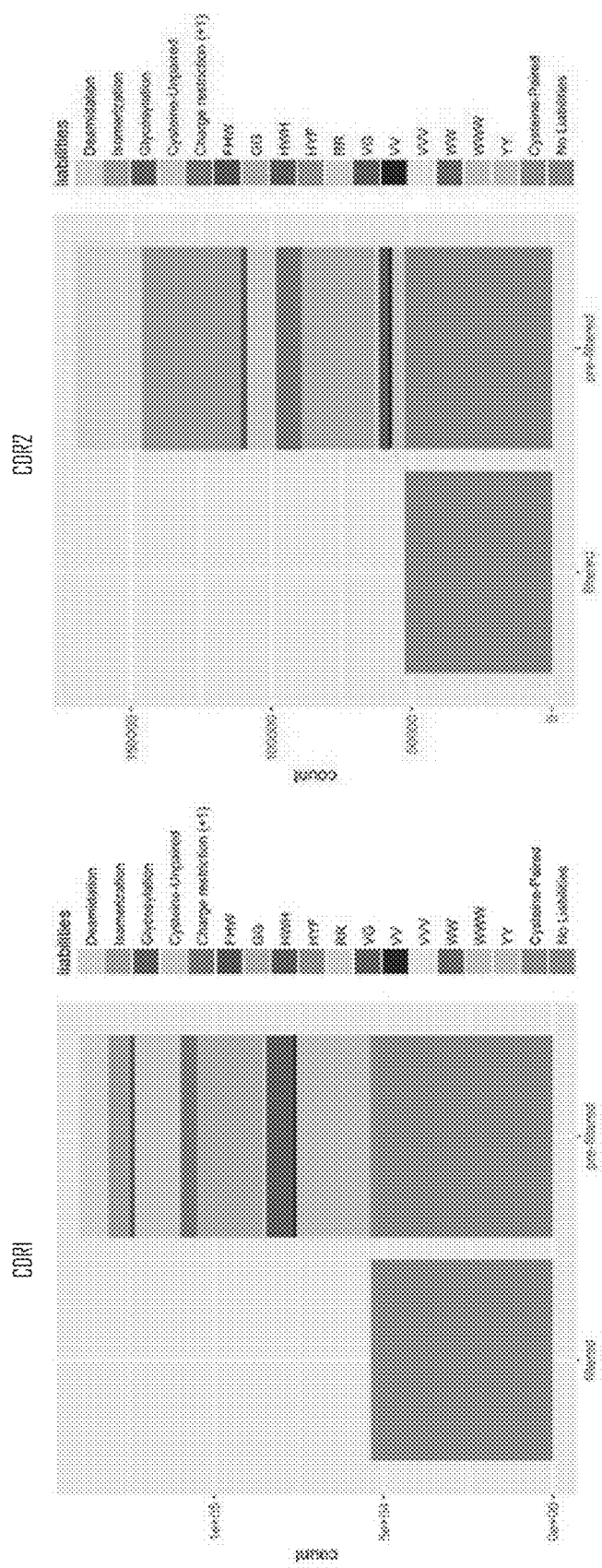
FIG. 9 includes graphs showing the presence of liabilities in heavy chain CDR1 (left panel) and CDR2 (right panel) regions before and after bioinformatic filtration.
Figure 10:
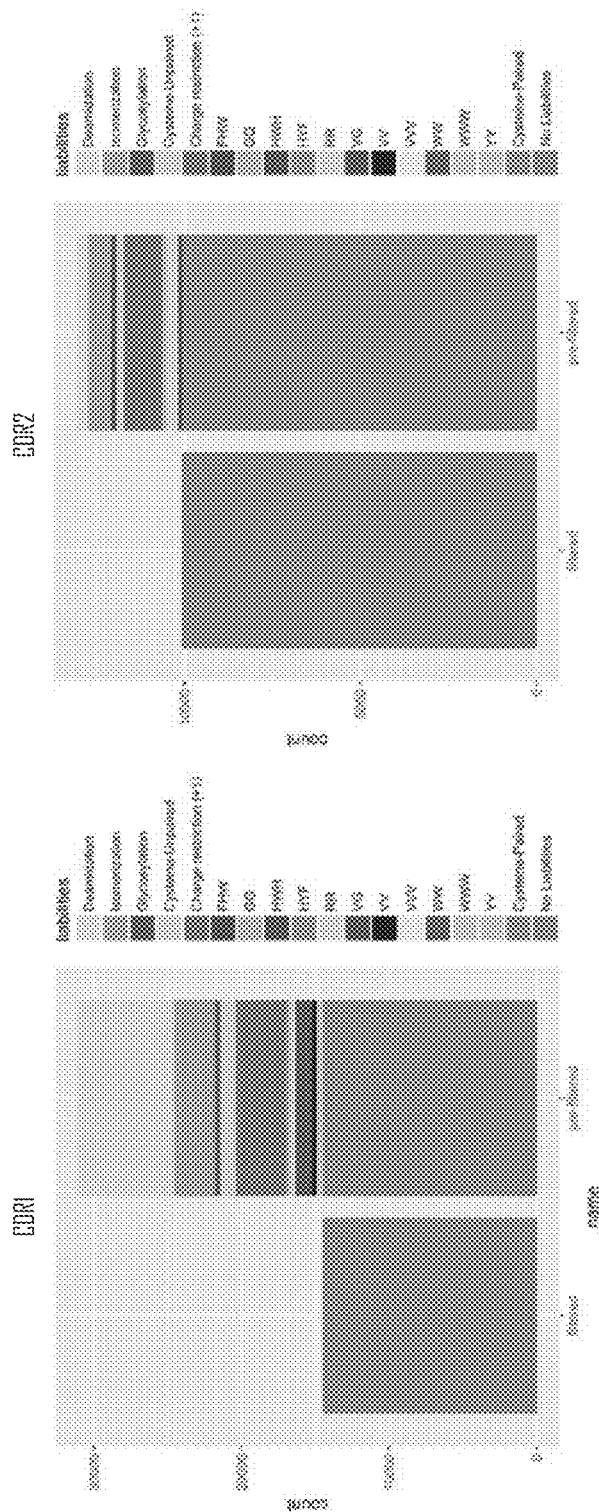
FIG. 10 includes graphs showing the presence of liabilities in Vκ CDR1 (left panel) and CDR2 (right panel) regions before and after bioinformatic filtration.
Figure 11:
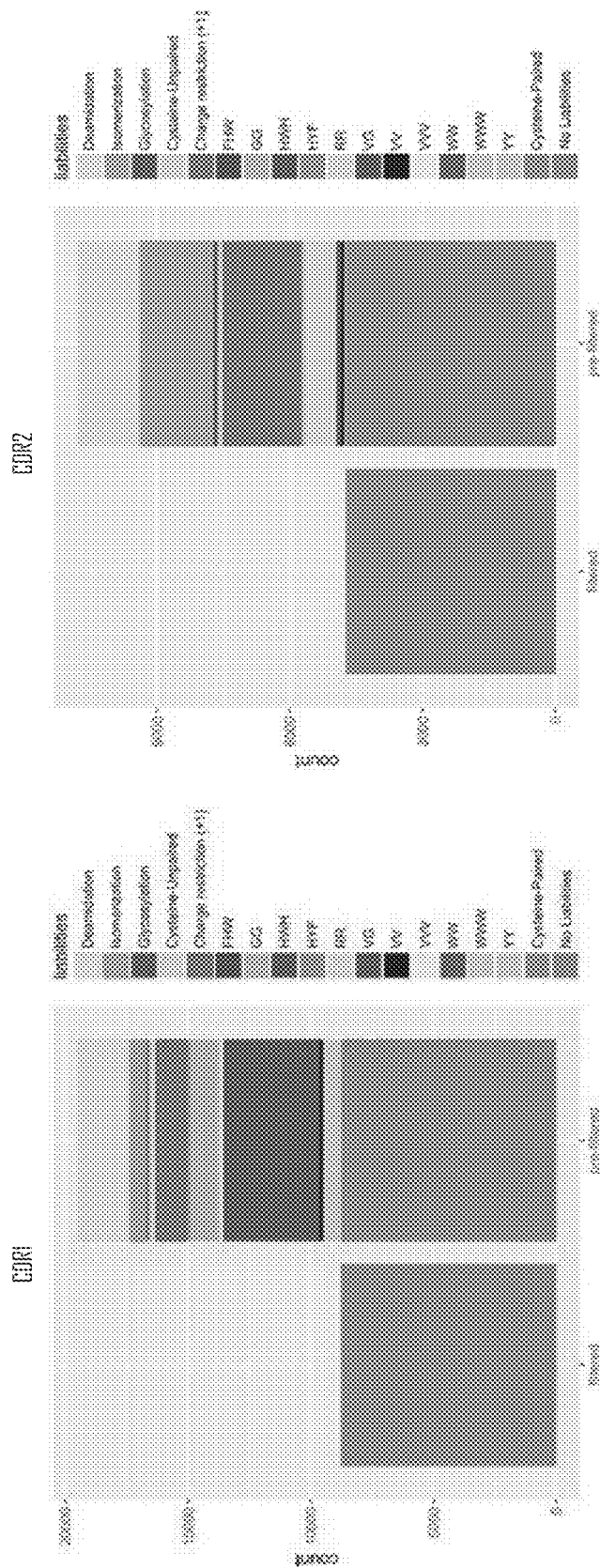
FIG. 11 includes graphs showing the presence of liabilities in Vλ CDR1 (left panel) and CDR2 (right panel) before and after bioinformatic filtration.
Figure 12:
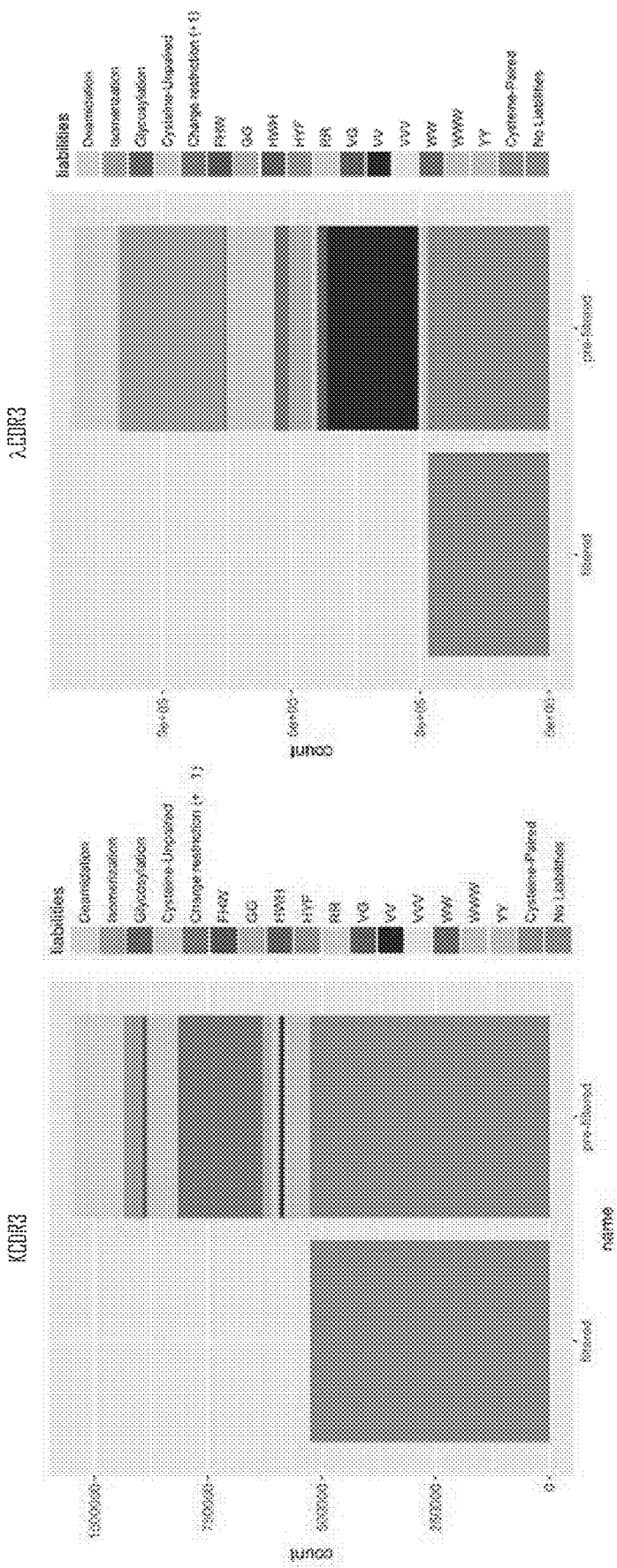
FIG. 12 includes graphs showing the presence of liabilities in Vκ CDR3 (left panel) ad Vλ CDR3 (right panel) before and after bioinformatic filtration.
Figure 13:
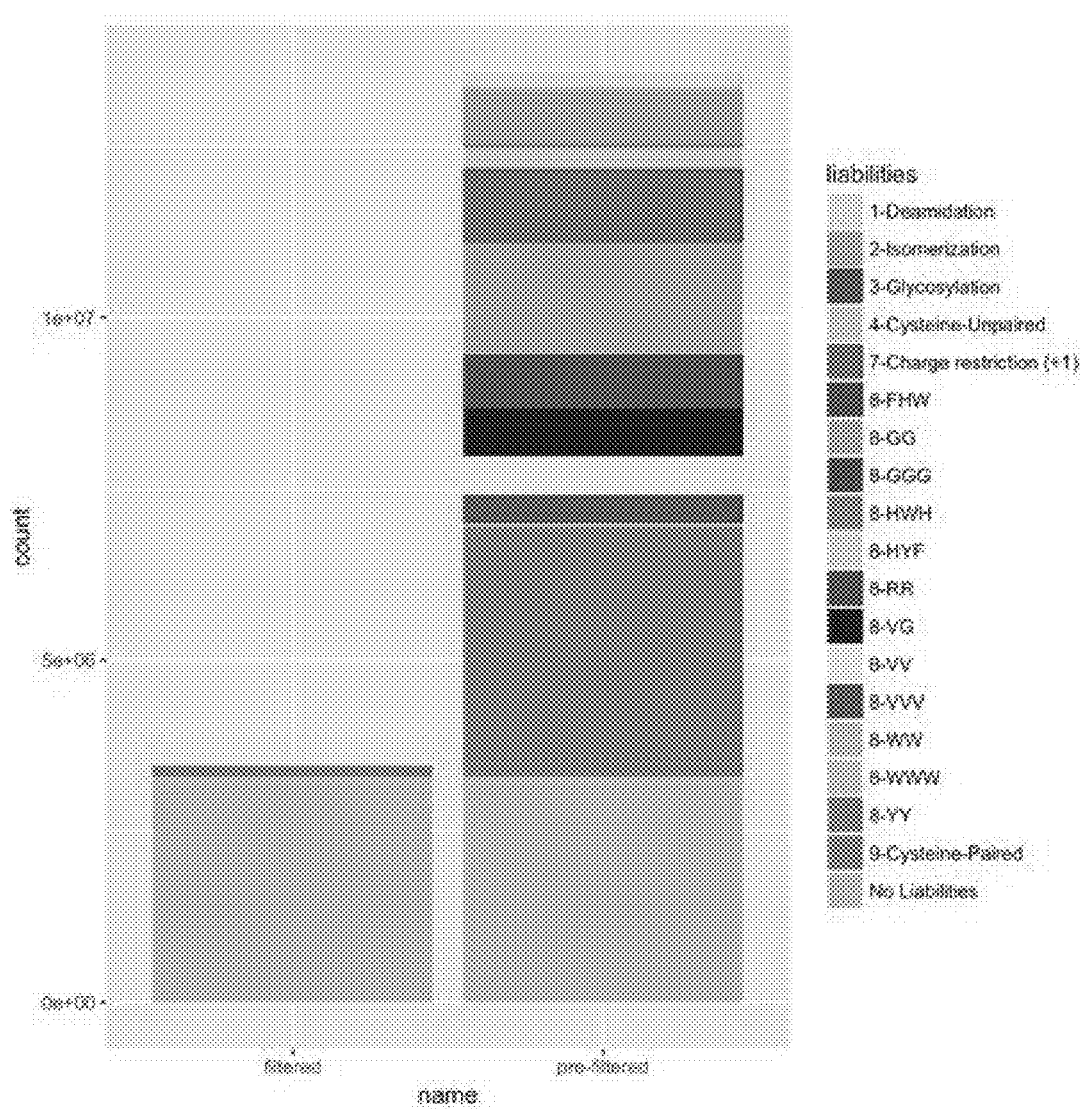
FIG. 13 includes a graph showing presence of liabilities in HC CDR3 before and after bioinformatic filtration.

Altogether, unique CDRs corresponding to the following heavy chain and light chain CDRs were identified showing both unique CDRs and CDRs including potential flanking scaffold oligos (in parentheses). The number of oligos is greater than the number of CDRs because of the need to synthesize some CDRs with different flanking sequences corresponding to different scaffolds:

~52,675 (66,020) LCDR1s;
~19,550 (23,854) LCDR2s;
~2,180,922 (2,617,051) LCDR3s;
~147,741 (167,376) HCDR1s;
~170,758 (202,170) HCDR2s; and
~13,588,754 HCDR3s Liabilities that were reduced to short sequences were used to identify CDRs containing them. For example, HCDR2 sequences containing liabilities such as deamidation, isomerization, glycosylation or unpaired cysteines are highlighted in pink (in FIG. 5). To underscore the importance of identifying liabilities and eliminating CDRs containing liabilities from the libraries, unpaired cysteines in HCDR3 were illustrated in FIGS. 6-8 as an example. Cysteines comprise up to 4% of HCDR3 amino acid and they need to be paired and structurally positioned, otherwise the presence of unpaired cysteines or poorly positioned cysteines would introduce undesirable structure or chemical reactivity into the CDR thus rendering the CDR non-functional or non-developable. The list of exemplary liabilities identified is described in Table 4, and it is clear that additional sequence-based liabilities can be similarly screened. The list of unique CDRs previously identified in Table 3 was examined for occurrence of the listed liabilities, and all CDRs containing a liability were computationally eliminated from the list of unique CDRs. FIGS. 9-13 reflects the extent of elimination of liabilities from the different CDR populations.

TABLE 4

| Liabilities to be Removed. | |
| --- | --- |
| Type of Liabilities | Exemplary Motif |
| Glycosylation-impacts stability, solubility, half-life, heterogeneity, and effector function. | NXS, → X = Any Amino Acid but Proline<br>NXT, → X = Any Amino Acid but Proline<br>NXC → X = Any Amino Acid but Proline |
| Deamidation-Therapeutic antibodies may undergo deamidation during manufacture and storage leading to protein structural changes, aggregation, change in pharmacokinetics, loss of activity and immunogenicity. | NG, NS, NT, NN, NA, NH, ND, GNF, GNY, GNT, or GNG |
| Isomerization-Asp residues can undergo isomerization and reported in CDRs. | DT, DH, DG, DS, DD |
| Known to increase charge heterogeneity Based on creation of synthetic library, selection against polyspecificity (PSR) and sequencing | GG, GGG, RR, VG, VV, VVV, WW, WWW, YY, WXW (X represents any amino acid residue) |

TABLE 3

Unique CDRs Identified and the Remaining Unique CDRs after Elimination of liabilities.

| Library | VH | VL | unique LCDR1 total | unique LCDR1 final | unique LCDR2 total | unique LCDR2 final | unique LCDR3 total | unique LCDR3 final |
| --- | --- | --- | --- | --- | --- | --- | --- | --- |
| 1 Abrilumab | VH1-24 | VK1-12 | 8,838 | 1,717 | 6,483 | 1,406 | 385,836 | 74,091 |
| 2 Mepolizumab | VH2-70 | VK4-1 | 6,039 | 103 | 685 | 140 | 130628 | 17,917 |
| 3 Crenezumab | VH3-7 | VK2D-29 | 4,668 | 50 | 1591 | 229 | 122745 | 32,092 |
| 4 Necitumumab | VH4-30-4 | VK3-11 | 13,345 | 1,910 | 685 | 972 | 436129 | 79,038^ |
| 5 Anifrolumab | VH5-51 | VK3-20 | 13,345 | 1,910 | 685 | 972 | 436129 | 79,038^ |
| 6 Evolocumab | VH1-18 | V12-14 | 19,785 | 1,696 | 10,792 | 1,197 | 1,105,584 | 94,371 |
| | | Total | 66,020 | 5,476 | 20,921 | 3,944 | 2,617,051 | 297,509 |

| Library | unique HCDR1 total | unique HCDR1 final | unique HCDR2 total | unique HCDR2 final | Unique HCDR3 total | Unique HCDR3 final | Theoretical diversity No HCDR3 | Theoretical diversity with 1e8 HCDR3's |
| --- | --- | --- | --- | --- | --- | --- | --- | --- |
| 1 Abrilumab | 19,635* | 2,860 | 31,412 | 2,171 | 13,588,754 | 1,791,801 | 1.11E+18 | 1.11E+26 |
| 2 Mepolizumab | 31,486 | 2,296 | 15,550 | 1,253 | | | 7.43E+14 | 7.43E+22 |
| 3 Crenezumab | 34,575 | 5,920 | 82,817 | 4,565 | | | 9.93E+15 | 9.93E+23 |
| 4 Necitumumab | 50,335 | 1,285 | 28,267 | 2,739 | | | 5.16E+17 | 5.16E+25 |
| 5 Anifrolumab | 11,710 | 1,979 | 12,712 | 669 | | | 1.94E+17 | 1.94E+25 |
| 6 Evolocumab | 19,635* | 2,860 | 31,412 | 2,171 | | | 1.19E+18 | 1.19E+26 |
| | 167,376 | 17,200 | 202,170 | 13,568 | 13,588,754 | 1,791,801 | 3.00E+18 | 3.00E+26 |

Sum of final CDRs (LCDR1-3 HCDR1-2): 337, 697.
*These identified CDRs are identical, but synthesized with different flanking regions corresponding to different VH1 genes (VH1-18 and VH1-24).
^These identified CDRs are identical, but synthesized with different flanking regions corresponding to different VK3 genes (VK3-20 and VK3-11).

TABLE 4-continued

Liabilities to be Removed.

| Type of Liabilities | Exemplary Motif |
|---|---|
| Single cluster in IL-13 human mAb HCDR3 which highly aggregating, alanine mutations increase solubility (aggregation) | FHW |
| Two aromatic tripeptides in HCDR3 mutated improve viscosity. Compatible with idea that 3 consecutive aromatics is bad news and should be eliminated | HYF, HVVH |
| Positive charge associated with poor developability properties. | Net Charge (+1) in LCDR1-3, HCDR1-2 |
| Unpaired cysteine can impact protein folding, function and stability. These reactive centers lead to formation of covalent aggregates and reduce protein stability | Unpaired Cysteine |
| Protease sensitivity (fragmentation) | DP, DG, DS, DV, DY, DF, DQ, DK, DL, DD |
| Integrin binding site | RGD, RYD, LDV, KGD |
| Lysine glycation site | KE, EK, or ED |
| Metal catalyzed fragmentation (X represents any amino acid residue) | HS, SH, KT, HXS, SXH |
| Polyspecificity, aggregation | $X_1X_2X_3$, in which each of $X_1$, $X_2$, and $X_3$ independent is F, I, L, V, W, or Y |
| Streptavidin binding motifs | HPQ, EPDW (SEQ ID NO: 117), PWXWL (SEQ ID NO: 118), GDWVFI (SEQ ID NO: 119), PWPWLG (SEQ ID NO: 120) (X represents any amino acid residue) |

Example 4: Elimination of CDRs Arising from Sequencing Errors

Following the removal of CDRs containing potential liabilities disclosed in Example 3 above, CDRs that may have arisen as a result of sequencing errors were also computationally eliminated. Sequencing errors are more likely when the CDRs sequenced are oversampled. In general, the more copies of a particular CDR, the more likely that it is real, and not the result of a sequencing error.

Figure 14:
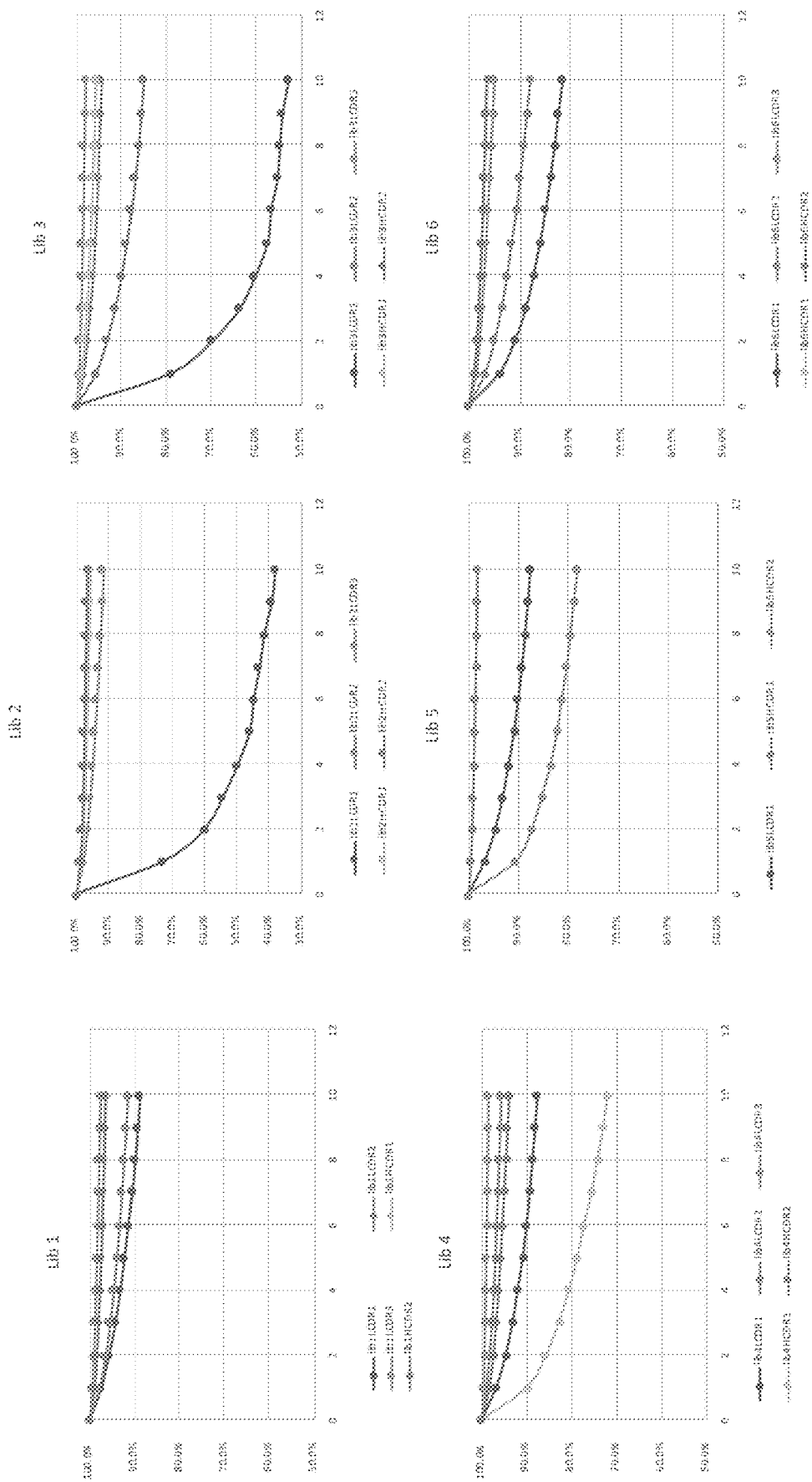
FIG. 14 includes charts showing the percentage of CDRs in each library that are excluded at different abundance threshold. Single thread of 4 reads is used across different libraries to exclude CDRs that arise by sequencing error.

The abundance of each unique CDR in the dataset was assessed after those containing liabilities had been removed. For each of the different libraries and individual CDRs, the percentage of sequences retained at different abundances (number of reads) was assessed. The more information retained, the more likely that rare CDRs are the result of sequencing errors, and not naturally occurring CDRs. The percentage of sequences eliminated for different CDRs except for HCDR3 at the application of different threshold numbers in each library is represented in FIG. 14. A threshold of 4 or more reads was evaluated for each unique CDR to represent the best balance between the number of unique CDRs and the retained sequence information. It is clear that different threshold numbers can be chosen depending upon the number of total reads, and the number of total unique CDRs identified. While different thresholds for each individual CDR for each library could be used, the single threshold of 4 reads was chosen to be consistent. CDRs with less than 4 reads were removed from the library.

Figure 15:
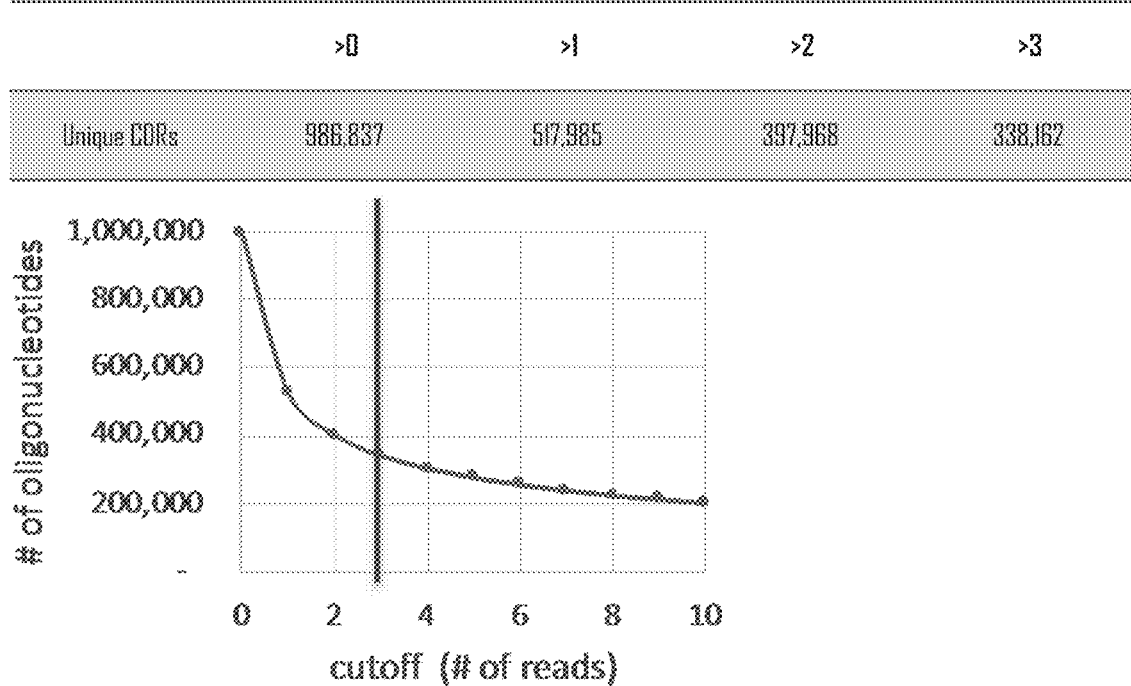
FIG. 15 includes a chart showing the number of CDRs remaining for all pooled CDRs except heavy chain CDR3 after exclusion at different threshold reads.
Figure 16:
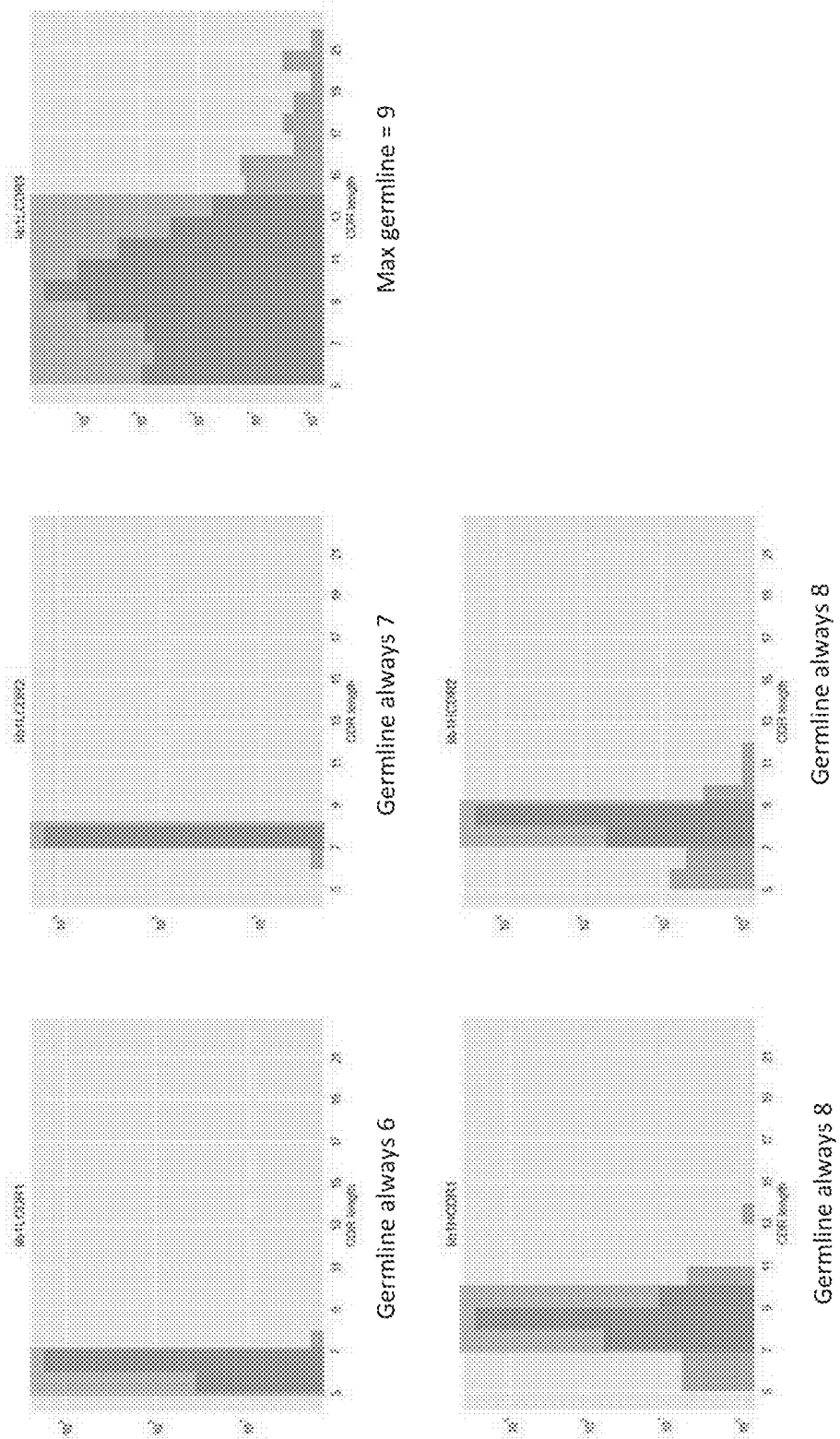
FIG. 16 includes graphs showing the length distribution of CDRs in Library 1 (using scaffold derived from abrilumab). The germline length for each CDR is indicated under each graph and the CDRs outside of the highlighted region are eliminated for anomalous length.
Figure 17:
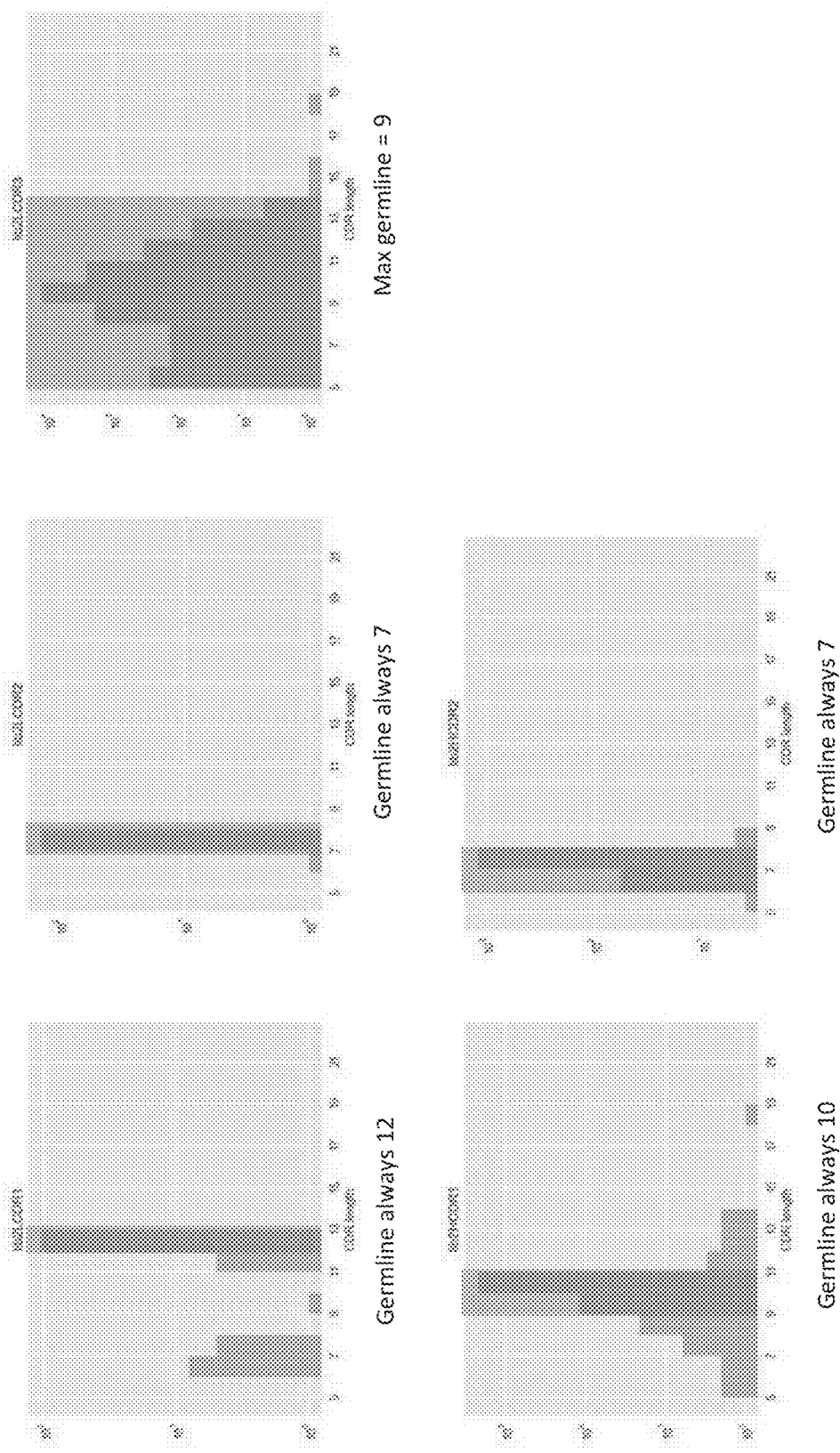
FIG. 17 includes graphs showing the length distribution of CDRs in Library 2 (using scaffold derived from mepolizumab). The germline length for each CDR is indicated under each graph and the CDRs outside of the highlighted region are eliminated for anomalous length.
Figure 18:
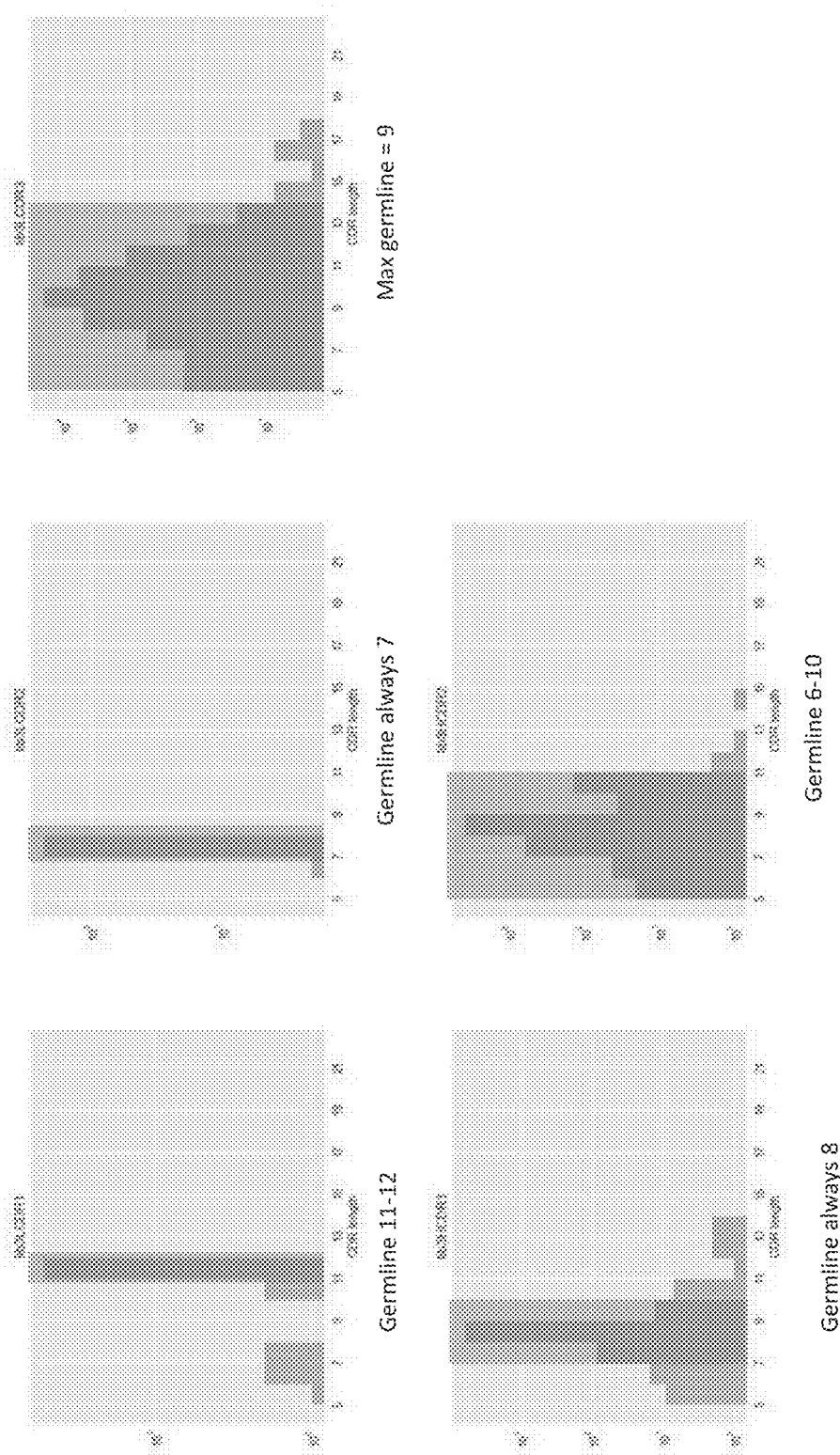
FIG. 18 includes graphs showing the length distribution of CDRs in Library 3 (using scaffold derived from crenezumab). The germline length for each CDR is indicated under each graph and the CDRs outside of the highlighted region are eliminated for anomalous length.
Figure 19:
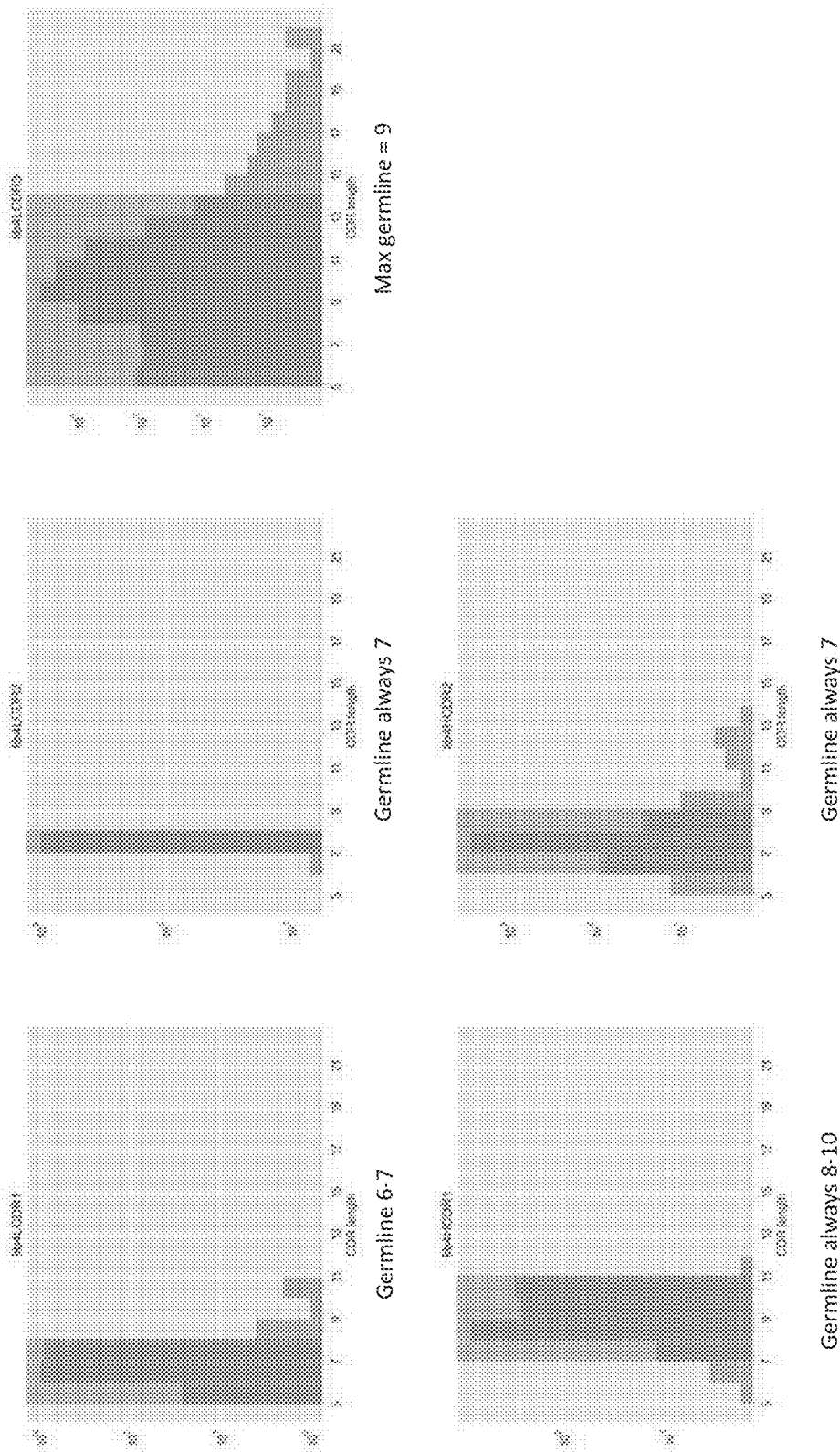
FIG. 19 includes graphs showing the length distribution of CDRs in Library 4 (using scaffold derived from necitumumab). The germline length for each CDR is indicated under each graph and the CDRs outside of the highlighted region are eliminated for anomalous length.
Figure 20:
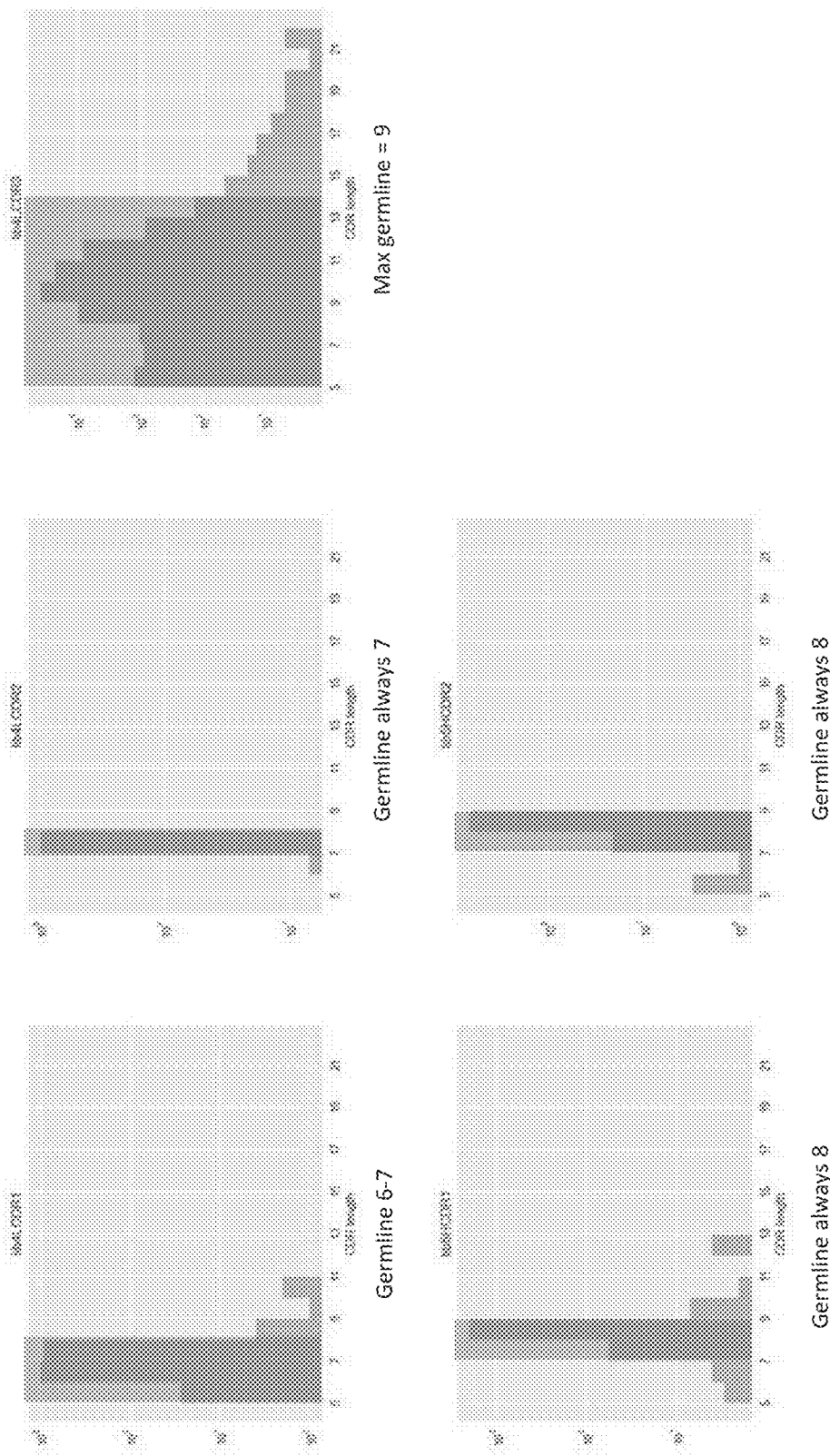
FIG. 20 includes graphs showing the length distribution of CDRs in Library 5 (using scaffold derived from anifrolumab). The germline length for each CDR is indicated under each graph and the CDRs outside of the highlighted region are eliminated for anomalous length.
Figure 22B:
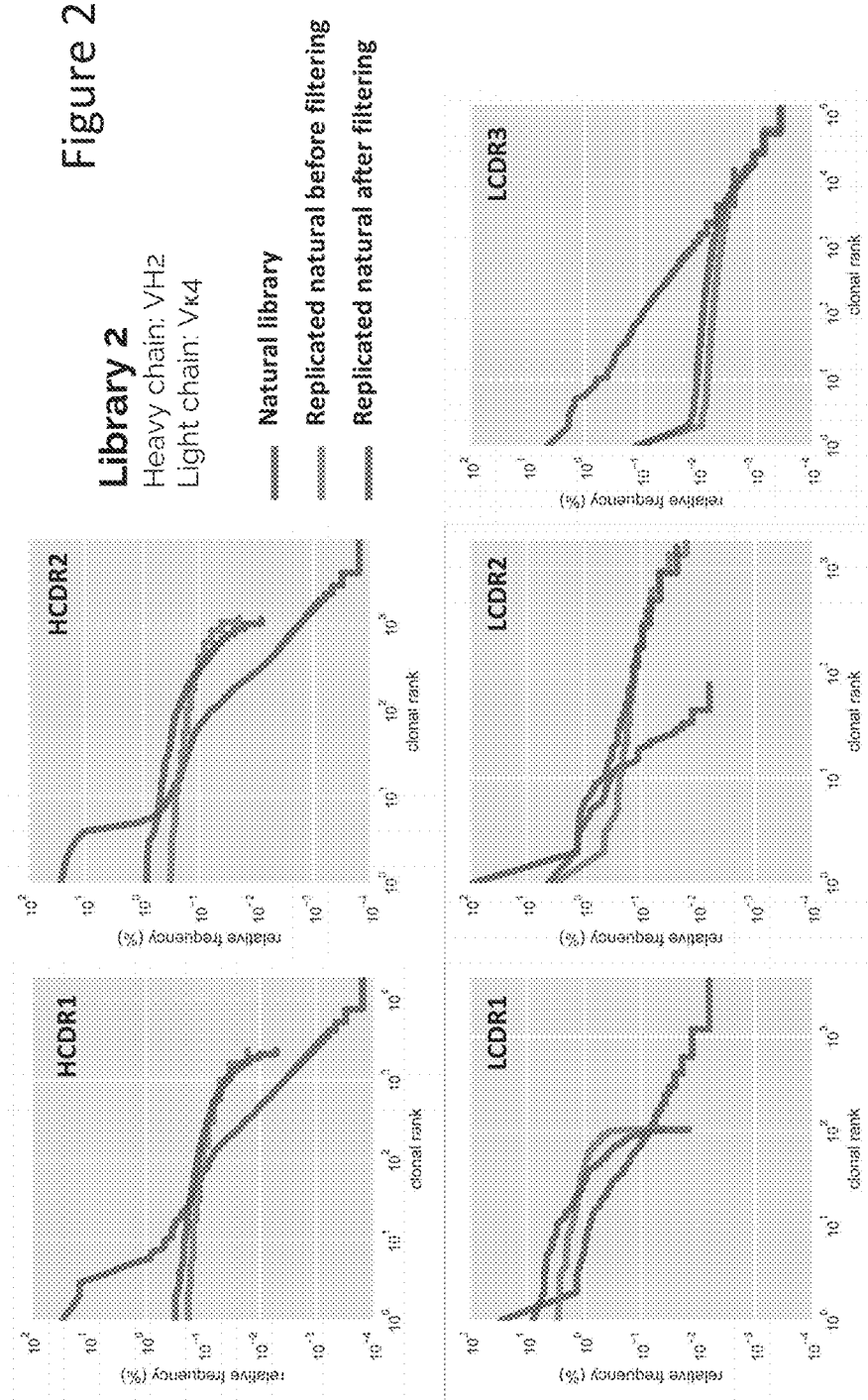
Figure 22F:
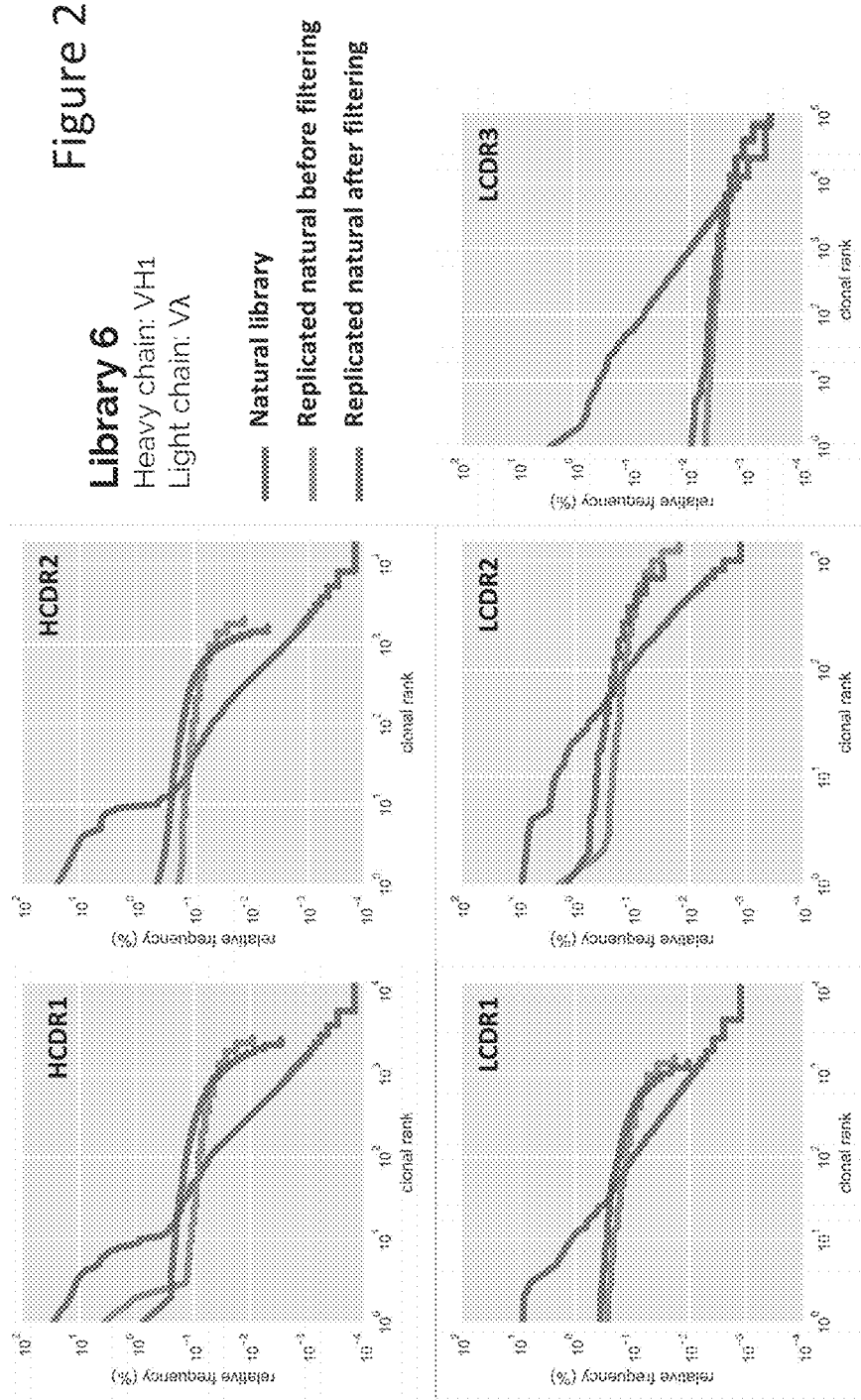
Figure 22I:
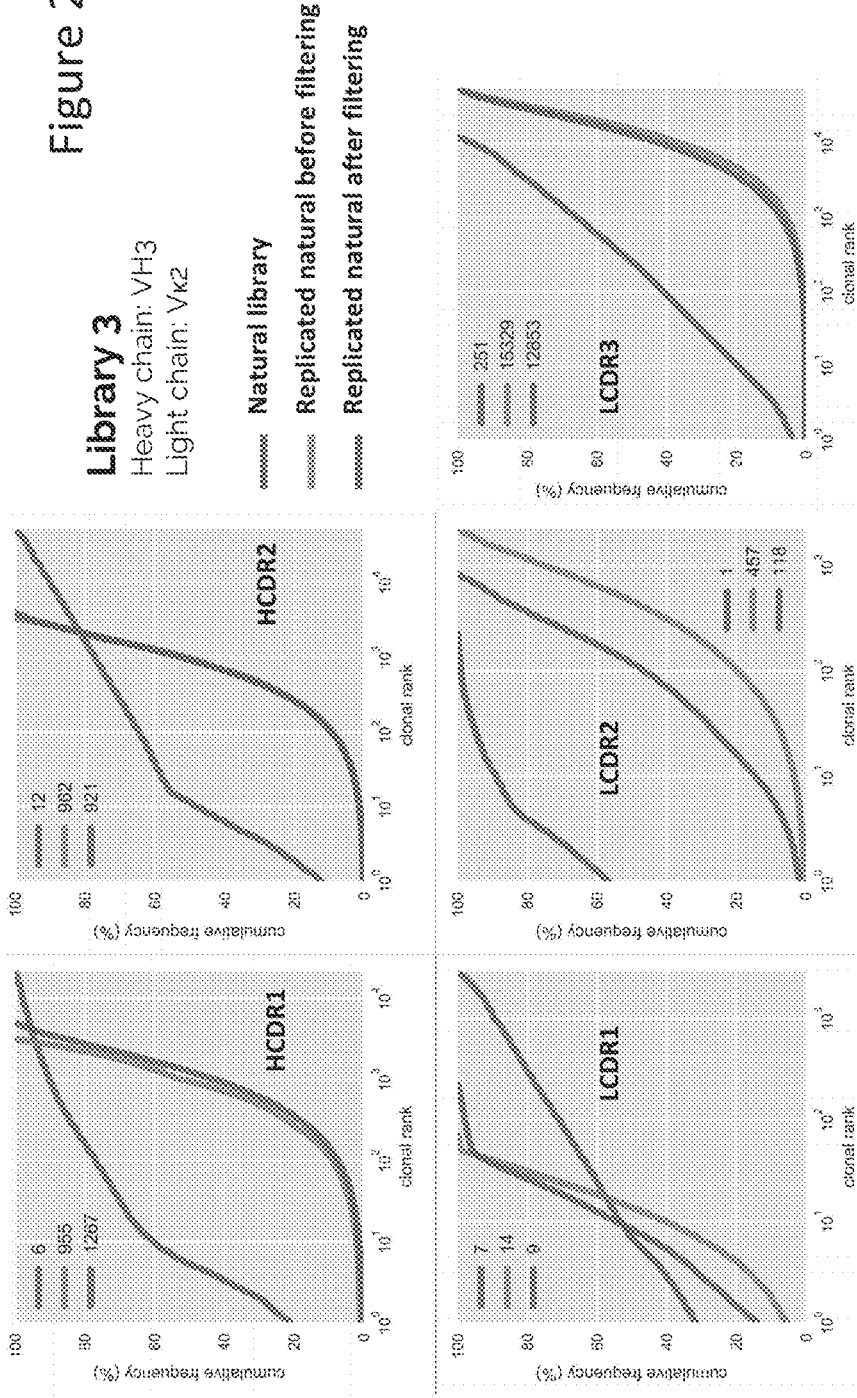
Figure 22L:
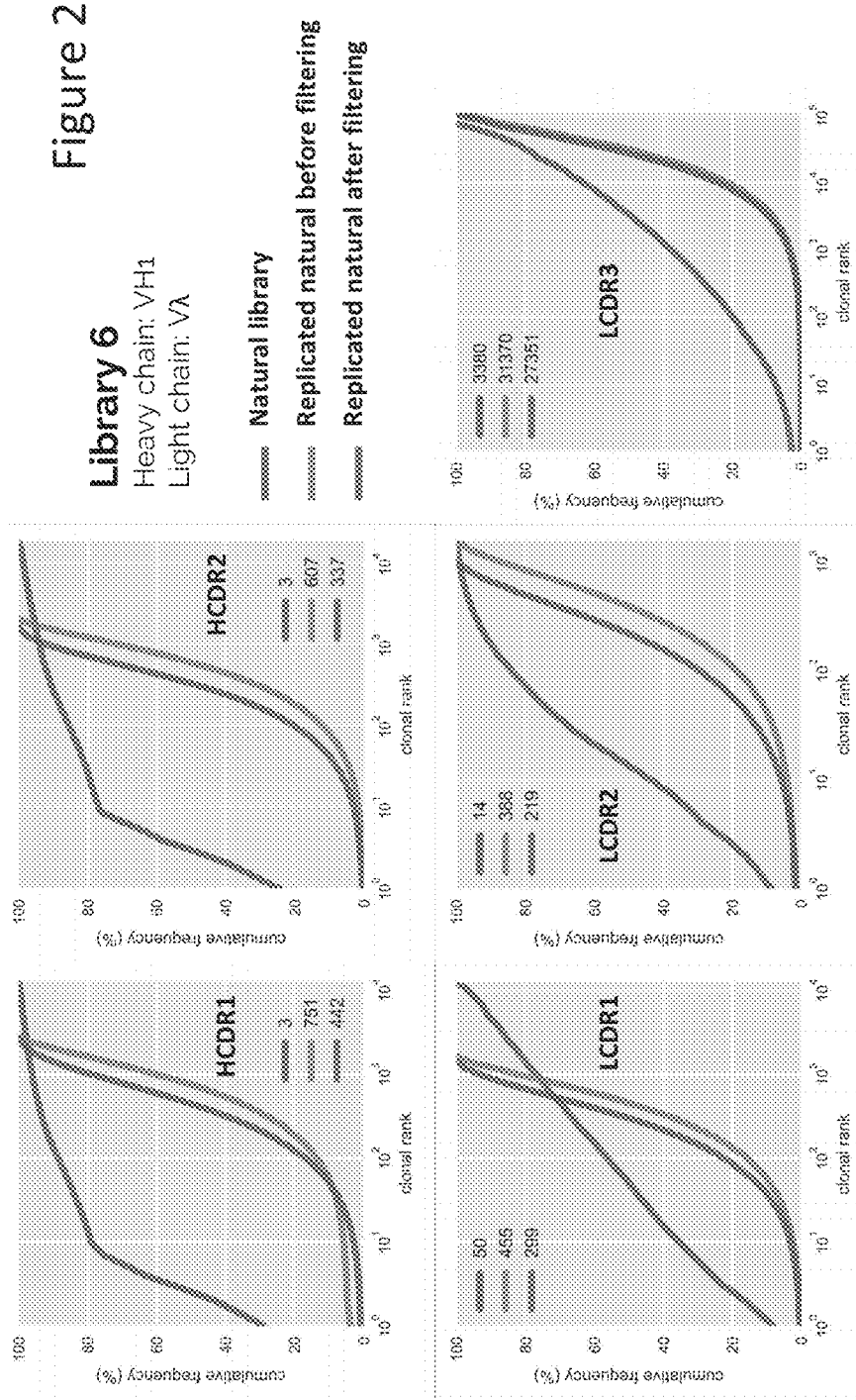

The use of different thresholds would be expected to yield different numbers of CDRs with different sequences as shown in FIG. 15.

Example 5: Elimination of CDRs Based on Anomalous Length

The lengths of germline CDRs are conserved, although they may vary during affinity maturation. CDRs of anomalous length are expected to reduce folding and expression of antibodies that contain them. CDRs with anomalous lengths were also computationally eliminated under the rules described in FIG. 4 and CDRs with a length outside of the pink shaded area were eliminated as shown FIGS. 16-21. The effects on the number of retained CDRs are indicated in Table 5 and Table 6. It is clear that alternative rules may be applied to the identification of naturally occurring CDRs that lack liabilities, and that as new liabilities are identified, they can be similarly eliminated. Furthermore, by carrying out next generation sequencing on CDRs experimentally selected for the presence of liabilities, such as polyreactivity or aggregation behavior, additional sequence liabilities can be identified and can be eliminated in other libraries created using this approach. As the numbers of CDRs sequenced increases, it is expected that the number of both unique CDRs, as well as the number of unique CDRs lacking liabilities will increase, so increasing the potential library diversity.

After the completion of these different informatic operations, the final number of unique CDRs identified as containing no liabilities, for each scaffold for this exemplary library is indicated in Table 3 showing both unique CDRs and CDRs including flanking scaffold oligos (in parentheses):

~3,566 (5,476) LCDR1s;
~2,972 (3,944) LCDR2s;
~218,471 (297,509) LCDR3s;
~14,340 (17,200) HCDR1s;
~11,397 (13,568) HCDR2s; and
~1,791,801 HCDR3s

TABLE 5

Number of CDRs Retained after Defined Length Restriction.

| Library 1 | No length restriction | Length Restriction | Difference | Library 2 | No length restriction | Length Restriction | Difference | Library 3 | No length restriction | Length Restriction | Difference |
|---|---|---|---|---|---|---|---|---|---|---|---|
| LCDR1 | 1,719 | 1,717 | −2 | LCDR1 | 122 | 103 | −19 | LCDR1 | 57 | 50 | −7 |
| LCDR2 | 1,409 | 1,406 | −3 | LCDR2 | 141 | 140 | −1 | LCDR2 | 231 | 229 | −2 |
| LCDR3 | 74,134 | 74,091 | −43 | LCDR3 | 17,920 | 17,917 | −3 | LCDR3 | 32,111 | 32,092 | −19 |
| HCDR1 | 2,878 | 2,860 | −18 | HCDR1 | 2,335 | 2,296 | −39 | HCDR1 | 5,956 | 5,920 | −36 |
| HCDR2 | 2,189 | 2,171 | −18 | HCDR2 | 1,262 | 1,253 | −9 | HCDR2 | 4,569 | 4,565 | −4 |
| Total | 82,329 | 82,245 | −84 | Total | 21,780 | 21,709 | −71 | Total | 42,924 | 42,856 | −68 |

TABLE 5-continued

Number of CDRs Retained after Defined Length Restriction.

| Library 4 | No length restriction | Length Restriction | Difference | Library 5 | No length restriction | Length Restriction | Difference | Library 6 | No length restriction | Length Restriction | Difference |
|---|---|---|---|---|---|---|---|---|---|---|---|
| LCDR1 | 1,917 | 1,910 | −7 | HCDR1 | 1,999 | 1,979 | −20 | LCDR1 | 1,697 | 1,696 | −1 |
| LCDR2 | 979 | 972 | −7 | HCDR2 | 673 | 669 | −4 | LCDR2 | 1,207 | 1,197 | −10 |
| LCDR3 | 79,141 | 79,038 | −103 | Total | 24,452 | 24,357 | −95 | LCDR3 | 94,383 | 94,371 | −12 |
| HCDR1 | 1,293 | 1,285 | −8 | | | | | HCDR1 | 2,878 | 2,860 | −18 |
| HCDR2 | 2,773 | 2,739 | −34 | | | | | HCDR2 | 2,189 | 2,171 | −18 |
| Total | 86,103 | 85,944 | −159 | | | | | Total | 102,354 | 102,295 | −59 |

TABLE 6

Total Number of CDRs.

| | No length restriction | Length Restriction | Difference |
|---|---|---|---|
| Total | 338,162 | 337,697 | −465 |

Example 6: Synthesis and Amplification of Oligonucleotides Corresponding to Final CDRs Oligonucleotides corresponding to those identified for HCDR1-2 and LCDR1-3 after the elimination steps as described in the above Examples were synthesized (Twist, Inc., San Francisco, CA), resulting in a total of 337,697 oligonucleotides coding for the selected CDRs. The CDR coding sequence in these oligonucleotides was flanked by 5' and 3' sequences homologous to the framework vectors, into which the CDR coding sequences were cloned. The homologous sequences were used for both amplification and insertion of the oligonucleotides into the yeast display vectors.

The combined pool of replicated natural CDRs amplified using primer pairs specific for each library scaffold and CDR position, cloned into the yeast display vectors described in Example 2 by homologous recombination, resulted in 30 different single CDR loop libraries (6 libraries, LCDR1-3, HCDR1-2). These were sorted for display, using a monoclonal antibody recognizing the SV5 tag by fluorescence activated cell sorting. For each of these libraries, this represents the diversity of replicated natural CDRs that are amplified using the specific primer pairs used (see below) that allow any level of display and are indicated as "Replicated natural before filtering" in FIG. 22.

FIG. 22A-F illustrates exemplary advantage of using synthetic oligonucleotides to encode HCDR1-2 and LCDR1-3 replicated natural diversity. Particularly for CDR1-2, the difference in abundance between the most and least abundant CDRs can be >300,000-fold, with the germline CDR1-2 sequences being by far the most abundant. When natural CDRs are synthesized, the distribution is always far flatter, as shown in FIGS. 22A-F, with the difference in abundance between the most and least abundant CDRs ranging from 10-200 fold, depending upon the CDR and library. The improvement in the diversity at each CDR using the approach described here is further illustrated in FIGS. 22G-L, where the cumulative distribution is indicated for each library and CDR position. The figures for each plot indicate the D50, the number of clones comprising the most abundant 50% of clones, which for all CDRs in all libraries is significantly higher for the replicated natural diversity, than for the natural diversity. In the case of HCDR3, the VDJ recombinatorial process (including addition of removal of nucleotides at the VD and DJ junctions) results in less variability in abundance between different HCDR3s.

The pool of oligonucleotides was subjected to amplification using the following primers:
  For LCDR1: F-L1-LCDR1 to F-L6-LCDR1 and R-L1-LCDR1 to R-L6-LCDR1
  For LCDR2: F-L1-LCDR2 to F-L6-LCDR2 and R-L1-LCDR2 to R-L6-LCDR2
  For LCDR3: F-L1-LCDR3 to F-L6-LCDR3 and R-L1-LCDR3 to R-L6-LCDR3
  For HCDR1: F-L1-HCDR1 to F-L1-HCDR1 and R-L1-HCDR1 to R-L1-HCDR1
  For HCDR2: F-L1-HCDR2 to F-L1-HCDR2 and R-L1-HCDR2 to R-L1-HCDR2

The exemplary amplification primer sequences and assembly primer sequences are provided in Table 7 and Table 8, respectively.

TABLE 7

Exemplary Amplification Primers.

| | Name | Sequence | Tm (° C.) | SEQ ID NO |
|---|---|---|---|---|
| 0 | F-L1-LCDR1 | GCTTCTGTTGGTGATCGTGTTACTATTACCTGTCGTGCTTCT | 77.9 | 181 |
| 1 | F-L2-LCDR1 | GTTTCTCTGGGTGAACGTGCTACCATCAACTGCAAATCTTCT | 77.9 | 182 |
| 2 | F-L3-LCDR1 | GTTACCCCAGGTGAACCAGCTTCTATTTCTTGTCGTTCTTCT | 77.9 | 183 |
| 3 | F-L4-LCDR1 | CTGTCTCCAGGTGAACGTGCCACTCTGTCTTGTCGTGCTTCT | 81.8 | 184 |
| 4 | F-L5-LCDR1 | CTGTCTCCAGGTGAACGTGCCACTCTGTCTTGTCGTGCTTCT | 81.8 | 185 |
| 5 | F-L6-LCDR1 | GGTTCTCCAGGTCAGTCTATCACCATCTCTTGTACCGGTACC | 80.9 | 186 |

TABLE 7-continued

Exemplary Amplification Primers.

| | Name | Sequence | Tm (° C.) | SEQ ID NO |
|---|---|---|---|---|
| 6 | R-L1-LCDR1 | CAGTTTTGGAGCTTTACCTGGTTTCTGCTGGTACCAAGCCAG | 79.9 | 187 |
| 7 | R-L2-LCDR1 | CAGTTTTGGTGGCTGACCTGGTTTCTGCTGGTACCAAGCCAG | 81.8 | 188 |
| 8 | R-L3-LCDR1 | CAGCTGTGGAGACTGACCTGGTTTCTGCAGGTACCAGTGCAG | 82.8 | 189 |
| 9 | R-L4-LCDR1 | CAGACGTGGAGCCTGACCTGGTTTCTGCTGGTACCAAGCCAG | 83.8 | 190 |
| 10 | R-L5-LCDR1 | CAGACGTGGAGCCTGACCTGGTTTCTGCTGGTACCAAGCCAG | 83.8 | 191 |
| 11 | R-L6-LCDR1 | CAGTTTTGGAGCTTTACCTGGGTGCTGCTGGTACCAAGAAAC | 79.9 | 192 |
| 12 | F-L1-LCDR2 | TACCAGCAGAAACCAGGTAAAGCTCCAAAACTGCTGATCTAC | 77.9 | 193 |
| 13 | F-L2-LCDR2 | TACCAGCAGAAACCAGGTCAGCCACCAAAACTGCTGATCTAC | 79.9 | 194 |
| 14 | F-L3-LCDR2 | TACCTGCAGAAACCAGGTCAGTCTCCACAGCTGCTGATCTAC | 80.9 | 195 |
| 15 | F-L4-LCDR2 | TACCAGCAGAAACCAGGTCAGGCTCCACGTCTGCTGATCTAC | 81.8 | 196 |
| 16 | F-L5-LCDR2 | TACCAGCAGAAACCAGGTCAGGCTCCACGTCTGCTGATCTAC | 81.8 | 197 |
| 17 | F-L6-LCDR2 | TACCAGCAGCACCCAGGTAAAGCTCCAAAACTGATGATCTAC | 78.9 | 198 |
| 19 | R-L1-LCDR2 | ATCGGTACCAGAACCAGAACCAGAGAAACGAGATGGAACACC | 79.9 | 199 |
| 19 | R-L2-LCDR2 | ATCGGTACCAGAACCAGAACCAGAGAAACGATCTGGAACACC | 79.9 | 200 |
| 20 | R-L3-LCDR2 | ATCGGTACCAGAACCAGAACCAGAGAAACGATCTGGAACACC | 79.9 | 201 |
| 21 | R-L4-LCDR2 | ATCGGTACCAGAACCAGAACCAGAGAAACGAGCTGGGATACC | 80.9 | 202 |
| 22 | R-L5-LCDR2 | ATCGGTACCAGAACCAGAACCAGACAGACGATCTGGGATACC | 80.9 | 203 |
| 23 | R-L6-LCDR2 | GGTGTTACCAGATTTAGAACCAGAGAAACGGTTAGAAACACC | 77.0 | 204 |
| 24 | F-L1-LCDR3 | ATCTCTTCTCTGCAGCCAGAAGATTTCGCTAACTACTACTGT | 77.0 | 205 |
| 25 | F-L2-LCDR3 | ATCTCTTCTCTGCAGGCTGAAGATGTTGCTGTTTACTACTGT | 77.0 | 206 |
| 26 | F-L3-LCDR3 | ATCTCTCGTGTTGAAGCTGAAGATGTTGGTGTTTACTACTGT | 76.0 | 207 |
| 27 | F-L4-LCDR3 | ATCTCTTCTCTGGAACCAGAAGATTTCGCTGTTTACTACTGT | 76.0 | 208 |
| 28 | F-L5-LCDR3 | ATCACCCGTCTGGAACCAGAAGATTTCGCTGTTTACTACTGT | 77.9 | 209 |
| 29 | F-L6-LCDR3 | ATCTCTGGTCTGCAGGCTGAAGATGAAGCTGATTACTACTGT | 77.9 | 210 |
| 30 | R-L1-LCDR3 | CGACCCTCCGGATTTGATTTCAACTTTGGTACCACCACCGAA | 79.9 | 211 |
| 31 | R-L6-LCDR3 | CGACCCTCCGGACAGAACGGTCAGTTTGGTACCACCACCGAA | 83.8 | 212 |
| 32 | F-L1-HCDR1 | AAAAAACCAGGTGCTTCTGTTAAAGTTTCTTGTAAAGTTTCT | 72.1 | 213 |
| 33 | F-L2-HCDR1 | GTTAAACCAACCCAGACCCTGACCCTGACCTGTACCGTTTCT | 80.9 | 214 |
| 34 | F-L3-HCDR1 | GTTCAGCCAGGTGGTTCTCTGCGTCTGTCTTGTGCTGCTTCT | 81.8 | 215 |
| 35 | F-L4-HCDR1 | GTTAAACCATCTCAGACCCTGTCTCTGACCTGTACCGTTTCT | 78.9 | 216 |
| 36 | F-L5-HCDR1 | AAAAAACCAGGTGAATCTCTGAAAATCTCTTGTAAAGGTTCT | 73.0 | 217 |
| 37 | F-L6-HCDR1 | AAAAAACCAGGTGCTTCTGTTAAAGTTTCTTGTAAAGCTTCT | 73.0 | 218 |
| 38 | R-L1-HCDR1 | CCATTCCAGACCTTTACCTGGAGCCTGACGAACCCAGTGGAT | 81.8 | 219 |
| 39 | R-L2-HCDR1 | CCATTCCAGAGCTTTACCTGGTGGCTGACGGATCCAGTTAAC | 80.9 | 220 |
| 40 | R-L3-HCDR1 | CAGTTCCAGACCTTTACCTGGAGCCTGACGAACCCAAGACAT | 80.9 | 221 |
| 41 | R-L4-HCDR1 | CCATTCCAGACCTTTACCTGGTGGCTGACGGATCCAAGACCA | 81.8 | 222 |
| 42 | R-L5-HCDR1 | AGATTCCAGACCTTTACCTGGAACCTGACGAACCCAAGCGAT | 79.9 | 223 |

TABLE 7-continued

Exemplary Amplification Primers.

| | Name | Sequence | Tm (° C.) | SEQ ID NO |
|---|---|---|---|---|
| 43 | R-L6-HCDR1 | CCATTCCAGACCCTGACCTGGAGCCTGACGAACCCAAGAGAT | 82.8 | 224 |
| 44 | F-L1-HCDR2 | GTTCGTCAGGCTCCAGGTAAAGGTCTGGAATGGATGGGTGGT | 81.8 | 225 |
| 45 | F-L2-HCDR2 | ATCCGTCAGCCACCAGGTAAAGCTCTGGAATGGCTGGCTATG | 81.8 | 226 |
| 46 | F-L3-HCDR2 | GTTCGTCAGGCTCCAGGTAAAGGTCTGGAACTGGTTGCTTCT | 80.9 | 227 |
| 47 | F-L4-HCDR2 | ATCCGTCAGCCACCAGGTAAAGGTCTGGAATGGATCGGTTAC | 80.9 | 228 |
| 48 | F-L5-HCDR2 | GTTCGTCAGGTTCCAGGTAAAGGTCTGGAATCTATGGGTATC | 78.9 | 229 |
| 49 | F-L6-HCDR2 | GTTCGTCAGGCTCCAGGTCAGGGTCTGGAATGGATGGGTTGG | 83.8 | 230 |
| 50 | R-L1-HCDR2 | TTCGGTCATGGTAACACGACCCTGGAATTTCTGAGCGTAGAT | 78.9 | 231 |
| 51 | R-L2-HCDR2 | AGAGATGGTCAGACGAGATTTCAGAGCAGAGTTGTAAACGAT | 77.0 | 232 |
| 52 | R-L3-HCDR2 | ACGAGAGATGGTGAAACGACCTTTAACAGAATCTGGGTAGTA | 77.0 | 233 |
| 53 | R-L4-HCDR2 | AACAGACATGGTAACACGAGATTTCAGAGATGGGTTGTAATC | 76.0 | 234 |
| 54 | R-L5-HCDR2 | AGCAGAGATGGTAACCTGACCCTGGAAAGATGGAGAGTAACG | 79.9 | 235 |
| 55 | R-L6-HCDR2 | GGTGGTCATGGTACCACGACCCTGCAGTTTCTGAGCGTAGTT | 81.8 | 236 |
| 56 | F-L1-HCDR3 | CTGTCTTCTCTGAAATCTGAGGACACGGCCGTGTATTACTGT | 78.9 | 237 |
| 57 | F-L2-HCDR3 | ATGACCAACATGGATCCTGTGGACACAGCCACATATTACTGT | 77.9 | 238 |
| 58 | F-L3-HCDR3 | ATGAACTCTCTGCGTGCCGAGGACACGGCTGTGTATTACTGT | 80.9 | 239 |
| 59 | F-L4-HCDR3 | GTTAACTCTGTTACCGCCGCGGACACGGCTGTGTATTACTGT | 80.9 | 240 |
| 60 | F-L5-HCDR3 | TGGTCTTCTCTGAAAGCCTCGGACACCGCCATTTATTACTGT | 78.9 | 241 |
| 61 | F-L6-HCDR3 | CTGCGTTCTCTGCGTTCTGACGACACGGCCGTGTATTACTGT | 81.8 | 242 |
| 62 | R-JH4 | GATTGGTTTGCCGCTAGCTGAGGAGACGGTGACCAGGGTTCC | 83.8 | 243 |
| 63 | R-JH6 | GATTGGTTTGCCGCTAGCTGAGGAGACGGTGACCGTGGTCCC | 84.8 | 244 |

TABLE 8

Exemplary Assembly Primers.

| | Name | Sequences | Tm (° C.) | SEQ ID NO |
|---|---|---|---|---|
| 64 | R-L1-LCDR1-ASS | GTAGATCAGCAGTTTTGGAGCTTT | 61.8 | 245 |
| 65 | R-L2-LCDR1-ASS | GTAGATCAGCAGTTTTGGTGG | 59.4 | 246 |
| 66 | R-L3-LCDR1-ASS | GTAGATCAGCAGCTGTGGAGA | 61.3 | 247 |
| 67 | R-L4-LCDR1-ASS | GTAGATCAGCAGACGTGGAG | 60.5 | 248 |
| 68 | R-L5-LCDR1-ASS | GTAGATCAGCAGACGTGGAG | 60.5 | 249 |
| 69 | R-L6-LCDR1-ASS | GTAGATCATCAGTTTTGGAGCTTTA | 60.9 | 250 |
| 70 | F-L1-LCDR2-ASS | CTGGCTTGGTACCAGCAGAAA | 61.3 | 251 |
| 71 | F-L2-LCDR2-ASS | CTGGCTTGGTACCAGCAGAAA | 61.3 | 252 |
| 72 | F-L3-LCDR2-ASS | CTGCACTGGTACCTGCAGAAA | 61.3 | 253 |
| 73 | F-L4-LCDR2-ASS | CTGGCTTGGTACCAGCAGAAA | 61.3 | 254 |
| 74 | F-L5-LCDR2-ASS | CTGGCTTGGTACCAGCAGAAA | 61.3 | 255 |
| 75 | F-L6-LCDR2-ASS | GTTTCTTGGTACCAGCAGCAC | 61.3 | 256 |
| 76 | R-L1-LCDR2-ASS | ACAGTAGTAGTTAGCGAAATCTTCT | 60.9 | 257 |
| 77 | R-L2-LCDR2-ASS | ACAGTAGTAAACAGCAACATCTTCA | 60.9 | 258 |
| 78 | R-L3-LCDR2-ASS | ACAGTAGTAAACACCAACATCTTCA | 60.9 | 259 |
| 79 | R-L4-LCDR2-ASS | ACAGTAGTAAACAGCGAAATCTTCT | 60.9 | 260 |
| 80 | R-L5-LCDR2-ASS | ACAGTAGTAAACAGCGAAATCTTCT | 60.9 | 261 |
| 81 | R-L6-LCDR2-ASS | ACAGTAGTAATCAGCTTCATCTTCA | 60.9 | 262 |

TABLE 8-continued

Exemplary Assembly Primers.

| Name | Sequences | Tm (° C.) | SEQ ID NO |
|------|-----------|-----------|-----------|
| 82 F-L1-LCDR3-ASS | GGTGTTCCATCTCGTTTCTCT | 59.4 | 263 |
| 83 F-L2-LCDR3-ASS | GGTGTTCCAGATCGTTTCTCT | 59.4 | 264 |
| 84 F-L3-LCDR3-ASS | GGTGTTCCAGATCGTTTCTCT | 59.4 | 265 |
| 85 F-L4-LCDR3-ASS | GGTATCCCAGCTCGTTTCTCT | 61.3 | 266 |
| 86 F-L5-LCDR3-ASS | GGTATCCCAGATCGTCTGTCT | 61.3 | 267 |
| 87 F-L6-LCDR3-ASS | GGTGTTTCTAACCGTTTCTCTG | 60.3 | 268 |
| 90 R-L1-HCDR1-ASS | ACCACCCATCCATTCCAGAC | 60.5 | 269 |
| 91 R-L2-HCDR1-ASS | CATAGCCAGCCATTCCAGAG | 60.5 | 270 |
| 92 R-L3-HCDR1-ASS | AGAAGCAACCAGTTCCAGACC | 61.3 | 271 |
| 93 R-L4-HCDR1-ASS | GTAACCGATCCATTCCAGACC | 61.3 | 272 |
| 94 R-L5-HCDR1-ASS | GATACCCATAGATTCCAGACCTTT | 61.8 | 273 |
| 95 R-L6-HCDR1-ASS | CCAACCCATCCATTCCAGAC | 60.5 | 274 |
| 96 F-L1-HCDR2-ASS | ATCCACTGGGTTCGTCAGG | 59.5 | 275 |
| 97 F-L2-HCDR2-ASS | GTTAACTGGATCCGTCAGCCA | 61.3 | 276 |
| 98 F-L3-HCDR2-ASS | ATGTCTTGGGTTCGTCAGGCT | 61.3 | 277 |
| 99 F-L4-HCDR2-ASS | TGGTCTTGGATCCGTCAGC | 59.5 | 278 |
| 100 F-L5-HCDR2-ASS | ATCGCTTGGGTTCGTCAGGTT | 61.3 | 279 |
| 101 F-L6-HCDR2-ASS | ATCTCTTGGGTTCGTCAGGCT | 61.3 | 280 |
| 102 R-L1-HCDR2-ASS | ACAGTAATACACGGCCGTGTC | 61.3 | 281 |
| 103 R-L2-HCDR2-ASS | ACAGTAATATGTGGCTGTGTCCA | 61.1 | 282 |
| 104 R-L3-HCDR2-ASS | ACAGTAATACACAGCCGTGTC | 59.4 | 283 |
| 105 R-L4-HCDR2-ASS | ACAGTAATACACAGCCGTGTC | 59.4 | 284 |
| 106 R-L5-HCDR2-ASS | ACAGTAATAAATGGCGGTGTCC | 60.3 | 285 |
| 107 R-L6-HCDR2-ASS | ACAGTAATACACGGCCGTGTC | 61.3 | 286 |
| 108 F-L1-HCDR3-ASS | ATCTACGCTCAGAAATTCCAGG | 60.3 | 287 |
| 109 F-L2-HCDR3-ASS | GTTTACAACTCTGCTCTGAAATCT | 60.1 | 288 |
| 110 F-L3-HCDR3-ASS | TACTACCCAGATTCTGTTAAAGGT | 60.1 | 289 |
| 111 F-L4-HCDR3-ASS | GATTACAACCCATCTCTGAAATCT | 60.1 | 290 |
| 112 F-L5-HCDR3-ASS | CGTTACTCTCCATCTTTCCAG | 59.4 | 291 |
| 113 F-L6-HCDR3-ASS | AACTACGCTCAGAAACTGCAG | 59.4 | 292 |
| 114 F-scfv-ASS | CGGATTGTCTTCAACCAACACAA | 61.1 | 293 |
| 115 R-scfv-ASS | CTCCTCCTGTTGAATCCAGG | 60.5 | 294 |
| 116 F-scfv | CAGTTAGATAAAAGAGGCGCG | 59.4 | 295 |
| 117 R-scfv | GCCCAGCAGTGGGTTTGG | 60.7 | 296 |
| 88 F-linker-ASS | TCCGGAGGGTCGACCATAA | 59.5 | 297 |
| 89 R-linker-ASS | GGTACCGCTCGAGGATAACTT | 61.3 | 298 |

While the diversity found in HCDR1-2 and LCDR1-3 can be covered by array-based oligonucleotide synthesis relatively easily, this may not be the case for HCDR3 in some instances, where the original diversity can easily exceed $10^8$ different HCDR3s. Even after liabilities and CDRs found fewer than 4 times may be eliminated, the number of different HCDR3s can exceed $10^7$ if NovaSeq ($3 \times 10^9$ reads) is used to assess diversity. This can be addressed either by limiting synthetic HCDR3 diversity to $<10^6$ sequences, which is tractable by array-based synthesis; or by combining synthetic HCDR1-2 and LCDR1-3 diversity with naturally diverse HCDR3 amplified from donor lymphocytes.

RNA from B lymphocytes from Leuko Paks from ten donors, comprising a total of $>10^9$ B cells, was isolated using the Miltenyi StraightFrom LeukoPak CD19 kit. cDNA was prepared using a primer annealing in the IgM constant region. HCDR3s were amplified from the cDNA using all possible combinations of the six forward primers (F-L1-HCDR3 to F1-L6-HCDR3) and the two reverse primers (R-JH4 and RJH6) described Table 7 and Table 8. This amplification appends sequences to the 5' and 3' ends homologous to the framework vectors, into which the HCDR3s are to be cloned.

Example 7: Cloning of CDRs into Single Site CDR Vectors and Selection for Functional CDRs Although natural replicated CDRs are synthesized based on criteria that should ensure their functionality (e.g., removal of liabilities), oligonucleotide synthesis may not be 100% accurate. In addition to the problem of incorrect sequences, other unidentified liabilities causing poor expression or polyreactivity may be encoded by the synthesized oligonucleotides. Selection of the functional CDRs can be an option to address this issue.

Each of the CDRs remaining from the elimination steps described above was cloned into the appropriate yeast display scaffold vector. The coding sequences of the exemplary scaffold are provided below:

>1 - abrilumab
(SEQ ID NO: 139)
cagttagataaaagaggcgcggcagcaagcggcgcgcatgccGATATCCAGATGACCCAGTCTCCATCTT
CTGTTTCTGCTTCTGTTGGTGATCGTGTTACTATTACCTGTCGTGCTTCTCAGGGTATCTCTTCTTGGCT -continued

```
GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC

CAGAAGATTTCGCTAACTACTACTGTCAGCAGGCTAACTCTTTCCCATGGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGGTTCAGTCTGGTGCTGAAGTTAAAAAACCAGGTGCTTCTGTTAAAGTTTCTT

GTAAAGTTTCTGGTTACACCCTGTCTGATCTGTCTATCCACTGGGTTCGTCAGGCTCCAGGTAAAGGTCT

GGAATGGATGGGTGGTTTCGATCCACAGGATGGTGAAACCATCTACGCTCAGAAATTCCAGGGTCGTGTT

ACCATGACCGAAGATACCTCTACCGATACCGCTTACATGGAACTGTCTTCTCTGAAATCTGAGGACACGG

CCGTGTATTACTGTGCTACCGGTTCTTCTTCTTCTTGGTTCGATCCATGGGGTCAGGGAACCCTGGTCAC

CGTCTCCTCAgctagcggcaaaccaatcccaaacccactgctgggc
```

>1a - abrilumab dLCDR1
(SEQ ID NO: 140)
```
cagttagataaaagaggcgcggcagcaagcggcgcgcatgccGATATCCAGATGACCCAGTCTCCATCTT CTGTTTCTGCTTCTGTTGGTGATCGTGTTACTATTACCTGTCGTGCTTCTagagaccatggccagtaagg ccggtctctCTGGCTTGGTACCAGCAGAAACCAGGTAAAGCTCCAAAACTGCTGATCTACGGTGCTTCTA

ACCTGGAATCTGGTGTTCCATCTCGTTTCTCTGGTTCTGGTTCTGGTACCGATTTCACCCTGACCATCTC

TTCTCTGCAGCCAGAAGATTTCGCTAACTACTACTGTCAGCAGGCTAACTCTTTCCCATGGACCTTCGGT

GGTGGTACCAAAGTTGAAATCAAATCCGGAGGGTCGACCATAACTTCGTATAATGTATACTATACGAAGT

TATCCTCGAGCGGTACCCAGGTTCAGCTGGTTCAGTCTGGTGCTGAAGTTAAAAAACCAGGTGCTTCTGT

TAAAGTTTCTTGTAAAGTTTCTGGTTACACCCTGTCTGATCTGTCTATCCACTGGGTTCGTCAGGCTCCA

GGTAAAGGTCTGGAATGGATGGGTGGTTTCGATCCACAGGATGGTGAAACCATCTACGCTCAGAAATTCC

AGGGTCGTGTTACCATGACCGAAGATACCTCTACCGATACCGCTTACATGGAACTGTCTTCTCTGAAATC

TGAGGACACGGCCGTGTATTACTGTGCTACCGGTTCTTCTTCTTCTTGGTTCGATCCATGGGGTCAGGGA

ACCCTGGTCACCGTCTCCTCAgctagcggcaaaccaatcccaaacccactgctgggc
```

>1b - abrilumab dLCDR2
(SEQ ID NO: 141)
```
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACagagaccatggccagtaaggc cggtctctGGTGTTCCATCTCGTTTCTCTGGTTCTGGTTCTGGTACCGATTTCACCCTGACCATCTCTTC

TCTGCAGCCAGAAGATTTCGCTAACTACTACTGTCAGCAGGCTAACTCTTTCCCATGGACCTTCGGTGGT

GGTACCAAAGTTGAAATCAAATCCGGAGGGTCGACCATAACTTCGTATAATGTATACTATACGAAGTTAT

CCTCGAGCGGTACCCAGGTTCAGCTGGTTCAGTCTGGTGCTGAAGTTAAAAAACCAGGTGCTTCTGTTAA

AGTTTCTTGTAAAGTTTCTGGTTACACCCTGTCTGATCTGTCTATCCACTGGGTTCGTCAGGCTCCAGGT

AAAGGTCTGGAATGGATGGGTGGTTTCGATCCACAGGATGGTGAAACCATCTACGCTCAGAAATTCCAGG

GTCGTGTTACCATGACCGAAGATACCTCTACCGATACCGCTTACATGGAACTGTCTTCTCTGAAATCTGA

GGACACGGCCGTGTATTACTGTGCTACCGGTTCTTCTTCTTCTTGGTTCGATCCATGGGGTCAGGGAACC

CTGGTCACCGTCTCCTCAgctagcggcaaaccaatcccaaacccactgctgggc
```

>1c - abrilumab dLCDR3
(SEQ ID NO: 142)
```
cagttagataaaagaggcgcggcagcaagcggcgcgcatgccGATATCCAGATGACCCAGTCTCCATCTT

CTGTTTCTGCTTCTGTTGGTGATCGTGTTACTATTACCTGTCGTGCTTCTCAGGGTATCTCTTCTTGGCT

GGCTTGGTACCAGCAGAAACCAGGTAAAGCTCCAAAACTGCTGATCTACGGTGCTTCTAACCTGGAATCT

GGTGTTCCATCTCGTTTCTCTGGTTCTGGTTCTGGTACCGATTTCACCCTGACCATCTCTTCTCTGCAGC
```

```
CAGAAGATTTCGCTAACTACTACTGTagagaccatggccagtaaggccggtctctTTCGGTGGTGGTACC
AAAGTTGAAATCAAATCCGGAGGGTCGACCATAACTTCGTATAATGTATACTATACGAAGTTATCCTCGA
GCGGTACCCAGGTTCAGCTGGTTCAGTCTGGTGCTGAAGTTAAAAAACCAGGTGCTTCTGTTAAAGTTTC
TTGTAAAGTTTCTGGTTACACCCTGTCTGATCTGTCTATCCACTGGGTTCGTCAGGCTCCAGGTAAAGGT
CTGGAATGGATGGGTGGTTTCGATCCACAGGATGGTGAAACCATCTACGCTCAGAAATTCCAGGGTCGTG
TTACCATGACCGAAGATACCTCTACCGATACCGCTTACATGGAACTGTCTTCTCTGAAATCTGAGGACAC
GGCCGTGTATTACTGTGCTACCGGTTCTTCTTCTTCTTGGTTCGATCCATGGGGTCAGGGAACCCTGGTC
ACCGTCTCCTCAgctagcggcaaaccaatcccaaacccactgctgggc >1d - abrilumab dHCDR1
                                                         (SEQ ID NO: 143)
cagttagataaaagaggcgcggcagcaagcggcgcgcatgccGATATCCAGATGACCCAGTCTCCATCTT
CTGTTTCTGCTTCTGTTGGTGATCGTGTTACTATTACCTGTCGTGCTTCTCAGGGTATCTCTTCTTGGCT
GGCTTGGTACCAGCAGAAACCAGGTAAAGCTCCAAAACTGCTGATCTACGGTGCTTCTAACCTGGAATCT
GGTGTTCCATCTCGTTTCTCTGGTTCTGGTTCTGGTACCGATTTCACCCTGACCATCTCTTCTCTGCAGC
CAGAAGATTTCGCTAACTACTACTGTCAGCAGGCTAACTCTTTCCCATGGACCTTCGGTGGTGGTACCAA
AGTTGAAATCAAATCCGGAGGGTCGACCATAACTTCGTATAATGTATACTATACGAAGTTATCCTCGAGC
GGTACCCAGGTTCAGCTGGTTCAGTCTGGTGCTGAAGTTAAAAAACCAGGTGCTTCTGTTAAAGTTTCTT
GTAAAGTTTCTagagaccatggccagtaaggccggtctctATCCACTGGGTTCGTCAGGCTCCAGGTAAA
GGTCTGGAATGGATGGGTGGTTTCGATCCACAGGATGGTGAAACCATCTACGCTCAGAAATTCCAGGGTC
GTGTTACCATGACCGAAGATACCTCTACCGATACCGCTTACATGGAACTGTCTTCTCTGAAATCTGAGGA
CACGGCCGTGTATTACTGTGCTACCGGTTCTTCTTCTTCTTGGTTCGATCCATGGGGTCAGGGAACCCTG
GTCACCGTCTCCTCAgctagcggcaaaccaatcccaaacccactgctgggc >1e - abrilumab dHCDR2
                                                         (SEQ ID NO: 144)
cagttagataaaagaggcgcggcagcaagcggcgcgcatgccGATATCCAGATGACCCAGTCTCCATCTT
CTGTTTCTGCTTCTGTTGGTGATCGTGTTACTATTACCTGTCGTGCTTCTCAGGGTATCTCTTCTTGGCT
GGCTTGGTACCAGCAGAAACCAGGTAAAGCTCCAAAACTGCTGATCTACGGTGCTTCTAACCTGGAATCT
GGTGTTCCATCTCGTTTCTCTGGTTCTGGTTCTGGTACCGATTTCACCCTGACCATCTCTTCTCTGCAGC
CAGAAGATTTCGCTAACTACTACTGTCAGCAGGCTAACTCTTTCCCATGGACCTTCGGTGGTGGTACCAA
AGTTGAAATCAAATCCGGAGGGTCGACCATAACTTCGTATAATGTATACTATACGAAGTTATCCTCGAGC
GGTACCCAGGTTCAGCTGGTTCAGTCTGGTGCTGAAGTTAAAAAACCAGGTGCTTCTGTTAAAGTTTCTT
GTAAAGTTTCTGGTTACACCCTGTCTGATCTGTCTATCCACTGGGTTCGTCAGGCTCCAGGTAAAGGTCT
GGAATGGATGGGTGGTagagaccatggccagtaaggccggtctctATCTACGCTCAGAAATTCCAGGGTC
GTGTTACCATGACCGAAGATACCTCTACCGATACCGCTTACATGGAACTGTCTTCTCTGAAATCTGAGGA
CACGGCCGTGTATTACTGTGCTACCGGTTCTTCTTCTTCTTGGTTCGATCCATGGGGTCAGGGAACCCTG
GTCACCGTCTCCTCAgctagcggcaaaccaatcccaaacccactgctgggc >1f - abrilumab dHCDR3
                                                         (SEQ ID NO: 145)
cagttagataaaagaggcgcggcagcaagcggcgcgcatgccGATATCCAGATGACCCAGTCTCCATCTT
CTGTTTCTGCTTCTGTTGGTGATCGTGTTACTATTACCTGTCGTGCTTCTCAGGGTATCTCTTCTTGGCT
GGCTTGGTACCAGCAGAAACCAGGTAAAGCTCCAAAACTGCTGATCTACGGTGCTTCTAACCTGGAATCT
GGTGTTCCATCTCGTTTCTCTGGTTCTGGTTCTGGTACCGATTTCACCCTGACCATCTCTTCTCTGCAGC
CAGAAGATTTCGCTAACTACTACTGTCAGCAGGCTAACTCTTTCCCATGGACCTTCGGTGGTGGTACCAA
```

-continued

AGTTGAAATCAAATCCGGAGGGTCGACCATAACTTCGTATAATGTATACTATACGAAGTTATCCTCGAGC

GGTACCCAGGTTCAGCTGGTTCAGTCTGGTGCTGAAGTTAAAAAACCAGGTGCTTCTGTTAAAGTTTCTT

GTAAAGTTTCTGGTTACACCCTGTCTGATCTGTCTATCCACTGGGTTCGTCAGGCTCCAGGTAAAGGTCT

GGAATGGATGGGTGGTTTCGATCCACAGGATGGTGAAACCATCTACGCTCAGAAATTCCAGGGTCGTGTT

ACCATGACCGAAGATACCTCTACCGATACCGCTTACATGGAACTGTCTTCTCTGAAATCTGAGGACACGG

CCGTGTATTACTGTagagaccatggccagtaaggccggtctctGGAACCCTGGTCACCGTCTCCTCAgct agcggcaaaccaatcccaaacccactgctgggc >2 - mepolizumab
(SEQ ID NO: 146)
cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACGGT

GCTTCTACCCGTGAATCTGGTGTTCCAGATCGTTTCTCTGGTTCTGGTTCTGGTACCGATTTCACCCTGA

CCATCTCTTCTCTGCAGGCTGAAGATGTTGCTGTTTACTACTGTCAGAACGTTCACTCTTTCCCATTCAC

CTTCGGTGGTGGTACCAAAGTTGAAATCAAATCCGGAGGGTCGACCATAACTTCGTATAATGTATACTAT

ACGAAGTTATCCTCGAGCGGTACCCAGGTTACCCTGCGTGAATCTGGTCCAGCTCTGGTTAAACCAACCC

AGACCCTGACCCTGACCTGTACCGTTTCTGGTTTCTCTCTGTCTGCTTACTCTGTTAACTGGATCCGTCA

GCCACCAGGTAAAGCTCTGGAATGGCTGGCTATGATCTGGGGTGATGGTAAAATCGTTTACAACTCTGCT

CTGAAATCTCGTCTGACCATCTCTAAAGATACCTCTAAAAACCAGGTTGTTCTGACCATGACCAACATGG

ATCCTGTGGACACAGCCACATATTACTGTGCTGGTGATGGTTACTACCCATACGCTATGGATAACTGGGG

TCAGGGAACCCTGGTCACCGTCTCCTCAgctagcggcaaaccaatcccaaacccactgctgggc

>2a - mepolizumab dLCDR1
(SEQ ID NO: 147)
cagttagataaaagaggcgcggcagcaagcggcgcgcatgccGATATCGTTATGACCCAGTCTCCAGATT CTCTGGCTGTTTCTCTGGGTGAACGTGCTACCATCAACTGCAAATCTTCTagagaccatggccagtaagg ccggtctctCTGGCTTGGTACCAGCAGAAACCAGGTCAGCCACCAAAACTGCTGATCTACGGTGCTTCTA

CCCGTGAATCTGGTGTTCCAGATCGTTTCTCTGGTTCTGGTTCTGGTACCGATTTCACCCTGACCATCTC

TTCTCTGCAGGCTGAAGATGTTGCTGTTTACTACTGTCAGAACGTTCACTCTTTCCCATTCACCTTCGGT

GGTGGTACCAAAGTTGAAATCAAATCCGGAGGGTCGACCATAACTTCGTATAATGTATACTATACGAAGT

TATCCTCGAGCGGTACCCAGGTTACCCTGCGTGAATCTGGTCCAGCTCTGGTTAAACCAACCCAGACCCT

GACCCTGACCTGTACCGTTTCTGGTTTCTCTCTGTCTGCTTACTCTGTTAACTGGATCCGTCAGCCACCA

GGTAAAGCTCTGGAATGGCTGGCTATGATCTGGGGTGATGGTAAAATCGTTTACAACTCTGCTCTGAAAT

CTCGTCTGACCATCTCTAAAGATACCTCTAAAAACCAGGTTGTTCTGACCATGACCAACATGGATCCTGT

GGACACAGCCACATATTACTGTGCTGGTGATGGTTACTACCCATACGCTATGGATAACTGGGGTCAGGGA

ACCCTGGTCACCGTCTCCTCAgctagcggcaaaccaatcccaaacccactgctgggc

>2b - mepolizumab dLCDR2
(SEQ ID NO: 148)
cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACaga gaccatggccagtaaggccggtctctGGTGTTCCAGATCGTTTCTCTGGTTCTGGTTCTGGTACCGATTT

CACCCTGACCATCTCTTCTCTGCAGGCTGAAGATGTTGCTGTTTACTACTGTCAGAACGTTCACTCTTTC

CCATTCACCTTCGGTGGTGGTACCAAAGTTGAAATCAAATCCGGAGGGTCGACCATAACTTCGTATAATG

TATACTATACGAAGTTATCCTCGAGCGGTACCCAGGTTACCCTGCGTGAATCTGGTCCAGCTCTGGTTAA

-continued

ACCAACCCAGACCCTGACCCTGACCTGTACCGTTTCTGGTTTCTCTCTGTCTGCTTACTCTGTTAACTGG
ATCCGTCAGCCACCAGGTAAAGCTCTGGAATGGCTGGCTATGATCTGGGGTGATGGTAAAATCGTTTACA
ACTCTGCTCTGAAATCTCGTCTGACCATCTCTAAAGATACCTCTAAAAACCAGGTTGTTCTGACCATGAC
CAACATGGATCCTGTGGACACAGCCACATATTACTGTGCTGGTGATGGTTACTACCCATACGCTATGGAT
AACTGGGGTCAGGGAACCCTGGTCACCGTCTCCTCAgctagcggcaaaccaatcccaaacccactgctgg
gc >2c - mepolizumab dLCDR3 (SEQ ID NO: 149)
cagttagataaaagaggcgcggcagcaagcggcgcgcatgccGATATCGTTATGACCCAGTCTCCAGATT
CTCTGGCTGTTTCTCTGGGTGAACGTGCTACCATCAACTGCAAATCTTCTCAGTCTCTGCTGAACTCTGG
TAACCAGAAAAACTACCTGGCTTGGTACCAGCAGAAACCAGGTCAGCCACCAAAACTGCTGATCTACGGT
GCTTCTACCCGTGAATCTGGTGTTCCAGATCGTTTCTCTGGTTCTGGTTCTGGTACCGATTTCACCCTGA
CCATCTCTTCTCTGCAGGCTGAAGATGTTGCTGTTTACTACTGTagagaccatggccagtaaggccggtc
tctTTCGGTGGTGGTACCAAAGTTGAAATCAAATCCGGAGGGTCGACCATAACTTCGTATAATGTATACT
ATACGAAGTTATCCTCGAGCGGTACCCAGGTTACCCTGCGTGAATCTGGTCCAGCTCTGGTTAAACCAAC
CCAGACCCTGACCCTGACCTGTACCGTTTCTGGTTTCTCTCTGTCTGCTTACTCTGTTAACTGGATCCGT
CAGCCACCAGGTAAAGCTCTGGAATGGCTGGCTATGATCTGGGGTGATGGTAAAATCGTTTACAACTCTG
CTCTGAAATCTCGTCTGACCATCTCTAAAGATACCTCTAAAAACCAGGTTGTTCTGACCATGACCAACAT
GGATCCTGTGGACACAGCCACATATTACTGTGCTGGTGATGGTTACTACCCATACGCTATGGATAACTGG
GGTCAGGGAACCCTGGTCACCGTCTCCTCAgctagcggcaaaccaatcccaaacccactgctgggc >2d - mepolizumab dHCDR1 (SEQ ID NO: 150)
cagttagataaaagaggcgcggcagcaagcggcgcgcatgccGATATCGTTATGACCCAGTCTCCAGATT
CTCTGGCTGTTTCTCTGGGTGAACGTGCTACCATCAACTGCAAATCTTCTCAGTCTCTGCTGAACTCTGG
TAACCAGAAAAACTACCTGGCTTGGTACCAGCAGAAACCAGGTCAGCCACCAAAACTGCTGATCTACGGT
TTCTACCCGTGAATCTGGTGTTCCAGATCGTTTCTCTGGTTCTGGTTCTGGTACCGATTTCACCCTGA
CCATCTCTTCTCTGCAGGCTGAAGATGTTGCTGTTTACTACTGTCAGAACGTTCACTCTTTCCCATTCAC
CTTCGGTGGTGGTACCAAAGTTGAAATCAAATCCGGAGGGTCGACCATAACTTCGTATAATGTATACTAT
ACGAAGTTATCCTCGAGCGGTACCCAGGTTACCCTGCGTGAATCTGGTCCAGCTCTGGTTAAACCAACCC
AGACCCTGACCCTGACCTGTACCGTTTCTagagaccatggccagtaaggccggtctctGTTAACTGGATC
CGTCAGCCACCAGGTAAAGCTCTGGAATGGCTGGCTATGATCTGGGGTGATGGTAAAATCGTTTACAACT
CTGCTCTGAAATCTCGTCTGACCATCTCTAAAGATACCTCTAAAAACCAGGTTGTTCTGACCATGACCAA
CATGGATCCTGTGGACACAGCCACATATTACTGTGCTGGTGATGGTTACTACCCATACGCTATGGATAAC
TGGGGTCAGGGAACCCTGGTCACCGTCTCCTCAgctagcggcaaaccaatcccaaacccactgctgggc >2e - mepolizumab dHCDR2 (SEQ ID NO: 151)
cagttagataaaagaggcgcggcagcaagcggcgcgcatgccGATATCGTTATGACCCAGTCTCCAGATT
CTCTGGCTGTTTCTCTGGGTGAACGTGCTACCATCAACTGCAAATCTTCTCAGTCTCTGCTGAACTCTGG
TAACCAGAAAAACTACCTGGCTTGGTACCAGCAGAAACCAGGTCAGCCACCAAAACTGCTGATCTACGGT
GCTTCTACCCGTGAATCTGGTGTTCCAGATCGTTTCTCTGGTTCTGGTTCTGGTACCGATTTCACCCTGA
CCATCTCTTCTCTGCAGGCTGAAGATGTTGCTGTTTACTACTGTCAGAACGTTCACTCTTTCCCATTCAC
CTTCGGTGGTGGTACCAAAGTTGAAATCAAATCCGGAGGGTCGACCATAACTTCGTATAATGTATACTAT
ACGAAGTTATCCTCGAGCGGTACCCAGGTTACCCTGCGTGAATCTGGTCCAGCTCTGGTTAAACCAACCC -continued

AGACCCTGACCCTGACCTGTACCGTTTCTGGTTTCTCTCTGTCTGCTTACTCTGTTAACTGGATCCGTCA

GCCACCAGGTAAAGCTCTGGAATGGCTGGCTATGagagaccatggccagtaaggccggtctctATCGTTT

ACAACTCTGCTCTGAAATCTCGTCTGACCATCTCTAAAGATACCTCTAAAAACCAGGTTGTTCTGACCAT

GACCAACATGGATCCTGTGGACACAGCCACATATTACTGTGCTGGTGATGGTTACTACCCATACGCTATG

GATAACTGGGGTCAGGGAACCCTGGTCACCGTCTCCTCAgctagcggcaaaccaatcccaaacccactgc tgggc

>2f - mepolizumab dHCDR3
(SEQ ID NO: 152)
cagttagataaaagaggcgcggcagcaagcggcgcgcatgccGATATCGTTATGACCCAGTCTCCAGATT

CTCTGGCTGTTTCTCTGGGTGAACGTGCTACCATCAACTGCAAATCTTCTCAGTCTCTGCTGAACTCTGG

TAACCAGAAAAACTACCTGGCTTGGTACCAGCAGAAACCAGGTCAGCCACCAAAACTGCTGATCTACGGT

GCTTCTACCCGTGAATCTGGTGTTCCAGATCGTTTCTCTGGTTCTGGTTCTGGTACCGATTTCACCCTGA

CCATCTCTTCTCTGCAGGCTGAAGATGTTGCTGTTTACTACTGTCAGAACGTTCACTCTTTCCCATTCAC

CTTCGGTGGTGGTACCAAAGTTGAAATCAAATCCGGAGGGTCGACCATAACTTCGTATAATGTATACTAT

ACGAAGTTATCCTCGAGCGGTACCCAGGTTACCCTGCGTGAATCTGGTCCAGCTCTGGTTAAACCAACCC

AGACCCTGACCCTGACCTGTACCGTTTCTGGTTTCTCTCTGTCTGCTTACTCTGTTAACTGGATCCGTCA

GCCACCAGGTAAAGCTCTGGAATGGCTGGCTATGATCTGGGGTGATGGTAAAATCGTTTACAACTCTGCT

CTGAAATCTCGTCTGACCATCTCTAAAGATACCTCTAAAAACCAGGTTGTTCTGACCATGACCAACATGG

ATCCTGTGGACACAGCCACATATTACTGTagagaccatggccagtaaggccggtctctGGAACCCTGGTC

ACCGTCTCCTCAgctagcggcaaaccaatcccaaacccactgctgggc

>3 - crenezumab
(SEQ ID NO: 153)
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTGGTTTCACCTTCTCTTCTTACGGTATGTCTTGGGTTCGTCAGGC

TCCAGGTAAAGGTCTGGAACTGGTTGCTTCTATCAACTCTAACGGTGGTTCTACCTACTACCCAGATTCT

GTTAAAGGTCGTTTCACCATCTCTCGTGATAACGCTAAAAACTCTCTGTACCTGCAGATGAACTCTCTGC

GTGCCGAGGACACGGCTGTGTATTACTGTGCTTCTGGTGATTACTGGGGTCAGGGGACCACGGTCACCGT

CTCCTCAgctagcggcaaaccaatcccaaacccactgctgggc

>3a - crenezumab dLCDR1
(SEQ ID NO: 154)
cagttagataaaagaggcgcggcagcaagcggcgcgcatgccGATATCGTTATGACCCAGTCTCCACTGT CTCTGCCAGTTACCCCAGGTGAACCAGCTTCTATTTCTTGTCGTTCTTCTagagaccatggccagtaagg ccggtctctCTGCACTGGTACCTGCAGAAACCAGGTCAGTCTCCACAGCTGCTGATCTACAAAGTTTCTA

ACCGTTTCTCTGGTGTTCCAGATCGTTTCTCTGGTTCTGGTTCTGGTACCGATTTCACCCTGAAAATCTC

TCGTGTTGAAGCTGAAGATGTTGGTGTTTACTACTGTTCTCAGTCTACCCACGTTCCATGGACCTTCGGT

GGTGGTACCAAAGTTGAAATCAAATCCGGAGGGTCGACCATAACTTCGTATAATGTATACTATACGAAGT

TATCCTCGAGCGGTACCGAAGTTCAGCTGGTTGAATCTGGTGGTGGTCTGGTTCAGCCAGGTGGTTCTCT

GCGTCTGTCTTGTGCTGCTTCTGGTTTCACCTTCTCTTCTTACGGTATGTCTTGGGTTCGTCAGGCTCCA

-continued

```
GGTAAAGGTCTGGAACTGGTTGCTTCTATCAACTCTAACGGTGGTTCTACCTACTACCCAGATTCTGTTA

AAGGTCGTTTCACCATCTCTCGTGATAACGCTAAAAACTCTCTGTACCTGCAGATGAACTCTCTGCGTGC

CGAGGACACGGCTGTGTATTACTGTGCTTCTGGTGATTACTGGGGTCAGGGGACCACGGTCACCGTCTCC

TCAgctagcggcaaaccaatcccaaacccactgctgggc
```

>3b - crenezumab dLCDR2
(SEQ ID NO: 155)
```
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACagagac catggccagtaaggccggtctctGGTGTTCCAGATCGTTTCTCTGGTTCTGGTTCTGGTACCGATTTCAC

CCTGAAAATCTCTCGTGTTGAAGCTGAAGATGTTGGTGTTTACTACTGTTCTCAGTCTACCCACGTTCCA

TGGACCTTCGGTGGTGGTACCAAAGTTGAAATCAAATCCGGAGGGTCGACCATAACTTCGTATAATGTAT

ACTATACGAAGTTATCCTCGAGCGGTACCGAAGTTCAGCTGGTTGAATCTGGTGGTGGTCTGGTTCAGCC

AGGTGGTTCTCTGCGTCTGTCTTGTGCTGCTTCTGGTTTCACCTTCTCTTCTTACGGTATGTCTTGGGTT

CGTCAGGCTCCAGGTAAAGGTCTGGAACTGGTTGCTTCTATCAACTCTAACGGTGGTTCTACCTACTACC

CAGATTCTGTTAAAGGTCGTTTCACCATCTCTCGTGATAACGCTAAAAACTCTCTGTACCTGCAGATGAA

CTCTCTGCGTGCCGAGGACACGGCTGTGTATTACTGTGCTTCTGGTGATTACTGGGGTCAGGGGACCACG

GTCACCGTCTCCTCAgctagcggcaaaccaatcccaaacccactgctgggc
```

>3c - crenezumab dLCDR3
(SEQ ID NO: 156)
```
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTagagaccatggccagtaaggccggtctct

TTCGGTGGTGGTACCAAAGTTGAAATCAAATCCGGAGGGTCGACCATAACTTCGTATAATGTATACTATA

CGAAGTTATCCTCGAGCGGTACCGAAGTTCAGCTGGTTGAATCTGGTGGTGGTCTGGTTCAGCCAGGTGG

TTCTCTGCGTCTGTCTTGTGCTGCTTCTGGTTTCACCTTCTCTTCTTACGGTATGTCTTGGGTTCGTCAG

GCTCCAGGTAAAGGTCTGGAACTGGTTGCTTCTATCAACTCTAACGGTGGTTCTACCTACTACCCAGATT

CTGTTAAAGGTCGTTTCACCATCTCTCGTGATAACGCTAAAAACTCTCTGTACCTGCAGATGAACTCTCT

GCGTGCCGAGGACACGGCTGTGTATTACTGTGCTTCTGGTGATTACTGGGGTCAGGGGACCACGGTCACC

GTCTCCTCAgctagcggcaaaccaatcccaaacccactgctgggc
```

>3d - crenezumab dHCDR1
(SEQ ID NO: 157)
```
cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTagagaccatggccagtaaggccggtctctATGTCTTGGGTTCGT

CAGGCTCCAGGTAAAGGTCTGGAACTGGTTGCTTCTATCAACTCTAACGGTGGTTCTACCTACTACCCAG
```

-continued

ATTCTGTTAAAGGTCGTTTCACCATCTCTCGTGATAACGCTAAAAACTCTCTGTACCTGCAGATGAACTC

TCTGCGTGCCGAGGACACGGCTGTGTATTACTGTGCTTCTGGTGATTACTGGGGTCAGGGGACCACGGTC

ACCGTCTCCTCAgctagcggcaaaccaatcccaaacccactgctgggc

>3e - crenezumab dHCDR2

(SEQ ID NO: 158)

cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTGGTTTCACCTTCTCTTCTTACGGTATGTCTTGGGTTCGTCAGGC

TCCAGGTAAAGGTCTGGAACTGGTTGCTTCTagagaccatggccagtaaggccggtctctTACTACCCAG

ATTCTGTTAAAGGTCGTTTCACCATCTCTCGTGATAACGCTAAAAACTCTCTGTACCTGCAGATGAACTC

TCTGCGTGCCGAGGACACGGCTGTGTATTACTGTGCTTCTGGTGATTACTGGGGTCAGGGGACCACGGTC

ACCGTCTCCTCAgctagcggcaaaccaatcccaaacccactgctgggc

>3f - crenezumab dHCDR3

(SEQ ID NO: 159)

cagttagataaaagaggcgcggcagcaagcggcgcgcatgccGATATCGTTATGACCCAGTCTCCACTGT

CTCTGCCAGTTACCCCAGGTGAACCAGCTTCTATTTCTTGTCGTTCTTCTCAGTCTCTGGTTTACTCTAA

CGGTGATACCTACCTGCACTGGTACCTGCAGAAACCAGGTCAGTCTCCACAGCTGCTGATCTACAAAGTT

TCTAACCGTTTCTCTGGTGTTCCAGATCGTTTCTCTGGTTCTGGTTCTGGTACCGATTTCACCCTGAAAA

TCTCTCGTGTTGAAGCTGAAGATGTTGGTGTTTACTACTGTTCTCAGTCTACCCACGTTCCATGGACCTT

CGGTGGTGGTACCAAAGTTGAAATCAAATCCGGAGGGTCGACCATAACTTCGTATAATGTATACTATACG

AAGTTATCCTCGAGCGGTACCGAAGTTCAGCTGGTTGAATCTGGTGGTGGTCTGGTTCAGCCAGGTGGTT

CTCTGCGTCTGTCTTGTGCTGCTTCTGGTTTCACCTTCTCTTCTTACGGTATGTCTTGGGTTCGTCAGGC

TCCAGGTAAAGGTCTGGAACTGGTTGCTTCTATCAACTCTAACGGTGGTTCTACCTACTACCCAGATTCT

GTTAAAGGTCGTTTCACCATCTCTCGTGATAACGCTAAAAACTCTCTGTACCTGCAGATGAACTCTCTGC

GTGCCGAGGACACGGCTGTGTATTACTGTagagaccatggccagtaaggccggtctctGGGACCACGGTC

ACCGTCTCCTCAgctagcggcaaaccaatcccaaacccactgctgggc

>4 - necitumumab (SEQ ID NO: 160)

cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACGATGCTTCTAACCGTGCTACC

GGTATCCCAGCTCGTTTCTCTGGTTCTGGTTCTGGTACCGATTTCACCCTGACCATCTCTTCTCTGGAAC

CAGAAGATTTCGCTGTTTACTACTGTCACCAGTACGGTTCTACCCCACTGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGCAGGAATCTGGTCCAGGTCTGGTTAAACCATCTCAGACCCTGTCTCTGACCT

GTACCGTTTCTGGTGGTTCTATCTCTTCTGGTGATTACTACTGGTCTTGGATCCGTCAGCCACCAGGTAA

AGGTCTGGAATGGATCGGTTACATCTACTACTCTGGTTCTACCGATTACAACCCATCTCTGAAATCTCGT

GTTACCATGTCTGTTGATACCTCTAAAAACCAGTTCTCTCTGAAAGTTAACTCTGTTACCGCCGCGGACA

CGGCTGTGTATTACTGTGCTCGTGTTTCTATCTTCGGTGTTGGTACCTTCGATTACTGGGGTCAGGGAAC

CCTGGTCACCGTCTCCTCAgctagcggcaaaccaatcccaaacccactgctgggc

>4a - necitumumab dLCDR1
(SEQ ID NO: 161)
cagttagataaaagaggcgcggcagcaagcggcgcgcatgccGAAATCGTTATGACCCAGTCTCCAGCTA CCCTGTCTCTGTCTCCAGGTGAACGTGCCACTCTGTCTTGTCGTGCTTCTagagaccatggccagtaagg ccggtctctCTGGCTTGGTACCAGCAGAAACCAGGTCAGGCTCCACGTCTGCTGATCTACGATGCTTCTA

ACCGTGCTACCGGTATCCCAGCTCGTTTCTCTGGTTCTGGTTCTGGTACCGATTTCACCCTGACCATCTC

TTCTCTGGAACCAGAAGATTTCGCTGTTTACTACTGTCACCAGTACGGTTCTACCCCACTGACCTTCGGT

GGTGGTACCAAAGTTGAAATCAAATCCGGAGGGTCGACCATAACTTCGTATAATGTATACTATACGAAGT

TATCCTCGAGCGGTACCCAGGTTCAGCTGCAGGAATCTGGTCCAGGTCTGGTTAAACCATCTCAGACCCT

GTCTCTGACCTGTACCGTTTCTGGTGGTTCTATCTCTTCTGGTGATTACTACTGGTCTTGGATCCGTCAG

CCACCAGGTAAAGGTCTGGAATGGATCGGTTACATCTACTACTCTGGTTCTACCGATTACAACCCATCTC

TGAAATCTCGTGTTACCATGTCTGTTGATACCTCTAAAAACCAGTTCTCTCTGAAAGTTAACTCTGTTAC

CGCCGCGGACACGGCTGTGTATTACTGTGCTCGTGTTTCTATCTTCGGTGTTGGTACCTTCGATTACTGG

GGTCAGGGAACCCTGGTCACCGTCTCCTCAgctagcggcaaaccaatcccaaacccactgctgggc

>4b - necitumumab dLCDR2
(SEQ ID NO: 162)
cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACagagaccatggccagtaaggc cggtctctGGTATCCCAGCTCGTTTCTCTGGTTCTGGTTCTGGTACCGATTTCACCCTGACCATCTCTTC

TCTGGAACCAGAAGATTTCGCTGTTTACTACTGTCACCAGTACGGTTCTACCCCACTGACCTTCGGTGGT

GGTACCAAAGTTGAAATCAAATCCGGAGGGTCGACCATAACTTCGTATAATGTATACTATACGAAGTTAT

CCTCGAGCGGTACCCAGGTTCAGCTGCAGGAATCTGGTCCAGGTCTGGTTAAACCATCTCAGACCCTGTC

TCTGACCTGTACCGTTTCTGGTGGTTCTATCTCTTCTGGTGATTACTACTGGTCTTGGATCCGTCAGCCA

CCAGGTAAAGGTCTGGAATGGATCGGTTACATCTACTACTCTGGTTCTACCGATTACAACCCATCTCTGA

AATCTCGTGTTACCATGTCTGTTGATACCTCTAAAAACCAGTTCTCTCTGAAAGTTAACTCTGTTACCGC

CGCGGACACGGCTGTGTATTACTGTGCTCGTGTTTCTATCTTCGGTGTTGGTACCTTCGATTACTGGGGT

CAGGGAACCCTGGTCACCGTCTCCTCAgctagcggcaaaccaatcccaaacccactgctgggc

>4c - necitumumab dLCDR3
(SEQ ID NO: 163)
cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACGATGCTTCTAACCGTGCTACC

GGTATCCCAGCTCGTTTCTCTGGTTCTGGTTCTGGTACCGATTTCACCCTGACCATCTCTTCTCTGGAAC

CAGAAGATTTCGCTGTTTACTACTGTagagaccatggccagtaaggccggtctctTTCGGTGGTGGTACC

AAAGTTGAAATCAAATCCGGAGGGTCGACCATAACTTCGTATAATGTATACTATACGAAGTTATCCTCGA

GCGGTACCCAGGTTCAGCTGCAGGAATCTGGTCCAGGTCTGGTTAAACCATCTCAGACCCTGTCTCTGAC

CTGTACCGTTTCTGGTGGTTCTATCTCTTCTGGTGATTACTACTGGTCTTGGATCCGTCAGCCACCAGGT

AAAGGTCTGGAATGGATCGGTTACATCTACTACTCTGGTTCTACCGATTACAACCCATCTCTGAAATCTC

GTGTTACCATGTCTGTTGATACCTCTAAAAACCAGTTCTCTCTGAAAGTTAACTCTGTTACCGCCGCGGA

```
CACGGCTGTGTATTACTGTGCTCGTGTTTCTATCTTCGGTGTTGGTACCTTCGATTACTGGGGTCAGGGA

ACCCTGGTCACCGTCTCCTCAgctagcggcaaaccaatcccaaacccactgctgggc
```

>4d - necitumumab dHCDR1

(SEQ ID NO: 164)

```
cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACGATGCTTCTAACCGTGCTACC

GGTATCCCAGCTCGTTTCTCTGGTTCTGGTTCTGGTACCGATTTCACCCTGACCATCTCTTCTCTGGAAC

CAGAAGATTTCGCTGTTTACTACTGTCACCAGTACGGTTCTACCCCACTGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGCAGGAATCTGGTCCAGGTCTGGTTAAACCATCTCAGACCCTGTCTCTGACCT

GTACCGTTTCTagagaccatggccagtaaggccggtctctTGGTCTTGGATCCGTCAGCCACCAGGTAAA

GGTCTGGAATGGATCGGTTACATCTACTACTCTGGTTCTACCGATTACAACCCATCTCTGAAATCTCGTG

TTACCATGTCTGTTGATACCTCTAAAAACCAGTTCTCTCTGAAAGTTAACTCTGTTACCGCCGCGGACAC

GGCTGTGTATTACTGTGCTCGTGTTTCTATCTTCGGTGTTGGTACCTTCGATTACTGGGGTCAGGGAACC

CTGGTCACCGTCTCCTCAgctagcggcaaaccaatcccaaacccactgctgggc
```

>4e - necitumumab dHCDR2

(SEQ ID NO: 165)

```
cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACGATGCTTCTAACCGTGCTACC

GGTATCCCAGCTCGTTTCTCTGGTTCTGGTTCTGGTACCGATTTCACCCTGACCATCTCTTCTCTGGAAC

CAGAAGATTTCGCTGTTTACTACTGTCACCAGTACGGTTCTACCCCACTGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGCAGGAATCTGGTCCAGGTCTGGTTAAACCATCTCAGACCCTGTCTCTGACCT

GTACCGTTTCTGGTGGTTCTATCTCTTCTGGTGATTACTACTGGTCTTGGATCCGTCAGCCACCAGGTAA

AGGTCTGGAATGGATCGGTTACagagaccatggccagtaaggccggtctctGATTACAACCCATCTCTGA

AATCTCGTGTTACCATGTCTGTTGATACCTCTAAAAACCAGTTCTCTCTGAAAGTTAACTCTGTTACCGC

CGCGGACACGGCTGTGTATTACTGTGCTCGTGTTTCTATCTTCGGTGTTGGTACCTTCGATTACTGGGGT

CAGGGAACCCTGGTCACCGTCTCCTCAgctagcggcaaaccaatcccaaacccactgctgggc
```

>4f - necitumumab dHCDR3

(SEQ ID NO: 166)

```
cagttagataaaagaggcgcggcagcaagcggcgcgcatgccGAAATCGTTATGACCCAGTCTCCAGCTA

CCCTGTCTCTGTCTCCAGGTGAACGTGCCACTCTGTCTTGTCGTGCTTCTCAGTCTGTTTCTTCTTACCT

GGCTTGGTACCAGCAGAAACCAGGTCAGGCTCCACGTCTGCTGATCTACGATGCTTCTAACCGTGCTACC

GGTATCCCAGCTCGTTTCTCTGGTTCTGGTTCTGGTACCGATTTCACCCTGACCATCTCTTCTCTGGAAC

CAGAAGATTTCGCTGTTTACTACTGTCACCAGTACGGTTCTACCCCACTGACCTTCGGTGGTGGTACCAA

AGTTGAAATCAAATCCGGAGGGTCGACCATAACTTCGTATAATGTATACTATACGAAGTTATCCTCGAGC

GGTACCCAGGTTCAGCTGCAGGAATCTGGTCCAGGTCTGGTTAAACCATCTCAGACCCTGTCTCTGACCT

GTACCGTTTCTGGTGGTTCTATCTCTTCTGGTGATTACTACTGGTCTTGGATCCGTCAGCCACCAGGTAA

AGGTCTGGAATGGATCGGTTACATCTACTACTCTGGTTCTACCGATTACAACCCATCTCTGAAATCTCGT

GTTACCATGTCTGTTGATACCTCTAAAAACCAGTTCTCTCTGAAAGTTAACTCTGTTACCGCCGCGGACA

CGGCTGTGTATTACTGTagagaccatggccagtaaggccggtctctGAACCCTGGTCACCGTCTCCTCA gctagcggcaaaccaatcccaaacccactgctgggc
```

-continued

>5 - anifrolumab
(SEQ ID NO: 167)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTGGTTACATCTTCACCAACTACTGGATCGCTTGGGTTCGTCAGGTTCCAGGTAAAGG

TCTGGAATCTATGGGTATCATCTACCCAGGTGATTCTGATATCCGTTACTCTCCATCTTTCCAGGGTCAG

GTTACCATCTCTGCTGATAAATCTATCACCACCGCTTACCTGCAGTGGTCTTCTCTGAAAGCCTCGGACA

CCGCCATTTATTACTGTGCTCGTCACGATATCGAAGGTTTCGATTACTGGGGTCGTGGAACCCTGGTCAC

CGTCTCCTCAgctagcggcaaaccaatcccaaacccactgctgggc

>5a - anifrolumab dLCDR1
(SEQ ID NO: 168)
cagttagataaaagaggcgcggcagcaagcggcgcgcatgccGAAATCGTTCTGACCCAGTCTCCAGGTA CCCTGTCTCTGTCTCCAGGTGAACGTGCCACTCTGTCTTGTCGTGCTTCTagagaccatggccagtaagg ccggtctctCTGGCTTGGTACCAGCAGAAACCAGGTCAGGCTCCACGTCTGCTGATCTACGGTGCTTCTT

CTCGTGCTACCGGTATCCCAGATCGTCTGTCTGGTTCTGGTTCTGGTACCGATTTCACCCTGACCATCAC

CCGTCTGGAACCAGAAGATTTCGCTGTTTACTACTGTCAGCAGTACGATTCTTCTGCTATCACCTTCGGT

GGTGGTACCAAAGTTGAAATCAAATCCGGAGGGTCGACCATAACTTCGTATAATGTATACTATACGAAGT

TATCCTCGAGCGGTACCGAAGTTCAGCTGGTTCAGTCTGGTGCTGAAGTTAAAAAACCAGGTGAATCTCT

GAAAATCTCTTGTAAAGGTTCTGGTTACATCTTCACCAACTACTGGATCGCTTGGGTTCGTCAGGTTCCA

GGTAAAGGTCTGGAATCTATGGGTATCATCTACCCAGGTGATTCTGATATCCGTTACTCTCCATCTTTCC

AGGGTCAGGTTACCATCTCTGCTGATAAATCTATCACCACCGCTTACCTGCAGTGGTCTTCTCTGAAAGC

CTCGGACACCGCCATTTATTACTGTGCTCGTCACGATATCGAAGGTTTCGATTACTGGGGTCGTGGAACC

CTGGTCACCGTCTCCTCAgctagcggcaaaccaatcccaaacccactgctgggc

>5b - anifrolumab dLCDR2
(SEQ ID NO: 169)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACagagaccatggccagtaa ggccggtctctGGTATCCCAGATCGTCTGTCTGGTTCTGGTTCTGGTACCGATTTCACCCTGACCATCAC

CCGTCTGGAACCAGAAGATTTCGCTGTTTACTACTGTCAGCAGTACGATTCTTCTGCTATCACCTTCGGT

GGTGGTACCAAAGTTGAAATCAAATCCGGAGGGTCGACCATAACTTCGTATAATGTATACTATACGAAGT

TATCCTCGAGCGGTACCGAAGTTCAGCTGGTTCAGTCTGGTGCTGAAGTTAAAAAACCAGGTGAATCTCT

GAAAATCTCTTGTAAAGGTTCTGGTTACATCTTCACCAACTACTGGATCGCTTGGGTTCGTCAGGTTCCA

GGTAAAGGTCTGGAATCTATGGGTATCATCTACCCAGGTGATTCTGATATCCGTTACTCTCCATCTTTCC

AGGGTCAGGTTACCATCTCTGCTGATAAATCTATCACCACCGCTTACCTGCAGTGGTCTTCTCTGAAAGC

CTCGGACACCGCCATTTATTACTGTGCTCGTCACGATATCGAAGGTTTCGATTACTGGGGTCGTGGAACC

CTGGTCACCGTCTCCTCAgctagcggcaaaccaatcccaaacccactgctgggc

-continued

>5c - anifrolumab dLCDR3
(SEQ ID NO: 170)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTagagaccatggccagtaaggccggtctctTTCGGTGGTGGT

ACCAAAGTTGAAATCAAATCCGGAGGGTCGACCATAACTTCGTATAATGTATACTATACGAAGTTATCCT

CGAGCGGTACCGAAGTTCAGCTGGTTCAGTCTGGTGCTGAAGTTAAAAAACCAGGTGAATCTCTGAAAAT

CTCTTGTAAAGGTTCTGGTTACATCTTCACCAACTACTGGATCGCTTGGGTTCGTCAGGTTCCAGGTAAA

GGTCTGGAATCTATGGGTATCATCTACCCAGGTGATTCTGATATCCGTTACTCTCCATCTTTCCAGGGTC

AGGTTACCATCTCTGCTGATAAATCTATCACCACCGCTTACCTGCAGTGGTCTTCTCTGAAAGCCTCGGA

CACCGCCATTTATTACTGTGCTCGTCACGATATCGAAGGTTTCGATTACTGGGGTCGTGGAACCCTGGTC

ACCGTCTCCTCAgctagcggcaaaccaatcccaaacccactgctgggc

>5d - anifrolumab dHCDR1
(SEQ ID NO: 171)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTagagaccatggccagtaaggccggtctctATCGCTTGGGTTCGTCAGGTTCCAGGT

AAAGGTCTGGAATCTATGGGTATCATCTACCCAGGTGATTCTGATATCCGTTACTCTCCATCTTTCCAGG

GTCAGGTTACCATCTCTGCTGATAAATCTATCACCACCGCTTACCTGCAGTGGTCTTCTCTGAAAGCCTC

GGACACCGCCATTTATTACTGTGCTCGTCACGATATCGAAGGTTTCGATTACTGGGGTCGTGGAACCCTG

GTCACCGTCTCCTCAgctagcggcaaaccaatcccaaacccactgctgggc

>5e - anifrolumab dHCDR2
(SEQ ID NO: 172)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTGGTTACATCTTCACCAACTACTGGATCGCTTGGGTTCGTCAGGTTCCAGGTAAAGG

TCTGGAATCTATGGGTATCagagaccatggccagtaaggccggtctctCGTTACTCTCCATCTTTCCAGG

GTCAGGTTACCATCTCTGCTGATAAATCTATCACCACCGCTTACCTGCAGTGGTCTTCTCTGAAAGCCTC

GACACCGCCATTTATTACTGTGCTCGTCACGATATCGAAGGTTTCGATTACTGGGGTCGTGGAACCCTG

GTCACCGTCTCCTCAgctagcggcaaaccaatcccaaacccactgctgggc

>5f - anifrolumab dHCDR3
(SEQ ID NO: 173)
cagttagataaaagaggcgcggcagcaagcggcgcgcatgccGAAATCGTTCTGACCCAGTCTCCAGGTA

CCCTGTCTCTGTCTCCAGGTGAACGTGCCACTCTGTCTTGTCGTGCTTCTCAGTCTGTTTCTTCTTCTTT

CCTGGCTTGGTACCAGCAGAAACCAGGTCAGGCTCCACGTCTGCTGATCTACGGTGCTTCTTCTCGTGCT

ACCGGTATCCCAGATCGTCTGTCTGGTTCTGGTTCTGGTACCGATTTCACCCTGACCATCACCCGTCTGG

AACCAGAAGATTTCGCTGTTTACTACTGTCAGCAGTACGATTCTTCTGCTATCACCTTCGGTGGTGGTAC

CAAAGTTGAAATCAAATCCGGAGGGTCGACCATAACTTCGTATAATGTATACTATACGAAGTTATCCTCG

AGCGGTACCGAAGTTCAGCTGGTTCAGTCTGGTGCTGAAGTTAAAAAACCAGGTGAATCTCTGAAAATCT

CTTGTAAAGGTTCTGGTTACATCTTCACCAACTACTGGATCGCTTGGGTTCGTCAGGTTCCAGGTAAAGG

TCTGGAATCTATGGGTATCATCTACCCAGGTGATTCTGATATCCGTTACTCTCCATCTTTCCAGGGTCAG

GTTACCATCTCTGCTGATAAATCTATCACCACCGCTTACCTGCAGTGGTCTTCTCTGAAAGCCTCGGACA

CCGCCATTTATTACTGTagagaccatggccagtaaggccggtctctGGAACCCTGGTCACCGTCTCCTCA gctagcggcaaaccaatcccaaacccactgctgggc >6 - evolocumab
(SEQ ID NO: 174)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTGGTTACACCCTGACCTCTTACGGTATCTCTTGGGTTCGTCAGGCTCCAGGTCA

GGGTCTGGAATGGATGGGTTGGGTTTCTTTCTACAACGGTAACACCAACTACGCTCAGAAACTGCAGGGT

CGTGGTACCATGACCACCGATCCATCTACCTCTACCGCTTACATGGAACTGCGTTCTCTGCGTTCTGACG

ACACGGCCGTGTATTACTGTGCTCGTGGTTACGGTATGGATGTTTGGGGTCAGGGGACCACGGTCACCGT

CTCCTCAgctagcggcaaaccaatcccaaacccactgctgggc

>6a - evolocumab dLCDR1
(SEQ ID NO: 175)
cagttagataaaagaggcgcggcagcaagcggcgcgcatgccGAATCTGCTCTGACCCAGCCAGCTTCTG TTTCTGGTTCTCCAGGTCAGTCTATCACCATCTCTTGTACCGGTACCagagaccatggccagtaaggccg gtctctGTTTCTTGGTACCAGCAGCACCCAGGTAAAGCTCCAAAACTGATGATCTACGAAGTTTCTAACC

GTCCATCTGGTGTTTCTAACCGTTTCTCTGGTTCTAAATCTGGTAACACCGCTTCTCTGACCATCTCTGG

TCTGCAGGCTGAAGATGAAGCTGATTACTACTGTAACTCTTACACCTCTACCTCTATGGTTTTCGGTGGT

GGTACCAAACTGACCGTTCTGTCCGGAGGGTCGACCATAACTTCGTATAATGTATACTATACGAAGTTAT

CCTCGAGCGGTACCGAAGTTCAGCTGGTTCAGTCTGGTGCTGAAGTTAAAAAACCAGGTGCTTCTGTTAA

AGTTTCTTGTAAAGCTTCTGGTTACACCCTGACCTCTTACGGTATCTCTTGGGTTCGTCAGGCTCCAGGT

CAGGGTCTGGAATGGATGGGTTGGGTTTCTTTCTACAACGGTAACACCAACTACGCTCAGAAACTGCAGG

GTCGTGGTACCATGACCACCGATCCATCTACCTCTACCGCTTACATGGAACTGCGTTCTCTGCGTTCTGA

CGACACGGCCGTGTATTACTGTGCTCGTGGTTACGGTATGGATGTTTGGGGTCAGGGGACCACGGTCACC

GTCTCCTCAgctagcggcaaaccaatcccaaacccactgctgggc

-continued

>6b - evolocumab dLCDR2
(SEQ ID NO: 176)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACagagaccatggccag taaggccggtctctGGTGTTTCTAACCGTTTCTCTGGTTCTAAATCTGGTAACACCGCTTCTCTGACCAT

CTCTGGTCTGCAGGCTGAAGATGAAGCTGATTACTACTGTAACTCTTACACCTCTACCTCTATGGTTTTC

GGTGGTGGTACCAAACTGACCGTTCTGTCCGGAGGGTCGACCATAACTTCGTATAATGTATACTATACGA

AGTTATCCTCGAGCGGTACCGAAGTTCAGCTGGTTCAGTCTGGTGCTGAAGTTAAAAAACCAGGTGCTTC

TGTTAAAGTTTCTTGTAAAGCTTCTGGTTACACCCTGACCTCTTACGGTATCTCTTGGGTTCGTCAGGCT

CCAGGTCAGGGTCTGGAATGGATGGGTTGGGTTTCTTTCTACAACGGTAACACCAACTACGCTCAGAAAC

TGCAGGGTCGTGGTACCATGACCACCGATCCATCTACCTCTACCGCTTACATGGAACTGCGTTCTCTGCG

TTCTGACGACACGGCCGTGTATTACTGTGCTCGTGGTTACGGTATGGATGTTTGGGGTCAGGGGACCACG

GTCACCGTCTCCTCAgctagcggcaaaccaatcccaaacccactgctgggc

>6c - evolocumab dLCDR3
(SEQ ID NO: 177)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTagagaccatggccagtaaggccggtctctTTCGGTGGT

GGTACCAAACTGACCGTTCTGTCCGGAGGGTCGACCATAACTTCGTATAATGTATACTATACGAAGTTAT

CCTCGAGCGGTACCGAAGTTCAGCTGGTTCAGTCTGGTGCTGAAGTTAAAAAACCAGGTGCTTCTGTTAA

AGTTTCTTGTAAAGCTTCTGGTTACACCCTGACCTCTTACGGTATCTCTTGGGTTCGTCAGGCTCCAGGT

CAGGGTCTGGAATGGATGGGTTGGGTTTCTTTCTACAACGGTAACACCAACTACGCTCAGAAACTGCAGG

GTCGTGGTACCATGACCACCGATCCATCTACCTCTACCGCTTACATGGAACTGCGTTCTCTGCGTTCTGA

CGACACGGCCGTGTATTACTGTGCTCGTGGTTACGGTATGGATGTTTGGGGTCAGGGGACCACGGTCACC

GTCTCCTCAgctagcggcaaaccaatcccaaacccactgctgggc

>6d - evolocumab dHCDR1
(SEQ ID NO: 178)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCTGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTagagaccatggccagtaaggccggtctctATCTCTTGGGTTCGTCAGGCTCCA

GGTCAGGGTCTGGAATGGATGGGTTGGGTTTCTTTCTACAACGGTAACACCAACTACGCTCAGAAACTGC

AGGGTCGTGGTACCATGACCACCGATCCATCTACCTCTACCGCTTACATGGAACTGCGTTCTCTGCGTTC

TGACGACACGGCCGTGTATTACTGTGCTCGTGGTTACGGTATGGATGTTTGGGGTCAGGGGACCACGGTC

ACCGTCTCCTCAgctagcggcaaaccaatcccaaacccactgctgggc

```
>6e - evolocumab dHCDR2
                                                          (SEQ ID NO: 179)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTGGTTACACCCTGACCTCTTACGGTATCTCTTGGGTTCGTCAGGCTCCAGGTCA

GGGTCTGGAATGGATGGGTTGGagagaccatggccagtaaggccggtctctAACTACGCTCAGAAACTGC

AGGGTCGTGGTACCATGACCACCGATCCATCTACCTCTACCGCTTACATGGAACTGCGTTCTCTGCGTTC

TGACGACACGGCCGTGTATTACTGTGCTCGTGGTTACGGTATGGATGTTTGGGGTCAGGGGACCACGGTC

ACCGTCTCCTCAgctagcggcaaaccaatcccaaacccactgctgggc

>6f - evolocumab dHCDR3
                                                          (SEQ ID NO: 180)
cagttagataaaagaggcgcggcagcaagcggcgcgcatgccGAATCTGCTCTGACCCAGCCAGCTTCTG

TTTCTGGTTCTCCAGGTCAGTCTATCACCATCTCTTGTACCGGTACCTCTTCTGATGTTGGTGGTTACAA

CTCTGTTTCTTGGTACCAGCAGCACCCAGGTAAAGCTCCAAAACTGATGATCTACGAAGTTTCTAACCGT

CCATCTGGTGTTTCTAACCGTTTCTCTGGTTCTAAATCGGTAACACCGCTTCTCTGACCATCTCTGGTC

TGCAGGCTGAAGATGAAGCTGATTACTACTGTAACTCTTACACCTCTACCTCTATGGTTTTCGGTGGTGG

TACCAAACTGACCGTTCTGTCCGGAGGGTCGACCATAACTTCGTATAATGTATACTATACGAAGTTATCC

TCGAGCGGTACCGAAGTTCAGCTGGTTCAGTCTGGTGCTGAAGTTAAAAAACCAGGTGCTTCTGTTAAAG

TTTCTTGTAAAGCTTCTGGTTACACCCTGACCTCTTACGGTATCTCTTGGGTTCGTCAGGCTCCAGGTCA

GGGTCTGGAATGGATGGGTTGGGTTTCTTTCTACAACGGTAACACCAACTACGCTCAGAAACTGCAGGGT

CGTGGTACCATGACCACCGATCCATCTACCTCTACCGCTTACATGGAACTGCGTTCTCTGCGTTCTGACG

ACACGGCCGTGTATTACTGTagagaccatggccagtaaggccggtctctGGGACCACGGTCACCGTCTCC

TCAgctagcggcaaaccaatcccaaacccactgctgggc
```

Sequences 1-6 refer to the coding sequence of the exemplary scaffolds as indicated and sequences 1a-1f, 2a-2f, 3a-3f, 4a-4f, 5a-5f, and 6a-6f refer to sequences in which cloning sites were inserted flanking the corresponding CDRs of each exemplary scaffold as indicated.

Figure 24:
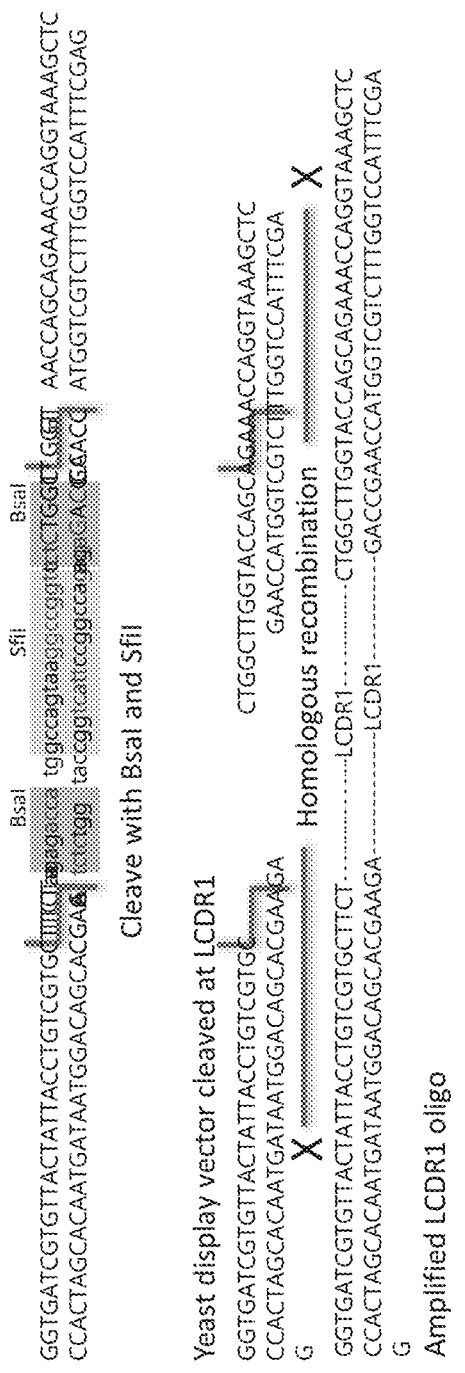
FIG. 24 is a diagram showing an exemplary process of inserting oligonucleotides encoding LC CDR1s into a yeast display vector. Nucleic acid sequences representing part of a yeast display vector to be cleaved with BsaI and SfiI correspond to SEQ ID NOs: 103-104 (from top to bottom). Sequences of the cleaved vector (middle) correspond to SEQ ID NOs: 105-108 (labeled from top to bottom then left to right). Sequences of the amplified LCDR1 oligo (middle) correspond to SEQ ID NOs: 109-112 (labeled top to bottom then left to right). Homologous recombination produces the amplified LCDR1 inserted into the yeast display vector (bottom), which corresponds to SEQ ID NOs: 113-116 (labeled top to bottom then left to right).
Figure 25A:
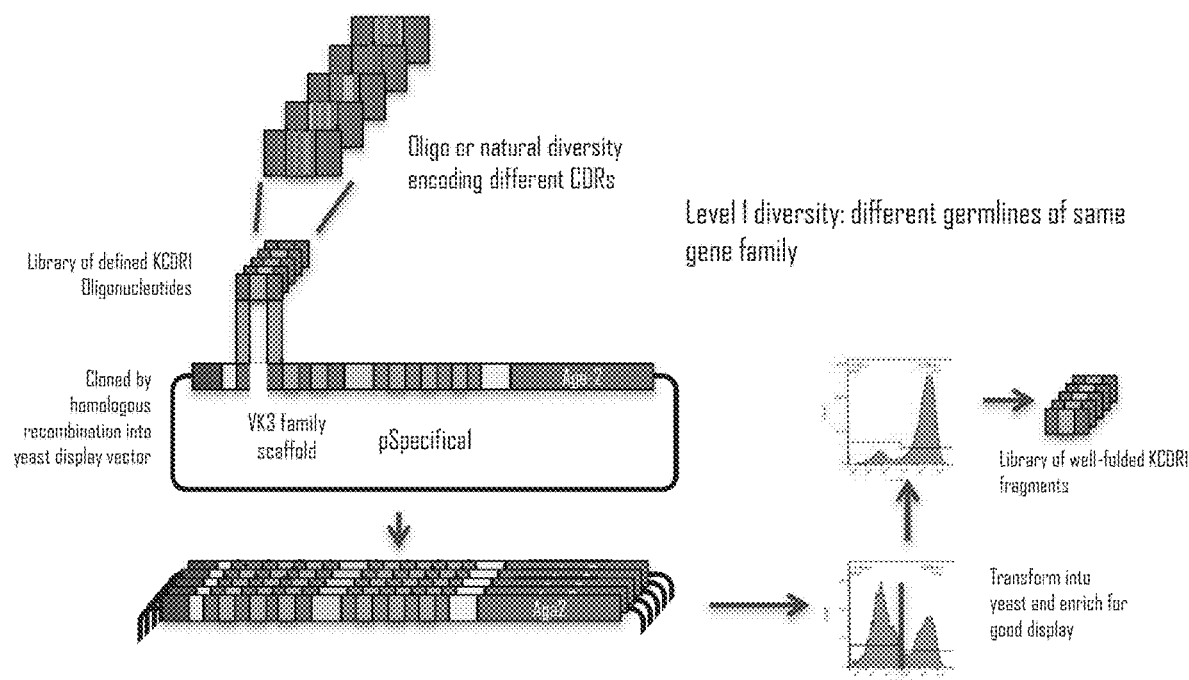
FIG. 25A is a diagram illustrating an exemplary process of isolating well expressed antibody CDRs by sorting yeast displaying single CDR loop libraries after cloning, using VK chains comprising functional KCDR1 as an example.
Figure 25B:
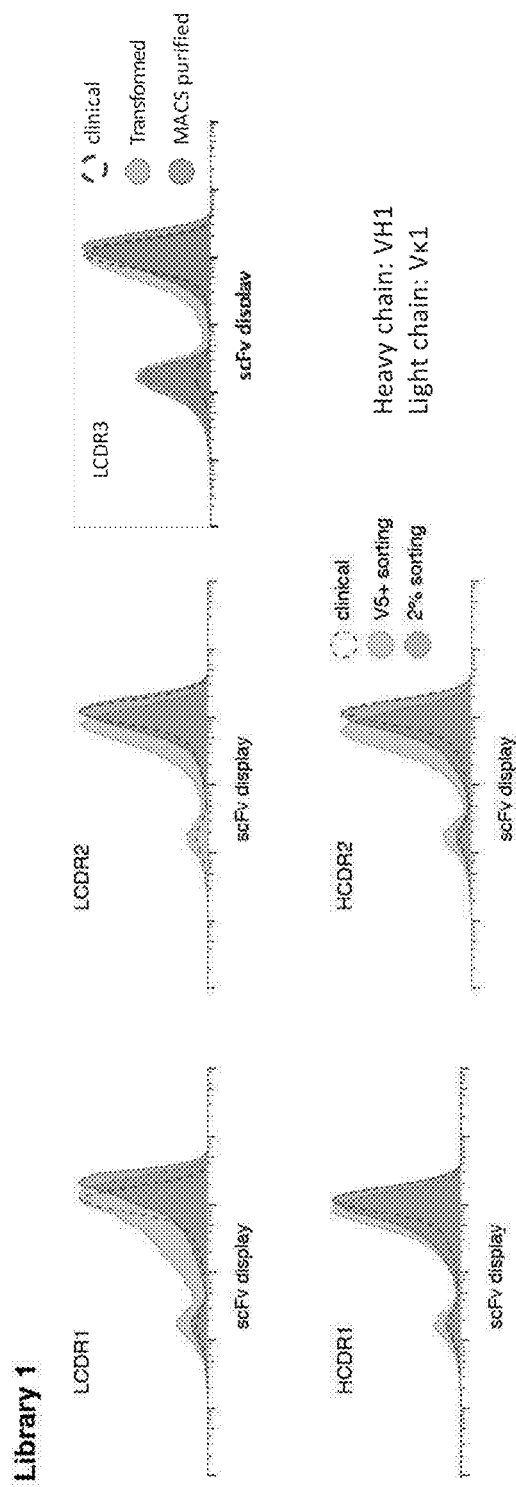
Figure 25C:
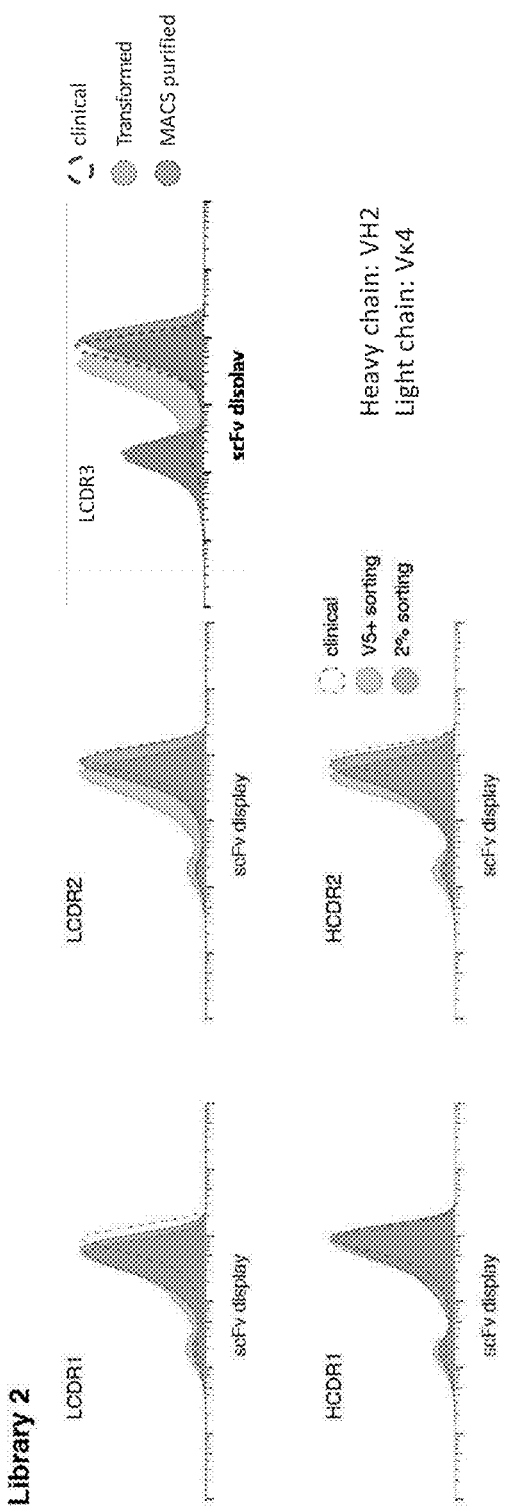
Figure 25E:
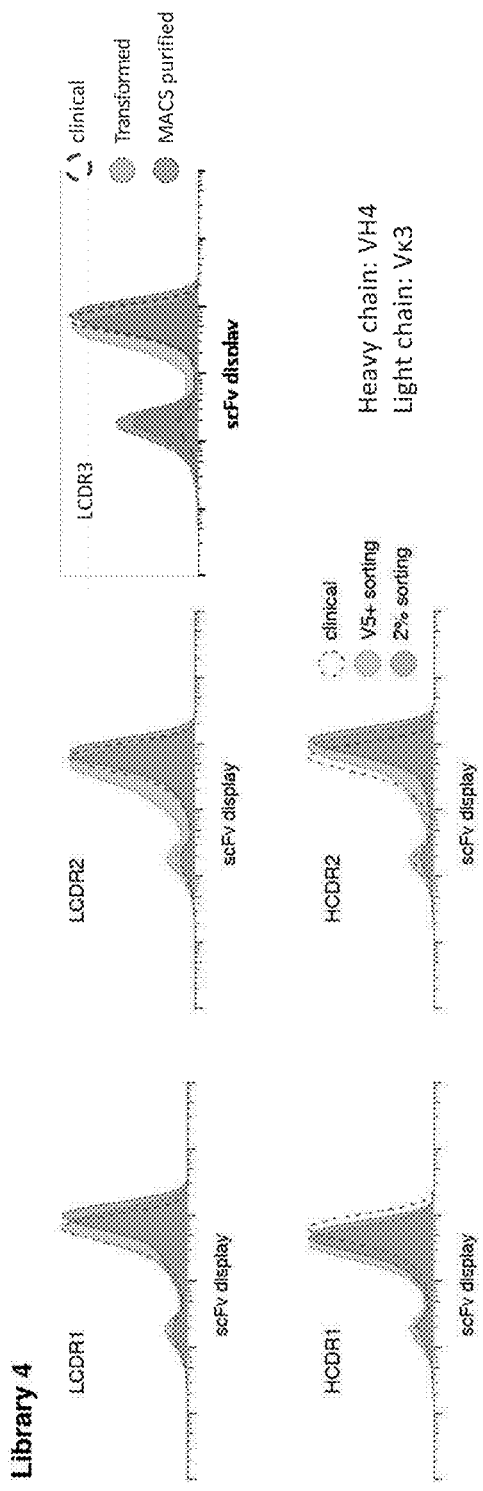
Figure 25F:
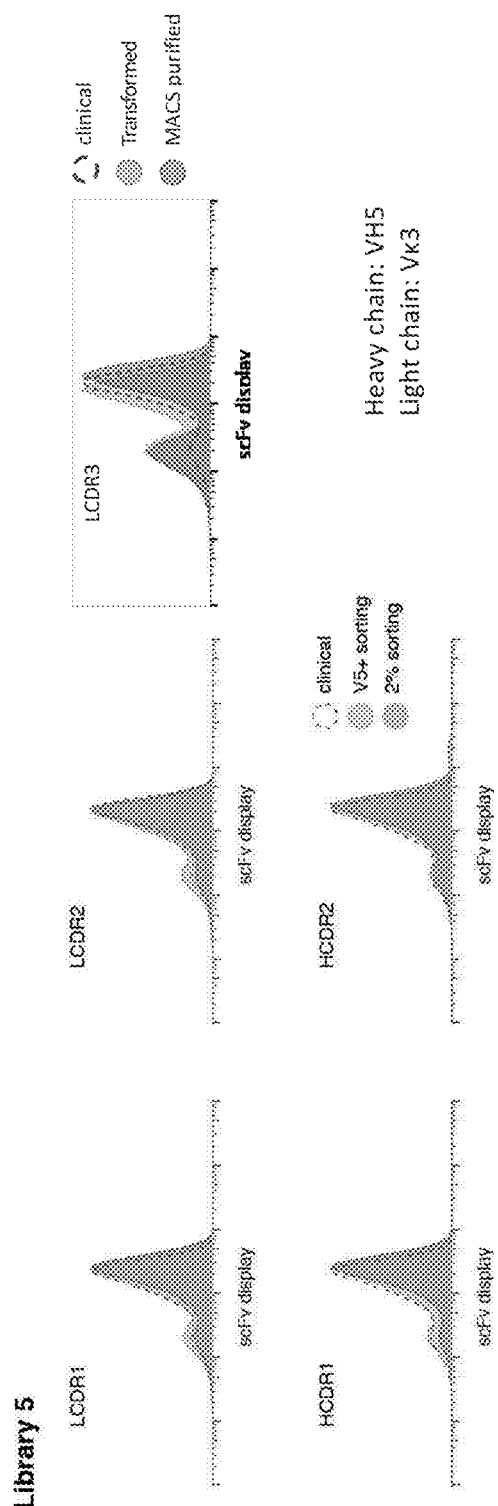
Figure 25G:
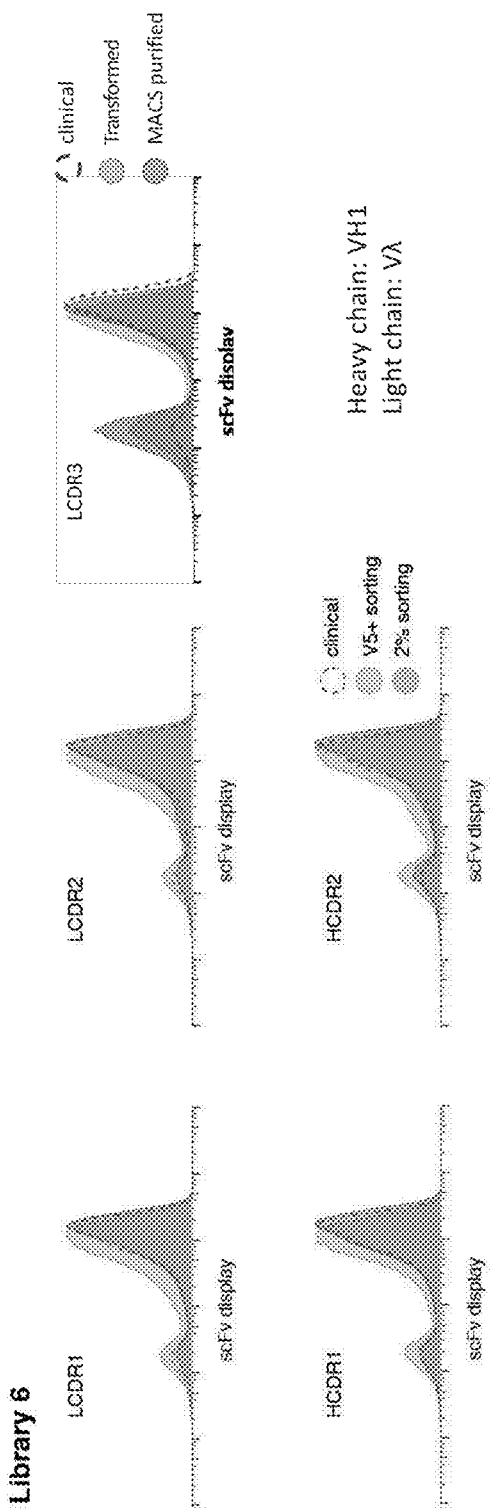

Using LCDR1 of library 1 as an example, the LCDR1 scaffold vector was digested with BsaI and SfiI leaving a gap at the site of LCDR1, as shown in FIG. 24. The cleaved vector and the collection of LCDR1 oligonucleotides were then transformed into yeast. Inside yeast cells, homologous recombination between the vector and the LCDR1 oligonucleotides results in insertion of the LCDR1 oligonucleotides into the LCDR1 scaffold vector. The entire population of LCDR1 yeast scaffold vectors carrying each of the LCDR1 oligonucleotides identified above constitutes a LCDR1 yeast display library (FIG. 25). For the LCDR1 scaffold vector, all portions of the VH and VL domains are constant except for the LCDR1 that is assessed. Selection for functional LCDR1 was carried out by sorting for display (i.e., expression). After the display of the scFv is induced, the yeast cells are stained with fluorescent-labelled antibody that detects scFv display (using the mAb recognizing the SV5 tag). For CDR1-2 libraries, the populations are analyzed by flow cytometry and sorted by fluorescence activated cell sorting by gating the top 2% most fluorescent cells among the positive population—this ensures the enrichment for CDRs that promote high levels of display. In FIGS. 22A-L, the population after this stringent 2% sorting is indicated as "Replicated natural after filtering". At least a 10-fold number of cells is sorted as compared to the theoretical diversity to ensure recovery of all possible clones. For LCDR3, after scFv display induction and staining with fluorescent-labelled antibody that detects the scFv display (SV5), the positive population (scFv displaying) is purified using MACS (magnetic-activated cell sorting) employing magnetic nanoparticles that recognize the primary antibody (SV5) used. The higher the level of the scFv display, the higher the probability of the cell binding the nanoparticles—especially when competition is employed by having a number of cells that far exceeds the binding capacity of the nanoparticles, thus, enriching for well displaying sequences, analogously to fluorescence activated cell sorting of the most fluorescent 2% for the CDR1-2 described above. The MACS technique is preferentially employed for LCDR3 due to the capacity of purifying a large number of cells in a short span of time, since the theoretical diversity of the LCDR3 is several fold higher than CDR1-2.

Figure 23:
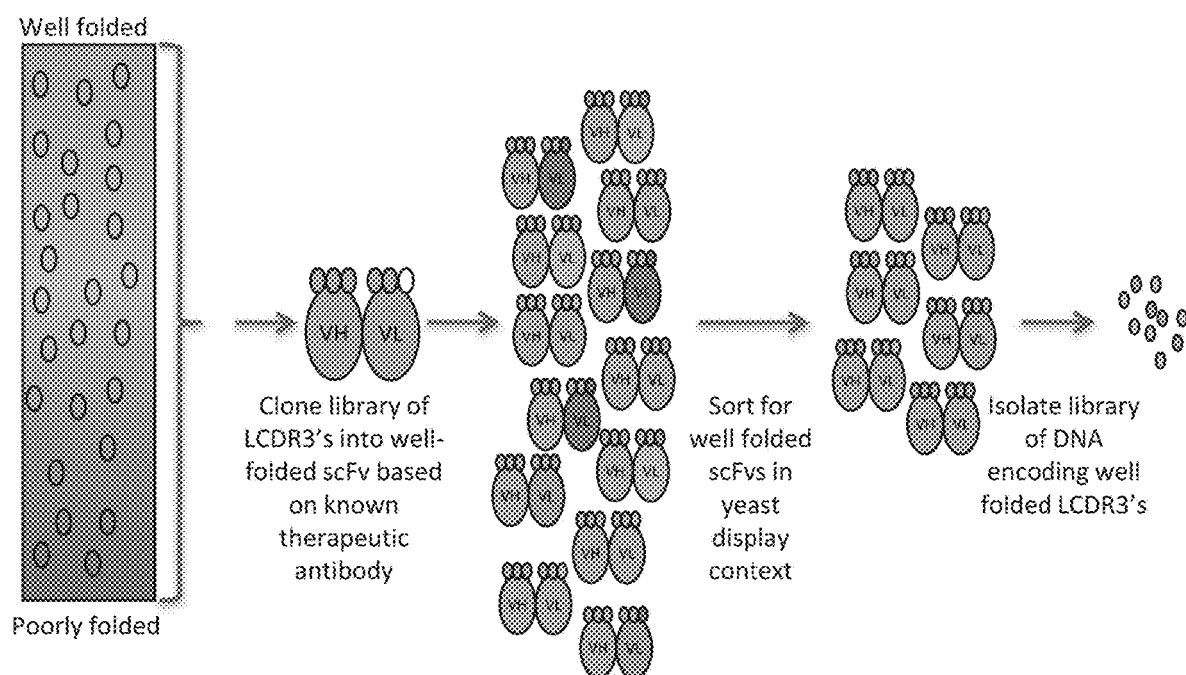
FIG. 23 is a diagram illustrating an exemplary process for selecting for functional CDRs, for example, well folded LC CDR3s.

Although scFvs are used in this example for yeast display, the format of CDR-specific scaffold vectors can be VH, VL, scFv, Fab or full-length immunoglobulin, the requirement being that display can be carried out. By sorting libraries of single CDRs cloned into well folded scaffolds, those CDRs that contain stop codons, frameshifts, or are poorly expressed or polyreactive may be eliminated. Effective display on the yeast surface has been previously correlated with improved stability and folding in diverse proteins (Cherf, G. M. and J. R. Cochran (2015). "Applications of Yeast Surface Display for Protein Engineering." Methods Mol Biol 1319: 155-175; Pavoor, T. V., et al., (2012). "An enhanced approach for engineering thermally stable proteins using yeast display." Protein engineering, design & selection: PEDS 25(10): 625-630; Pepper, L. R., et al., (2008). "A decade of yeast surface display technology: where are we now?" Comb Chem High Throughput Screen 11(2): 127-134; Xu, L., et al., (2013). "Rapid optimization and prototyping for therapeutic antibody-like molecules." MAbs 5(2): 237-254). After each CDR library is sorted, a collection of well expressed, non-polyreactive CDRs is obtained by isolating DNA from yeast cells expressing well folded CDRs. Schematic illustrations of how functional CDR libraries are cloned and sorted are shown in FIGS. 23-25. The non-filtered and filtered libraries for the 6 different scaffolds are show in FIGS. 25B-G: the populations are analyzed by flow cytometry and expression levels (x axis) are represented as a histogram. The analysis shows a clear improvement after enrichment (top 2% by fluorescence activated cell sorting for CDRs 1-2, and magnetic activated cell sorting for LCDR3), with most libraries showing display levels exceeding that of the original clinical candidate from which the scaffolds were generated.

In the examples provided here, we have sorted for improved expression levels. However, a similar approach can be taken using any selective method that distinguishes yeast displaying antibodies with desirable properties (e.g. high expression, low polyreactivity, good developability) from yeast displaying antibodies with undesirable properties (e.g. low expression, high polyreactivity, poor developability). For example, to select antibodies with reduced polyreactivity, clones displaying antibodies (scFvs, Fabs, IgGs, or other antibody fragment) that do not bind to polyspecificity reagents would be selected. Examples of such polyspecificity reagents include those described in (Hotzel, I. et al. A strategy for risk mitigation of antibodies with fast clearance. MAbs 4, 753-760, doi:10.4161/mabs.22189 (2012); Xu, Y. et al. Addressing polyspecificity of antibodies selected from an in vitro yeast presentation system: a FACS-based, high-throughput selection and analytical tool. Protein Eng Des Sel 26, 663-670, doi:10.1093/protein/gzt047 (2013); Kelly, R. L. et al. Chaperone proteins as single component reagents to assess antibody nonspecificity. MAbs 9, 1036-1040, doi: 10.1080/19420862.2017.1356529 (2017).)

Example 8: Assembly of Full Length scFv Library

Figure 26:
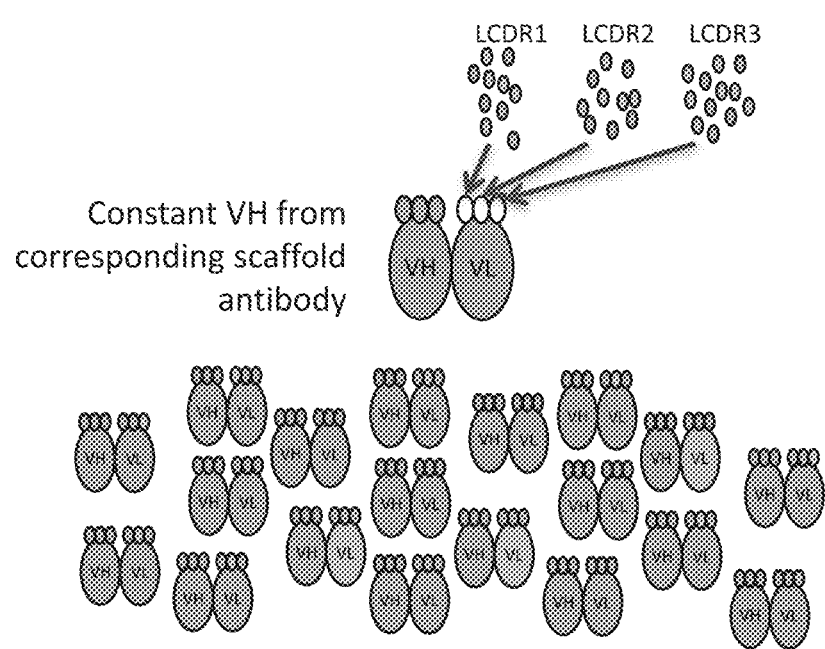
FIG. 26 is a diagram illustrating the pairing between a constant VH chain and VL chains with diversity in LC CDRs to select functional antibodies.
Figure 27:
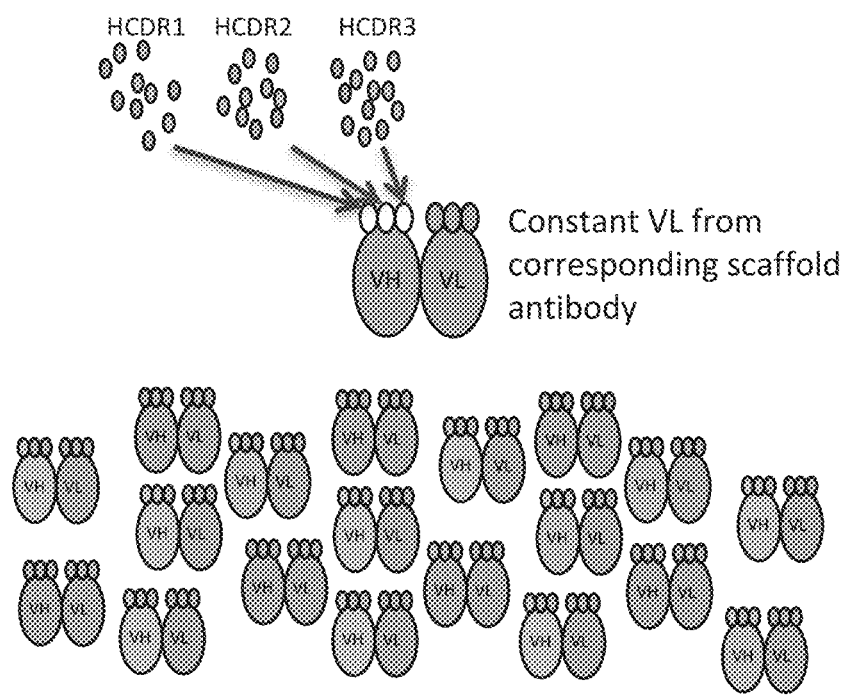
FIG. 27 is a diagram illustrating pairing between a constant VL chain and VH chains with diversity in VH CDRs for selection of functional antibodies.
Figure 28:
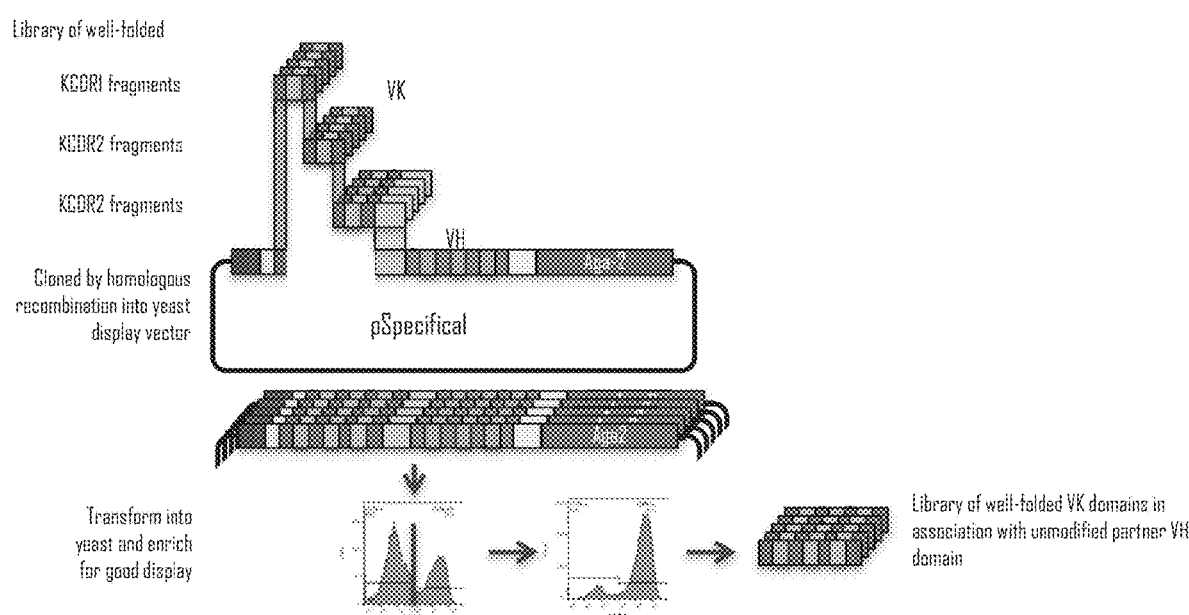
FIG. 28 is a diagram illustrating construction of an exemplary antibody library comprising VL chains having well-folded LC CDRs selected via yeast display and unmodified VH domains.
Figure 29:
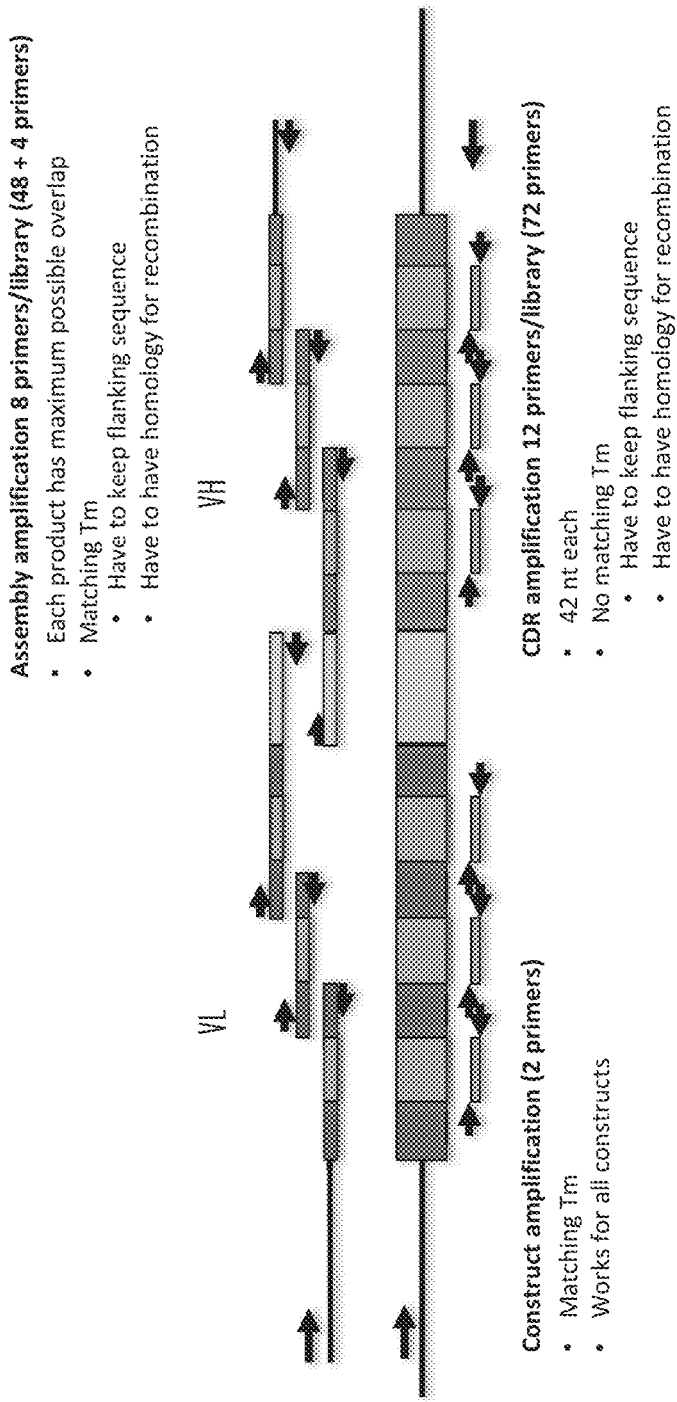
FIG. 29 is a diagram illustrating an exemplary process of amplifying and assembling VH and VL CDRs into a preselected VH or VL scaffold.
Figure 30:
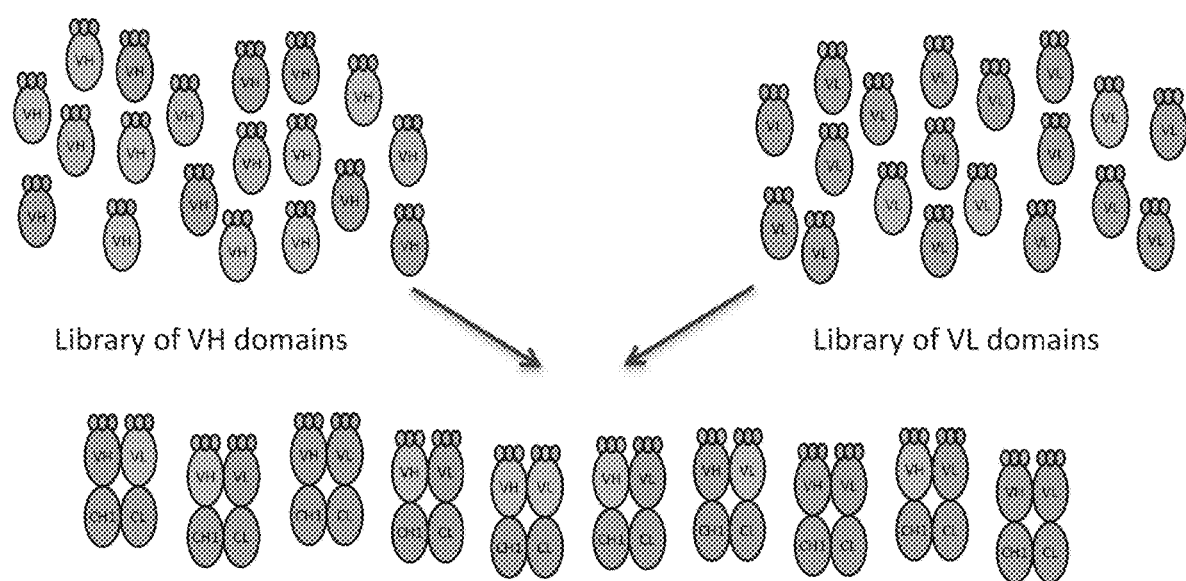
FIG. 30 is a diagram illustrating construction of an exemplary Fab antibody library via combining a library of VH domains and a library of VL domains.
Figure 31:
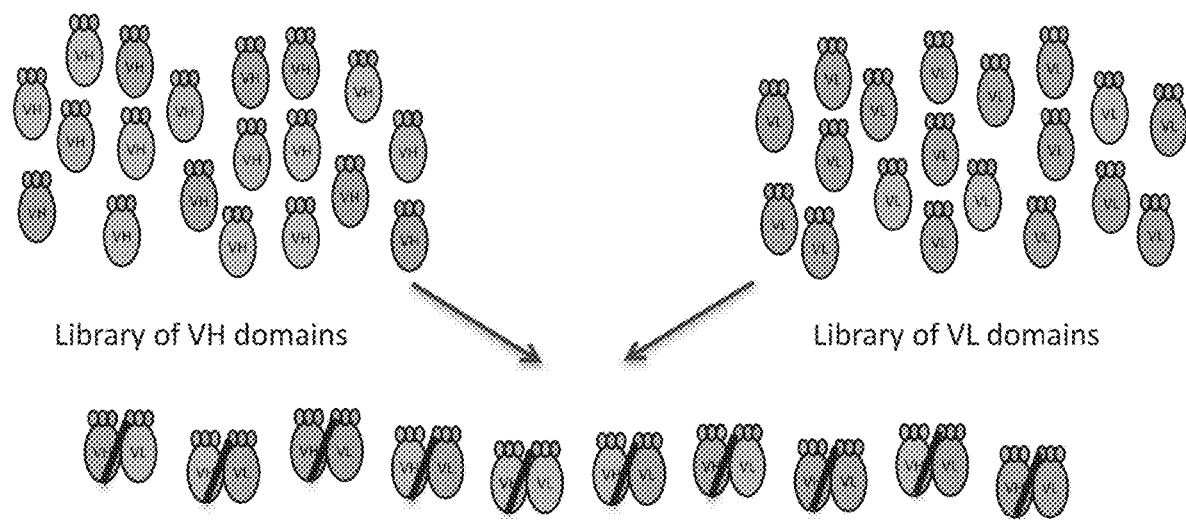
FIG. 31 is a diagram illustrating construction of an exemplary scFv antibody library via combining a library of VH domains and a library of VL domains.
Figure 32:
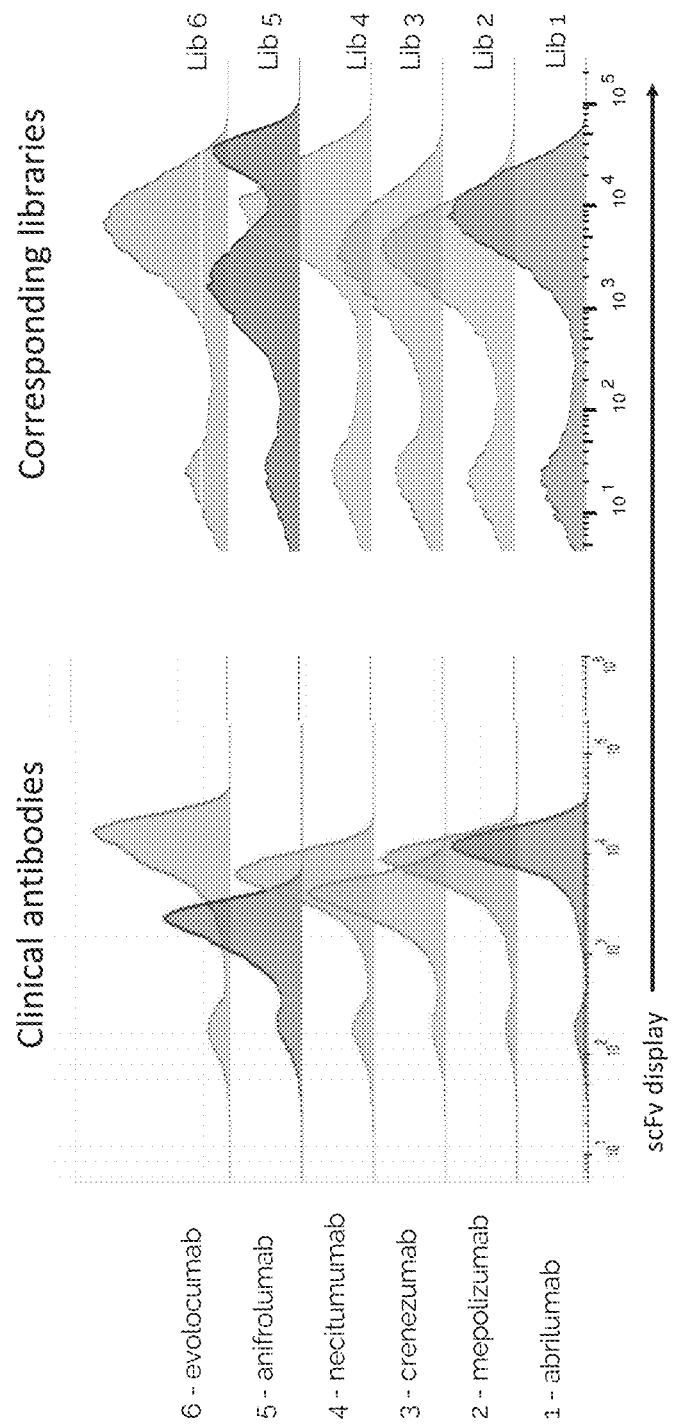
FIG. 32 is a flow plot of scFvs corresponding to the clinical candidates used as scaffolds compared to the corresponding libraries. The double peak for library 5 is thought to be due to the presence of a smaller truncated product, which was eliminated in the final phage display libraries.

Once each individual CDR library was screened for expression and developability, the VH and VL CDRs were assembled into full length VH or VL domains. Individual CDRs in VL and VH were amplified with the flanking sequence using the primers described in Table 7 and Table 8. This was carried out as illustrated in FIGS. 29-31, with the VH and VL first assembled from their constituent CDR fragments and flanking framework regions, and then combined into complete scFvs or Fabs. An alternative approach would be to assemble each full length VH or VL within the context of their non-modified VL or VH partner chains as illustrated in FIGS. 26-28. This alternative approach would allow sorting (by FACS or MACS) for VH or VL libraries that are functional within the context of their unmodified partner chains. However, we found that the direct assembly of complete scFvs directly from libraries of filtered CDRs led to highly functional scFv libraries without the need for this intermediate step, as illustrated in FIG. 32, which shows that the peak display level of scFvs derived from the clinical antibodies used as scaffolds is similar to that for the corresponding libraries, except that the distribution of library display levels is broader than that of the clinical candidate antibodies used as scaffolds, and includes some scFvs that are displayed better than the parental clinical scaffold scFv. The functional antibody library can be assembled within the context of different display vectors, including phage, yeast or mammalian display vectors.

Example 9: Cloning into a Phage Display Vector (pDAN5)

Once the scFv or Fab libraries were assembled, they were ligated into a phage display vector, such as pDAN5 to explore their functionality. This vector contains a cloning site upstream of the g3 of the filamentous phage, comprised by the restriction enzyme sites for BssHII and NheI. The scFv/Fabs created in Example 8 were amplified with flanking primers containing the BssHII restriction site upstream of the light chain and the NheI downstream of the heavy chain. The PCR product was then digested with the same enzymes to generate cohesive ends. The pDAN5 plasmid was cultivated in E. coli, extracted by alkaline lysis and purified by cesium chloride/ethidium bromide gradient. The plasmid was digested with the same enzymes and the backbone purified by agarose gel electrophoresis extraction followed by chromatography to remove contaminants. The backbone was ligated to the scFv/Fab library using T4 DNA ligase overnight at 16° C. The ligation was purified and electrotransformed into electrocompetent E. coli TG1 cells. The transformed cells were plated out on agar plates containing carbenicillin and glucose to select for bacteria that received the plasmid. Analysis of the scFv libraries by PacBio sequencing revealed >90% open reading frames (Table 9), and essentially no clone duplication (Table 10).

TABLE 9

Percentage of open reading frames in scFv libraries as assessed by PacBio sequencing.

| Library | sequences analyzed | correct frame | ORFs | ORF % |
| --- | --- | --- | --- | --- |
| Lib1 | 6,510 | 6,103 | 6,050 | 93% |
| Lib2 | 5,699 | 5,403 | 5,355 | 94% |
| Lib3 | 7,012 | 6,623 | 6,583 | 94% |
| Lib4 | 9,168 | 8,660 | 8,613 | 94% |
| Lib5 | 7,640 | 7,282 | 7,242 | 95% |
| Lib6 | 5,378 | 5,027 | 5,005 | 93% |

TABLE 10

Analysis of library diversity by PacBio.

| library | No. reads | Full-Length | | HCDR3 + LCDR3 | | HCDR3 | | LCDR3 | | HCDR2 | | LCDR2 | | HCDR1 | | LCDR1 | |
|---|---|---|---|---|---|---|---|---|---|---|---|---|---|---|---|---|---|
| | | No. | % | No. | % | No. | % | No. | % | No. | % | No. | % | No. | % | No. | % |
| 1 | 6000 | 5998 | 99.97 | 5998 | 99.97 | 5851 | 97.52 | 5679 | 94.65 | 1786 | 29.77 | 2224 | 37.07 | 2158 | 35.97 | 1328 | 22.13 |
| 2 | 5265 | 5258 | 99.87 | 5258 | 99.87 | 4740 | 90.03 | 4675 | 88.79 | 1927 | 36.60 | 1796 | 34.11 | 2267 | 43.06 | 481 | 9.14 |
| 3 | 6496 | 6493 | 99.95 | 6493 | 99.95 | 6300 | 96.98 | 5828 | 89.72 | 3077 | 47.37 | 1329 | 20.46 | 3676 | 56.59 | 438 | 6.74 |
| 4 | 8423 | 8420 | 99.96 | 8420 | 99.96 | 8137 | 96.60 | 7965 | 94.56 | 2538 | 30.13 | 1355 | 16.09 | 2525 | 29.98 | 1399 | 16.61 |
| 5 | 7030 | 7029 | 99.99 | 7015 | 99.79 | 6457 | 91.85 | 6263 | 89.09 | 1780 | 25.32 | 1873 | 26.64 | 2684 | 38.18 | 2090 | 29.73 |
| 6 | 4899 | 4898 | 99.98 | 4898 | 99.98 | 4735 | 96.65 | 4725 | 96.45 | 1639 | 33.46 | 1148 | 23.43 | 1833 | 37.42 | 1545 | 31.54 |

Example 10: Creation of Bacteriophage Particles, Including Western Blot

The transformed bacteria were cultivated in a shaking flask containing liquid 2×YT media+carbenicillin+glucose (the glucose is to inhibit scFv/Fab expression) at 37° C. until an OD600 nm of 0.5 was reached. The bacteria were superinfected with M13KO7 helper phage (at a multiplicity of infection of 5) for 30 min at 37° C. without shaking. The bacteria were centrifuged, the media removed and replaced with 2×YT media+carbenicillin+kanamycin and cultivated for 16 h at 25° C. in a shaker incubator.

Figure 33:
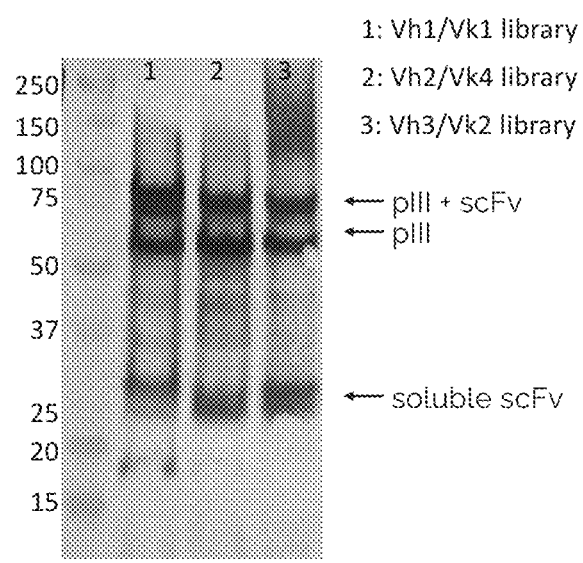
FIG. 33 shows a western blot of libraries 1-3 with the pIII and the scFv-pIII bands indicated.

To recover the phage particles, the cultures were centrifuged to separate the bacteria and the supernatant, where the phage is found. The supernatant was mixed with a 20% PEG 8000+2.5 M NaCl solution at a 5:1 ratio. This causes the phage to precipitate, allowing them to be harvested by centrifugation. The supernatant was discarded and the phage pellet was resuspended in a PBS solution. The display of the scFv/Fab by the phage was assessed by SDS-PAGE+western blot using an antibody that specifically recognizes the expression tag (SV5) as show in FIG. 33.

Figure 34:
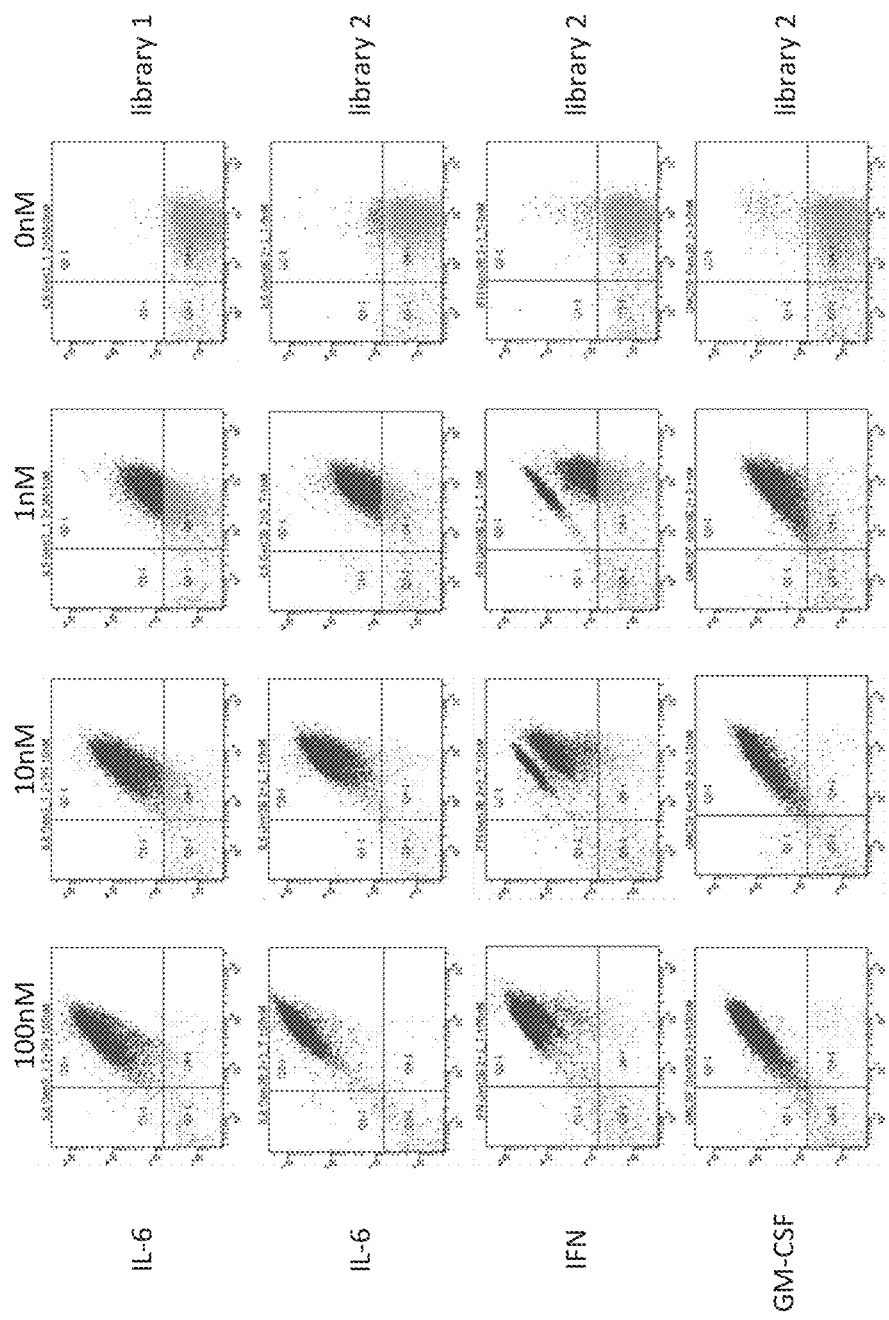
FIG. 34 shows binding of antibodies displayed on yeast binding to targets against which they were selected at different concentrations. Display on yeast followed two rounds of selection by phage display, and two rounds of yeast display. Library 1 and Library 2 represent two different libraries created using the same LCDR1-3 and HCDR1-2 diversity, and HCDR3 diversity from different donors.

Example 11: Antibody Selection by Combined Phage and Yeast Display Using the Library After construction and phage particle production, the library was screened against targets of interest. While selection can be carried out using phage display alone (Sblattero, D. & Bradbury, A. Exploiting recombination in single bacteria to make large phage antibody libraries. *Nat Biotechnol* 18, 75-80 (2000)), we prefer to combine phage and yeast display technologies (Ferrara, F. et al. Using phage and yeast display to select hundreds of monoclonal antibodies: application to antigen 85, a tuberculosis biomarker. *PLoS One* 7, e49535 (2012)). $10^{12}$ phage particles displaying the scFv library were used in two rounds of selection against the biotinylated recombinant human antigens of clinical interest—interleukin 6, interferon alpha, and GM-CSF—using the Kingfisher magnetic bead system: $2 \times 10^7$ streptavidin-conjugated magnetic beads (Dynabeads M-280) coated with the biotinylated proteins (100-400 nM) were washed, coated with the antigen, incubated with the phage particles and washed again to remove non-binders. Phage particles were then eluted by reducing the pH and infecting F' pilus-carrying bacteria (Ominmax-2T1, Thermo Fisher Scientific). The phages were propagated, and the selection cycle reiterated. After two rounds of phage enrichment, the scFvs were PCR amplified and transferred to an N-terminal yeast display system by homologous recombination (pSpec yeast display vector), in which the scFv is displayed fused to the N terminus of Aga-2. The transformed yeast was then induced for scFv display by adding galactose to the culture media. The induced yeast minilibraries were then used for another two to three rounds of enrichment against the biotinylated recombinant human antigens by fluorescence activated cell sorting. Up to 10,000 yeast cells with positive antigen binding signal were sorted and propagated in each round. Target concentration in the first sorting round was 100 nM, reduced to 10 nM and then 1 nM. After these rounds of phage and yeast sorting enrichment the recovered populations was analyzed by flow cytometry to test for binding against the antigens in decreasing concentration of antigen and in the absence of the antigen to check for non-specific binding to secondary reagents (FIG. 34). Results show that the library can successfully yield high affinity binders to all antigens tested.

Example 12: Affinity Determination of Selected Antibodies

Affinity determination of antibodies selected from the naïve library using the phage+yeast display protocol described in Example 11, was performed following the approaches described herein. Binding affinity of the antibody variants thus obtained to various targets (e.g., GM-CSF, IFN-α 2A and IL-6) was examined using a Carterra LSA machine. Briefly, supernatants from yeast expressing scFv-Fc fusions from selections against GM-CSF, IFN-α 2A and IL-6 were immobilized on a Carterra LSA HC200M chip with anti-human Fc. The chips were activated with 1:1:1 100 mM MES pH 5.5, 100 mM S—NHS, 400 mM EDC (all reconstituted in MES 5.5), and 100 μL of each were mixed in a vial immediately before running the assay. The polyclonal goat anti-human IgG was immobilized for 10-minute at 50 μg/mL followed by 7-minute deactivation with 1 M Ethanolamine pH 8.5.

Figure 37:
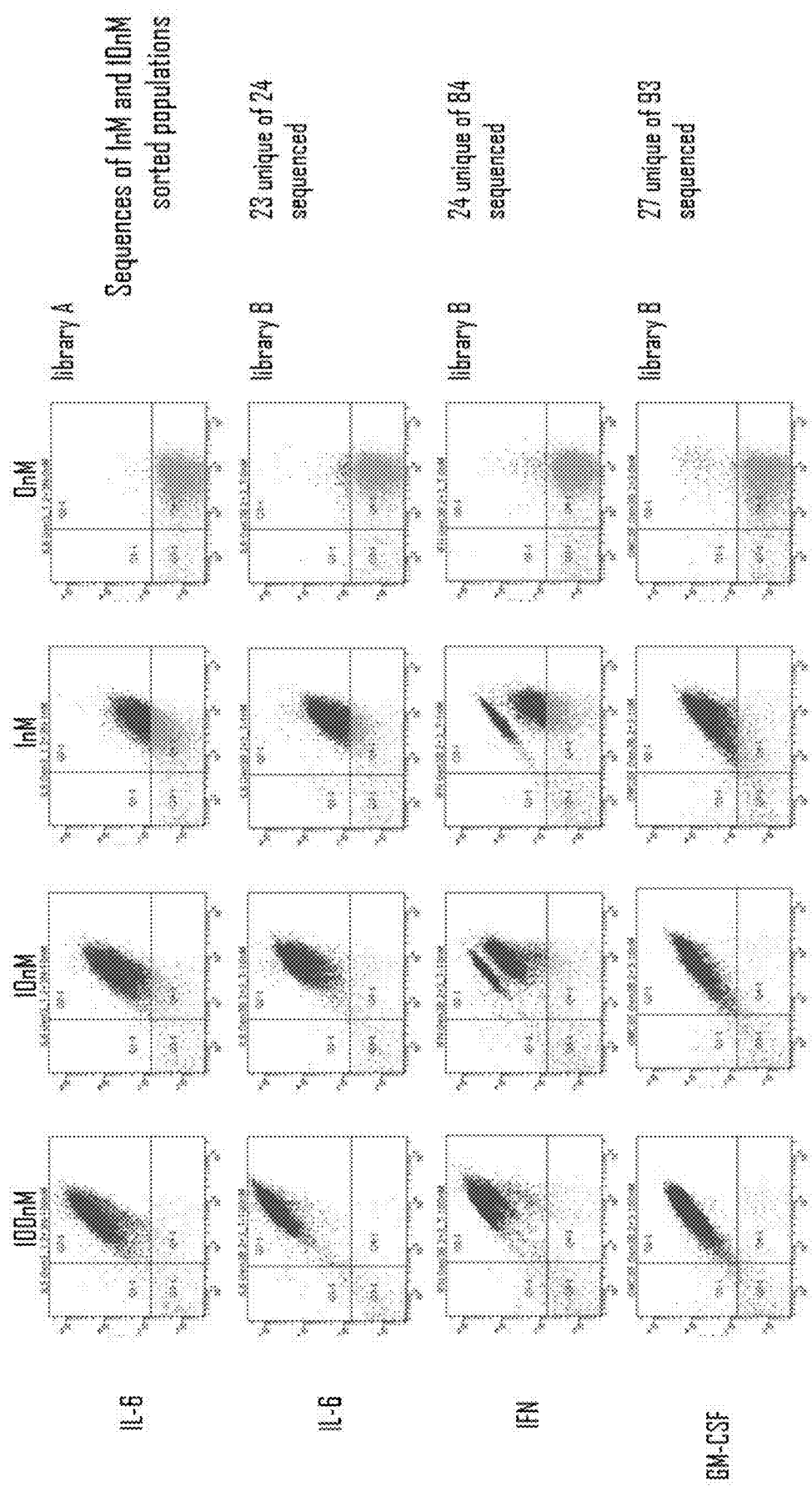
FIG. 37 includes diagrams showing clones binding to the indicated antigens at various concentrations (100 nM, 10 nM, 1 nm, or 0 nM) isolated from Library A or Library B.

The scFv-Fc supernatants were diluted two or three fold into HBSTE buffer and cycled for 12 minutes across the anti-Fc surface. Antigens were tested in a three-fold dilution series starting at 6 nM for IFN-2A and 167 nM for IL-6/GM-SCF. The antigen samples were tested from lowest to highest concentration. FIG. 37.

Data was processed using a floated Rmax parameter for the IFN-2A and GM-SCF clones that did not dissociate fully between binding cycles; some of the data were also fit using a bulk shift parameter.

Figure 38A:
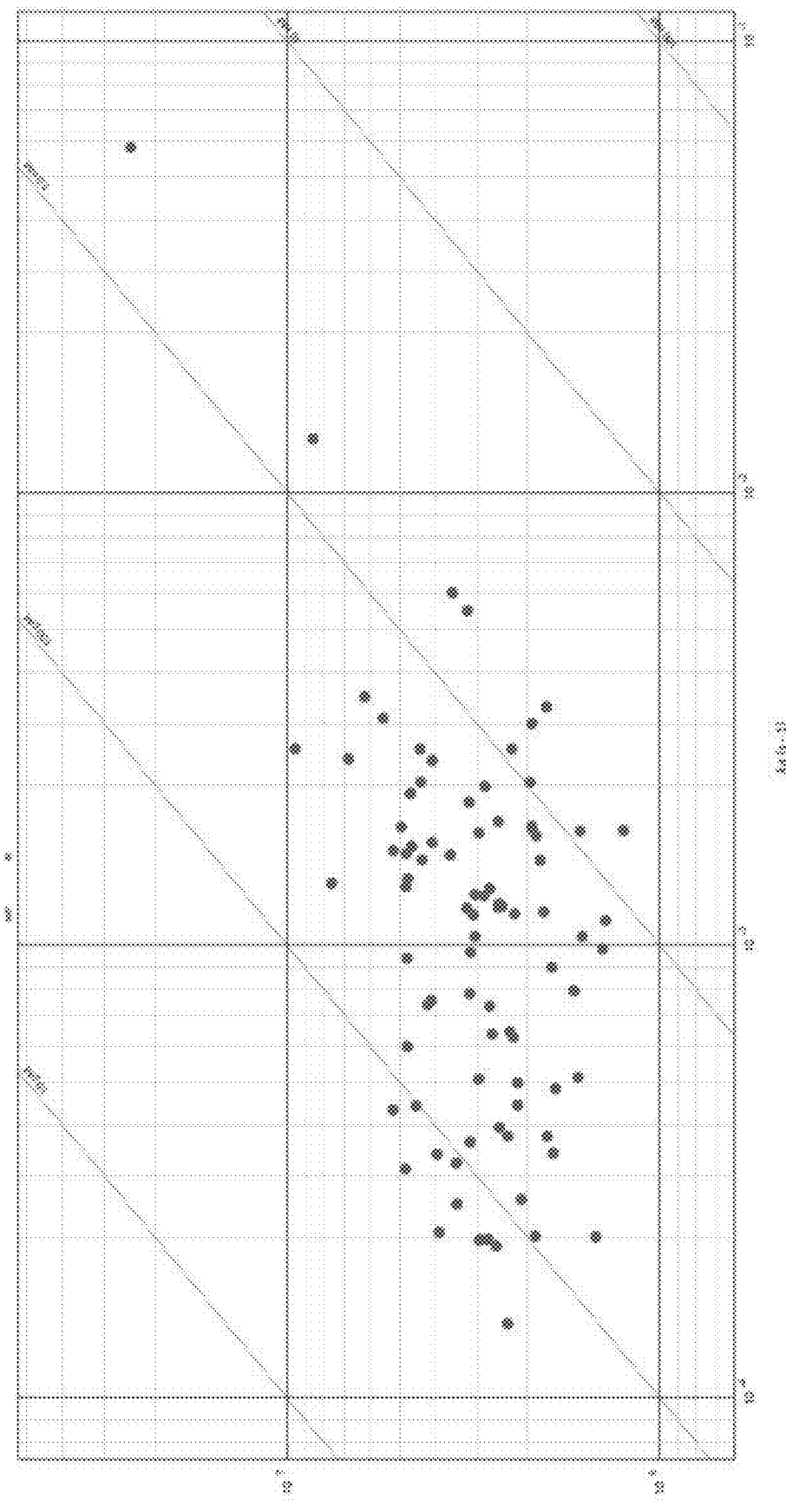
FIGS. 38A-38C include diagrams showing isolation of high affinity antibodies (having binding affinity at the sub-nanomolar level) from the libraries disclosed herein.
Figure 38B:
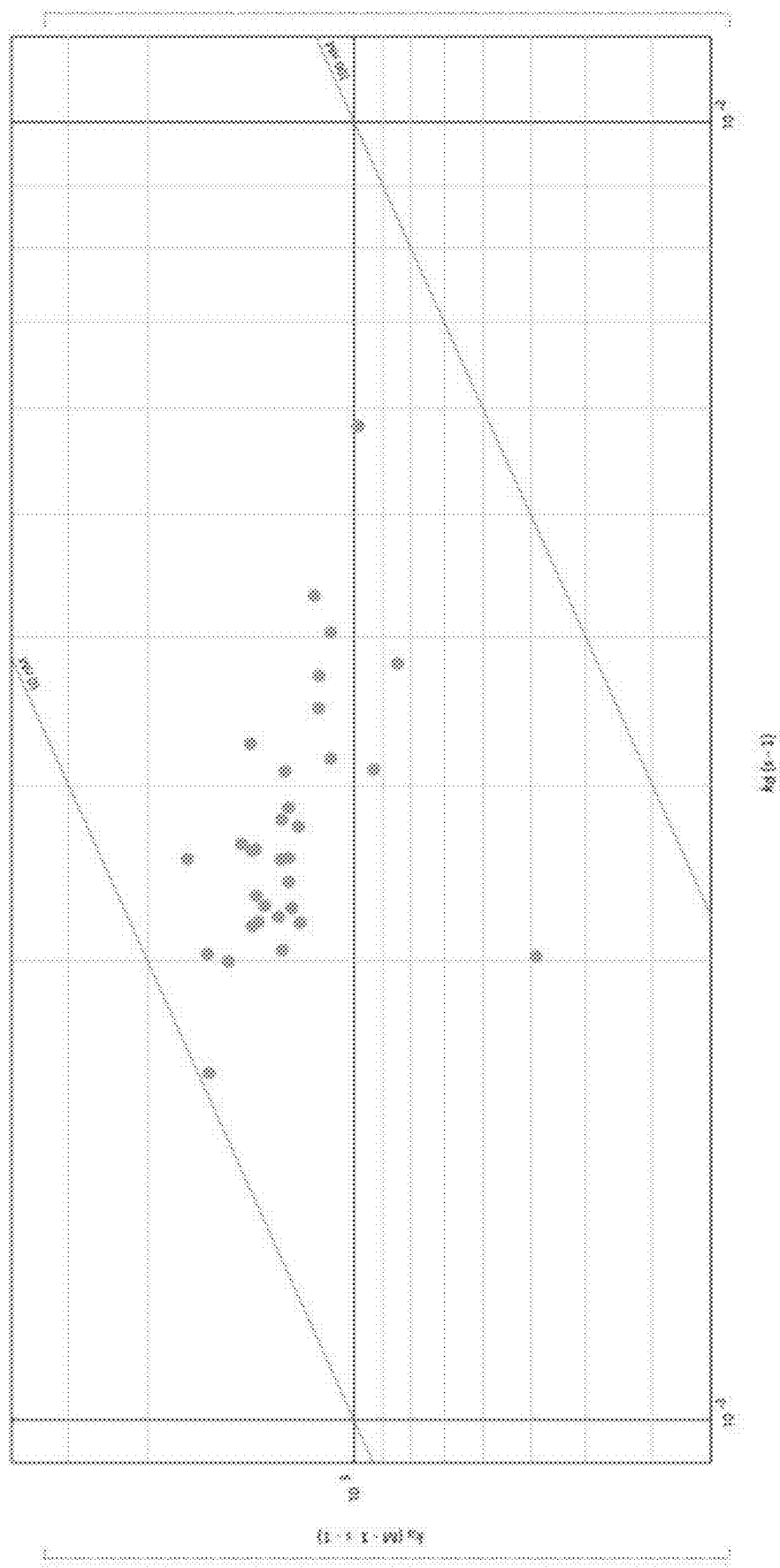
Figure 38C:
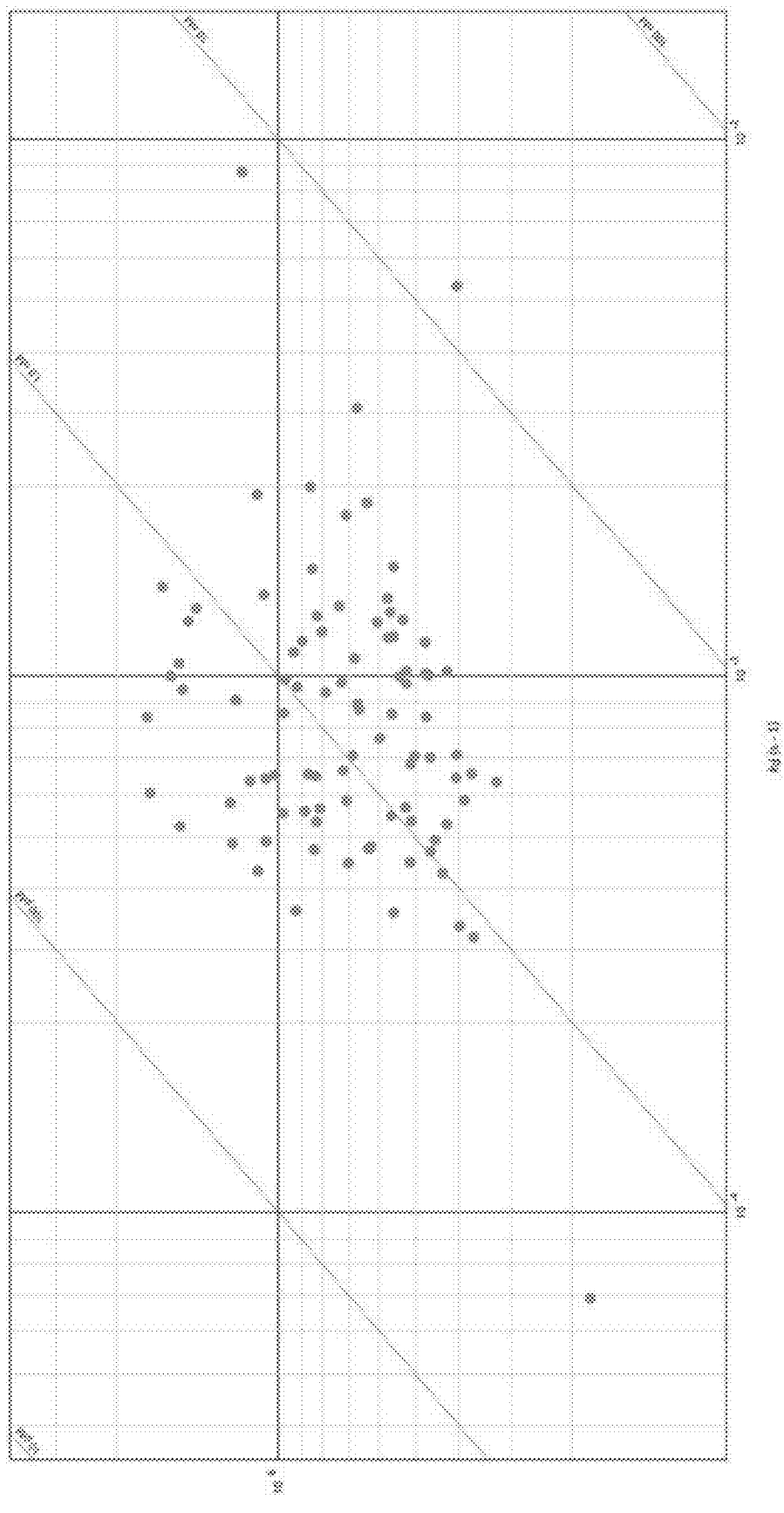

As shown in FIGS. 38A-38C, the affinities of antibodies selected directly from the library, constructed as described in Examples 1-10, are shown to be extremely potent, with many subnanomolar antibodies having been selected.

Figure 39:
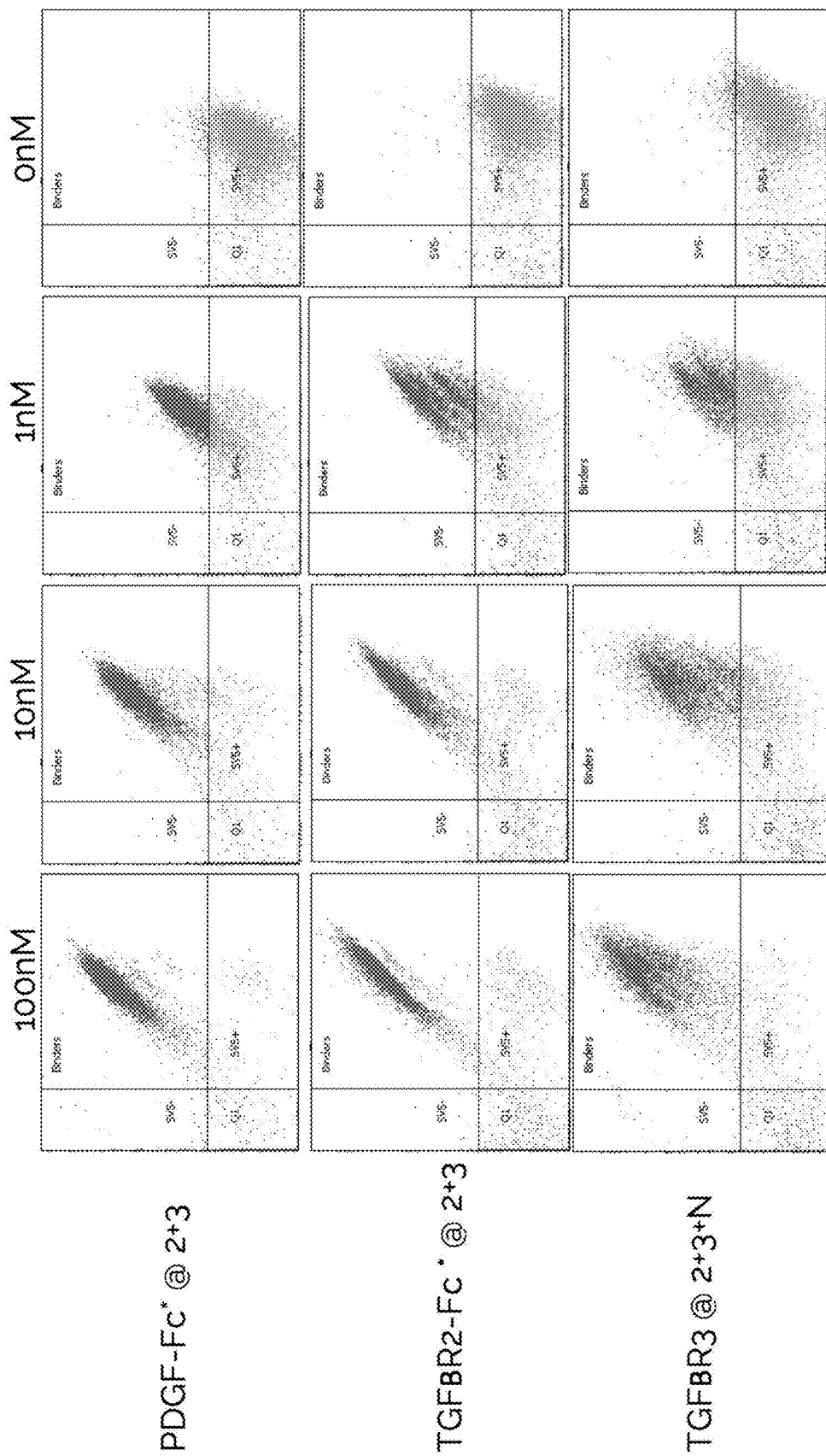
FIG. 39 is a diagram showing isolation of antibodies with high binding affinity to additional antigens, PDGF, TGFBR2, and TGFBR3, from the libraries disclosed herein.

Antibodies to additional targets, including PDGF, TGFBR2, and TGFBR3, were explored using this approach and similar results were observed. FIG. 39.

Example 13: Antibody Maturation

To select an optimized VL and VH pair and assemble the CDRs into a mature antibody, the following approach can be used. First, the VH is kept in unmodified form while the VLs in the LCDR libraries are shuffled. The remaining functional VLs are assembled with the unmodified VH and the formed antibodies are tested for functionality (FIG. 35). Likewise, the VL is kept unmodified and the VHs comprising synthetic HCDR1/2 and natural HCDR3 in the VH library is shuffled. Each of the remaining functional VH can be assembled with the unmodified VH and the newly formed antibodies are tested for their functions (FIG. 36).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for producing a human antibody library, comprising:
   deriving an antibody heavy chain from the heavy chain of a single human antibody heavy chain variable domain gene or from a single human therapeutic antibody;
   providing (a) a first plurality of nucleic acids encoding a population of naturally-occurring antibody heavy chain complementary determining region 1 (CDR1) fragments, (b) a second plurality of nucleic acids encoding a population of naturally-occurring antibody heavy chain complementary determining region 2 (CDR2) fragments, and (c) a third plurality of nucleic acids encoding a population of naturally-occurring heavy chain complementary determining region 3 (CDR3) fragments;
   inserting the first plurality of nucleic acids and/or the second plurality and/or the third plurality of nucleic acids into the CDR1 region and/or the CDR2 region and/or the CDR3 region, respectively, of an antibody heavy chain variable domain gene, thereby producing an antibody library;
   wherein at least 90% of the population of naturally-occurring antibody heavy chain CDR1 fragments, the population of antibody heavy chain CDR2 fragments, and optionally the population of antibody heavy chain CDR3 fragments is free of members comprising one or more of:
   (i) a glycosylation site,
   (ii) a deamidation site,
   (iii) an isomerization site,
   (iv) unpaired cysteine,
   (v) net charge greater than 1,
   (vi) a tripeptide motif containing at least two aromatic residues,
   (vii) a motif that promotes aggregation,
   (viii) a poly specificity site;
   (ix) a protease sensitive site,
   (x) an integrin binding site,
   (xi) a lysine glycation site,
   (xii) a metal catalyzed fragmentation site,
   (xiii) a poly specificity aggregation site; or
   (xiv) a streptavidin binding motif.

2. The method of claim 1, wherein the glycosylation site of (i) comprises the motif NXS, NXT, or NXC, in which X represents any naturally-occurring amino acid residue except for proline;
   the deamidation site of (ii) comprises the motif of NG, NS, NT, NN, NA, NH, ND, GNF, GNY, GNT, or GNG;
   the isomerization site of (iii) comprises the motif of DT, DH, DS, DG, or DD;
   the tripeptide of (vi) is HYF or HWH;
   the motif that promotes aggregation of (vii) comprises the motif of FHW;
   the polyspecificity site of (viii) comprises the motif GG, GGG, RR, VG, W, WV, WW, WWW, YY, or WXW, in which X represents any amino acid residue
   the protease cleavage site of (ix) comprises the motif of DX, in which X is P, G, S, V, Y, F, Q, K, L, or D;
   the integrin binding site of (x) comprises RGD, RYD, LDV, or KGD;
   the lysine glycation site of (xi) comprises KE, EK, or ED;
   the metal catalyzed fragmentation site of (xii) comprises the motif of HS, SH, KT, HXS, or SXH, in which X represents any amino acid residue;
   the polyspecificity aggregation site of (xiii) comprises a motif of X1X2X3, wherein each of X1, X2, and X3 independently is selected from the group consisting of F, I, L, V, W and Y; or
   the streptavidin binding motif of (xiv) comprises the motif HPQ, EPDW (SEQ ID NO: 117), PWXWL (SEQ ID NO: 118), in which X represents any amino acid residue, GDWVFI (SEQ ID NO: 119), or PWPWLG (SEQ ID NO: 120).

3. The method of claim 1, wherein the population of human antibody heavy chain CDR3 fragments is derived from B cells.

4. The method of claim 1, wherein the antibody heavy chain variable region gene is a human heavy chain variable region gene, which optionally is selected from the group consisting of VH1-24, VH2-70, VH3-7, VH4-30-4, VH5-51, VH1-18, VH1-69, VH3-23, VH5-10-1, VH3-9, and VH3-11.

5. The method of claim 4, wherein the human antibody heavy chain variable region gene is derived from a therapeutic antibody selected from the group consisting of abrilumab, mepolizumab, crenezumab, necitumumab, anifrolumab, and evoculumab.

6. The method of claim 4, wherein the human antibody heavy chain variable region gene is derived from a therapeutic antibody selected from the group consisting of abituzumab, adalimumab, alemtuzumab, alirocumab, bapineuzumab, benralizumab, brodalumab, canakinumab, certolizumab, clazakizumab, dacetuzumab, daclizumab, daratumumab, eculizumab, efalizumab, elotuzumab, epratuzumab, farletuzumab, fasinumab, ficlatuzumab, fletikumab, fresolimumab, fulranumab, gevokizumab, ibalizumab, lintuzumab, matuzumab, mavrilimumab, mogamulizumab, motavizumab, natalizumab, nivolumab, obinutuzumab, ofatumumab, olokizumab, omalizumab, onartuzumab, otelixizumab, otlertuzumab, palivizumab, panitumumab, panobacumab, pertuzumab, pinatuzumab, polatuzumab, radretumab, ramucirumab, reslizumab, romosozumab, sarilumab, secukinumab, sifalimumab, tabalumab, tigatuzumab, tildrakizumab, tocilizumab, tovetumab, trastuzumab, vedolizumab, veltuzumab, zalutumumab, and zanolimumab.

7. The method of claim 1, wherein the heavy chain CDR1, CDR2, and CDR3 fragments, the heavy chain variable domain gene, and optionally the light chain CDR1, CDR2, and CDR3 fragments, and the light chain variable domain gene are derived from naturally-occurring antibodies of a mammalian species.

8. The method of claim 7, wherein the mammalian species is human or camelid.

9. The method of claim 1, wherein the antibody library is a full-length antibody library, a Fab antibody library, a single-chain antibody library, or a single domain antibody library.

10. The library of claim 1, wherein the derived antibody heavy chain has up to 5 amino acid substitutions.

11. The library of claim 1, wherein the library contains at least $10^7$ unique CDR3 sequences.

12. The library of claim 1, wherein the library contains heavy chain CDR3 sequences with greater diversity than the heavy chain CDR1, heavy chain CDR2, light chain CDR 1, light chain CDR2, and light chain CDR3 diversity.

* * * * *